(12) United States Patent
Nicolaou et al.

(10) Patent No.: US 6,660,758 B1
(45) Date of Patent: Dec. 9, 2003

(54) EPOTHILONE ANALOGS

(75) Inventors: Kyriacos C. Nicolaou, La Jolla, CA (US); Yun He, San Diego, CA (US); Sacha Ninkovic, San Diego, CA (US); Joaquin Pastor, Madrid (ES); Frank Roschangar, Durham, NC (US); Francisco Sarabia, Torre De Benagalbón (ES); Hans Vallberg, Huddinge (SE); Dionisios Vourloumis, Apex, NC (US); Nicolas Winssinger, La Jolla, CA (US); Zhen Yang, Brookline, MA (US); Nigel Paul King, Camborne (GB); M. Ray Finlay, Killinchy (GB)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/319,885

(22) PCT Filed: Dec. 12, 1997

(86) PCT No.: PCT/EP97/07011

§ 371 (c)(1),
(2), (4) Date: Sep. 24, 1999

(87) PCT Pub. No.: WO98/25929

PCT Pub. Date: Jun. 18, 1998

Related U.S. Application Data

(60) Provisional application No. 60/032,864, filed on Dec. 13, 1996.

(51) Int. Cl.[7] .................... C07D 413/06; A01K 31/422
(52) U.S. Cl. ........................................ 514/374; 548/235
(58) Field of Search ........................... 548/235; 514/374

(56) References Cited

FOREIGN PATENT DOCUMENTS

| WO | 9310121 | 5/1993 |
| --- | --- | --- |
| WO | 9719086 | 5/1997 |
| WO | 9808849 | 3/1998 |
| WO | 9822461 | 5/1998 |
| WO | 9825929 | 6/1998 |
| WO | 98381912 | 9/1998 |
| WO | 9901124 | 1/1999 |
| WO | 9902514 | 1/1999 |
| WO | 9907692 | 2/1999 |
| WO | 9901124 | * 11/1999 ................ 548/235 |

OTHER PUBLICATIONS

Gabriel, et al., "The Chromimum–Refromatsky Reaction: Asymmetric Synthesis of the Aldol Fragment of Cytotoxic Epothilones from 3–(2–Bromoacyl)–2–oxazolidonones", *Tet. Lett. 38*: 1363–1366 (1997).

Taylor, et al., "Towards the Synthesis of Epothilone A: Enantioselective Preparation of the Thaizole Sidechain and Macrocyclic Ring Closure", *Tet. Lett. 38*: 2061–2064 (1997).

Su, et al., "Total Synthesis of (–)–Epothilone B: An Extension of the Suzuki Coupling Method and Insights into Structure–Activity Relationships of the Epothilones", *Angew. Chem. Int. Ed. Engl. 36*: 757–759 (1997).

Schinzer, et al., "Studies Towards the Total Synthesis of Epothilones: Asymmetric Synthesis of the Key Fragments", *Chem. Eur. J. 2*: 1477–1482 (1996).

Nicolaou, et al., "Total Synthesis of Oxazole and Cyclopropane–Containing Epothilone A Analogues by the Olefin Metathesis Approach", *Chem. Eur. J. 3*: 1957–1970 (1997).

Nicolaou, et al., "Total Synthesis of Oxazole– and Cyclopropane–Containing Epothilone B Analogues by the Macrolactonization Approach", *Chem. Eur. J. 3*: 1971–1986 (1997).

Nicolaou, et al., "Probing the Ring Size of Epothilones: Total Synthesis of [14]–, [15]–, [17]–, and [18]Epothilones", *Angew. Chem. Int. Ed. Engl. 37*: 81–84 (1998).

Nicolaou, et al., "Total Synthesis of Epothilone E and Analogues with Modified Side Chains through the Stille Coupling Reaction", *Angew. Chem. Int. Ed. Engl. 37*: 84–87 (1998).

Nicolaou, et al., "Total Synthesis of Epothilone E and Related Side–Chain Modified Analogues via a Stille Coupling Based Strategy", *Bioorg. Med. Chem. 7*: 665–697 (1999).

Schinzer, et al., "Total Synthesis of (–)–Epothilone A", *Ang. Chem. Int. Ed., Engl. 36(5)*: 523–524 (1997).

Yang, et al., "Total Synthesis of Epothilone A: The Olefin Metathesis Approach", *Ang. Chem. Int. Ed. Engl. 36*: 166–168 (1997).

Bollag, et al., "Epothilones, a New Class of Microtubule–stabilizing Agents with a Taxol–like Mechanism of Action", *Cancer Res. 55*:2325–2333 (1995).

Meng, et al., "Remote Effects in Macrolide Formation through Ring–Forming Olefin Metathesis: An Application to the Synthesis of Fully Active Epothilone Congeners", *Amer. Chem. Soc. 119*: 2733–2734 (1997).

Grever, et al., "The National Cancer Institute: Cancer Drug Discovery and Development Program", *Seminars Oncol. 19*: 622–638 (1992).

(List continued on next page.)

*Primary Examiner*—Robert Gerstl
(74) *Attorney, Agent, or Firm*—Donald G. Lewis

(57) ABSTRACT

Epothilone A, epothilone B, analogs of epothilone and libraries of epothilone analogs are synthesized. Epothilone A and B are known anticancers agents that derive their anticancer activity by the prevention of mitosis through the induction and stabilization of microtubule assembly. The analogs of epothilone are novel. Several of the analogs are demonstrated to have a superior cytotoxic activity as compared to epothilone A or epothilone B as demonstrated by their enhanced ability to induce the polymerization and stabilization of microtubules.

13 Claims, 101 Drawing Sheets

OTHER PUBLICATIONS

Mulzer, et al., "Synthesis of the C(1)–C(9) Segment of the Cytotoxic Macrolides Epothilon A and B", *Tetr. Lett. 37(51)*: 9179–9182 (1996).

Claus, et al., "Synthesis of the C1–C9 Segment of Epothilons", *Tetr. Lett. 38(8)*: 1359–1362 (1997).

Gabriel, et al., "The Chromium–Reformatsky Reaction: Asymmetric Synthesis of the Aldol Fragment of the Cytotoxic Epothilons from 3–(2–Bromoacyl)–2–oxazolidinones", *Teter. Lett. 38(8)*: 1363–1366 (1997).

Meng, et al., "Studies toward a Synthesis of Epothilone A: Use of Hydropyran Templates for the Management of Acyclic Stereochemical Relationships", *Org. Chem. 61*:7998–7999 (1996).

Bertinato, et al., "Studies toward a Synthesis of Epothilone A: Stereocontrolled Assembly for the Acyl Region and Models for Macrocyclization", *J. Org. Chem. 61*: 8000–8001 (1996).

Kowalski, et al., "Activities of the Microtubule–stabilizing Agents Epothilones A and B with Purified Tubulin and in Cells Resistant to Paclitaxel (Taxol)", *J. Biol. Chem. 272*: 2534–2541 (1997).

Schiff, et al., "Promotion of Microtubule Assembly in vitro by Taxols", *Nature 277*: 665–667 (1979).

Balog, et al., "Total Synthesis of (–)–Epothilone A", *Ang. Chem. Int. Ed. Engl.35(23/24)*: 2801–2803 (1996).

Hofle, et al., "Epothilone A and B–Novel 16–Membered Macrolides with Cytotoxic Activity: Isolation, Crystal Structure, and Conformation in Solution", *Ang. Chem. Int. Ed. Engl. 35 (13/14)*: 1567–1568 (1996).

Nicolaou, et al., "An Approach to Epothilones Based on Olefin Metathesis", *Ang. Chem. Int. Ed. Engl. 35 (20)*: 2399–2401 (1996).

Nicolaou, et al., "Total Synthesis of Epothilone A: The Macrolactonization Approach", *Ang. Chem. Int. Ed. Engl. 36(5)*: 525–527 (1997).

Nicolaou, et al., "Chemistry and Biology of Taxol", *Ang. Chem. Int. Ed. Engl. 33*: 15–44 (1994).

Winkler, et al., "A Model for the Taxol (Paclitaxel)/Epothilone Pharmacophore", *Bioorg. Med. Chem. Int. Ed. Engl. 33*: 2963–2966 (1996).

Nicolaou, et al., "Designed Epothilones: Combinatorial Synthesis, Tubulin Assembly Properties, and Cytotoxic Action against Taxol–Resistant Tumor Cells", *Ang. Chem. Int. Ed. Engl. 36 (19)*: 2097–2103 (1997).

Nicolaou, et al., "The Olefin Metathesis Approach to Epothilone A and Its Analogues", *J. Amer. Chem. Soc. 119*: 7960–7973 (1997).

Nicolaou, et al., "Total Synthesis of26–Hydroxy–Epothilone B and Related Analogs via a Macrolactonization Based Strategy", *Tetrahedron 54*: 7127–7166 (1998).

May, et al., "Total Synthesis of (–)–epothilone B", *Chem. Commun.*: 1597–1598 (1998).

Nicolaou, et al., "Total Synthesis of 26–hydroxyepothilone B and Related Analogues", *Chem. Commun.*: 2343–2344 (1997).

Su, et al., "Structure–Activity Relationships of the Epothilones and the First in vivo Comparison with Paxlitaxel", *Angew. Chem. Int. Ed. Engl 36*: 2093–2096 (1997).

Meng, et al., "Total Synthesis of Epothilones A and B", *J. Amer. Chem. Soc. 119*: 10073–10092 (1997).

Nicolaou, et al., "Synthesis of Epotnilones A and B in Solid and Solution Phase", *Nature 387*: 268–272 (1997).

Nicolaou, et al., "Total Syntheses of Epothilones A and B via a Macrolactonization–Based Strategy", *J. Amer. Chem. Soc. 119*: 7974–7991 (1997).

Balog, et al., "Stereoselective Synthesis and Evaluation of Compounds in the 8–Desmethylepothilone A Series: Some Surprising Observations Regarding their Chemical and Biological Properties", *Tetr. Lett. 38* : 4529–4532 (1997).

Nicolaou, et al., "Chemical Biology of Epothilones", *Angew. Chem. Int. Ed. Engl. 37*: 2014–2045 (1998).

White, et al., "Improved Synthesis of Epothilone B Employing Alkylation of an Alkyne for Assembly of Subunits", *Org. Lett. 1*: 1431–1434 (1999).

Sinha, et al., "Sets of Aldolase Antibodies with Antipodal Reactivities. Formal Synthesis of Epothilone E by Large–Scale Antibody–Catalyzed Resolution of Thiazole Aldol", *Org. Lett. 1*.: 1623–1626 (1999).

Sawada, et al., "Enantioselective Total Synthesis of Epothilone A Using Multifunctional Asymmetric Catalyses", *Angew. Chem. Int. Ed. Engl. 39*: 209–213 (2000).

Martin, et al., "How Stable are Epoxides? A Novel Synthesis of Epothilone B", *Angew. Chem. Int. Ed. Engl. 39*: 581–583 (2000).

* cited by examiner

1: R=H, epothilone A
2: R=Me, epothilone B

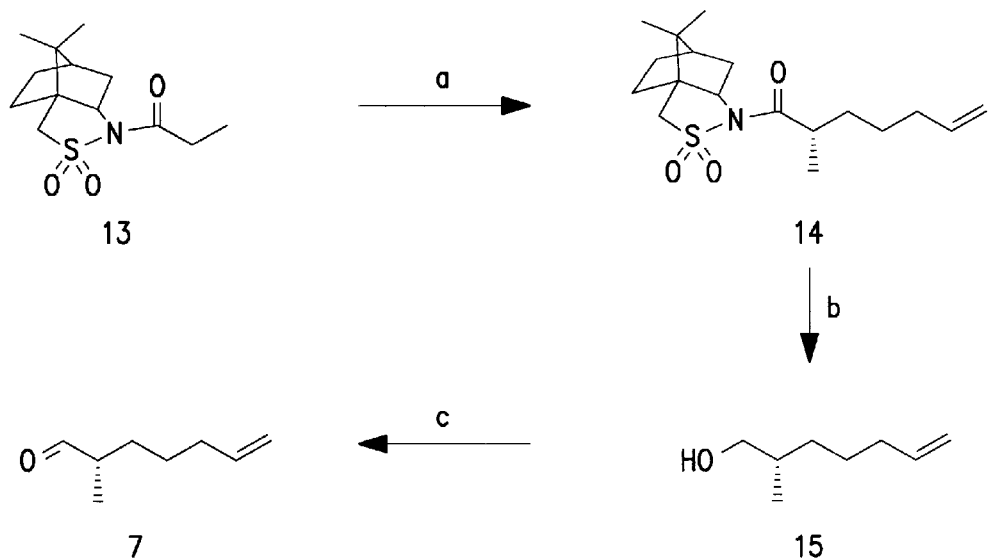
FIG. 3A
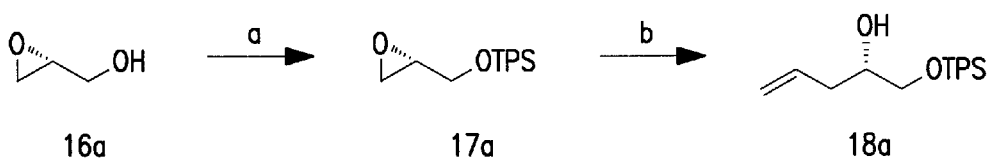
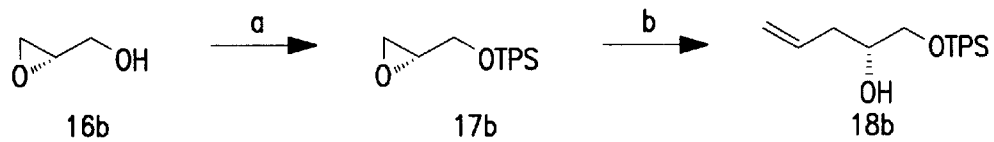
FIG. 3B
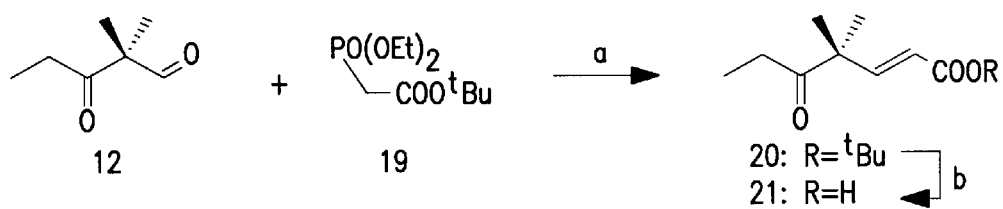
FIG. 3C

*Enders alkylation*
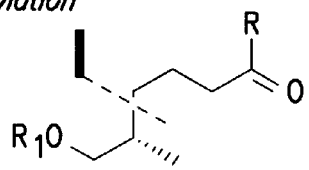
77: R=H
78: R=Me
+
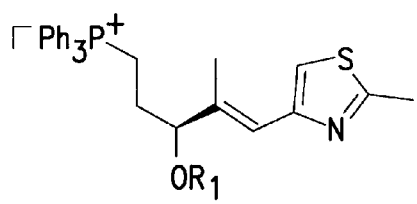
79
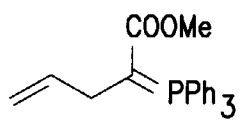
83
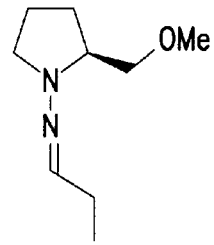
80
+
*Wittig olefination*
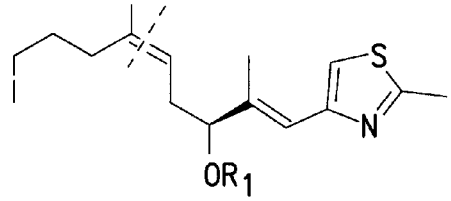
81
⇩
*Asymmetric allylboration*
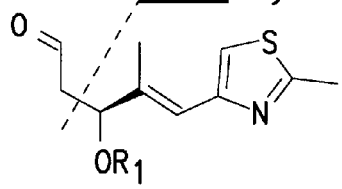
82
$R_1$ = TBS = Si$^t$BuMe$_2$
FIG. 11B

| Compound | Induction of tubulin assembly[a] EC$_{50}$ (mM) ± s.d. | Inhibition of human ovarian carcinoma cell growth[b] IC$_{50}$ nM (relative resistance) | | | |
|---|---|---|---|---|---|
| | | Parental | Taxol'-resistant β-tubulin mutants | | MDR-line |
| | | 1A9 | 1A9PTX10 | 1A9PTX22 | A2780AD |
| 1 | 14 ±0.4 | 2.0 | 19 (9.5) | 4.2 (2.1) | 2.4 (1.2) |
| 2 | 4.0 ±0.1 | 0.040 | 0.035 (0.88) | 0.045 (1.1) | 0.040 (1.0) |
| 71 | 3.3 ±0.2 | 2.0 | 33 (17) | 3.5 (1.8) | 1.5 (0.80) |
| 158 | 25 ±1 | 25 | >100 (>4) | 75 (3.0) | 22 (0.88) |
| 123 | 39 ±2 | 48 | >100 (>2) | 75 (1.6) | 24 (0.50) |
| 125 | 22 ±0.9 | 3.5 | 30 (8.6) | 5.5 (1.6) | 3.0 (0.86) |
| Taxol | 15 ±2 | 2.0 | 50 (25) | 43 (22) | >100 (>50) |

FIG. 23

1: X=S: epothilone A
161: X=O: epoxalone A

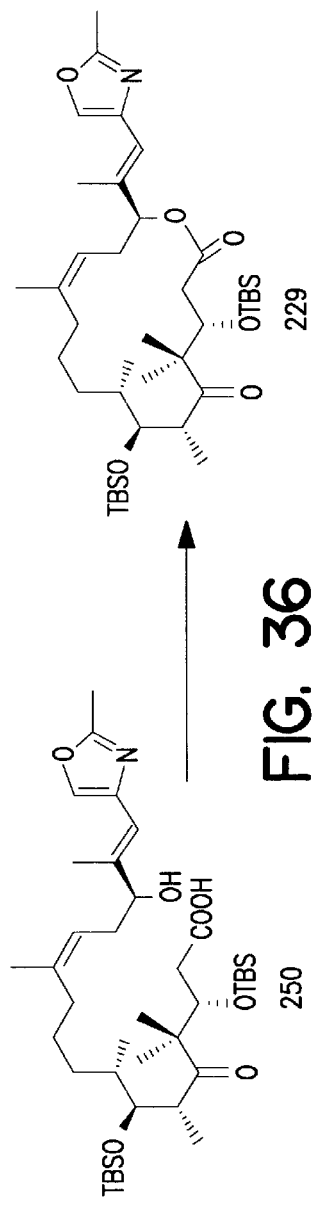

FIG. 54A

FIG. 54C
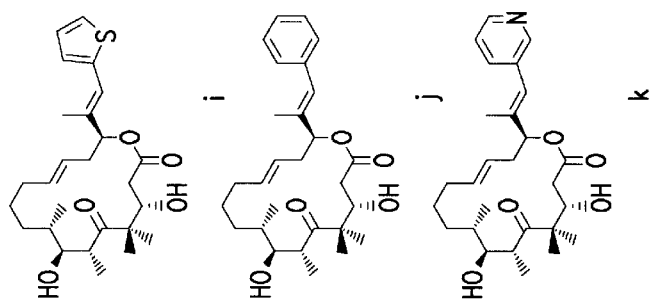
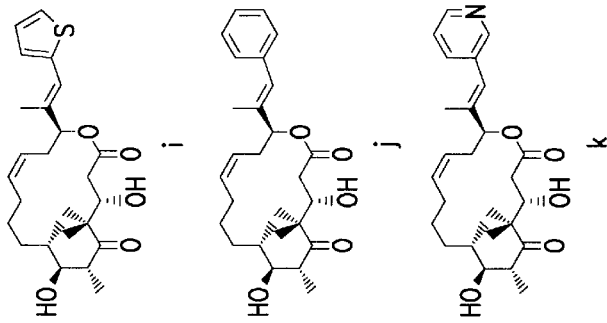
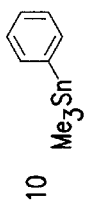

FIG. 55A

: R=CH$_2$OC(O)CH$_3$
: R=CH$_2$OC(O)$^t$Bu
: R=CH$_2$OC(O)Ph
: R=CHO
e → : R=COOH
f → : R=COOCH$_3$
: R=CH$_2$Cl
: R=CH$_2$OMe
: R=CH$_2$OCH$_2$Ph
: R=CH$_2$F
: R=CH=CH$_2$

: R=CH$_2$OC(O)CH$_3$
: R=CH$_2$OC(O)$^t$Bu
: R=CH$_2$OC(O)Ph
: R=CHO
e' → : R=COOH
f' → : R=COOCH$_3$
: R=CH$_2$Cl
: R=CH$_2$OMe

| Cmpd | Induction of tubulin polymerization | | | Inhibition of carcinoma cell growth [c] | | | |
|---|---|---|---|---|---|---|---|
| | Screening assay [a] | Quantitative glutamate assay [b] | | | Ovarian [d] | | Breast [e] |
| | | | Parental | | β-tubulin mutations | | |
| | | | 1A9 | | 1A9PTX10 | 1A9PTX22 | MCF7 |
| | % polymer formed with compound relative to that formed with GTP | EC$_{50}$ (μM) | IC$_{50}$ (nM) | | [RELATIVE RESISTANCE] [F] | | |
| Taxol™ | 50 | 4.7 | 1.4 | | 32 [23] | 38 [27] | 4.2 |
| 1 | 76 | 4.6 | 2.2 | | 20 [9.1] | 5.9 [2.7] | 5.1 |
| 2 | 98 | 3.4 | 0.13 | | 1.0 [7.7] | 0.31 [2.4] | 1.0 |
| 161 | 58 | 5.3 | 3.0 | | 25 [8.3] | 8.0 [2.7] | 6.1 |
| 233 | 93 | — | — | | 1.1 | 0.9 | — |
| 234 | 71 | 6.1 | 1.5 | | 11 [7.3] | 3.0 [2.0] | 6.2 |
| 58 | 92 | 6.2 | 2.0 | | 18 [9.0] | 3.0 [1.5] | 5.4 |
| 125 | 84 | 5.6 | 1.0 | | 8.5 [8.5] | 1.0 [1.0] | 1.8 |
| 171 | 64 | 7.8 | 3.5 | | 32 [9.1] | 9.5 [2.7] | >100 |
| 126 | 63 | 13 | 6.0 | | 30 [5.0] | 6.5 [1.1] | 14 |
| 172 | 46 | 8.1 | 4.8 | | 34 [7.1] | 9.0 [1.9] | 5.7 |

FIG. 66A

| | | | | | |
|---|---|---|---|---|---|
| 49 | 72 | 8.3 | 32 | >100 | 38 |
| 71 | 94 | 3.9 | 6.5 | 23 [3.5] | 9.3 |
| 168 | 75 | 6.1 | 68 | >100 | 74 |
| 231 | 93 | 3.3 | 8.0 | 30 [3.8] | >100 |
| 50 | 76 | 9.8 | 60 | >100 | >100 |
| 123 | 84 | 7.5 | 61 | >100 | 75 |
| 169 | 43 | 13 | >100 | – | >100 |
| 232 | 54 | 6.0 | 32 | >100 | 68 |
| 461 | 34 | 17 | >100 | – | >100 |
| 465 | 51 | 7.6 | 32 | >100 | 57 |
| 466 | 61 | 11 | 82 | >100 | 78 |

| | | | | | |
|---|---|---|---|---|---|
| | | | | 100 | |
| | | | | 9.0 [1.4] | |
| | | | | 90 | |
| | | | | 12 [1.5] | |
| | | | | 100 | |
| | | | | 85 | |
| | | | | – | |
| | | | | >100 | |
| | | | | – | |
| | | | | 70 | |
| | | | | >100 | |

FIG. 66B

Inhibition of human ovarian carcinoma cell growth

| Compound | Induction of tubulin assembly (%) | Parental 1A9 | Taxol-resistant PTX10 | Taxol-resistant PTX22 |
|---|---|---|---|---|
| | | $IC_{50}$ nM (relative resistance) | | |
| 1000g | 88 | 90 | >100 | >100 |
| 1000j | 83 | 0.65 | 6 | 4 |
| 1000k | 95 | 8.7 | 30 | 14 |
| 1000l | 66 | 60 | >100 | 93 |
| 1000d' | 87 | 5 | 24 | 3.1 |
| 1000g' | 69 | 0.25 | 0.50 | 0.55 |
| 1000i' | 41 | 25 | 55 | 20 |
| 1000j' | 93 | 0.15 | 0.55 | 0.15 |
| 1000k' | 94 | 0.63 | 4.7 | 0.95 |
| 1000l' | 79 | 0.27 | 8.5 | 0.45 |
| Taxol | 50 | 2 | 50 | 43 |
| Epothilone A | 72 | 2 | 19 | 4.2 |
| Epothilone B | 100 | 0.040 | 0.035 | 0.045 |

FIG. 71

EPOTHILONE ANALOGS

This application is a 371 of PCT/EP97/07011 filed Dec. 12, 1997 and claims benefit of: Ser. No. 60/032,864 filed Dec. 13, 1996.

This invention was made with government support under Contract No. CA 46446 by the National Institutes of Health. The government has certain rights in the invention.

TECHNICAL FIELD OF THE INVENTION

The present invention relates to epothilone A, epothilone B, epothilone analogs, libraries of epothilone analogs, and methods for producing such compounds using solid phase and solution phase chemistries, their use for the therapy of diseases or for the manufacture of pharmaceutical preparations for the treatment of diseases, as well as to novel intermediates used in the synthesis of said compounds.

BACKGROUND OF THE INVENTION

Epothilone A (1, FIG. 1) and epothilone B(2, FIG. 1) are natural substances isolated from myxobacteria Sorangium cellulosum strain 90. These natural substances exhibit cytotoxicity against taxol-resistant tumor cells and may prove to have a clinical utility comparable or superior to Taxol. (For Taxol references see: Horwitz et al. Nature 277, 665–667 (1979); Nicolaou et al. Angew. Chem. Int. Ed. Engl. 33, 15–44 (1994).) Like taxol, the epothilones are thought to exert their cytotoxicity by induction of microtubule assembly and stabilization. (Bollag et al. Cancer Res. 55, 2325–2333 (1995); Kowalski et al. J. Biol. Chem. 272, 2534–2541 (1997).) Epothilones are reported to be about 2000–5000 times more potent than Taxol with respect to the stabilization of microtubules. Despite the marked structural differences between the epothilones and Taxol™, the epothilones were found to bind to the same region on microtubules and to displace Taxol™ from its binding site. (Grever et al. Seminars in Oncology 1992, 19, 622–638; Bollag et al. Cancer Res. 1995, 55, 2325–2333; Kowalski et al. J. Biol. Chem. 1997, 272, 2534–2541; Horwitz et al. Nature 1979, 277, 665–667; Nicolaou et al. Angew. Chem. Int. Ed. Engl. 1994, 33, 15–44.) Epothilones A and B have generated intense interest amongst chemists, biologists and clinicians due to their novel molecular architecture, important biological action and intriguing mechanism of action. (Höfle et al. Angew. Chem. Int. Ed. Engl. 35, 1567–1569 (1996); Grever et al. Semin. Oncol. 19, 622–638 (1992); Bollag et al. Cancer Res. 55, 2325–2333 (1995); Kowalski et al. J. Biol. Chem. 272, 2534–2541 (1997); Nicolaou et al. Angew. Chem. Int. Ed. Engl. 35, 2399–2401 (1996); Meng et al. J. Org. Chem. 61, 7998–7999 (1996); Bertinato et al. J. Org. Chem. 61, 8000–8001 (1996); Schinzer et al. Chem. Eur. J. 2, 1477–1482 (1996); Mulzer et al. Tetrahedron Lett. 37, 9179–9182 (1996); Claus et al. Tetrahedron Lett. 38, 1359–1362 (1997); Gabriel et al. Tetrahedron Lett. 38, 1363–1366 (1997); Balog et al. Angew. Chem. Int. Ed. Engl. 35, 2801–2803 (1996); Yang et al. Angew. Chem. Int. Ed. Engl. 36, 166–168 (1997); Nicolaou et al. Angew. Chem. Int. Ed. Engl. 36, 525–527 (1997); Schinzer et al. Angew. Chem. Int. Ed. Engl. 36, 523–524 (1997); Meng et al. J. Am. Chem. Soc. 119, 2733–2734 (1997).)

What is needed are analogs of epothilone A and B and libraries of analogs of epothilone A and B that exhibit superior pharmacological properties in the area of microtubule stabilizing agents.

What is needed are methods for producing synthetic epothilone A, epothilone B, analogs of epothilone A and B, and libraries of epothilone analogs, including epothilone analogs possessing both optimum levels of microtubule stabilizing effects and cytotoxicity.

SUMMARY OF THE INVENTION

The invention provides new ways of synthesis for epothilone derivatives with advantageous pharmacological properties, especially due to better activities when compared with Taxol or (especially with regard to the preferred compounds) comparable or better activities than than epothilones A or B, which, without said methods, would have been inaccessible, as well as new synthetic methods for the synthesis of epothilone A and epothilone B.

In detail, the invention is directed to analogs of epothilone. More particularly, the invention is directed to compounds represented by the following structure (formula (I)):

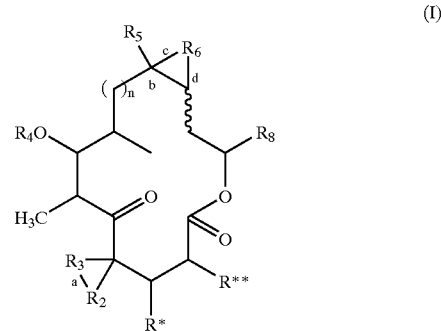

(I)

wherein n is 1 to 5, preferably 3 or in a broader aspect of the invention 1. In a preferred embodiment, either R* is —$OR_1$ and R** is hydrogen, or R* and R** together form a further bond so that a double bond is present between the two carbon atoms carrying R* and R**; $R_1$ is a radical selected from the group consisting of hydrogen (preferred) or methyl, or (in a broader aspect of the invention) a protecting group, especially from the group comprising tert-butyldimethylsilyl, trimethylsilyl, acetyl, benzoyl, and tertbutoxycarbonyl; $R_2$ is a radical selected from the group consisting of hydrogen, methylene and (preferably) methyl; $R_3$ is a radical selected from the group consisting of hydrogen, methylene and (preferably) methyl; $R_4$ is a radical selected from the group consisting of hydrogen (preferred) or methyl, or is a protecting group, preferably selected from the group consisting of tertbutyldimethylsilyl, trimethylsilyl, acetyl, benzoyl, and tertbutoxycarbonyl; $R_5$ is a radical selected from the group consisting of hydrogen, methyl, —CHO, —COOH, —$CO_2$Me, —$CO_2$(tert-butyl), —$CO_2$(isopropyl), —$CO_2$(phenyl), —$CO_2$(benzyl), —CONH (furfuryl), —$CO_2$(N-benzo-(2R,3S)-3-phenylisoserine), —CON(methyl)$_2$, —CON(ethyl)$_2$, —CONH(benzyl), —CH=$CH_2$, HC≡C—, and —$CH_2R_{11}$; $R_{11}$ is a radical selected from the group consisting of —OH, —O-Trityl, —O—($C_1$-$C_6$ alkyl), —($C_1$-$C_6$ alkyl), —O-benzyl, —O-allyl, —O—$COCH_3$, —O—$COCH_2$Cl, —O—$COCH_2CH_3$, —O—$COCF_3$, —O—$COCH(CH_3)_2$, —O—CO—C($CH_3)_3$, —O—CO(cyclopropane), —OCO (cyclohexane), —O—$COCH$=$CH_2$, —O—CO-Phenyl, —O-(2-furoyl), —O—(N-benzo-(2R,3S)-3-phenylisoserine), —O-cinnamoyl, —O-(acetylphenyl), —O-(2-thiophenesulfonyl), —S—($C_1$-$C_6$ alkyl), —SH, —S-Phenyl, —S-Benzyl, —S-furfuryl, —NH₂, —N₃, —NHCOCH₃, —NHCOCH₂Cl, —NHCOCH₂CH₃, —NHCOCF₃, —NHCOCH(CH₃)₂, —NHCO—C(CH₃)₃, —NHCO (cyclopropane), —NHCO(cyclohexane), —NHCOCH=CH₂, —NHCO-Phenyl, —NH(2-furoyl), —NH—(N-benzo-(2R,3S)-3-phenylisoserine), —NH-(cinnamoyl), —NH-(acetyl-phenyl), —NH-(2-thiophenesulfonyl), —F, —Cl, I, —CH₂CO₂H and methyl; $R_6$ is absent, methylene, or oxygen; $R_7$ is hydrogen; $R_8$ is a radical selected from the group represented by the for-mulas:

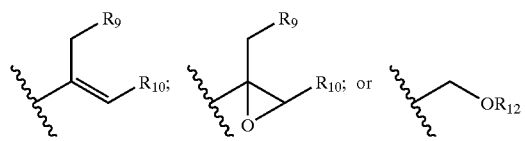

wherein $R_9$ is a radical selected from the group consisting of hydrogen and methyl; $R_{10}$ is a radical selected from the group represented by the formulas:

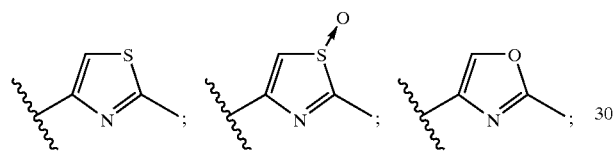

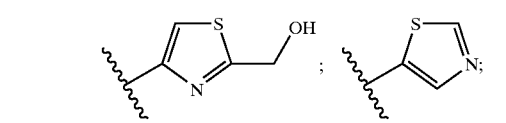

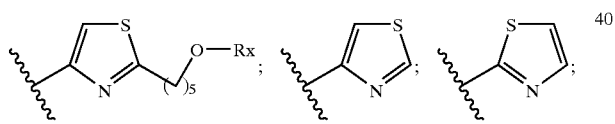

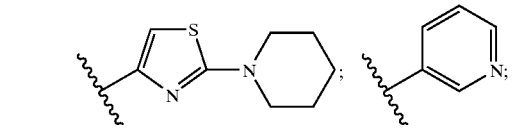

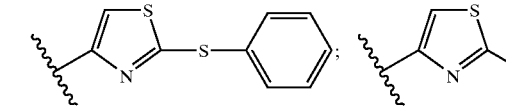

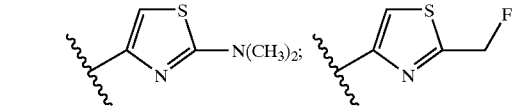

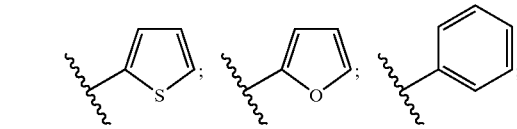

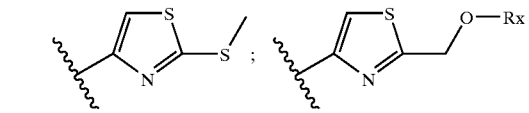

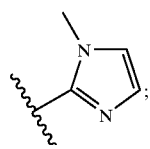

and (in a broader aspect of the invention)

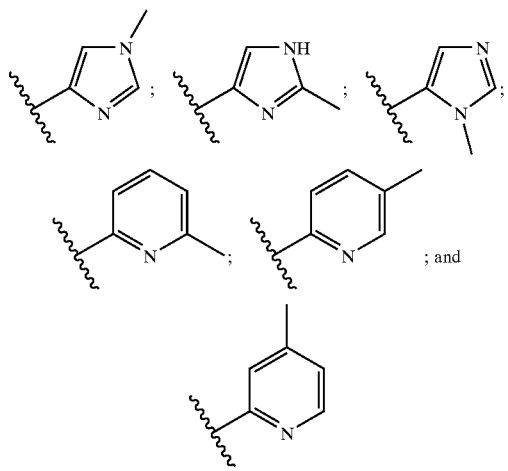

wherein Rx is acyl, especially lower alkanoyl, such as acetyl;

$R_{12}$ is a radical selected from the group consisting of hydrogen, methyl or a protecting group, preferably tertbutyldiphenylsilyl, tertbutyldimethylsilyl, trimethylsilyl, acetyl, benzoyl, tert-butoxycarbonyl and a group represented by any on of the following formulae

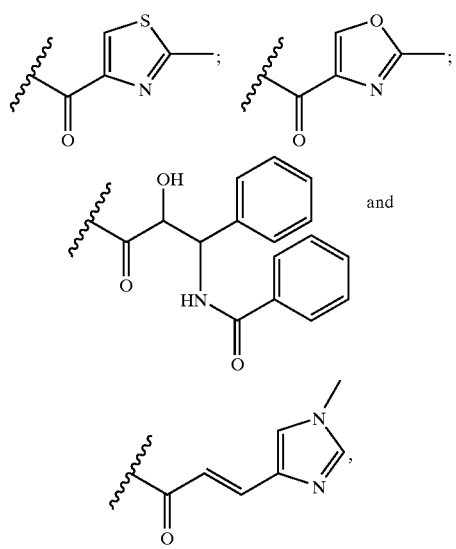

or (in a broader aspect of the invention) a salt thereof where a salt-forming group is present.

Preferably, the compound of the formula I has the formula IA

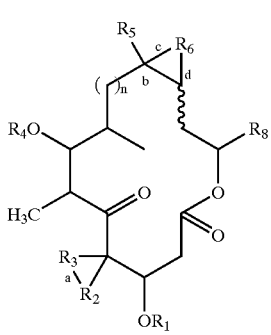

(IA)

wherein the moieties and symbols have the manings just defined for a compound of the formula I.

In the above structures, "a" can be either absent or a single bond; "b" can be either a single or double bond; "c" can be either absent or a single bond; "d" can be either absent or a single bond. However, the following provisos pertain:

1. If $R_2$ is methylene, then $R_3$ is methylene;
2. if $R_2$ and $R_3$ are both methylene, then "a" is a single bond;
3. if $R_2$ and $R_3$ are selected from the group consisting of hydrogen and methyl, then the single bond "a" is absent;
4. if n is 3, $R_2$ is methyl, $R_3$ is methyl, $R_5$ is selected from the group consisting of methyl and hydrogen, $R_6$ is oxygen, $R_7$ is hydrogen, $R_8$ is represented by the formula:

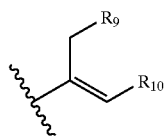

wherein $R_9$ is hydrogen, and $R_{10}$ is represented by the formula

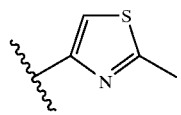

then $R_1$ and $R_4$ cannot both be simultaneously hydrogen or methyl or acetyl;

5. if $R_6$ is oxygen, then "c" and "d" are both a single bond and "b" is a single bond;
6. if $R_6$ is absent, then "c" and "d" are absent and "b" is a double bond;
7. if "b" is a double bond then $R_6$, "c", and "d" are absent;

Especially preferred is the use of said compounds for the treatment of resistant (especially drug resistant) tumours or for the preparation of a pharmaceutical preparation for the treatment of drug resistant tumors, or a pharmaceutical preparation for or a method for the treatment of a mammal, especially a human, having a proliferative disease that is resistant to treatment with other chemotherapeutic agents, especially Taxol, for or by administration to a mammal, especially a human, in need of such treatment, and especially the use of the protected forms of the compounds for the synthesis of the free compounds.

(Z:E ca 1:1); (b) 1.0 equivalent of CSA portionwise over 1 hour, methylene chloride:MeOH (1:1), 0° C.; then 25° C., 0.5 hour, 97%; (c) 2.0 equivalents of $SO_3$.pyr., 10.0 equivalents of DMSO, 5.0 equivalents of $Et_3N$, methylene chloride, 25° C., 0.5 hour, 95%; (d) 3.0 equivalents of LDA, THF, 0° C., 15 minutes; then 1.2 equivalents of 76 in THF, −78→−40° C., 0.5 hour; then 1.0 equivalent of 75' in THF at −78° C., high yield of 117a' and its 6S,7R-diastereoisomer 117b' (ca 1:1 ratio); (e) 3.0 equivalents of TBSOTf, 5.0 equivalents of 2,6-lutidine, methylene chloride, 0° C., 2 hours; (f) 2.0 equivalents of $K_2CO_3$, MeOH, 25° C., 15 minutes, 31% of 119' and 30% of 6S,7R-diastereoisomer 120' from 75'; (g) 6.0 equivalents of TBAF, THF, 25° C., 8 hours, 75%; (h) 1.3 equivalents of 2,4,6-trichlorobenzoylchloride, 2.2 equivalents of $Et_3N$, THF, 0° C., 1 hour; then add to a solution of 10.0 equivalents of 4-DMAP in toluene (0.002 M based on 73'), 25° C., 12 hours, 37% of 121; and 40% of 122; (i) 20% $CF_3COOH$ (by volume) in methylene chloride, −10→0° C., 1 hour, 91%; (j) same as i, 89%; (k) dimethyldioxirane, methylene chloride, −50° C., 75% (2:124 ca 5:1 ratio of diastereoisomers) or 1.5 equivalents of mCPBA, benzene, 3° C., 2 hours, 66% (2:124 ca 5:1 ratio of diastereoisomers) or methyl(trifluoromethyl) dioxirane, MeCN, 0° C., 85% (2:124 ca 5:1 ratio of diastereoisomers); (l) 1.5 equivalents mCPBA, benzene. 3° C., 2 hours, 73% (125:126 ca 4:1 ratio of stereoisomers) or methyl(trifluoromethyl)dioxirane, MeCN, 0° C., 86% (125:126 ca 1:1 ratio of diastereoisomers).

Figure 17:
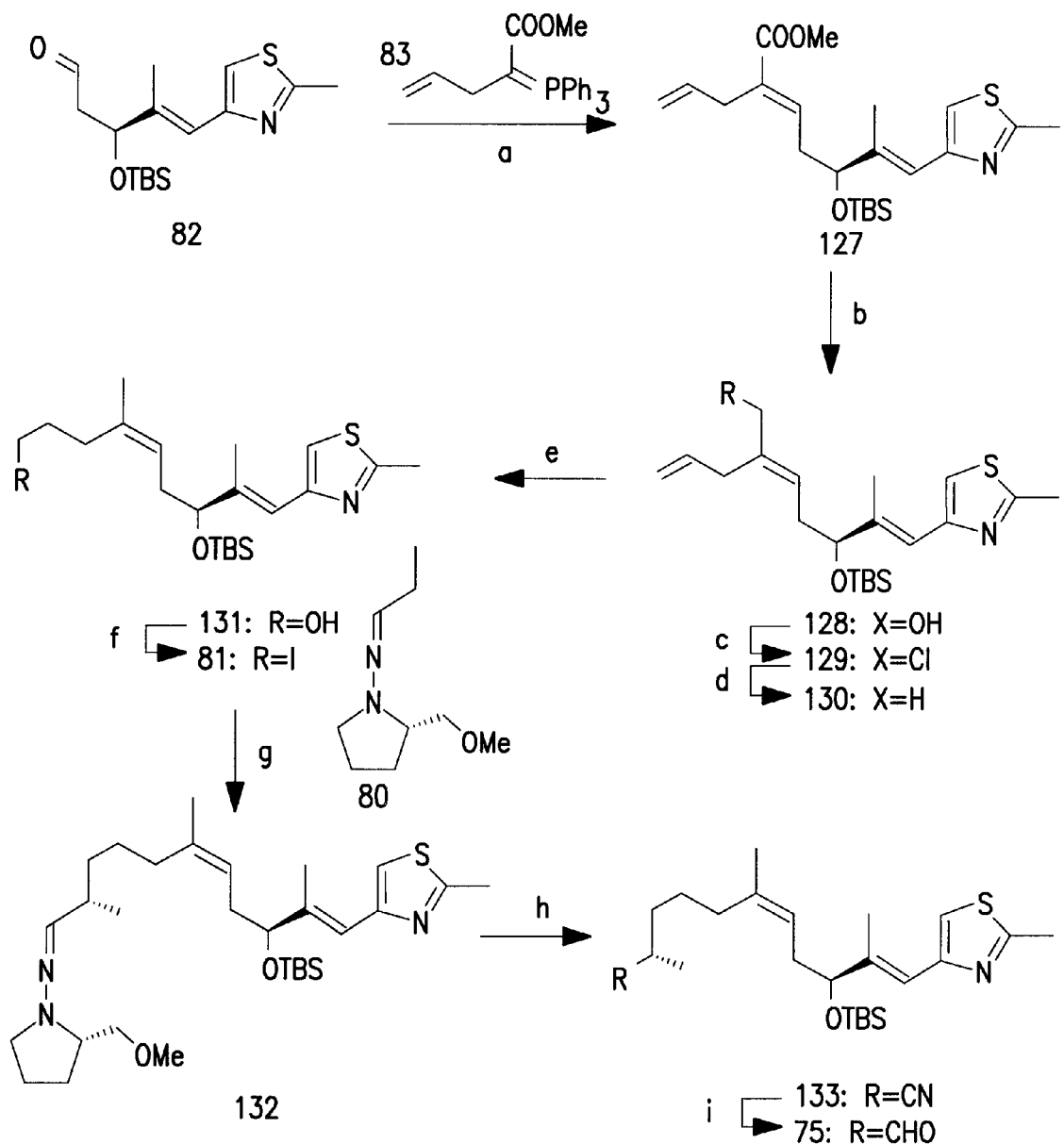

FIG. 17 illustrates the stereoselective synthesis of aldehyde 75 for epothilone B(2). Reagents and conditions: (a) 1.5 equivalents of 83, benzene, reflux, 5 hours, 95%; (b) 3.0 equivalents of DIBAL, methylene chloride, −78° C., 2 hours, 98%; (c) 2.0 equivalents of $Ph_3P$, $CCl_4$, reflux, 24 hours, 83%; (d) 2.0 equivalents of $LiEt_3BH$, THF, 0° C., 1 hour, 99%; (e) 1.2 equivalents of 9-BBN, THF, 0° C., 2 hours, 91%; (f) 1.5 equivalents of $I_2$, 3.0 equivalents of imidazole, 1.5 equivalents of $Ph_3P$, $Et_2O$:MeCN (3:1), 0° C., 0.5 hour, 92%; (g) 1.5 equivalents of 80, 1.5 equivalents of LDA, THF, 0° C., 8 hours; then 1.0 equivalent of 81 in THF, −100→−20° C., 10 hours, 70%; (h) 2.5 equivalents of monoperoxyphthalic acid, magnesium salt (MMPP), MeOH:phosphate buffer pH7 (1:1), 0° C., 1 hour, 80%; (i) 2.0 equivalents DIBAL, toluene, −78° C., 1 hour, 82%.

Figure 18:
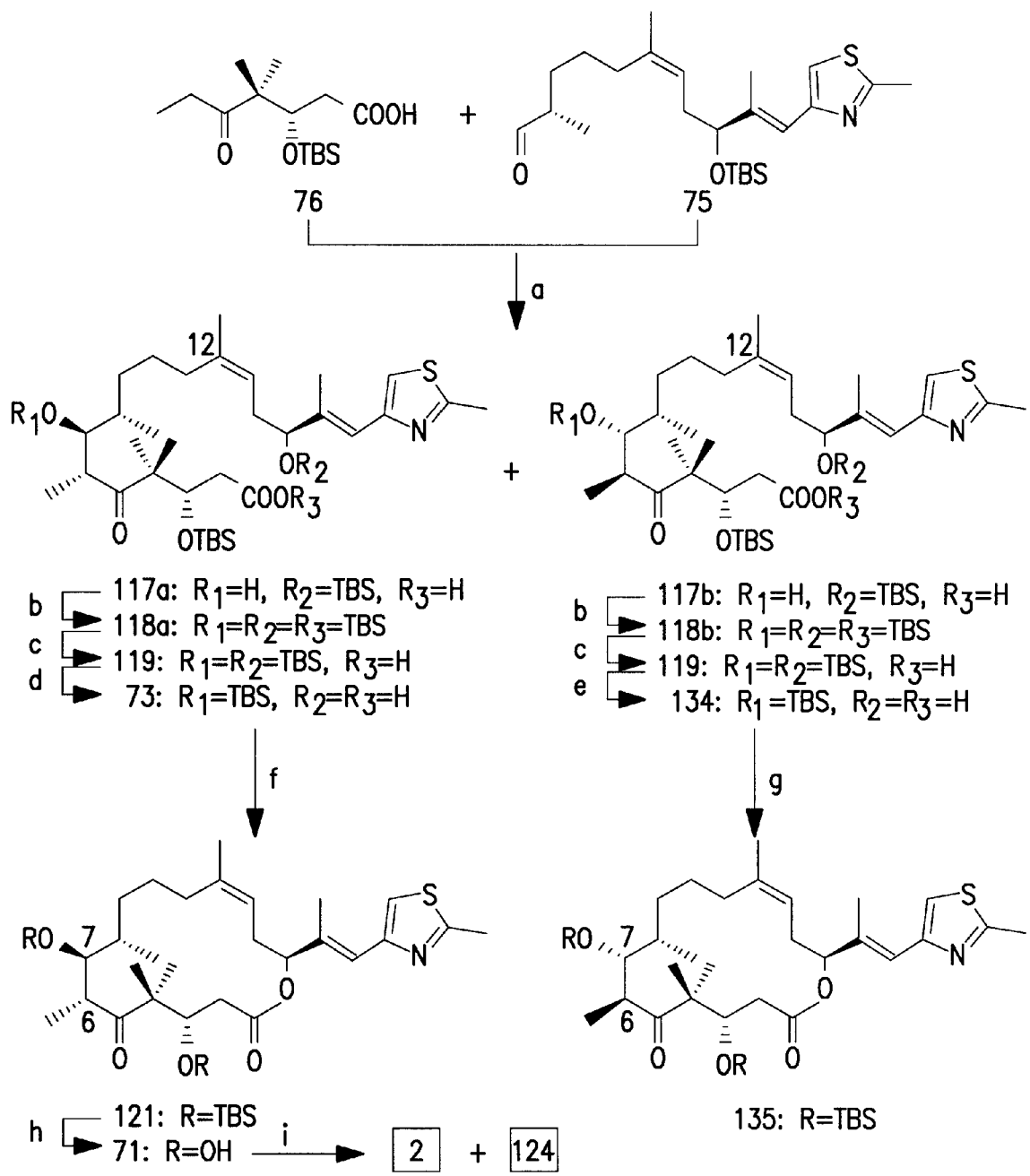

FIG. 18 illustrates the first stereoselective total synthesis of epothilone B(2). Reagents and conditions: (a) 3.0 equivalents of LDA, THF, 0° C., 15 minutes; then 1.2 equivalents of 76 in THF, −78→−40° C., 0.5 hour, then 1.0 equivalent of 75 in THF at −78° C., high yield of 117a and 6S,7R-diastereoisomer 117b (ca 1.3:1.0 ratio of diastereoisomers); (b) 3.0 equivalents of TBSOTf, 5.0 equivalents of 2,6-lutidine, methylene chloride, 0° C., 2 hours; (c) 2.0 equivalents of $K_2CO_3$, MeOH, 25° C., 15 minutes, 32% of 119 and 28% of 6S,7R-diastereoisomer 119 from 75; (d) 6.0 equivalents of TBAF, THF, 25° C., 8 hours, 73%; (e) same as d, 71%; (f) 5.0 equivalents of 2,4,6-trichlorobenzoylchloride, 6.0 equivalents of $Et_3N$, THF, 25° C., 15 minutes, then add to a solution of 10.0 equivalents of of 4-DMAP in toluene (0.002 M based on 73), 25° C., 12 hours, 77%; (g) same as f, 76%; (h) 20% $CF_3COOH$ (by volume) in methylene chloride, 0° C., 1 hour, 91%; (i) see FIG. 16.

Figure 19:
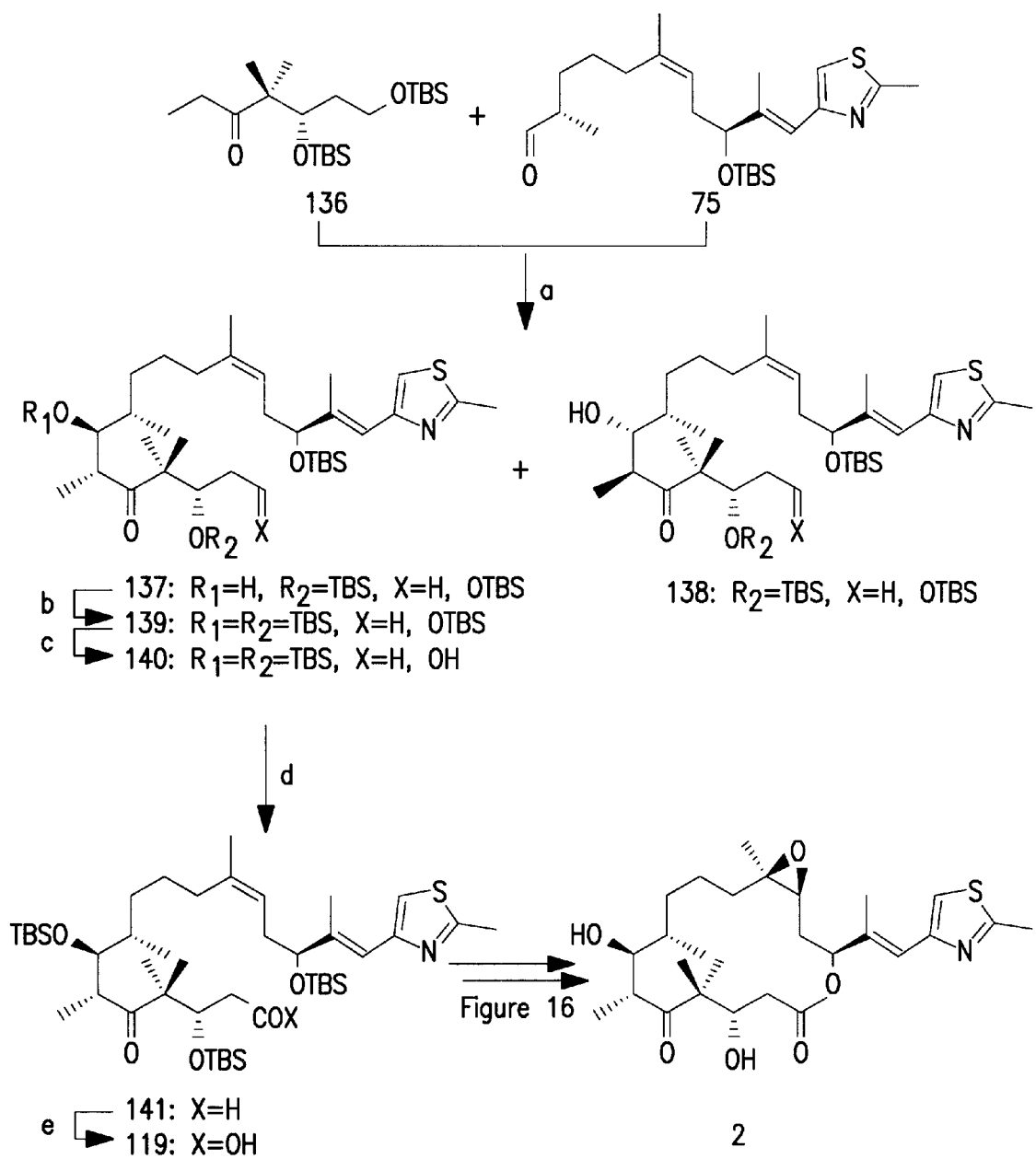

FIG. 19 illustrates the second stereoselective synthesis of epothilone B(2). Reagents and conditions: (a) 1.2 equivalents of LDA, THF, 0° C., 15 minutes; then 1.2 equivalents of 136 in THF, −78—−40° C., 1 hour; then 1.0 equivalent of 75 in THF at −78° C., 85% of 137 and 6S,7R-diastereoisomer 138 (ca 3:1 ratio); (b) 1.2 equivalents of TBSOTf, 2.0 equivalents of 2,6-lutidine, methylene chloride, 0° C., 2 hours, 96%; (c) 1.0 equivalent of CSA portionwise over 1 hour, methylene chloride:MeOH (1:1), 0 25° C., 0.5 hour, 85%; (c) 2.0 equivalents of $(COCl)_2$, 4.0 equivalents of DMSO, 6.0 equivalents of $Et_3N$, methylene chloride, −78→0° C., 1.5 hours, 95%; (d) 3.0 equivalents of $NaClO_2$, 4.0 equivalents of 2-methyl-2-butene, 1.5 equivalents of $NaH_2PO_4$, tBuOH:$H_2O$ (5:1), 25° C., 2 hours, 90%.

Figure 20:
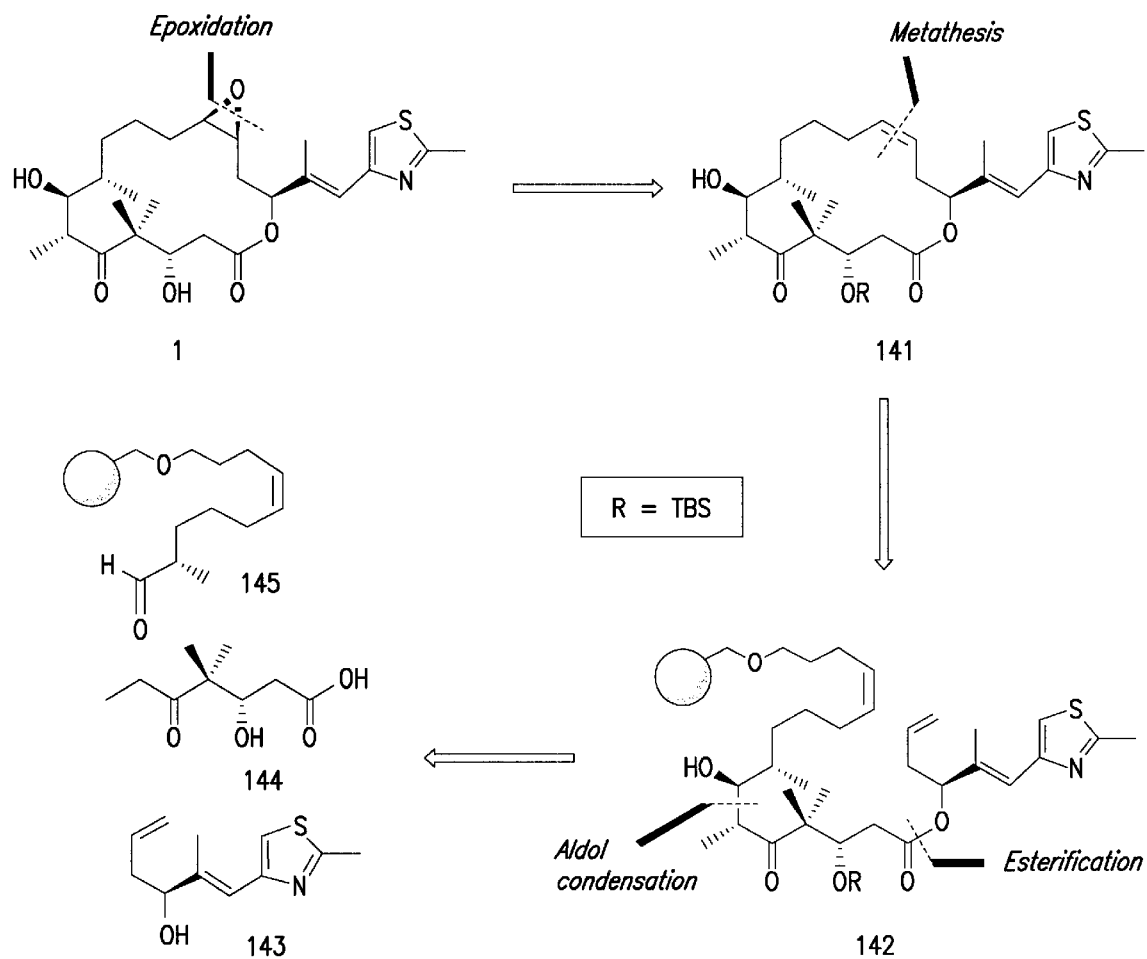

FIG. 20 illustrates the retrosynthetic analysis of epothilone A (1) by a solid phase olefin metathesis strategy wherein TBS=t-$BuMe_2Si$; filled circle=polystyrene.

Figure 21A:
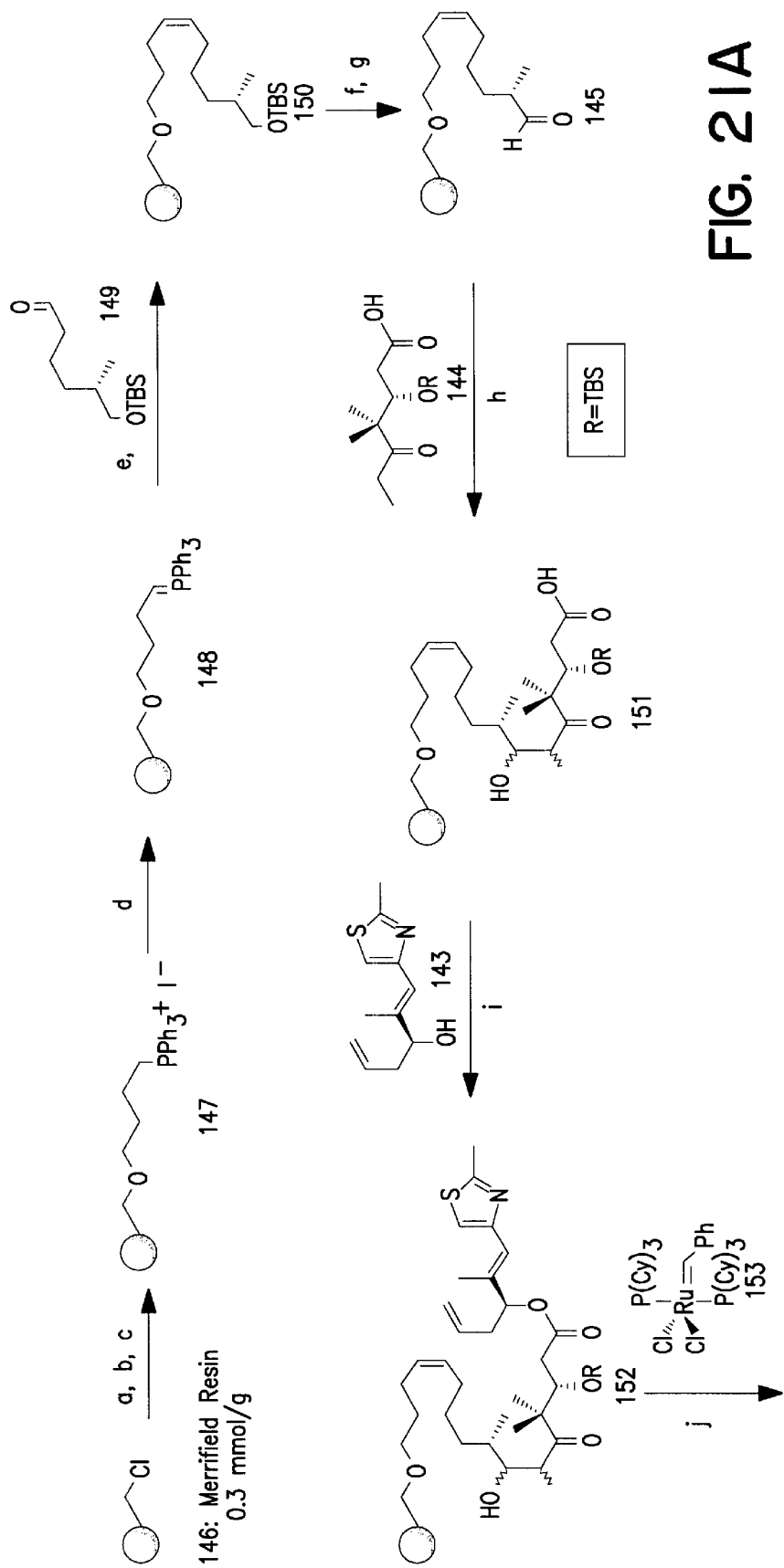
Figure 21B:
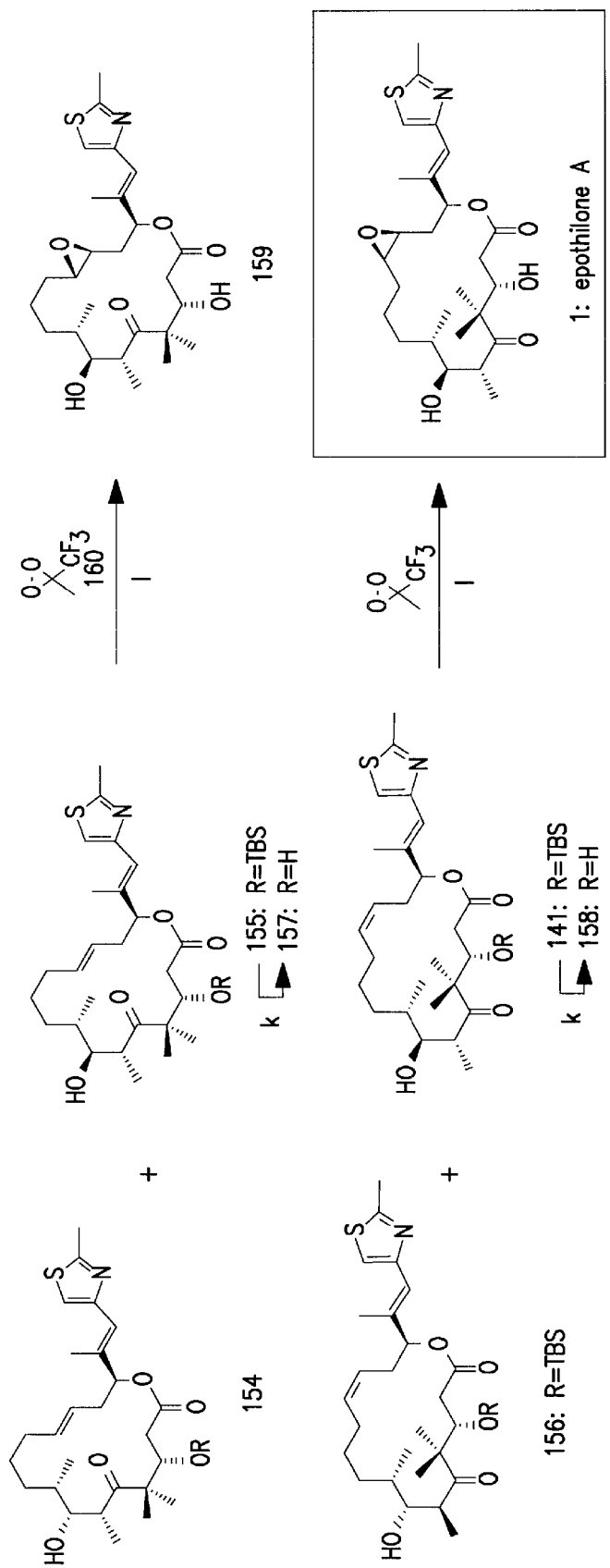

FIG. 21 illustrates the solid phase synthesis of epothilone a wherein: (a) 1,4-butanediol (5.0 eq.), NaH (5.0 eq.), n-$Bu_4NI$ (0.1 eq.), DMF, 25 C, 12 hours; (b) $Ph_3P$ (4.0 eq.), $I_2$ (4.0 eq.), imidazole (4.0 eq.), methylene chloride, 25 C, 3 hours; (c) $Ph_3P$ (10 eq.), 90 C, 12 hours (>90% for 3 steps based on mass gain of polymer); (d) NaHMDS (3.0 eq.), THF:DMSO (1:1), 25 C, 12 hours; (e) 149 (2.0 eq.), THF, 0 C, 3 hours (>70% based on aldehyde recovered from ozonolysis); (f) 10% HF.pyridine in THF, 25 C, 12 hours; (g) $(COCl)_2$ (4.0 eq.), DMSO (8.0 eq.), $Et_3N$ (12.5 eq.), −78 25° C.(ca. 95% for 2 steps)*; (h) 144 (2.0 eq.), LDA (2.2 eq), THF, −78 −40 C., 1 hour; then add resulting enolate to the resin suspended in a $ZnCl_2$ (2.0 eq.) solution in THF, −78→−40° C., 2.0 hours (ca. 90%)*; (i) 143 (5.0 eq.), DCC (5.0 eq), 4-DMAP (5.0 eq.), 25 C, 15 h (80% yield as determined by recovered heterocycle fragments obtained by treatment with NaOMe); (j) 153 (0.75 eq.), methylene chloride, 25 C, 48 hours (52%; 154:155:156:141=ca. 3:3:1:3); (k) 20% TFA in methylene chloride (v/v), 92% for 157 and 90% for 158; (l) 160 [methyl(trifluoromethyl) dioxirane], MeCN, 0° C., 2 hours (70% for 1, 45% for 159; in addition to these products, the corresponding α-epoxides were also obtained). NaHMDS=sodium bis(trimethylsilyl) amide; DMSO=dimethyl sulfoxide; LDA=lithium diisopropylamide; TBS=t-$BuMe_2Si$; 4-DMAP=4-dimethylaminopyridine. * Estimated yield. The reaction was monitored by infrared (IR) analysis of polymer-bound material and by TLC analysis of the products obtained by ozonolysis.

Figure 22:
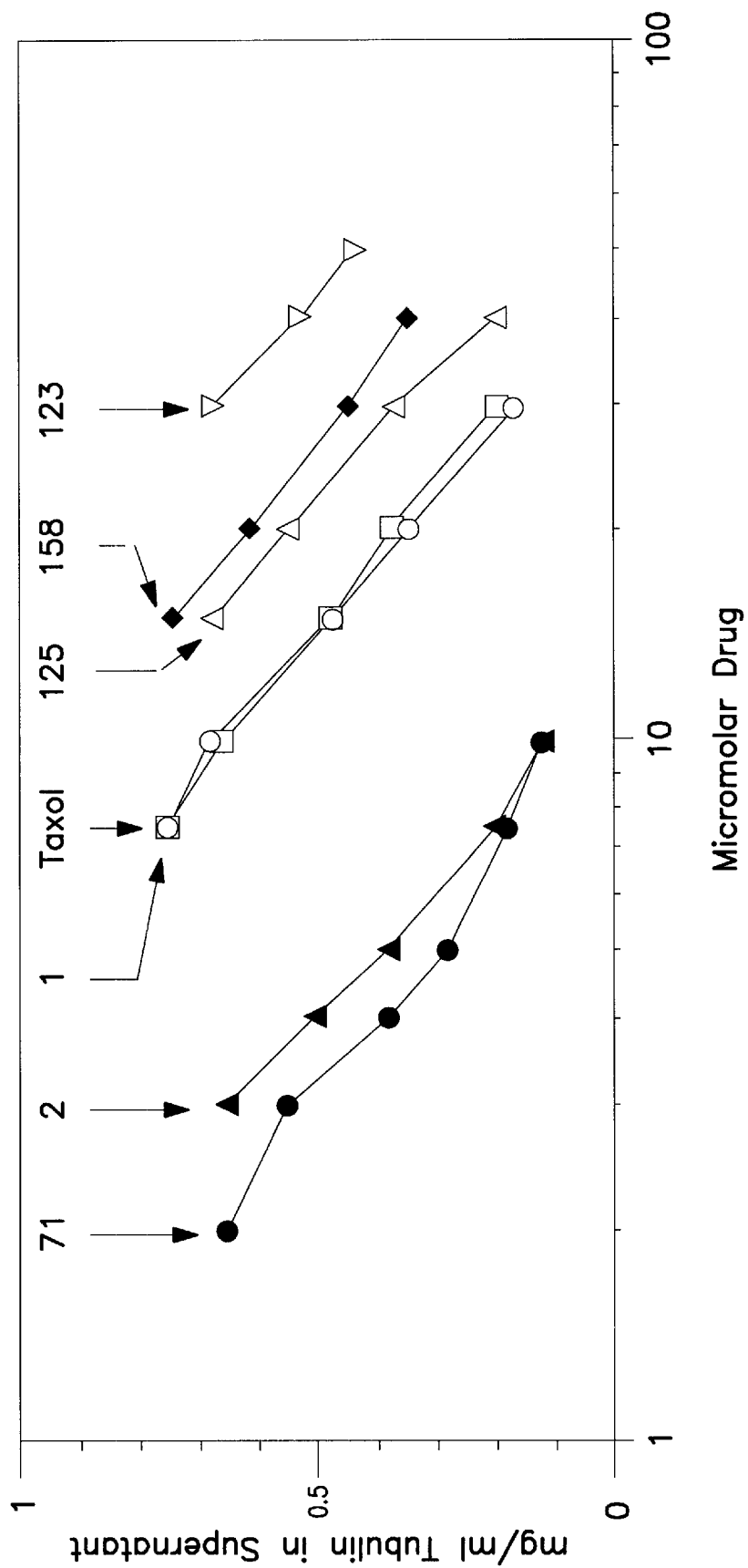

FIG. 22 illustrates activity of epothilones on tubulin assembly. Reaction mixtures contained purified tubulin at 1.0 mg/ml, 0.4 M monosodium glutamate, 5% dimethyl sulfoxide, and varying drug concentrations. Each compound was evaluated in three different experiments and average values are shown. Samples were incubated, centrifuged, and processed at room temperature (dark circle=71, $EC_{50}$=3.3±0.2 µM; dark triangle=2, $EC_{50}$=4.0±0.1 µM; open circle=1, $EC_{50}$=14±0.4 µM; open square=taxol, $EC_{50}$=15±2 µM; open triangle=125, $EC_{50}$=22±0.9 µM; dark square=158, $EC_{50}$=25±1 µM; open upside down triangle=123, $EC_{50}$=39±2 µM. The $EC_{50}$ is defined as the drug concentration that causes 50% of the tubulin to assemble into polymer. In the absence of drug, less than 5% of the tubulin was removed by centrifugation, while with high concentrations of the most active drugs, over 95% of the protein formed polymer. This suggests that at least 90% of the tubulin had the potential to interact with epothilones and taxoids. Although the $EC_{50}$ value obtained for Taxol was higher than that obtained in an alternate assay as described in Hofle et al. *Angew. Chem. Int Ed. Engl* 35, 1567–1569 (1996), the agent's role in these experiments was only as a control.

FIG. 23 provides a table of results from cytotoxicity experiments with 1A9, 1A9PTX10 (β-tubulin mutant), 1A9PTX22 (β-tubulin mutant) and A2780AD cell lines showing relative activities of epothilones A(1) and B(2) as compared with synthetic analogues 71, 158, 123 and 125 as inducers of tubulin assembly and inhibitors of human ovarian carcinoma cell growth. (a) See FIG. 22; (b) The growth of all cells lines was evaluated by quantitation of the protein in microtiter plates. The parental cell line 1A9, a clone of the A2780 cell line, was used to select two Taxol-resistant sublines (1A9PTX10 and 1A9PTX22). These sublines were selected by growth in the presence of Taxol and verapamil, a P-glycoprotein modulator. Two distinct point mutations in the β-tubulin isotype M40 gene were identified. In 1A9PTX10 amino acid residue 270 was changed from Phe (TTT) to Val (GTT), and in 1A9PTX22 residue 364 was changed from Ala (GCA) to Thr (ACA). The A2780AD line is a multidrug resistant (MDR) line expressing high levels of P-glycoprotein. Relative resistance refers to the ratio of the $IC_{50}$ value obtained with a resistant cell line to that obtained with the parental cell line.

Figure 24:
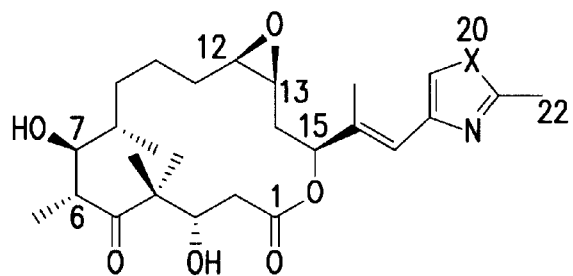

FIG. 24 illustrates the structure and numbering of epothilone A(1) and epoxalone A(2).

Figure 25:
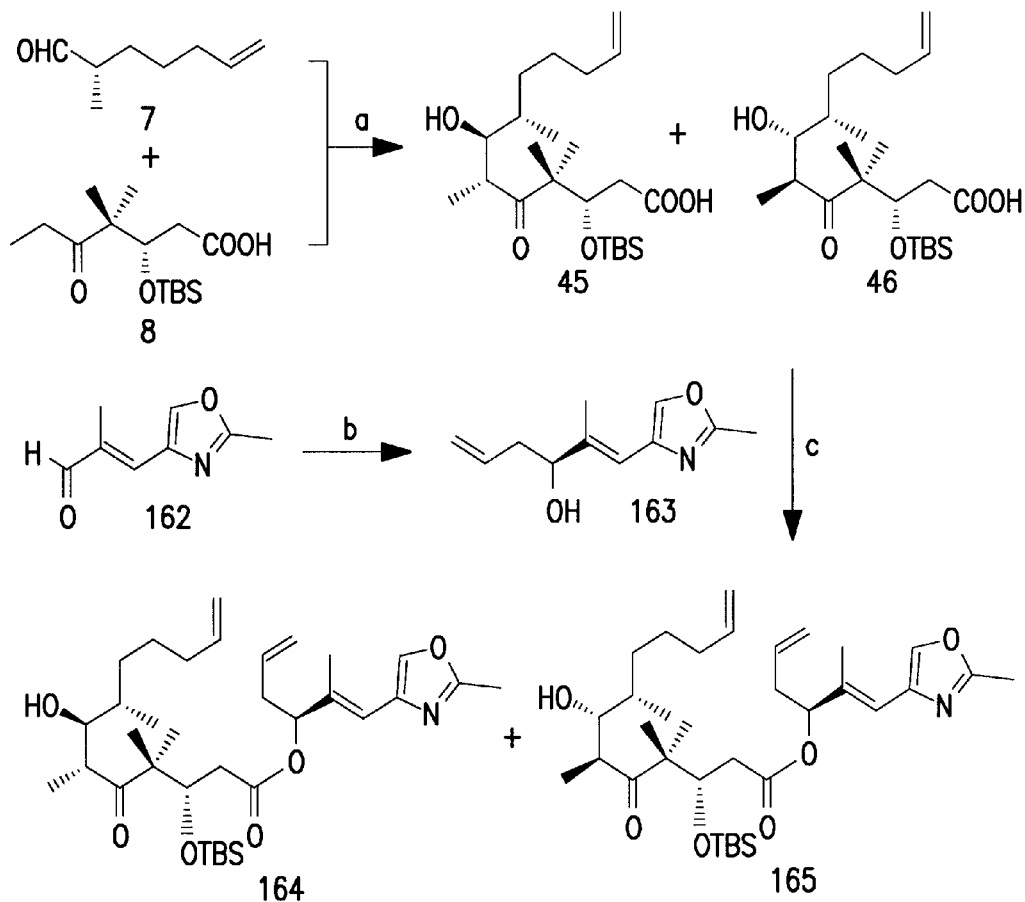

FIG. 25 illustrates the coupling of building blocks and construction of precursors 164 and 165. Reagents and conditions: (a) 2.4 equivalents of LDA, −40° C., THF, 1.5 hours, then 7 in THF, −40° C., 0.5 hour; 94% (45:46 ca 5:3); (b) 1.2 equivalents of (+)-Ipc$_2$B(allyl), Et$_2$O, −100° C., 0.5 hour, 91%; (c) 2.0 equivalents of 163, 1.5 equivalents of DCC, 1.5 equivalents of 4-DMAP, toluene, 25° C. 12 hours, 49% (164) plus 33% (165) for two steps. TBS=tert-butyldimethylsilyl; Ipc$_2$B(allyl)=diisopinocampheylallyl borane; LDA=lithium diisopropylamide; DCC=dicyclohexylcarbodiimide; 4-DMAP=4-dimethylaminopyridine.

Figure 26:
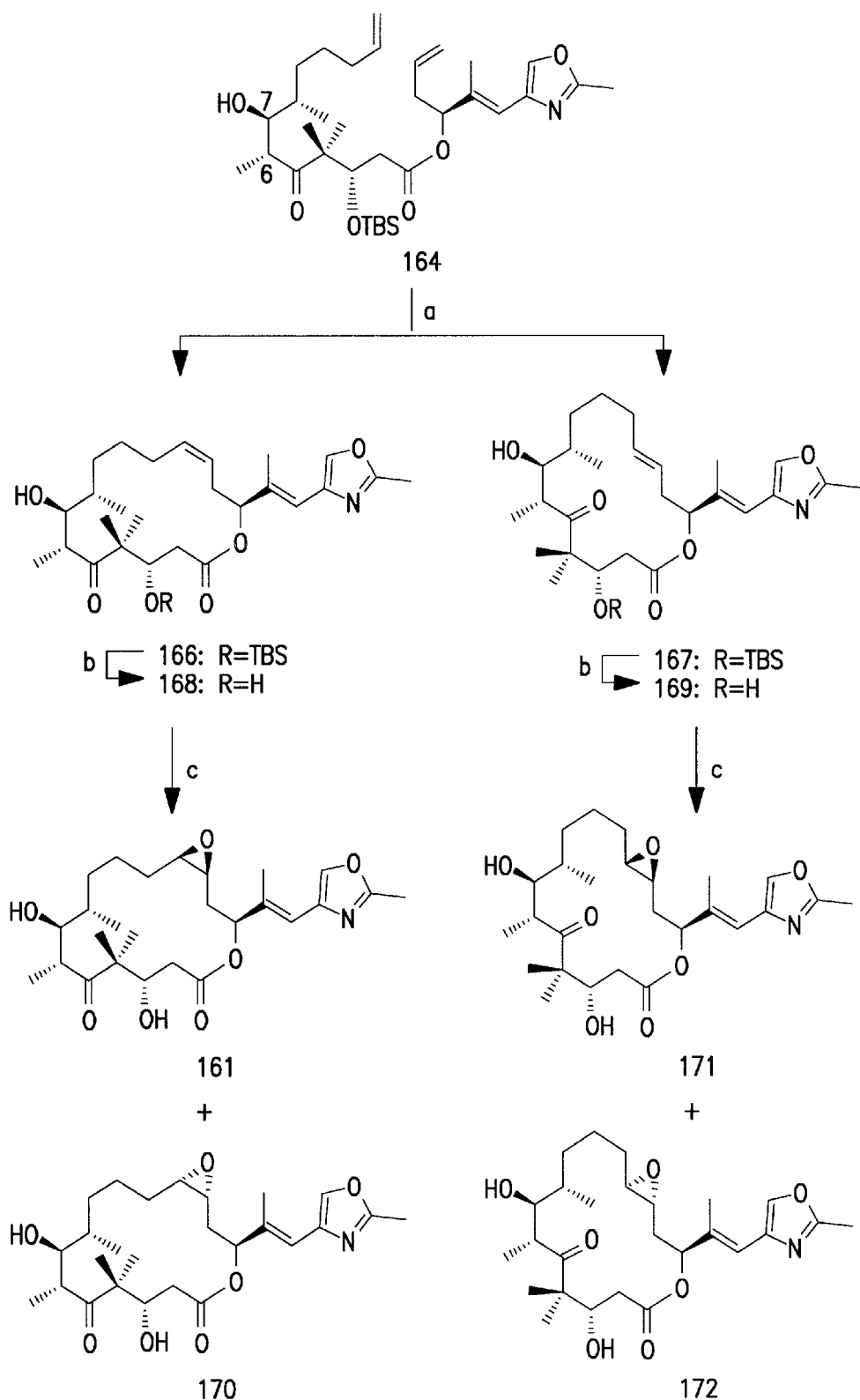

FIG. 26 illustrates the olefin metathesis of precursor 164 and synthesis of epoxalones 161, 171, 170 and 172. Reagents and conditions: (a) 20 mol % of RuCl$_2$(=CHPh)(PCy$_3$)$_2$ cat., CH$_2$Cl$_2$, 25° C., 20 hours, 40% (166) plus 29% (167); (b) 20% TFA in CH$_2$Cl$_2$, 2 h, 89% (168), 95% (169); (c) CH$_3$CN/Na$_2$EDTA (2:1), 10.0 equivalents of CF$_3$COCH$_3$, 8.0 equivalents of NaHCO$_3$, 3.0 equivalents of Oxone®, 0 C, 34% (161) plus 15% (170), 25% (171) plus 20% (172). TFA=trifluoroacetic acid. The tentative stereochemical assignments of epoxides 161, 171, 168, 169, 170 and 172 were based on the higher potencies at 161 and 171 in the tubulin polymerization assay as compared to those of 170 and 172 respectively (see FIG. 28).

Figure 27:
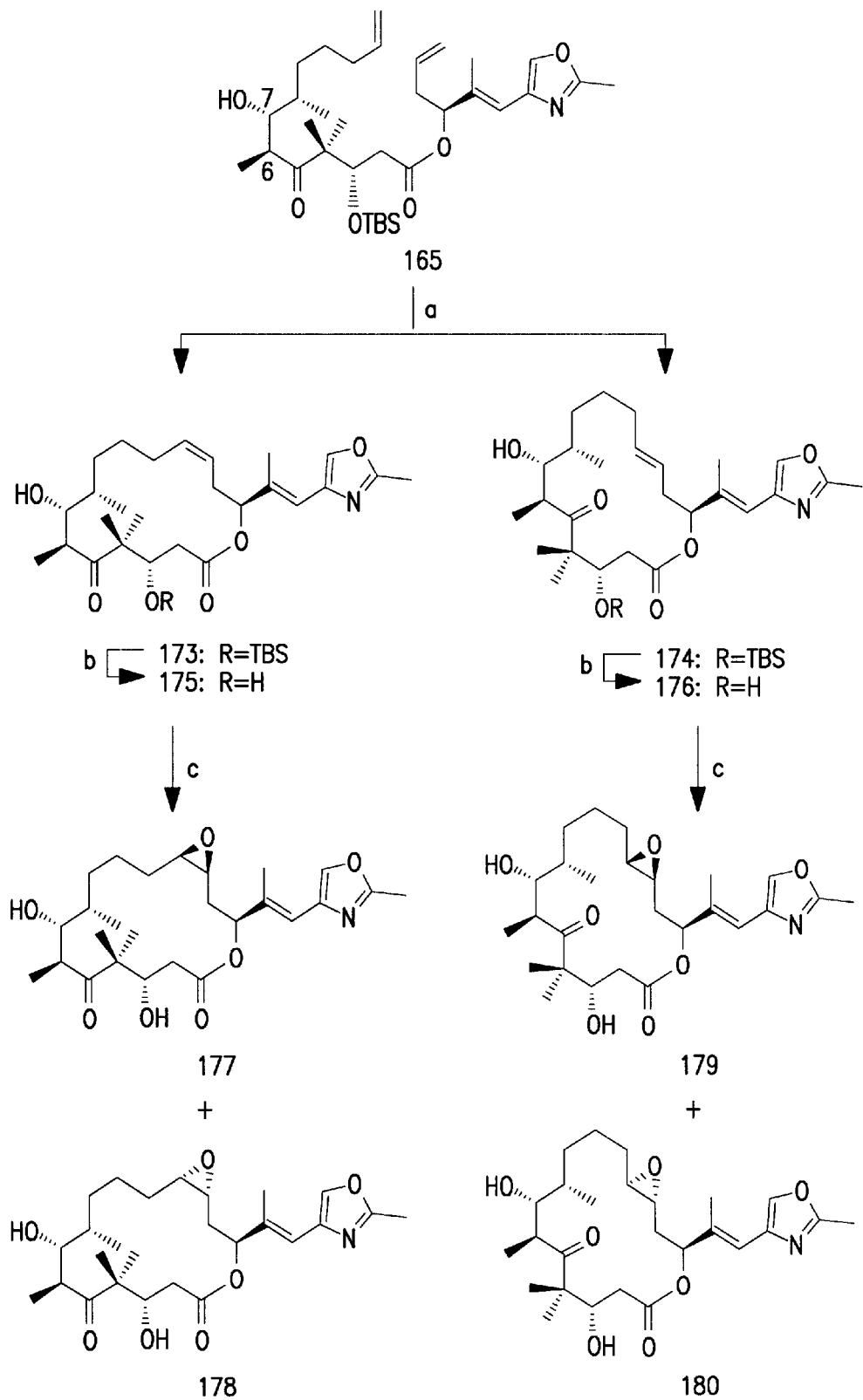

FIG. 27 illustrates the olefin metathesis of C6-7 diastereomeric precursor 165 and synthesis of epoxalones 175–180. Reagents and conditions. (a) 20 mol % of RuCl$_2$(=CHPh)(PCy$_3$)$_2$ cat., CH$_2$Cl$_2$, 25 C, 20 hours, 25% (173) plus 63% (174); (b) 20% TFA in CH$_2$Cl$_2$, 25 C, 2 hours, 75% (175), 72% (176); (c) CH$_3$CN/Na$_2$EDTA (2:1), 10.0 equivalents of CF$_3$COCH$_3$, 8.0 equivalents of NaHCO$_3$, 3.0 equivalents of Oxone®, 0° C., 38% (177) plus 17% (178), 22% (179) plus 13% (180).

Figure 28:
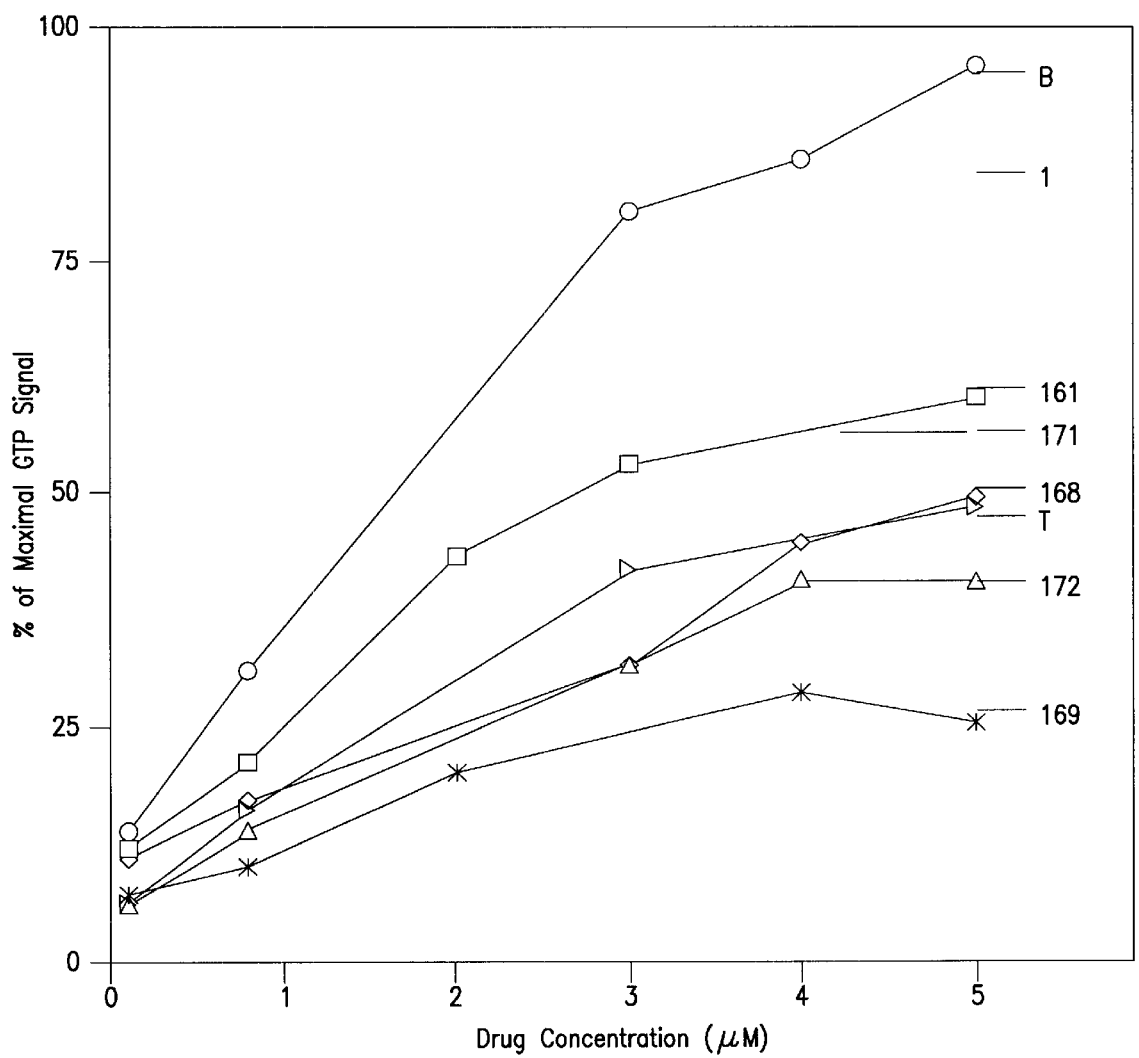

FIG. 28 illustrates the effect of epoxalones, epothilones and Taxol on tubulin polymerization. The Filtration-Colorimetric Assay was used for epothilones A and B except for the 30° C. incubation temperature (instead of 37 C) and the pure tubulin (instead of microtubule protein). After initial screening of all epoxalones (161, 168, 169, 170, 171, 172, 175, 176, 177, 178, 179, and 180) at 20 mM concentrations, the most potent ones (161, 168, 169, 171 and 172) were tested together with epothilones A(1) and B and Taxol at 01, 1.0, 2.0, 3.0, 4.0 and 5.0 mM. B=epothilone B; T=Taxol.

Figure 29A:
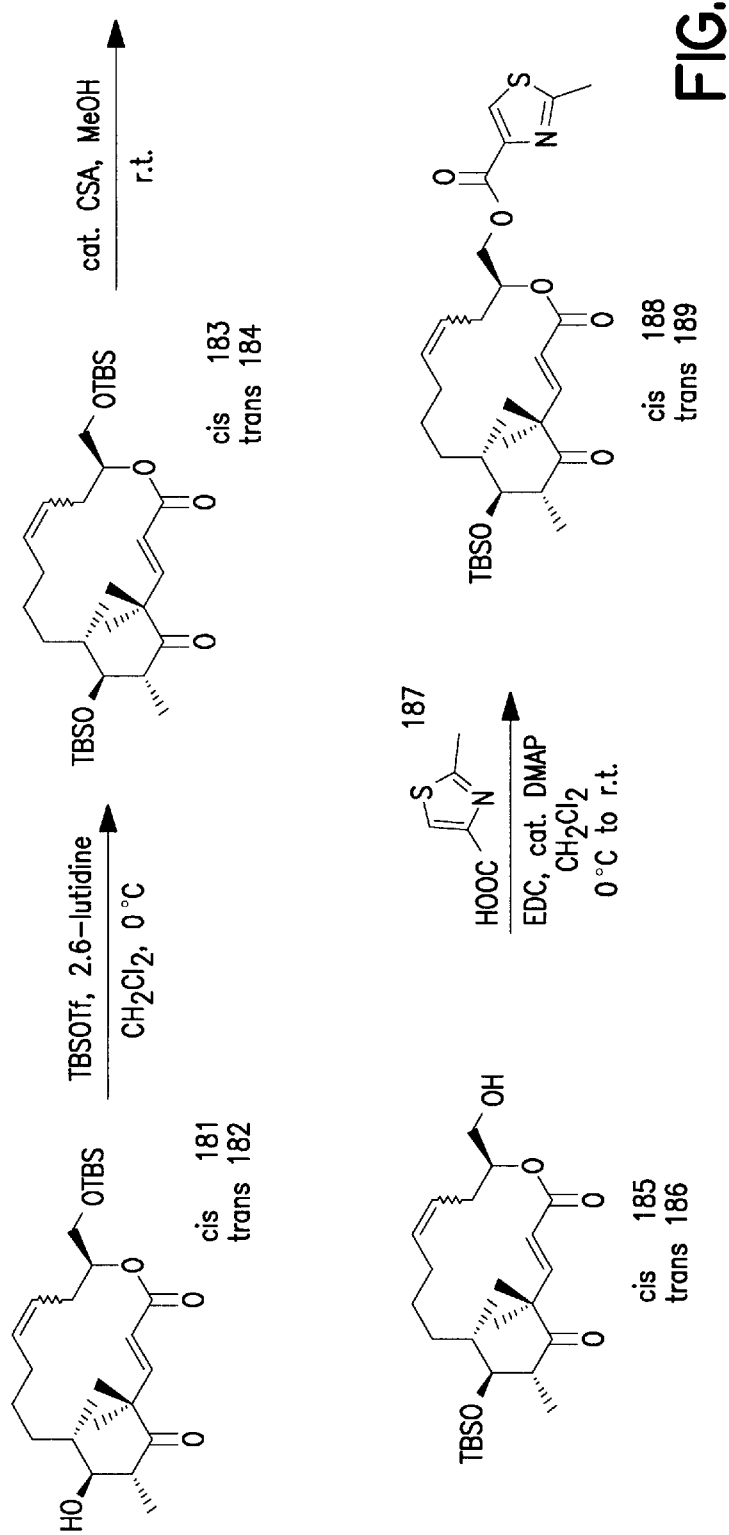
Figure 29B:
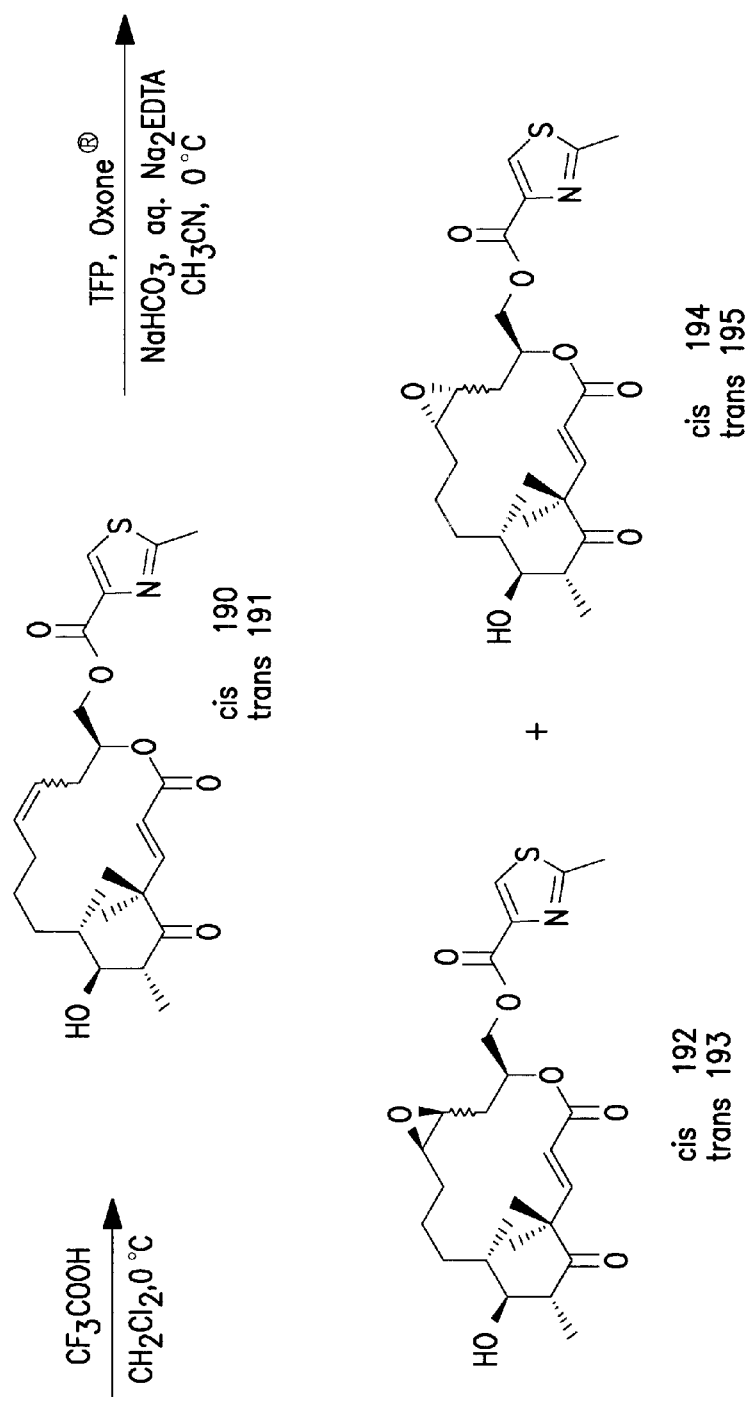

FIG. 29 illustrates the synthesis of epothilone analogs 192, 193, 194 and 195.

Figure 30A:
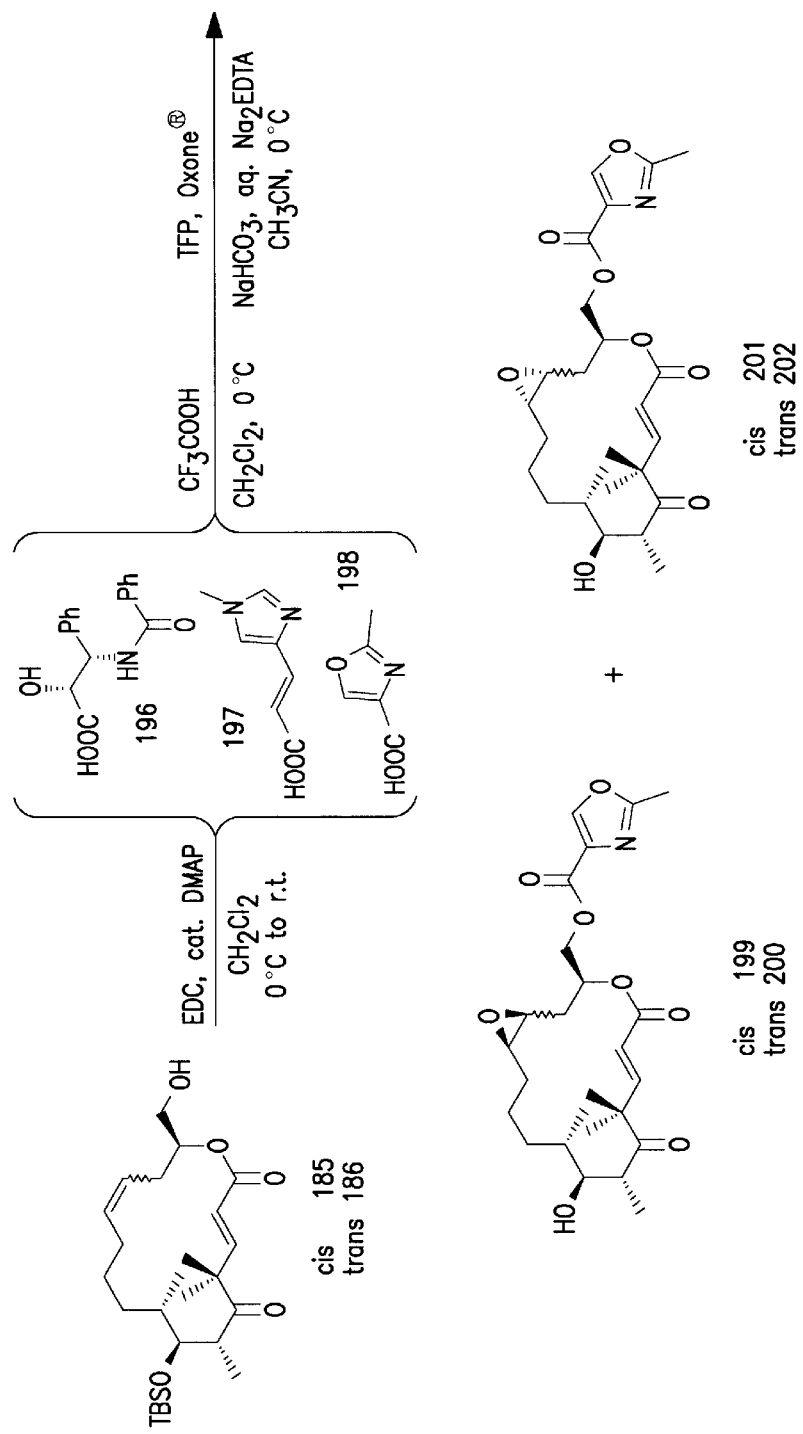
Figure 30B:
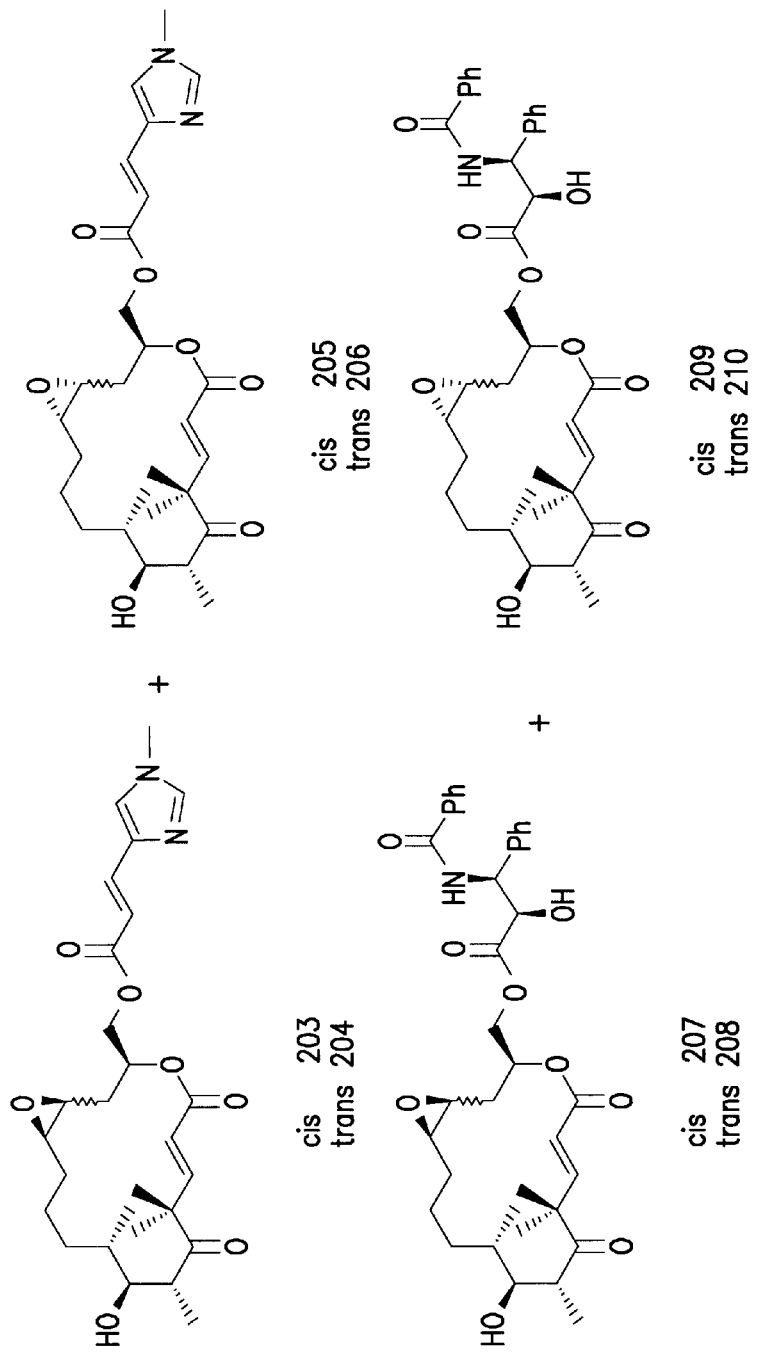

FIG. 30 illustrates the synthesis of epothilone analogs 199, 200, 201, 202, 203, 204, 205, 206, 207, 208, 209, and 210.

FIG. 31 illustrates the synthesis of phosphonium analog 220.

Figure 32A:
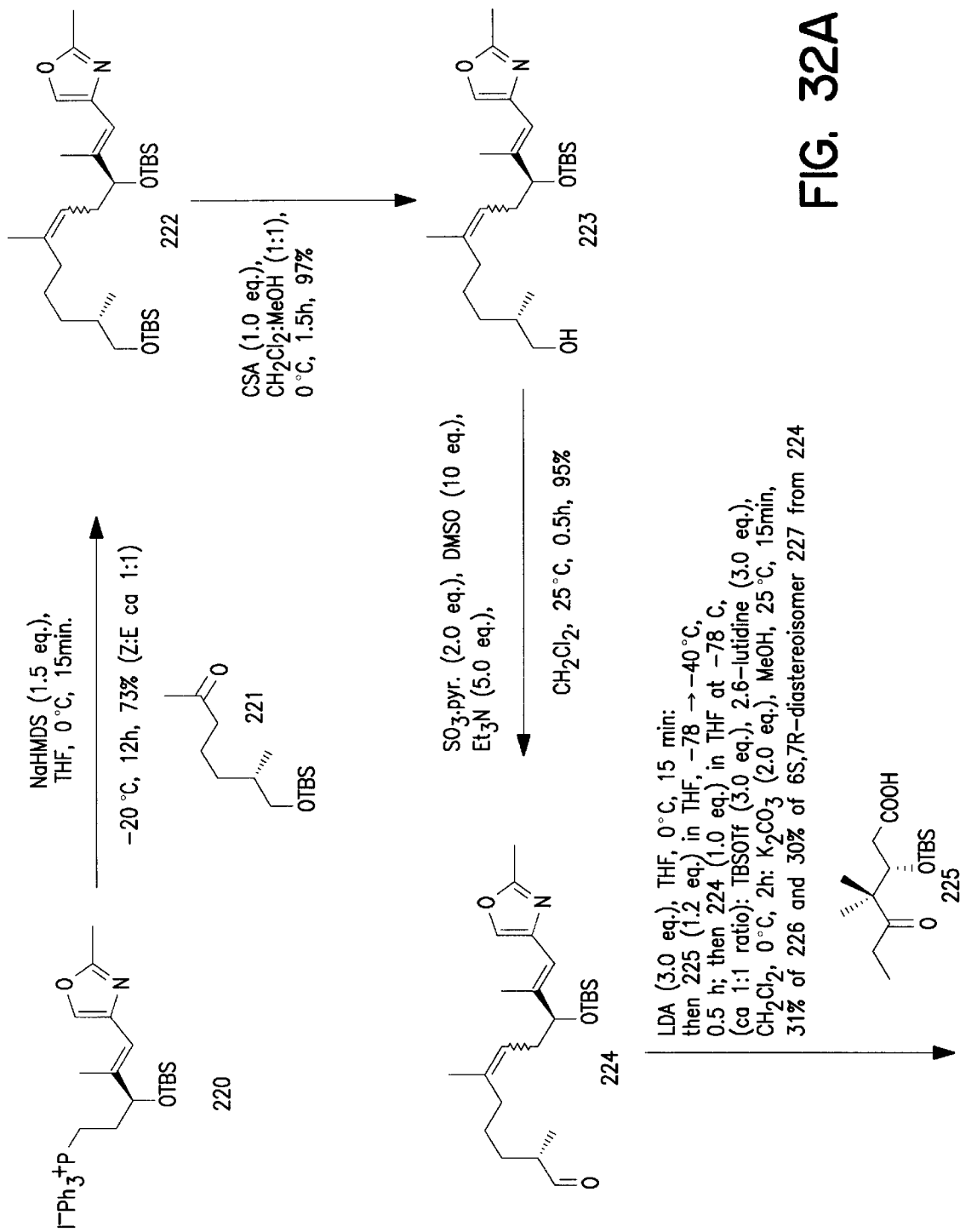
Figure 32B:
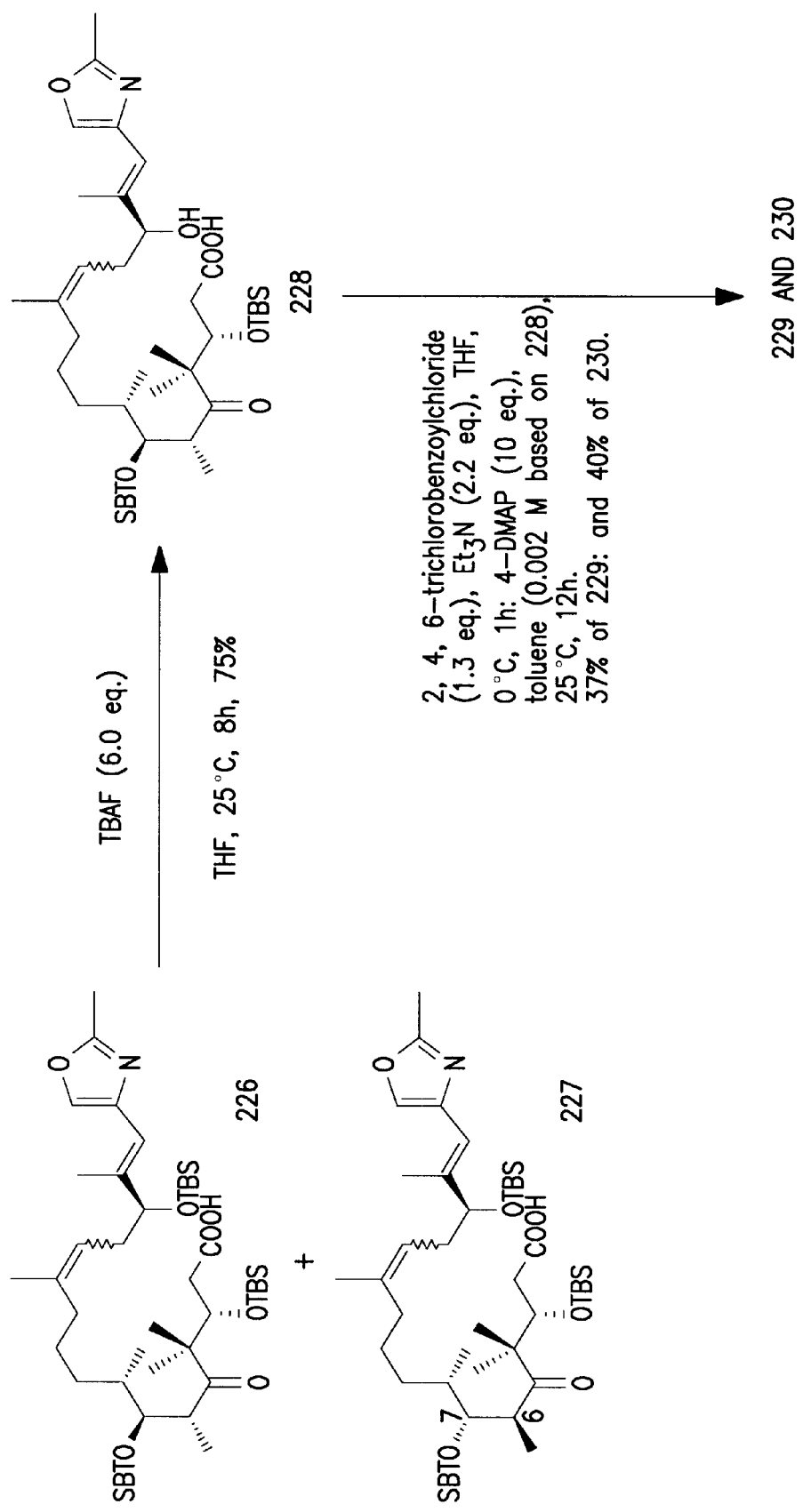

FIG. 32 illustrates the synthesis of epothilone advanced intermediate macrolides 229 and 230.

Figure 33:
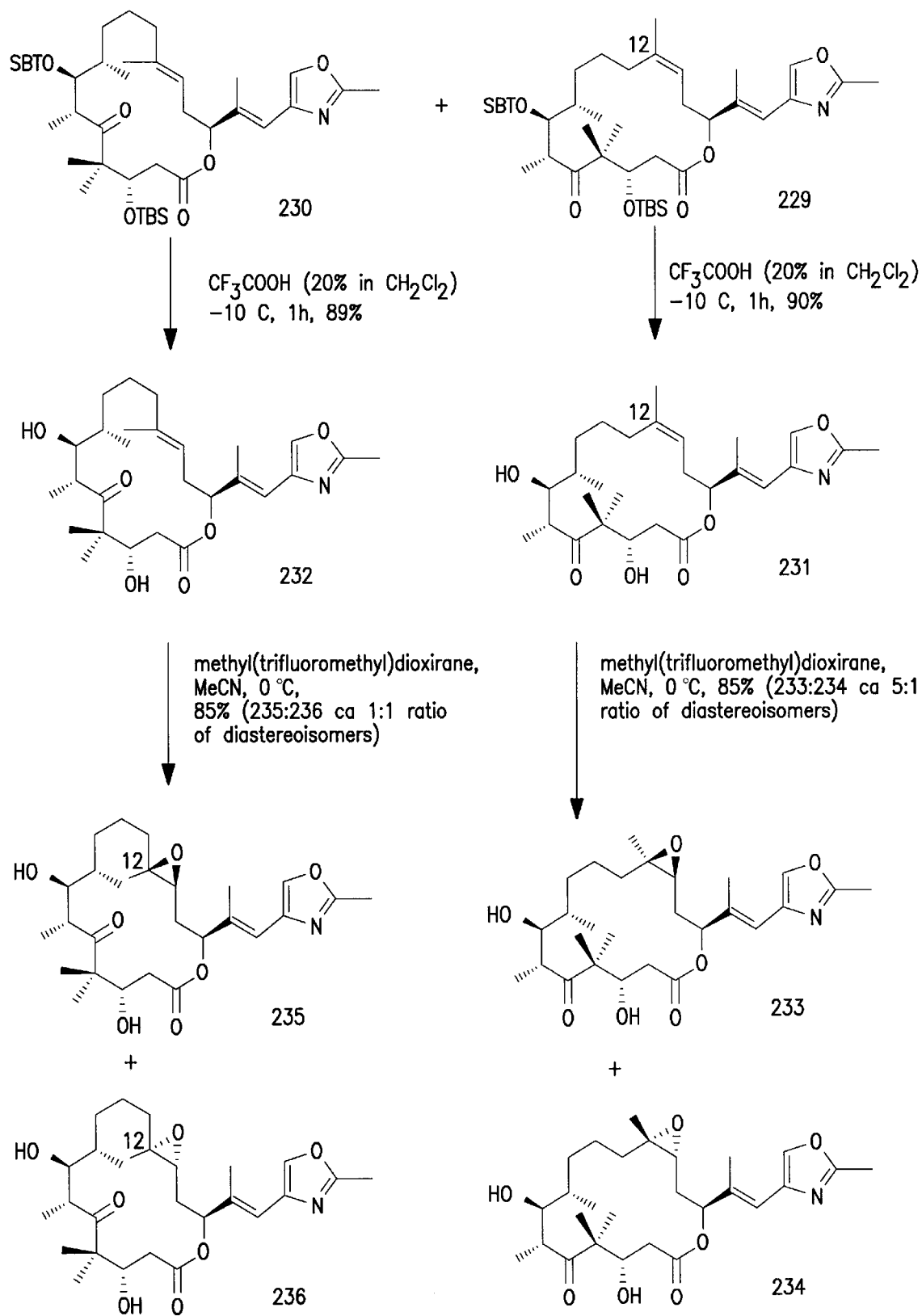

FIG. 33 illustrates the synthesis of epothilone analogs 233, 234, 235, and 236.

Figure 34A:
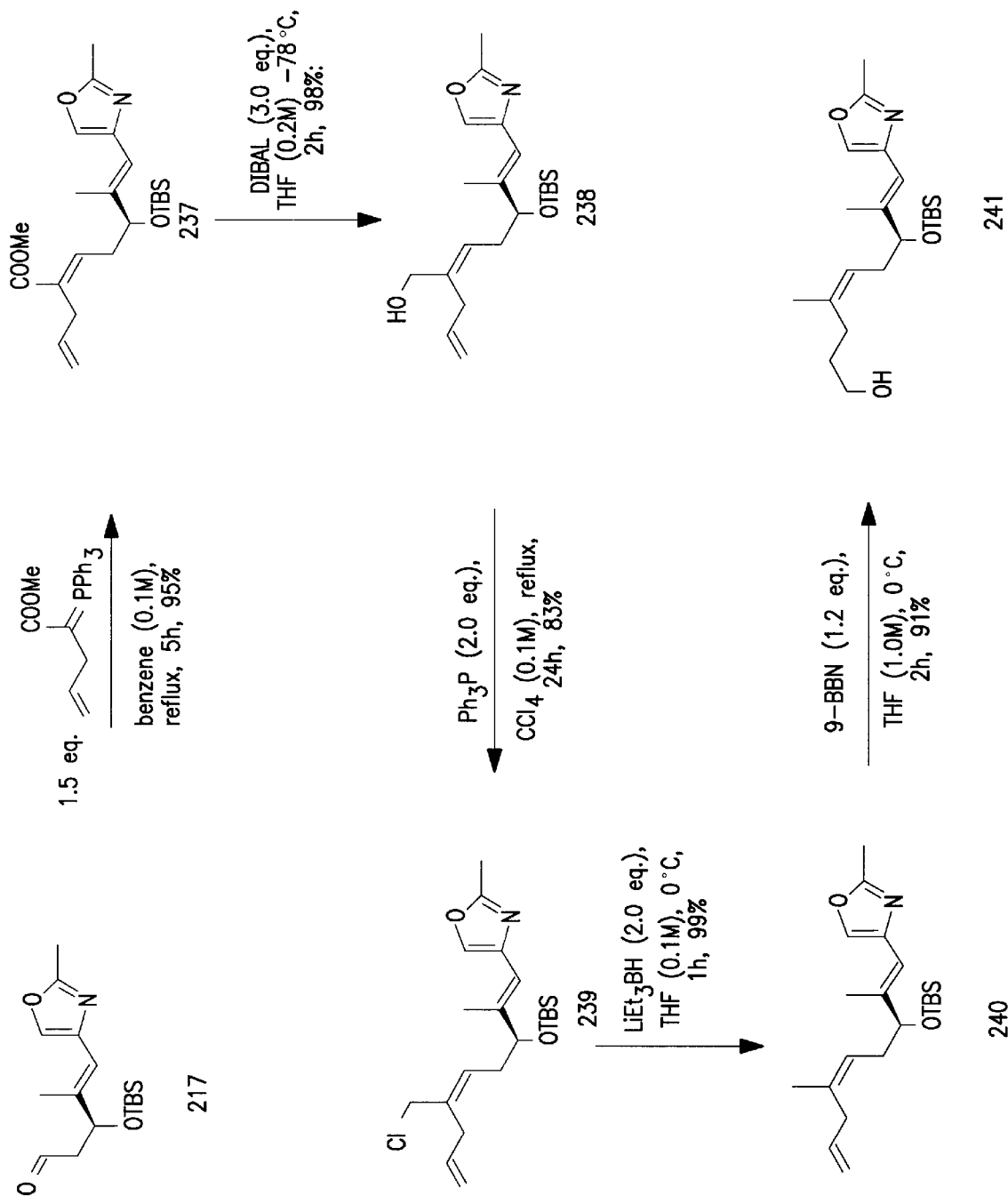
Figure 34B:
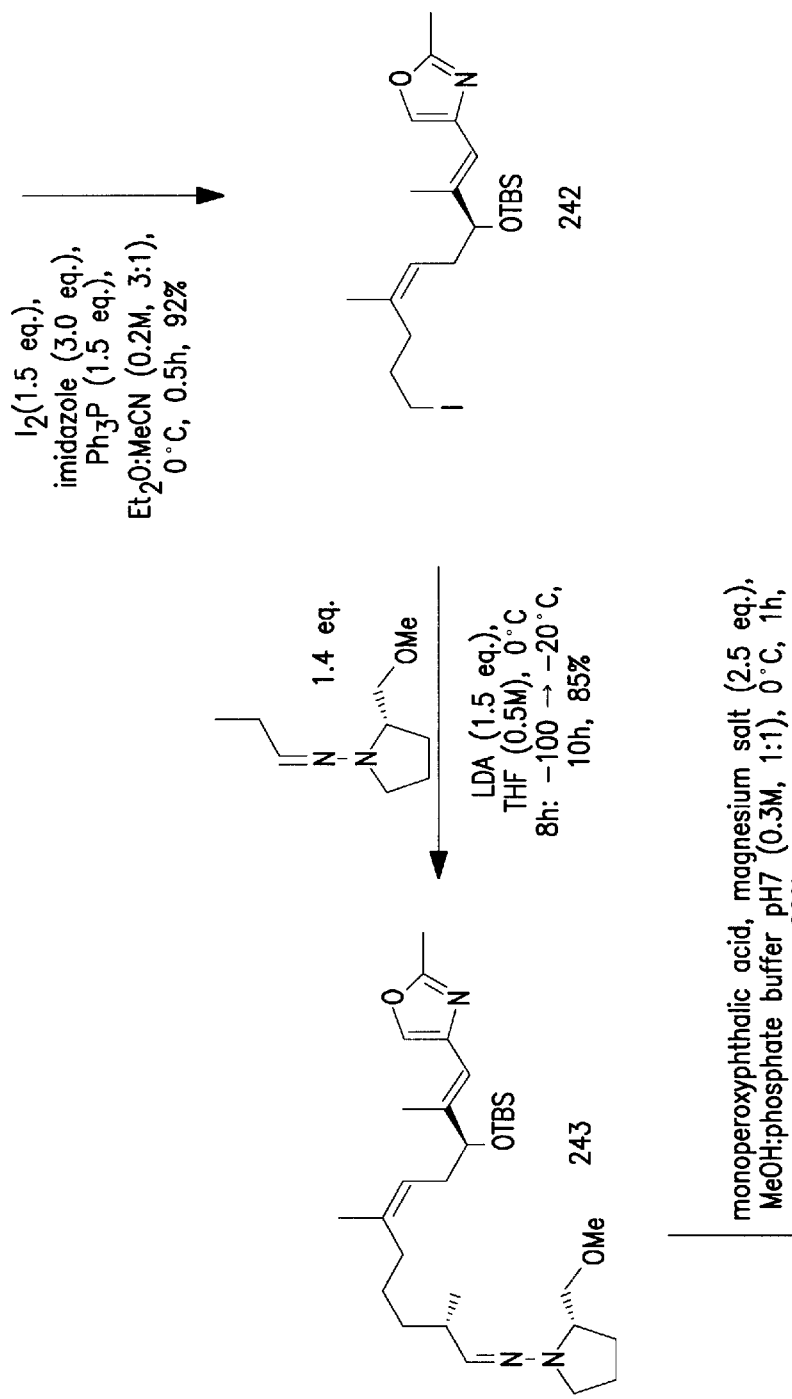

FIG. 34 illustrates the synthesis of advanced intermediate nitrile 244.

Figure 35A:
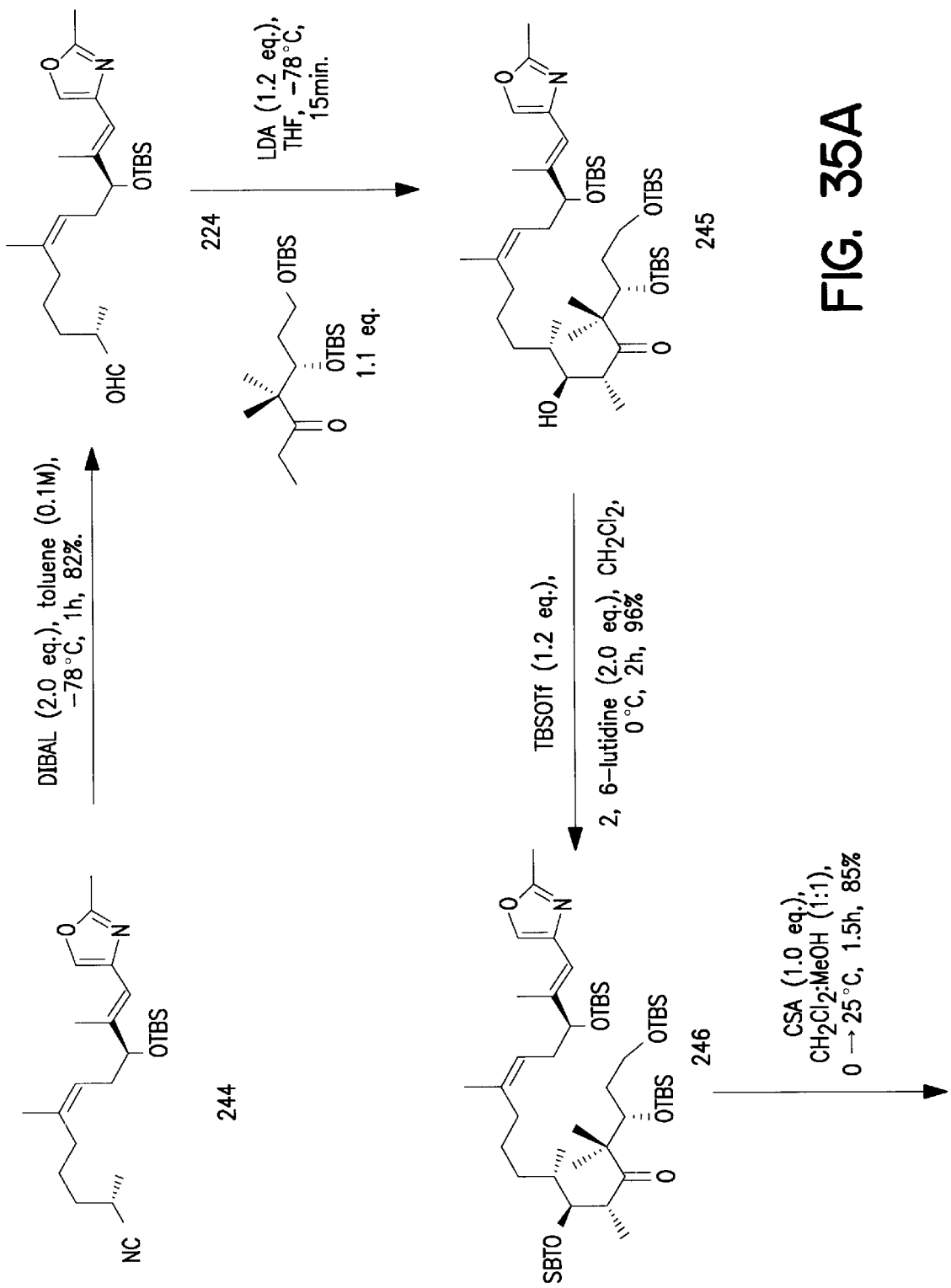
Figure 35B:
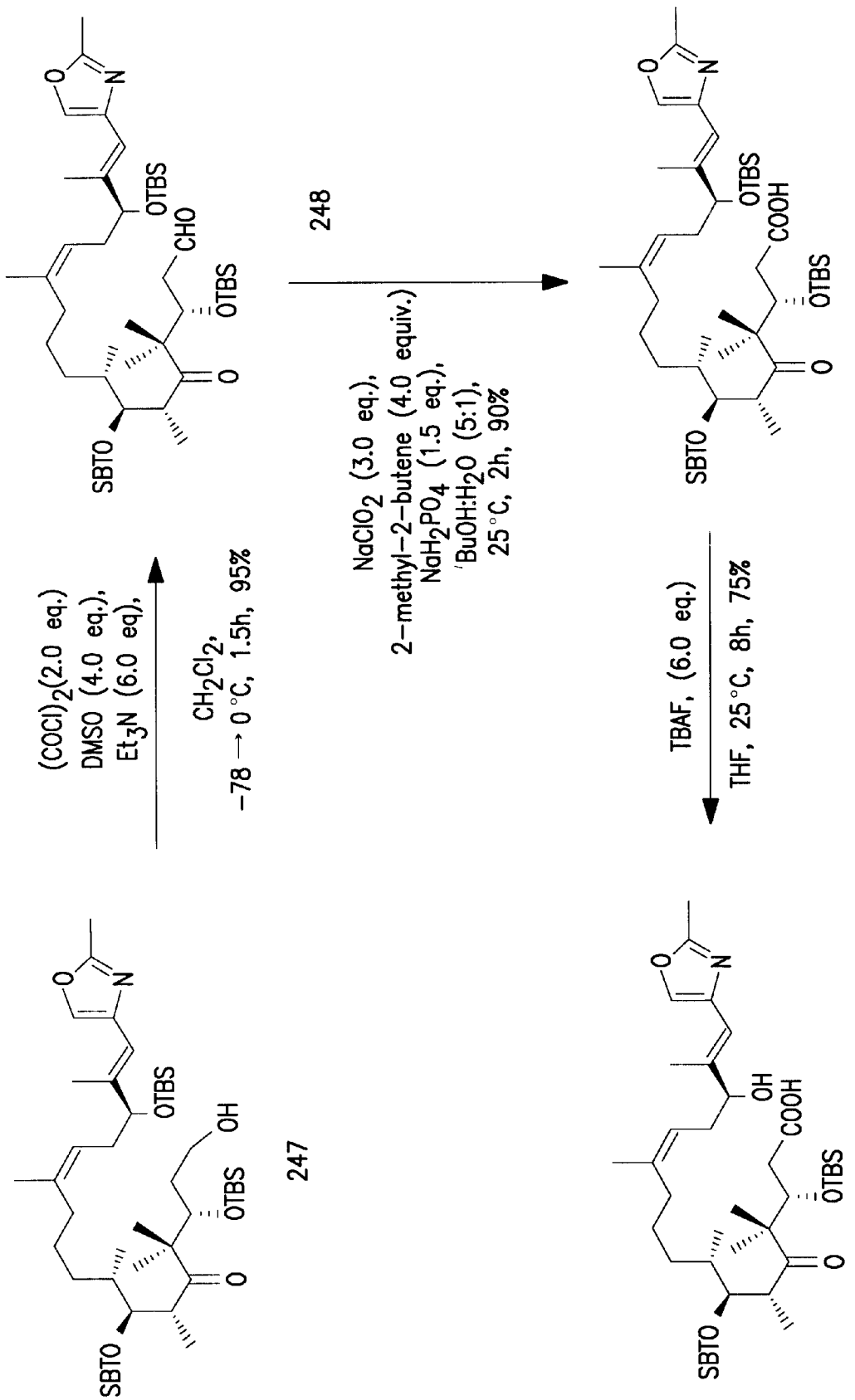

FIG. 35 illustrates the synthesis of epothilone analog 249.

FIG. 36 illustrates the synthesis of epothilone analog 229.

Figure 37B:
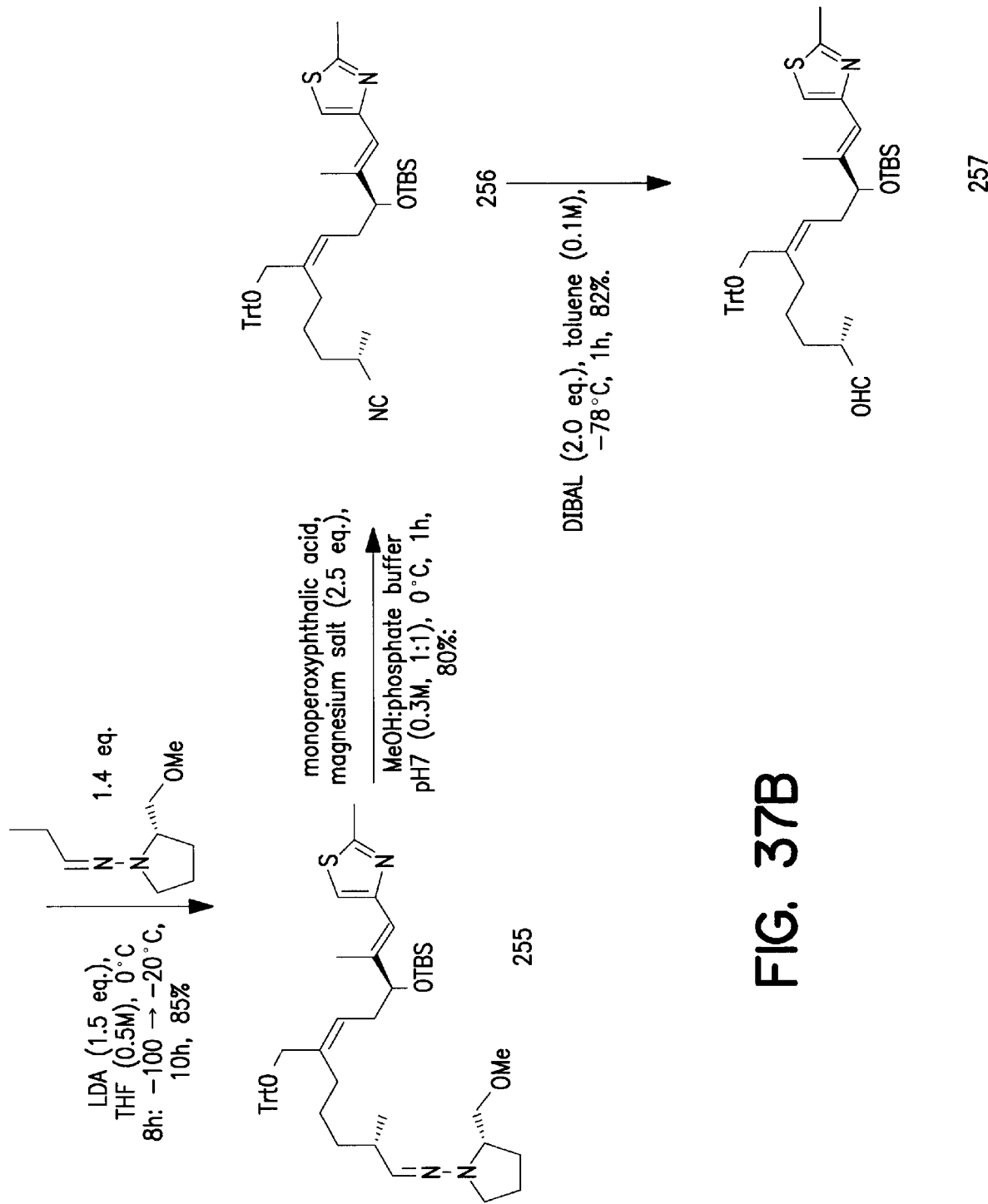

FIG. 37 illustrates the synthesis of advanced intermediate aldehyde 257.

Figure 38A:
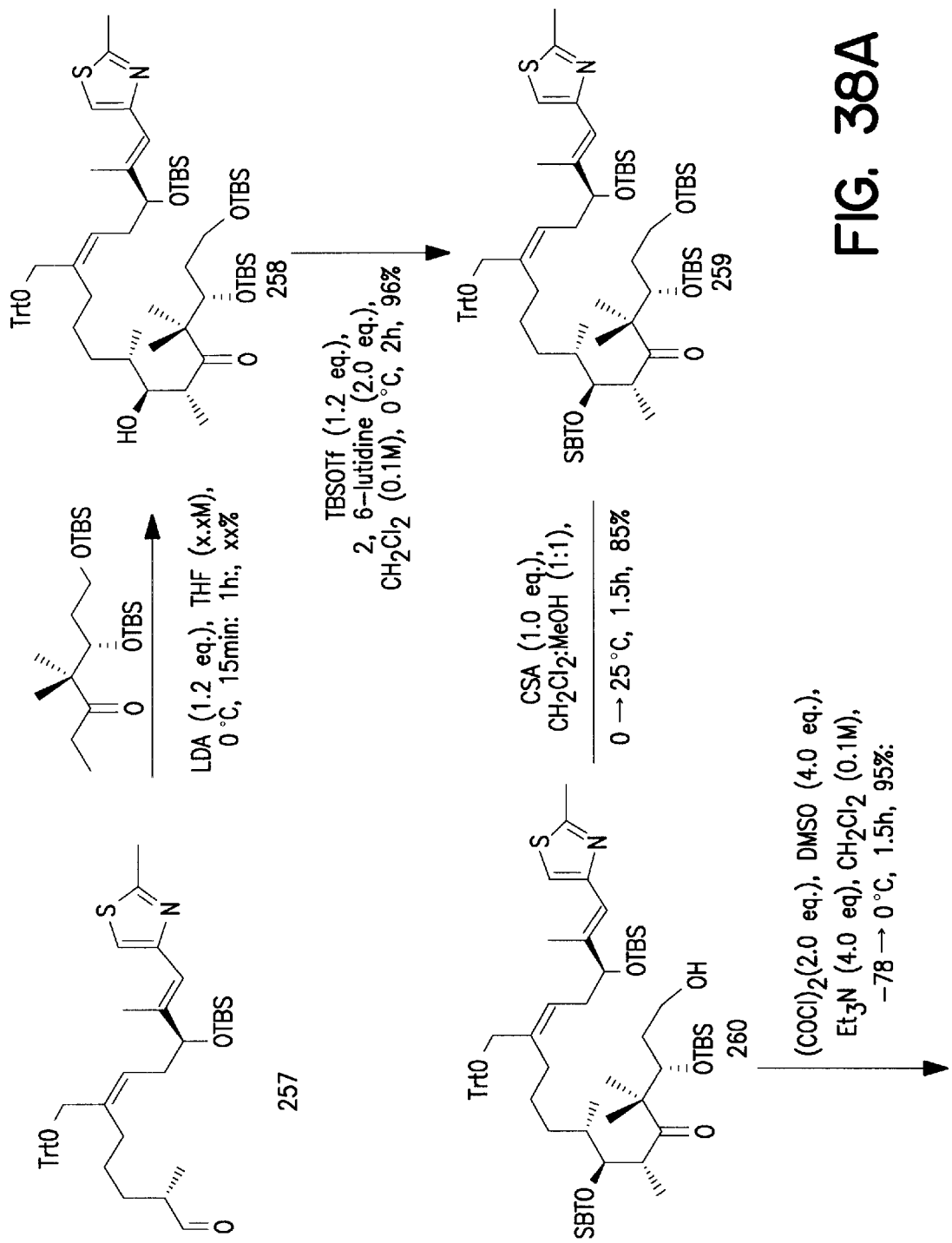
Figure 38B:
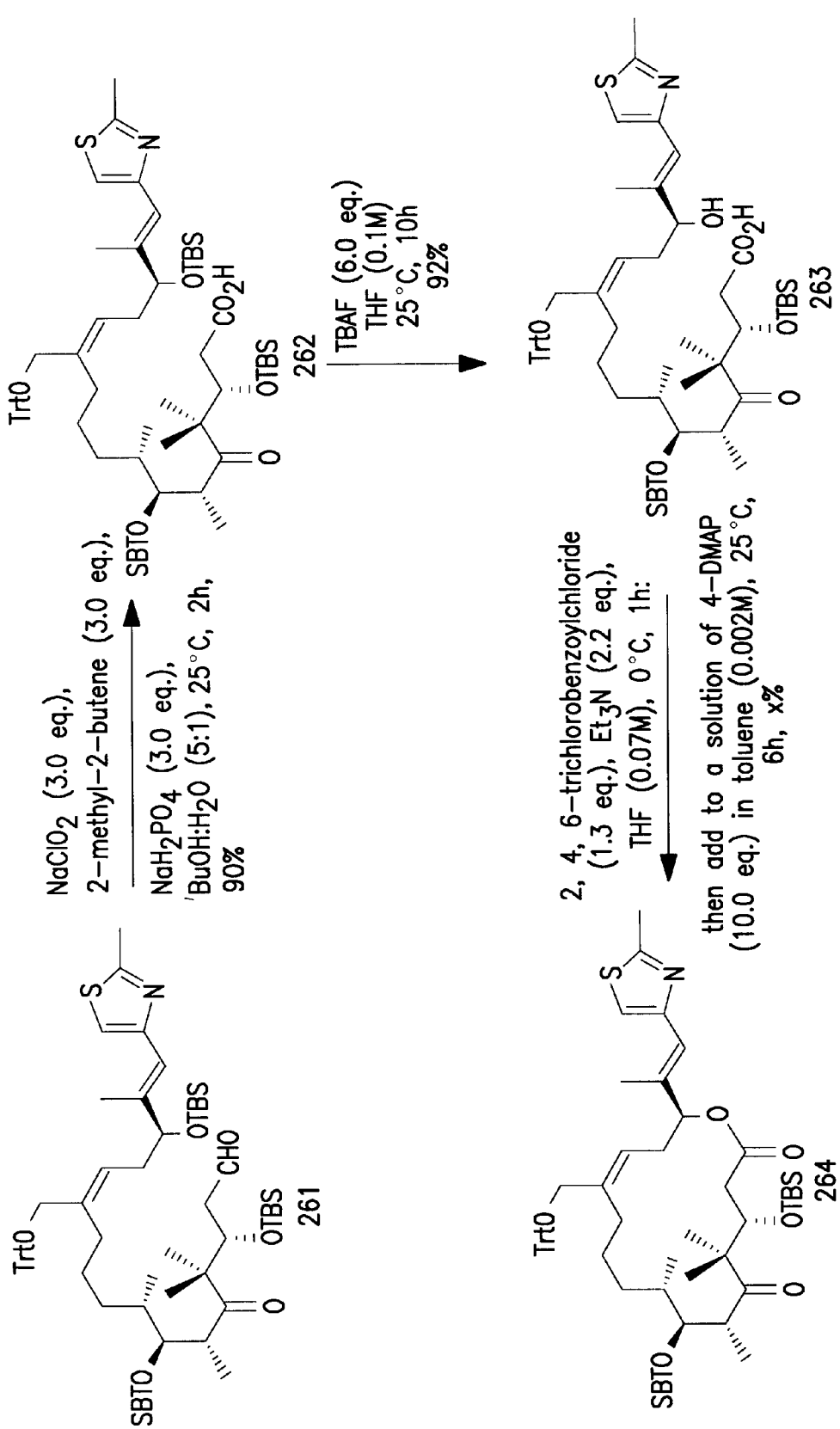

FIG. 38 illustrates the synthesis of epothilone analog 263.

Figure 39:
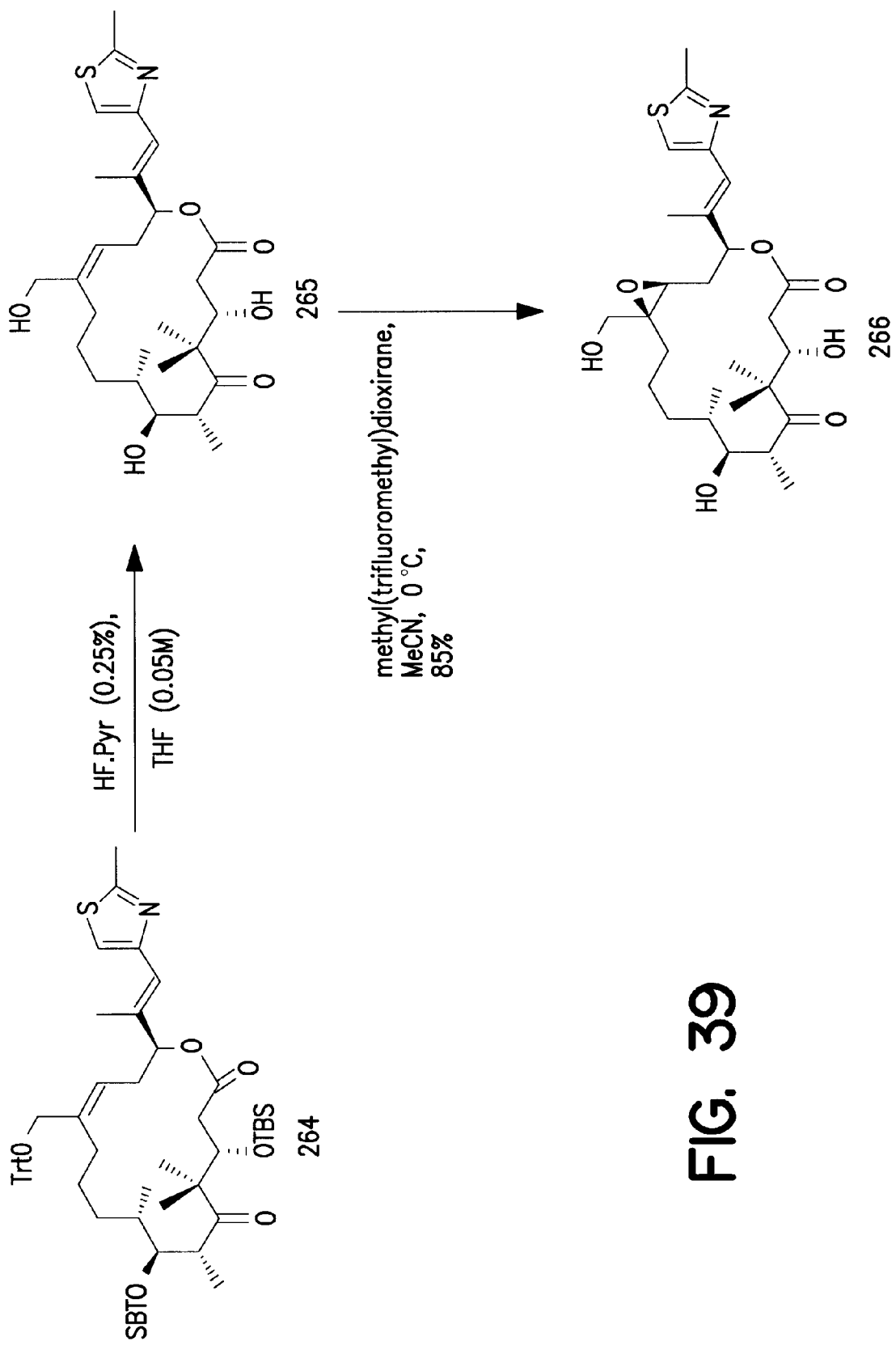

FIG. 39 illustrates the synthesis of epothilone analog 266.

Figure 40:
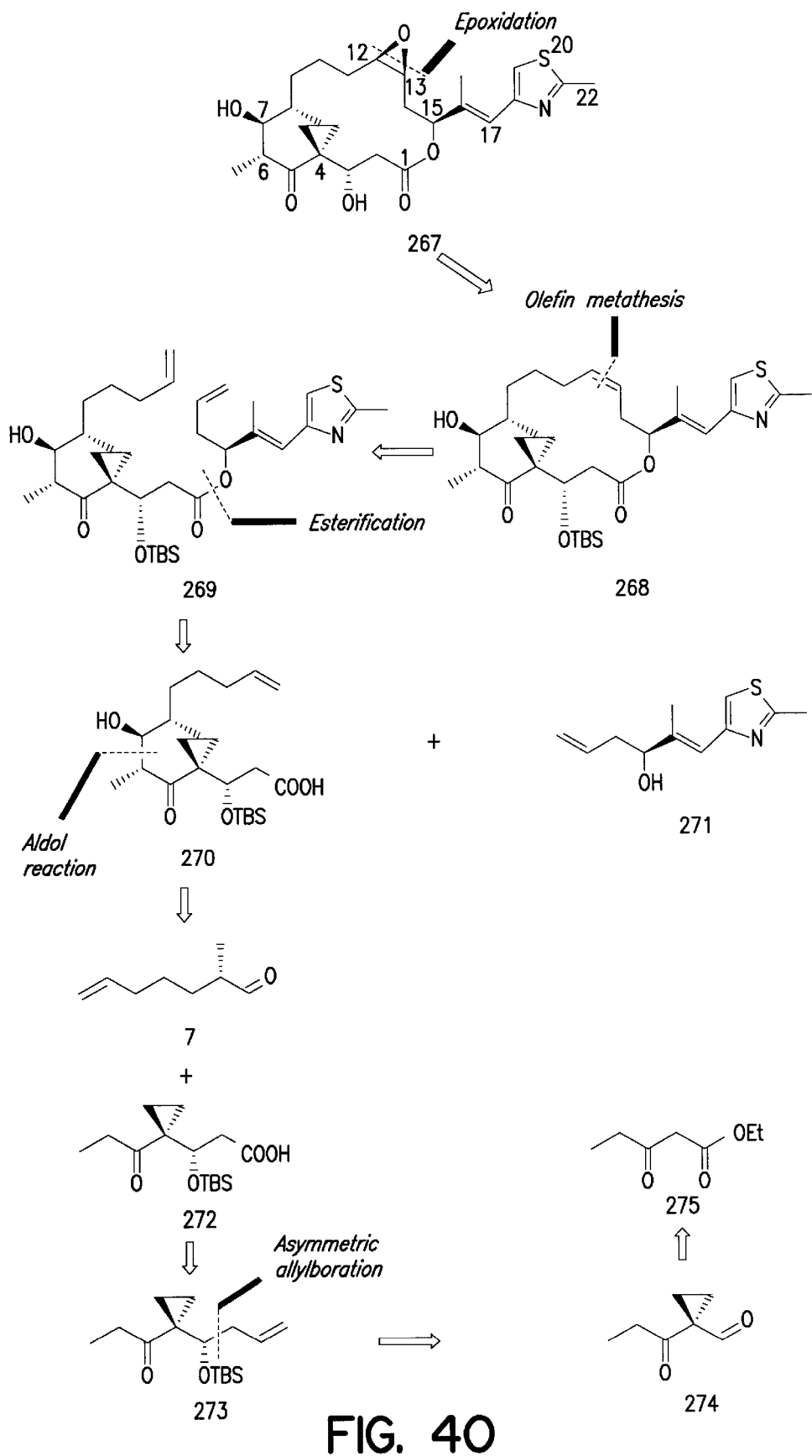

FIG. 40 illustrates the retrosynthetic analysis of 4,4-ethano epothilone A analog 267.

Figure 41:
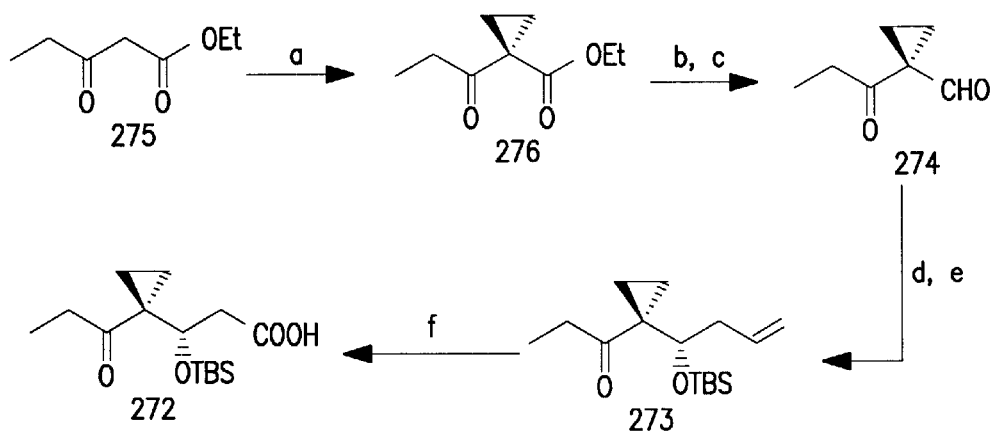

FIG. 41 illustrates the synthesis of ketoacid 272. Reagents and conditions: (a) 1.3 equiv of BrCH$_2$CH$_2$Br, 3.0 equiv of K$_2$CO$_3$, DMF, 25 C, 15 h, 60%; (b) 2.0 equiv of LiAlH$_4$, Et$_2$O, −20 to 0° C., 2.5 h, 93%; (c) 4.0 equiv of DMSO, 3.0 equiv of (COCl)2, 8.0 equiv of Et$_3$N, CH$_2$Cl$_2$, −78 to 0° C., 64%; (d) 1.1 equiv of (+)-Ipc2B(allyl), Et$_2$O, −100° C.; (e) 3.8 equiv of TBSOTf, 4.6 equiv of 2,6-lutidine, CH$_2$Cl$_2$, −78° C.; (f) 4.1 equiv of NaIO$_4$, 0.05 equiv of RuCl$_3$H$_2$O, MeCN:H$_2$O:CCl$_4$ (2:3:2), 25 C, 43% for 3 steps. DMSO=dimethyl sulfoxide; TBS=tert-butyldimethylsilyl; (+)-Ipc2B (allyl)=diisopinocampheylallyl borane.

Figure 42:
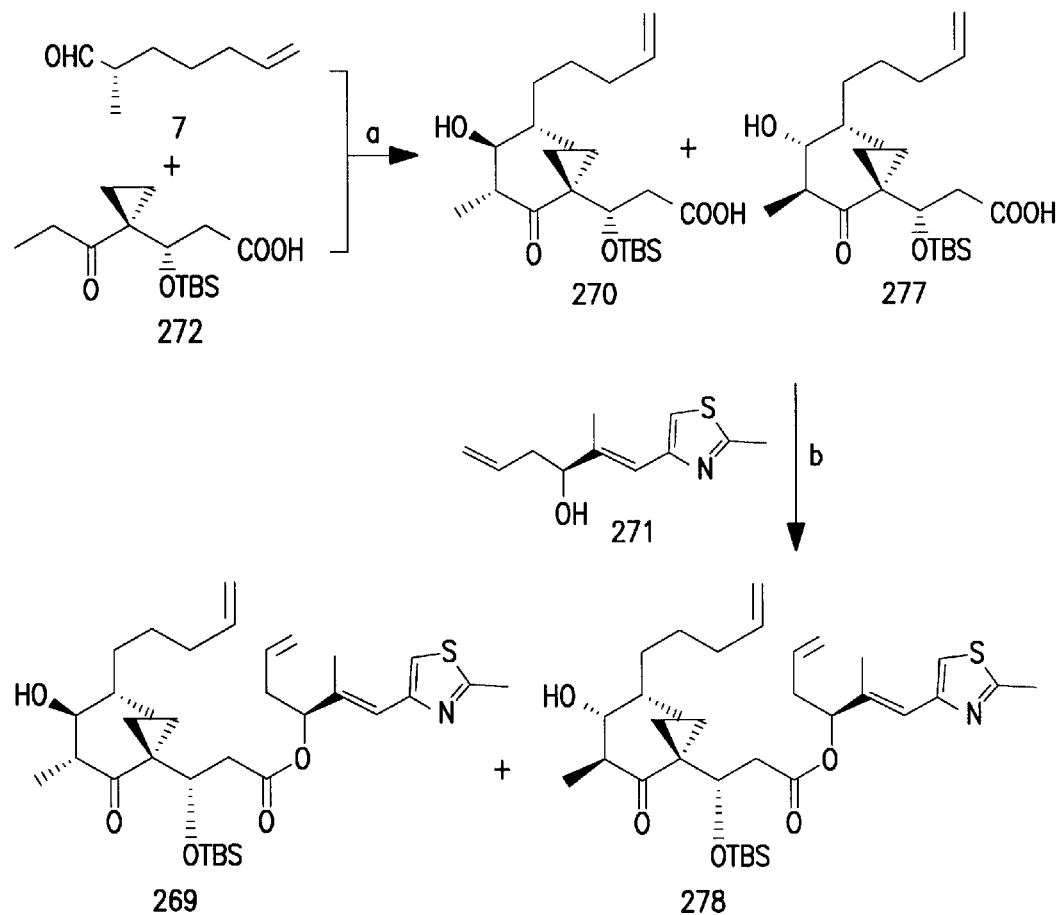

FIG. 42 illustrates the coupling of building blocks and construction of advanced intermediates 269 and 278. Reagents and conditions: (a) 2.4 equiv of LDA, −30° C., THF, 2 h, then 7 in THF, −30° C., 0.5 h, (29:36 ca. 2:3); (c) 2.5 equiv of 30, 1.2 equiv of EDC, 0.1 equiv 4-DMAP, CH$_2$Cl$_2$, 0♣25° C., 2 h, 15% (269) plus 36% (278) for two steps. TBS=tert-butyldimethylsilyl; LDA=lithium diisopropylamide; EDC=1-Ethyl-(3-dimethylaminopropyl)-3-carbodiimide hydrochloride; 4-DMAP=4-dimethylaminopyridine.

Figure 43:
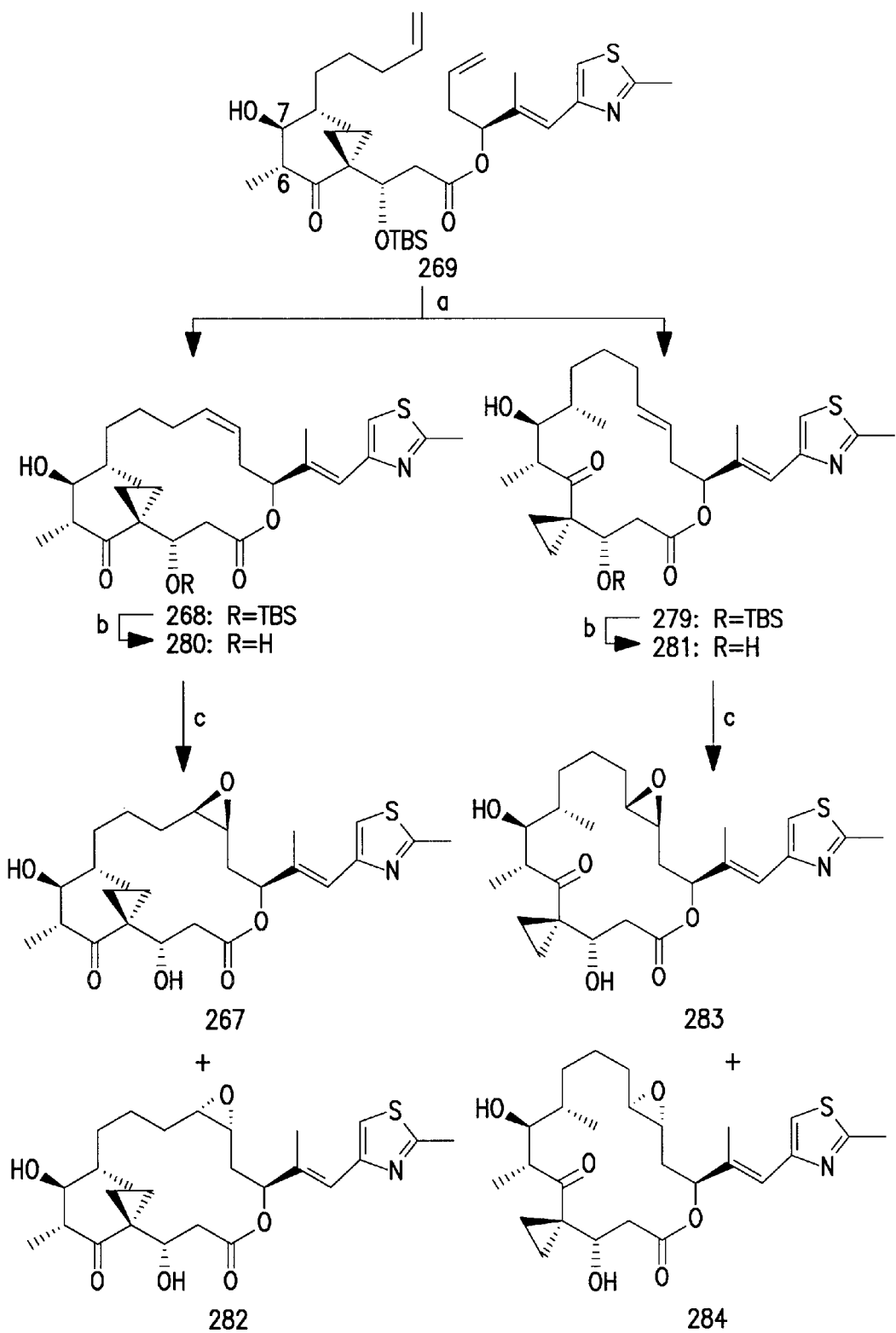

FIG. 43 illustrates an olefin metathesis of diene 269 and synthesis of 4,4-ethano epothilone A analogs and 282–284. Reagents and conditions: (a) 10 mol % of RuCl$_2$(=CHPh)(PCy$_3$)$_2$, CH$_2$Cl$_2$, 25 C, 2 h, 37% (268) plus 35% (279); (b) 25% HF.Py in THF, 0 to 25° C., 28 h, 65% (280), 62% (281); (c) CH$_2$Cl$_2$:CH$_3$CN:Na$_2$EDTA (1:2:1.5), 50 equiv of CF$_3$COCH$_3$, 11 equiv of NaHCO$_3$, 7.0 equiv of Oxone®, 0° C., 50% (267 or 282) plus 29% (282 or 267); 11% (283 or 284) plus 31% (284 or 283).

Figure 44:
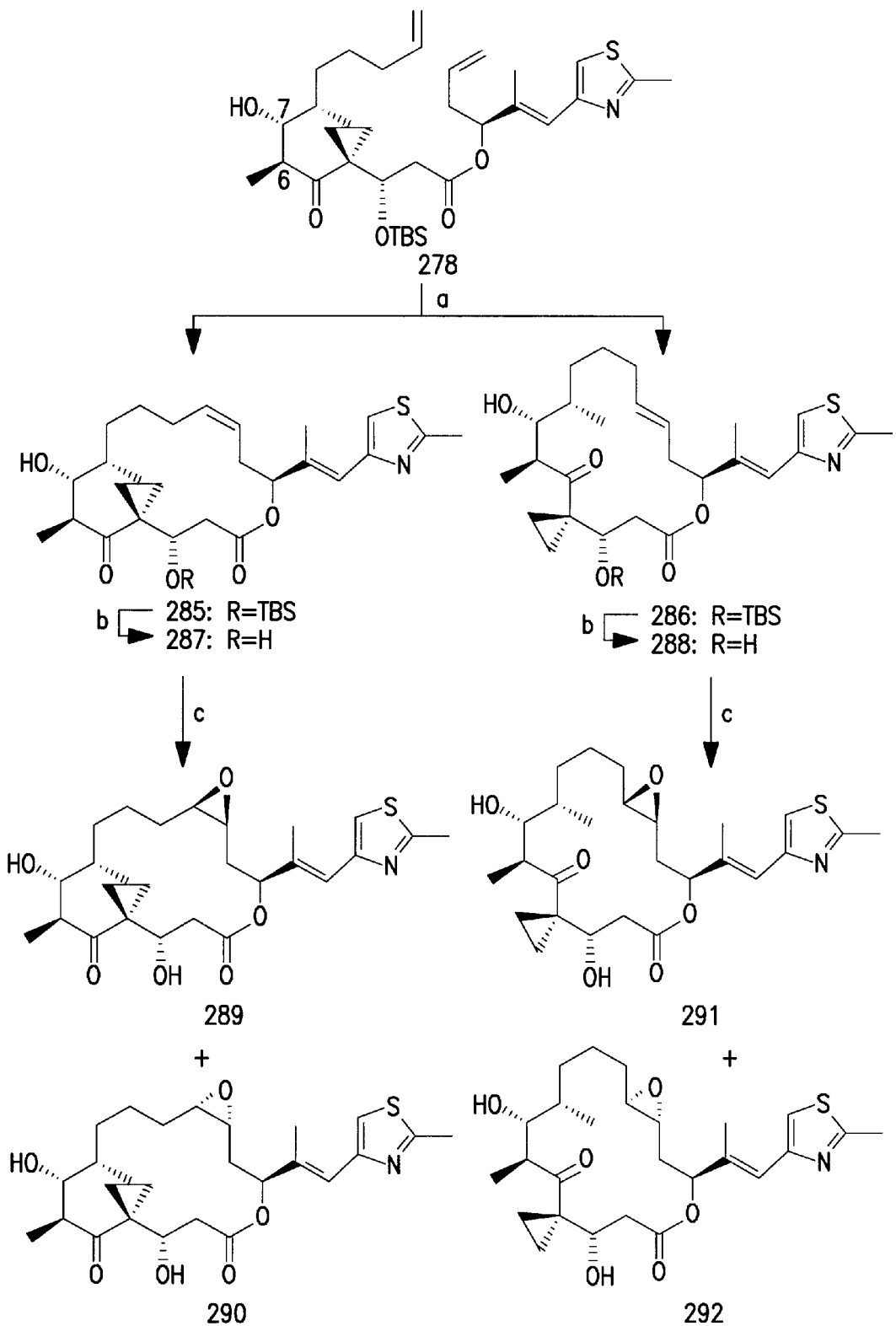

FIG. 44 illustrates the olefin metathesis of C6–C7 diastereomeric diene 278 and synthesis of 4,4-ethano epothilone A analogs 289–292. Reagents and conditions: (a) 9 mol % of RuCl$_2$(=CHPh)(PCy$_3$)$_2$, CH$_2$Cl$_2$, 25 C, 1 h, 18% (285) plus 58% (286); (b) 25% HF.Py in THF, 0 to 25° C., 22 h, 54% (287), 76% (288); (c) CH$_2$Cl$_2$:CH$_3$CN:Na$_2$EDTA (4:4:1), 50 equiv of CF$_3$COCH$_3$, 16 equiv of NaHCO$_3$, 10 equiv of Oxone®, 0° C., 39% (289 or 290) plus 35% (290 or 289); 22% (291 or 292) plus 27% (292 or 291).

Figure 45:
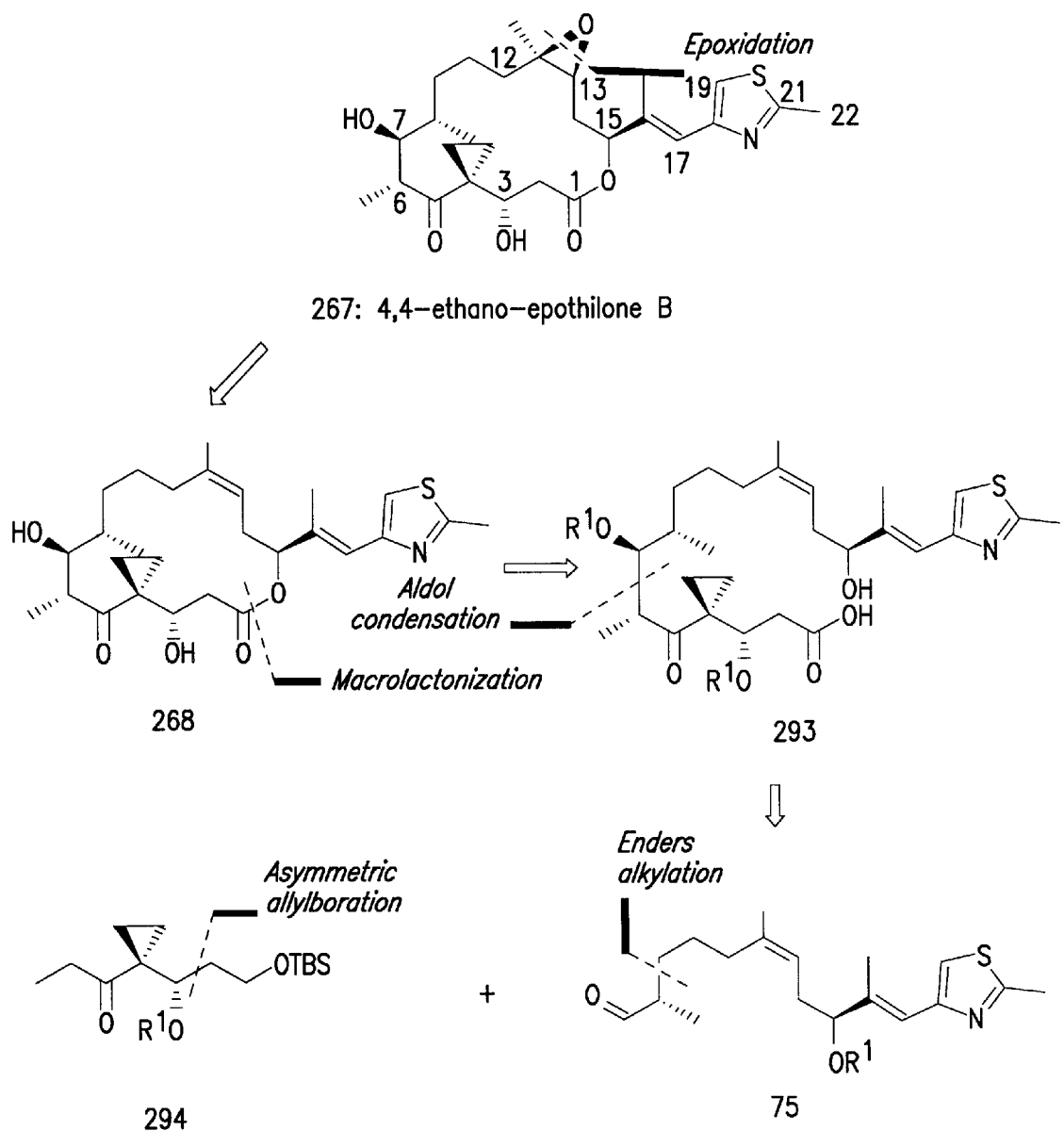

FIG. 45 illustrates the molecular structure and retrosynthetic analysis of the 4,4-ethano analog of epothilone B (267). R1=TBS=SitBuMe$_2$.

Figure 46:
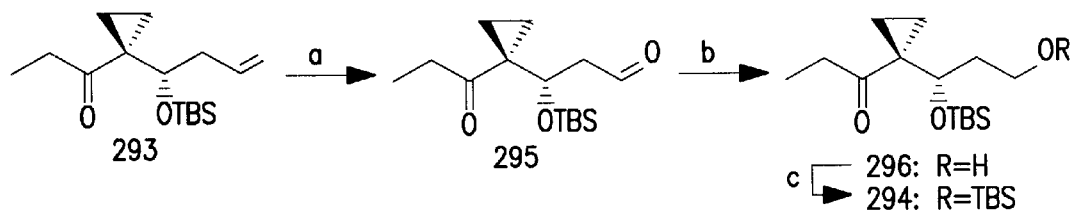

FIG. 46 illustrates the synthesis of ketone 294. Reagents and conditions: (a) O$_3$, CH$_2$Cl$_2$, −78° C., 0.5 h; then 1.2 equiv. Ph$_3$P, −78→25° C., 1 h, 90%; (b) 1.1 equiv. of LiAl(OtBu)$_3$H, THF, −78→0° C., 15 min; (c) 2.0 equiv. of TBSCl, 3.0 equiv. of Et$_3$N, 0.02 equiv. of 4-DMAP, CH$_2$Cl$_2$, 0→25° C., 12 h, 83% for 2 steps.

Figure 47A:
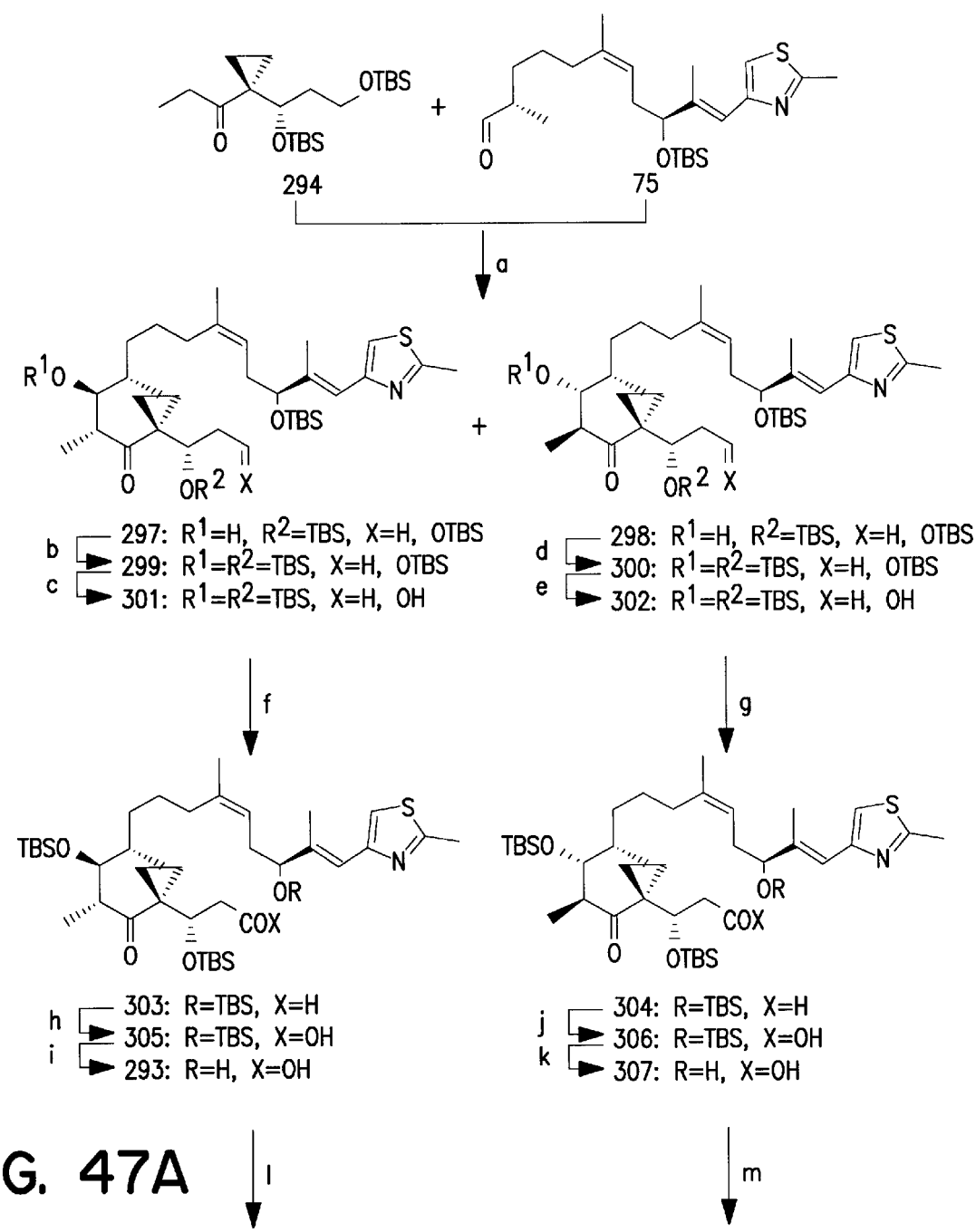
Figure 47B:
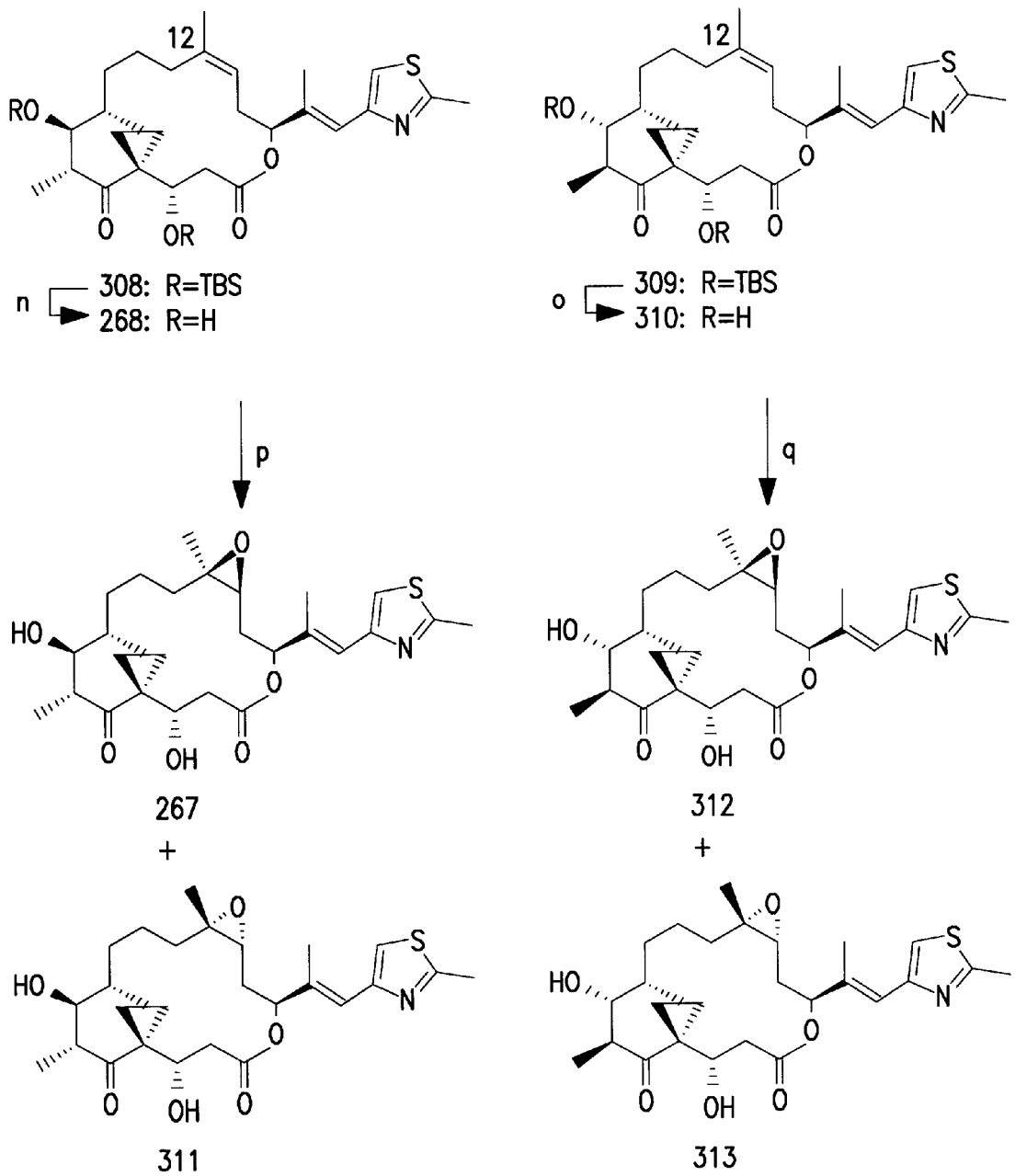

FIG. 47 illustrates the total synthesis of 4,4-ethano analogs of epothilone B. Reagents and conditions: (a) 1.5 equiv. of LDA, THF, 0° C., 15 min; then 1.4 equiv. of 294 in THF, −78→−60° C., 1 h; then 1.0 equiv. of 75 in THF at −78° C., 24% of 297 and 47% of its 6S,7R-diastereoisomer 298 (ca 1:2 ratio); (b) 1.2 equiv. of TBSOTf, 2.0 equiv. of 2,6-lutidine, $CH_2Cl_2$, 0° C., 2 h, 92%; (c) 1.0 equiv. of CSA portionwise, CH2Cl2:MeOH (1:1), 0 25° C., 0.5 h, 74%; (d) same as b, 89%; (e) same as c, 60%; (f) 2.0 equiv. of $(COCl)_2$, 4.0 equiv. of DMSO, 6.0 equiv. of $Et_3N$, CH2Cl2, −78→0° C., 1.0 h, 96%; (g) same as f, 69%; (h) 6.0 equiv. of $NaClO_2$, 10.0 equiv. of 2-methyl-2-butene, 3.0 equiv. of $NaH_2PO_4$, tBuOH:$H_2O$ (5:1), 25° C., 0.5 h, 91%; (i) 6.0 equiv. of TBAF, THF, 25° C., 8 h, 62%; (j) same as h, 99%; (k) same as i, 50%; (l) 1.1 equiv. of 2,4,6-trichlorobenzoylchloride, 2.2 equiv. of $Et_3N$, THF, 0° C., 1 h; then add to a solution of 2.0 equiv. of 4-DMAP in toluene (0.002 M based on 293), 25° C., 3 h, 70%; (m) same as 1, 72%; (n) 20% HF.pyr (by volume) in THF, 0→25° C., 24 h, 92%; (o) same as n, 90%; (p) methyl(trifluoromethyl) dioxirane, MeCN, 0° C., 86% (267:311 ca 8:1 ratio of diastereoisomers); (q) same as p, 89% (312:313 ca 2:1 ratio of diastereoisomers).

Figure 48:
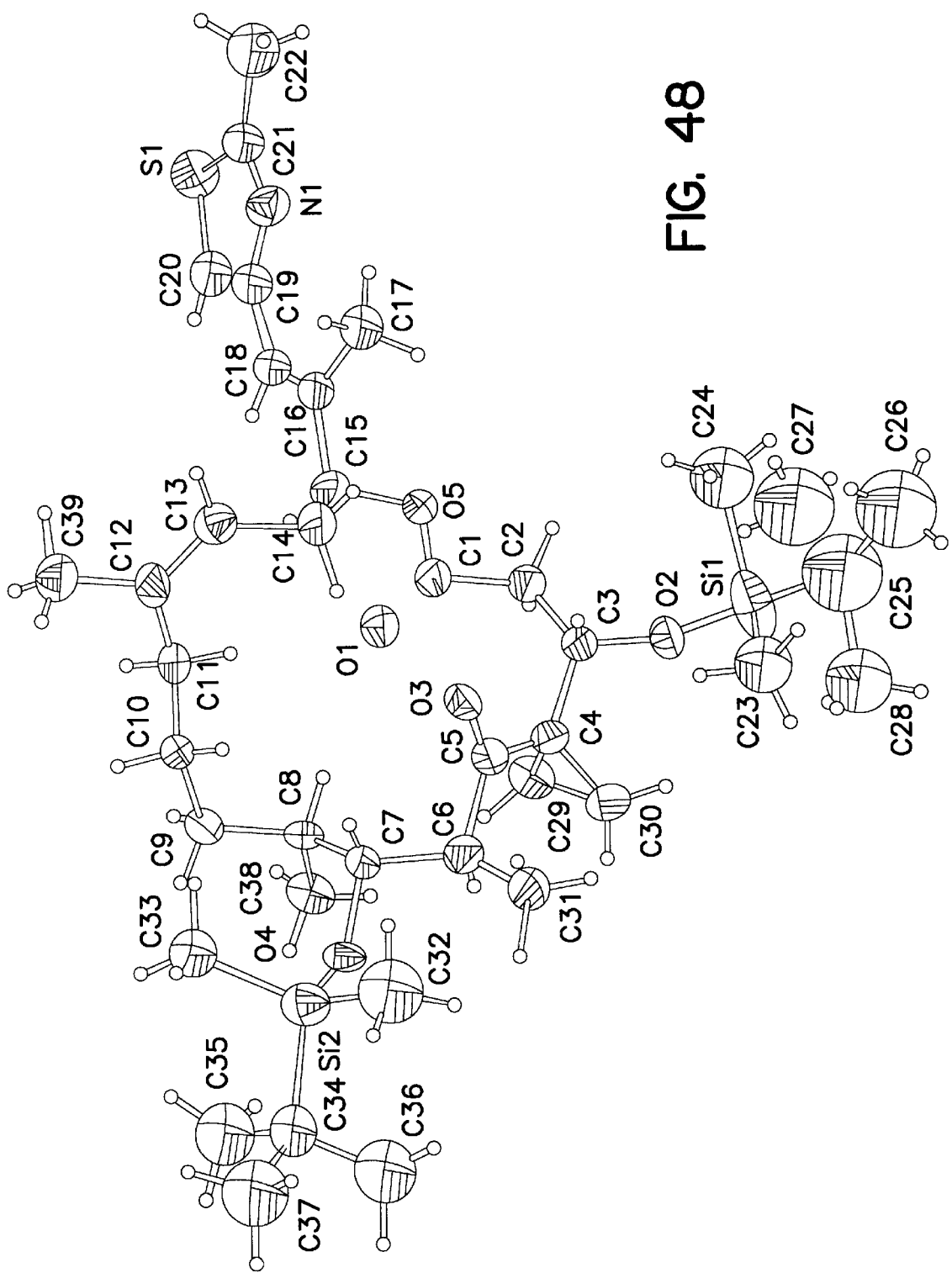

FIG. 48 illustrates ORTEP view of compound 309.

Figure 49A:
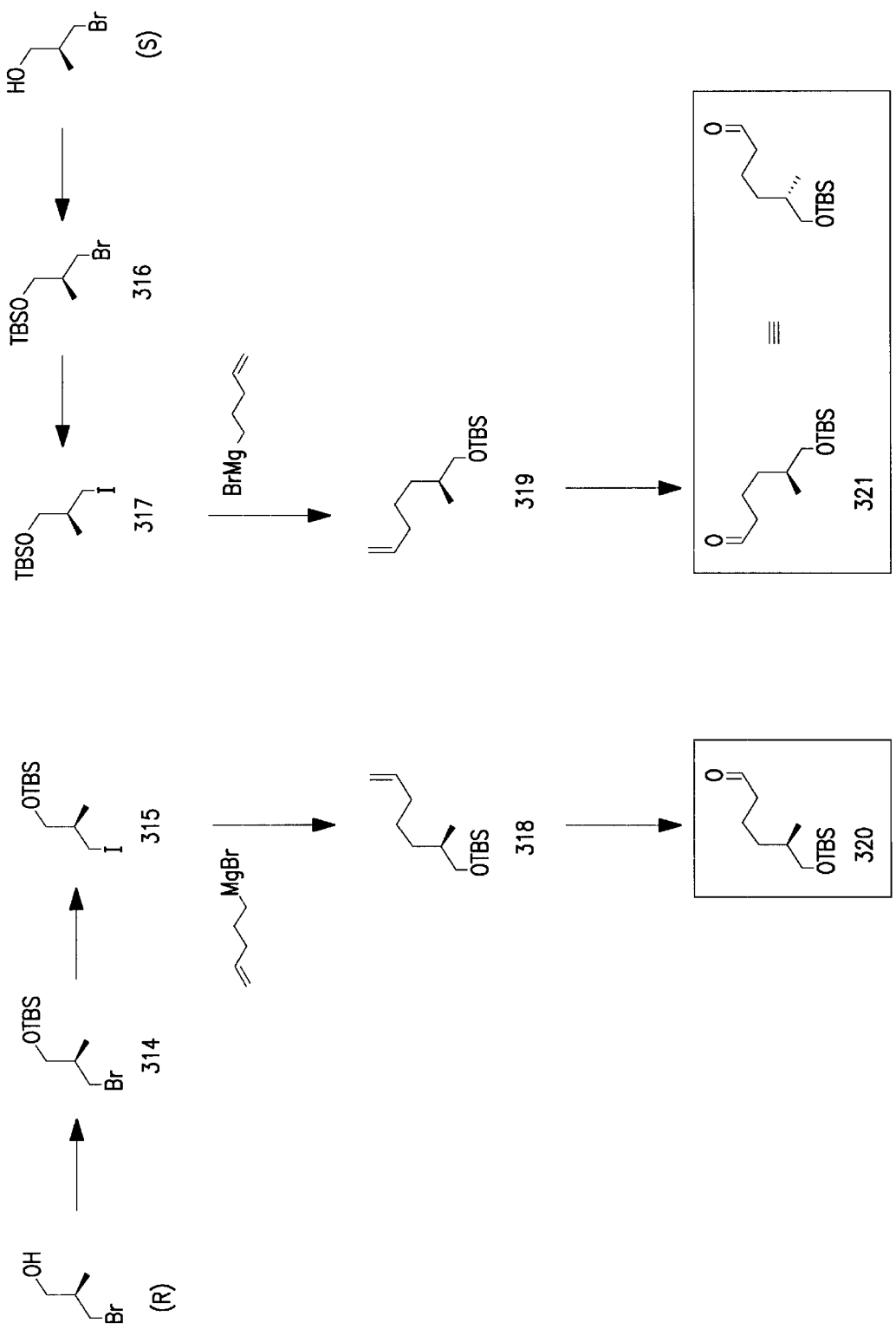
Figure 49B:
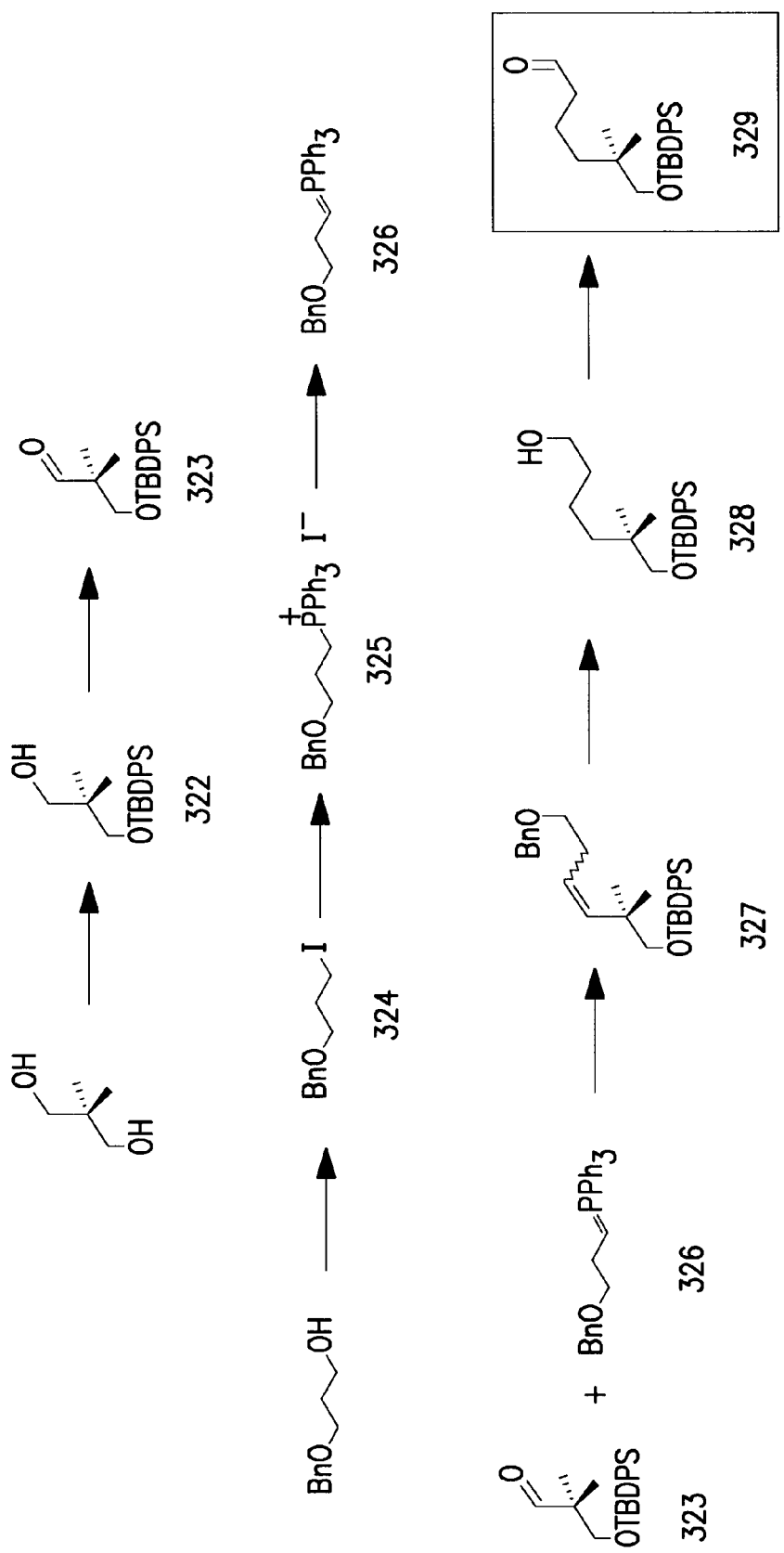

FIG. 49 illustrates the synthesis of key aldehydes 320, 321, 323 and 329.

Figure 50A:
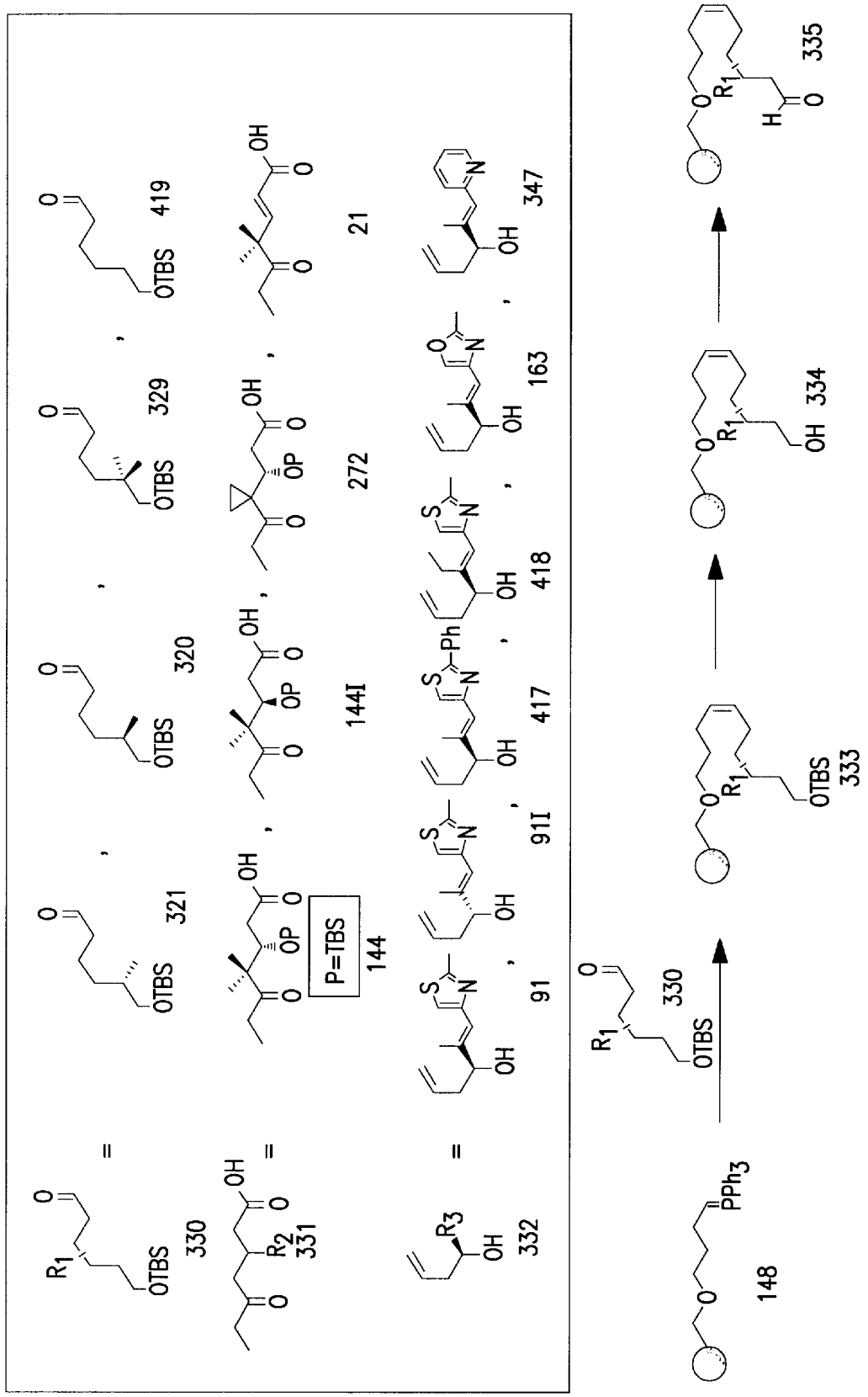
Figure 50B:
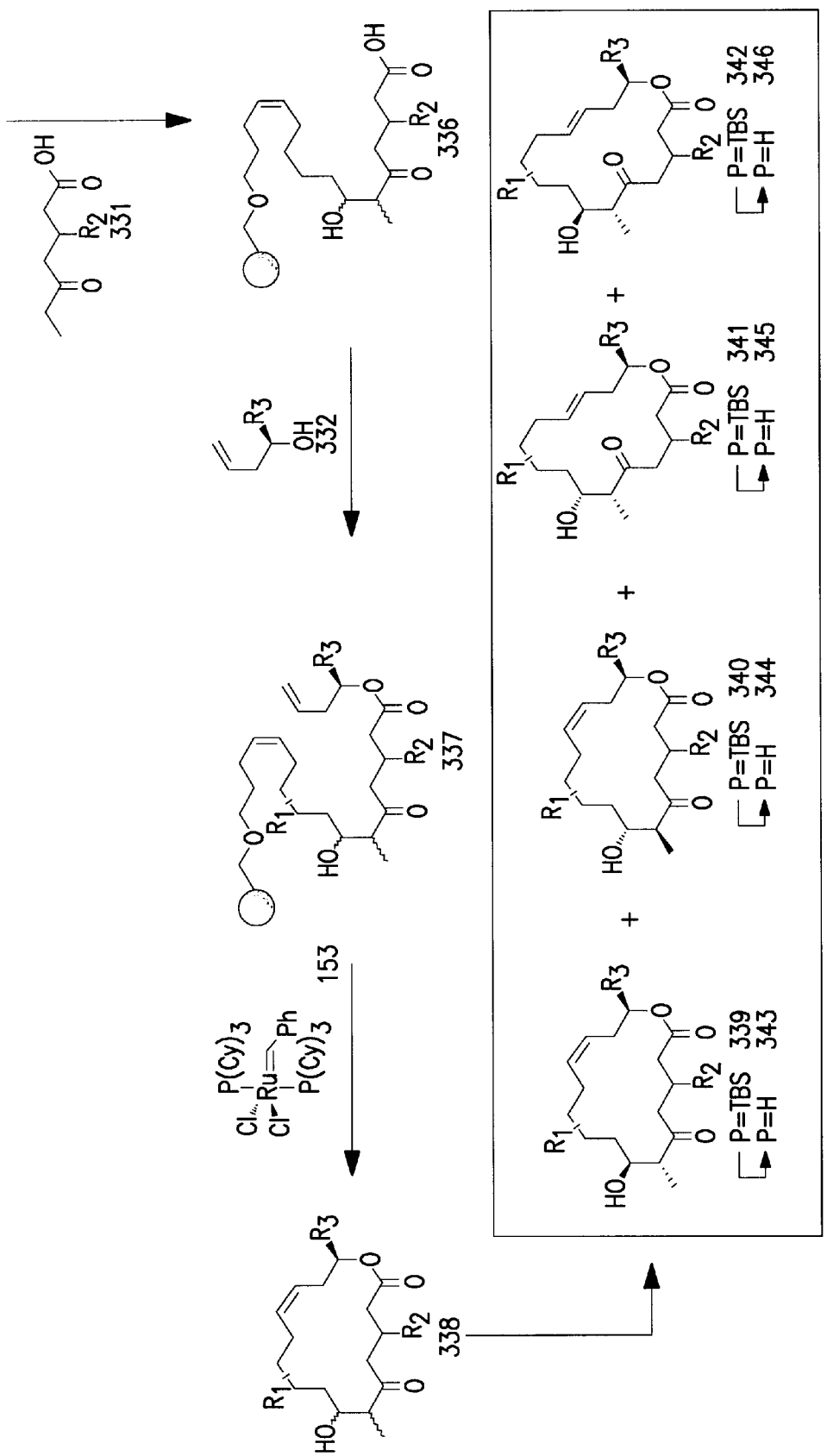

FIG. 50 illustrates the solid phase strategy for the synthesis of epothilone analogs with key intermediates 330, 331 and 332 and employing the metathesis approach.

Figure 51:
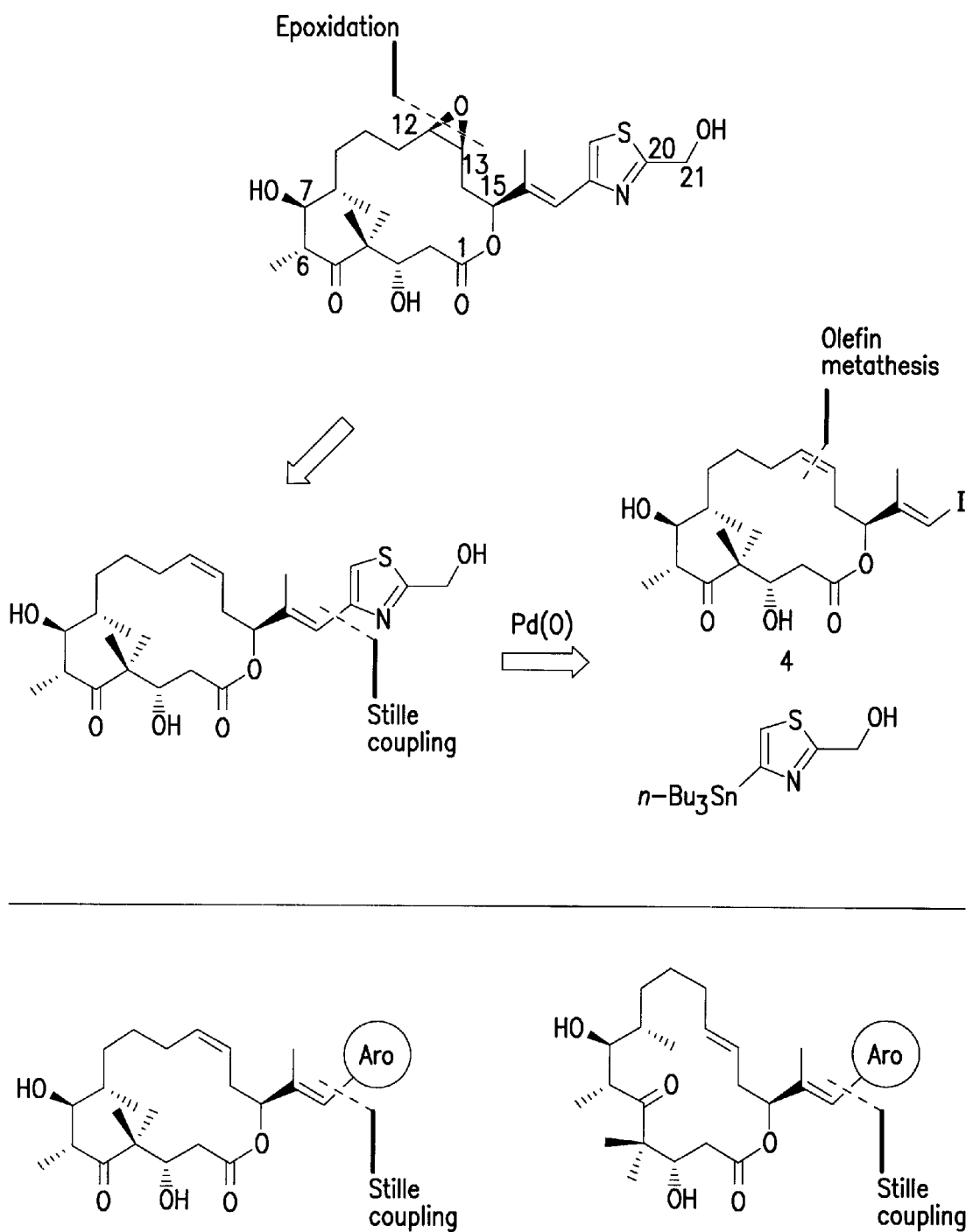

FIG. 51 illustrates the retrosynthetic analysis and strategy for the total synthesis of epothilone E and side chain epothilone analogs. Aro=aromatic moiety.

Figure 52:
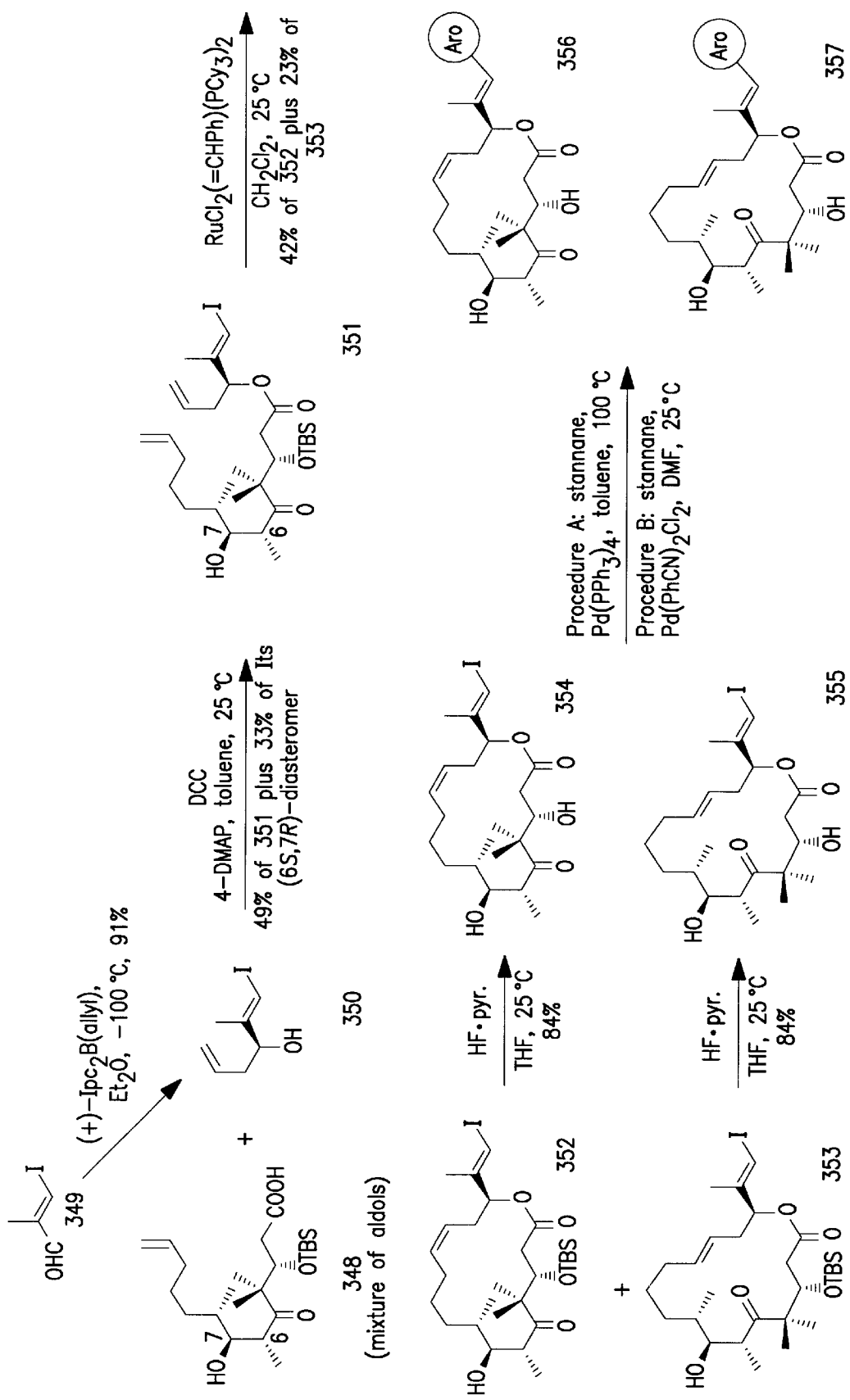

FIG. 52 illustrates the synthesis of epothilone analogs via the Stille coupling reaction.

Figure 53A:
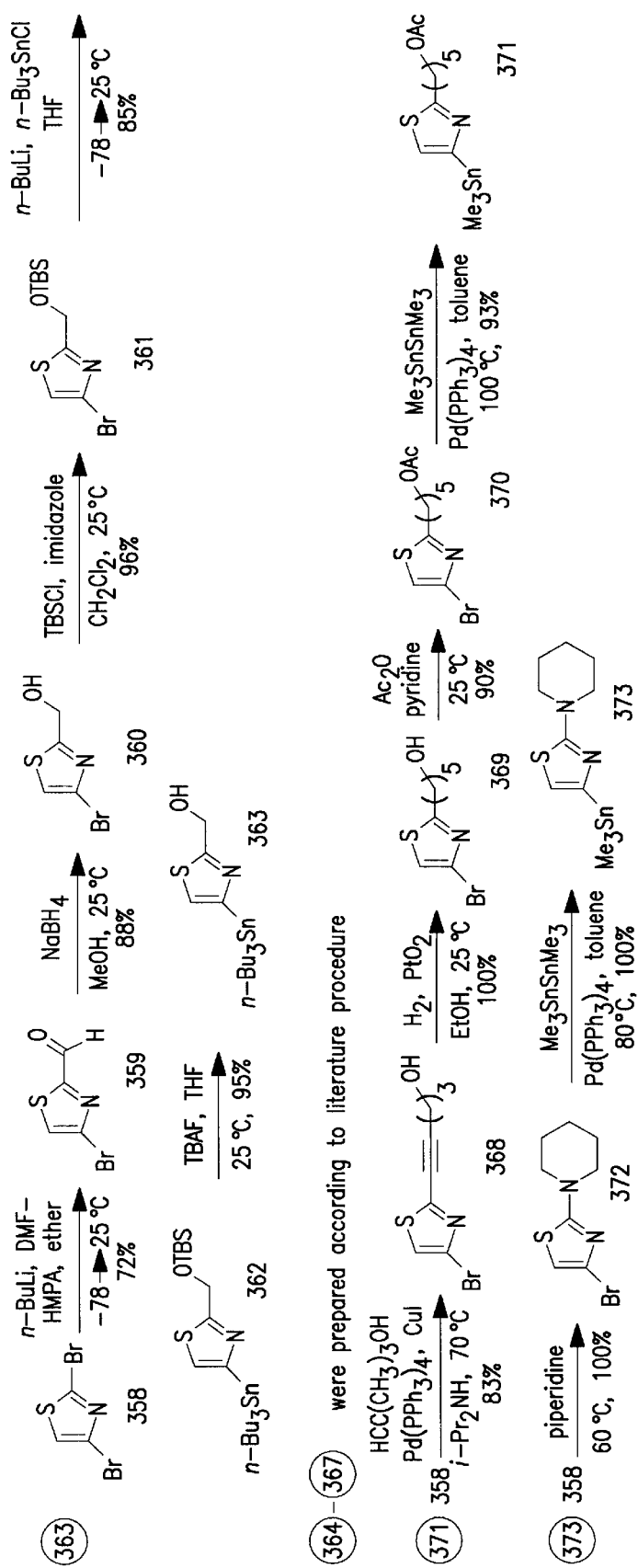
Figure 53B:
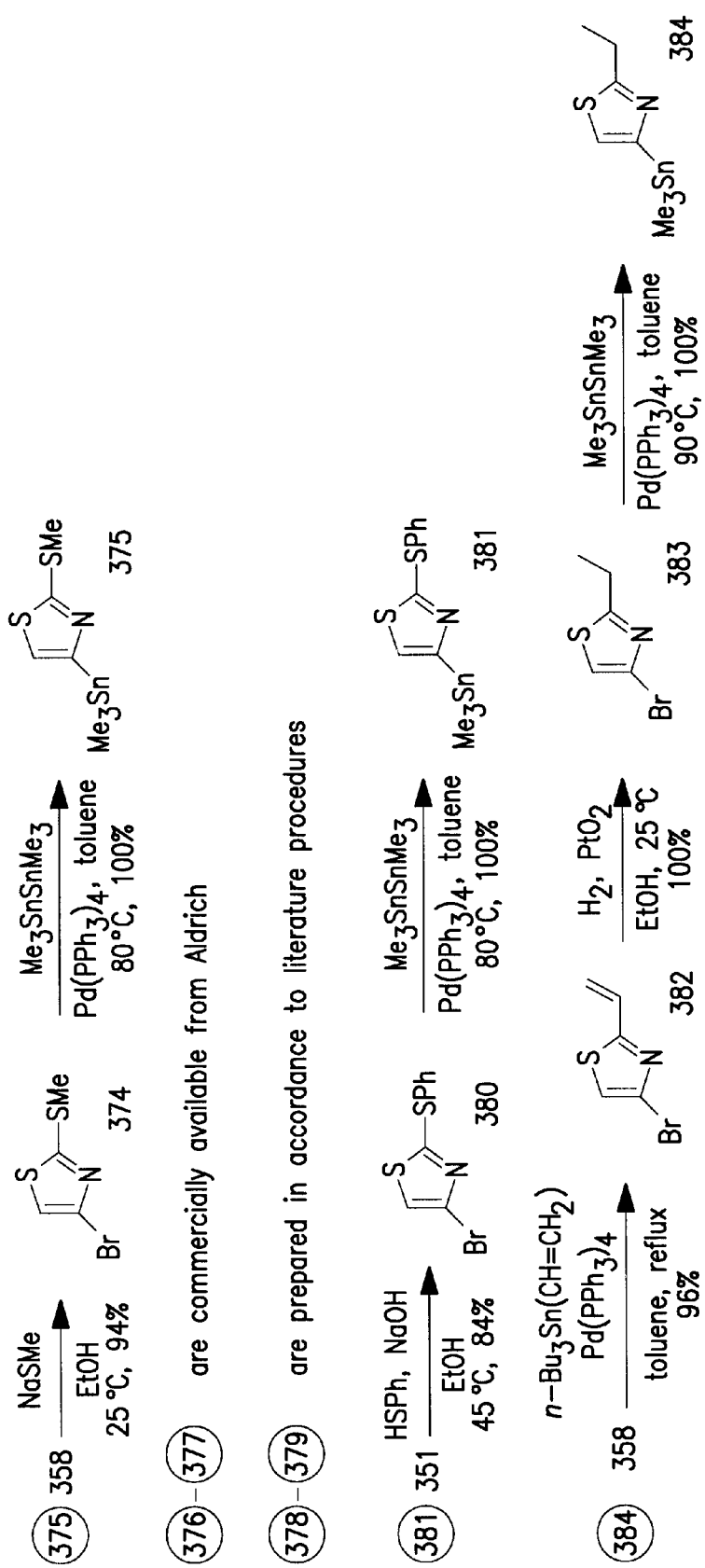
Figure 53C:
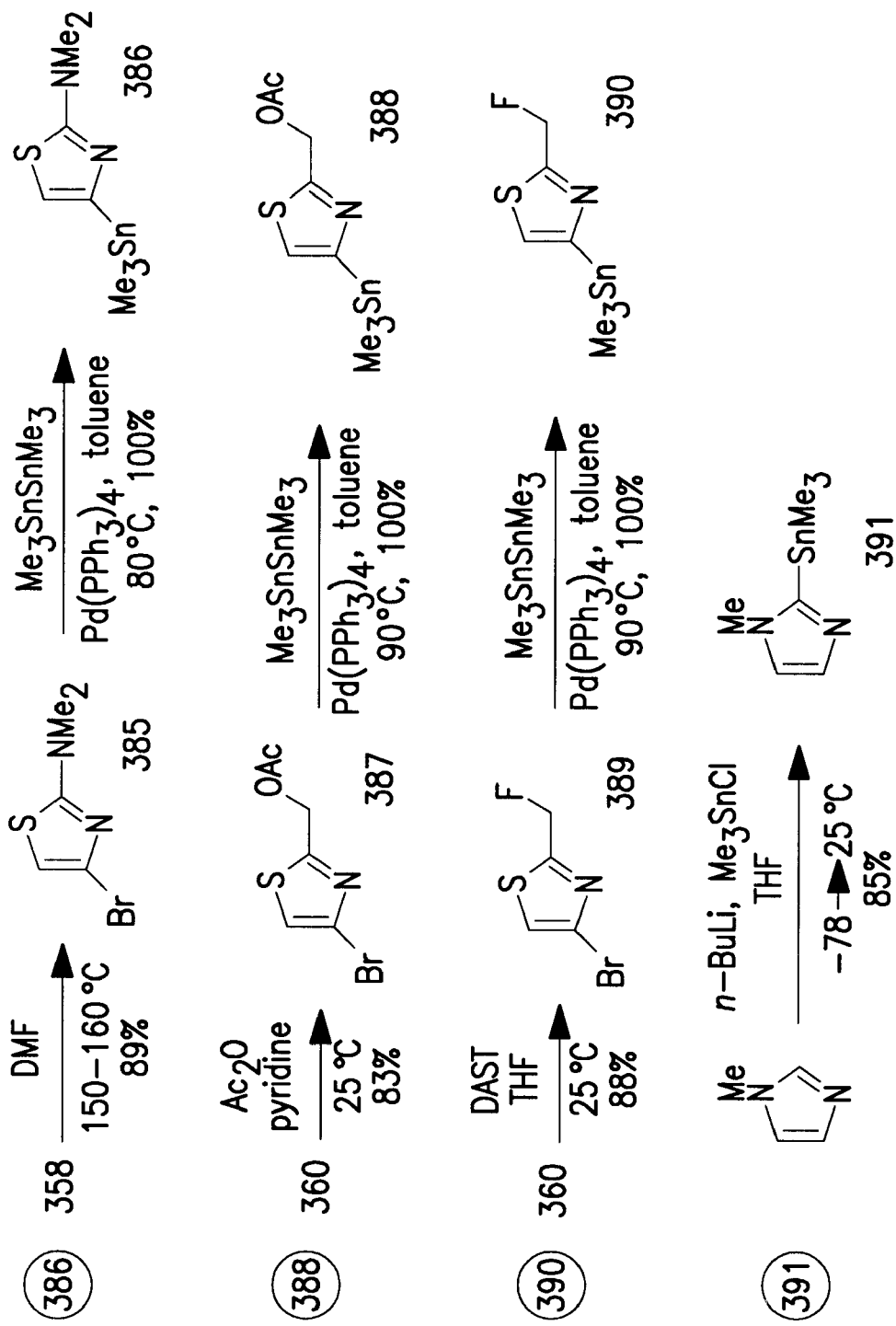

FIG. 53 illustrates the synthesis of recommended stannanes for the synthesis of epothilone analogs via the Stille coupling reaction.

Figure 54A:
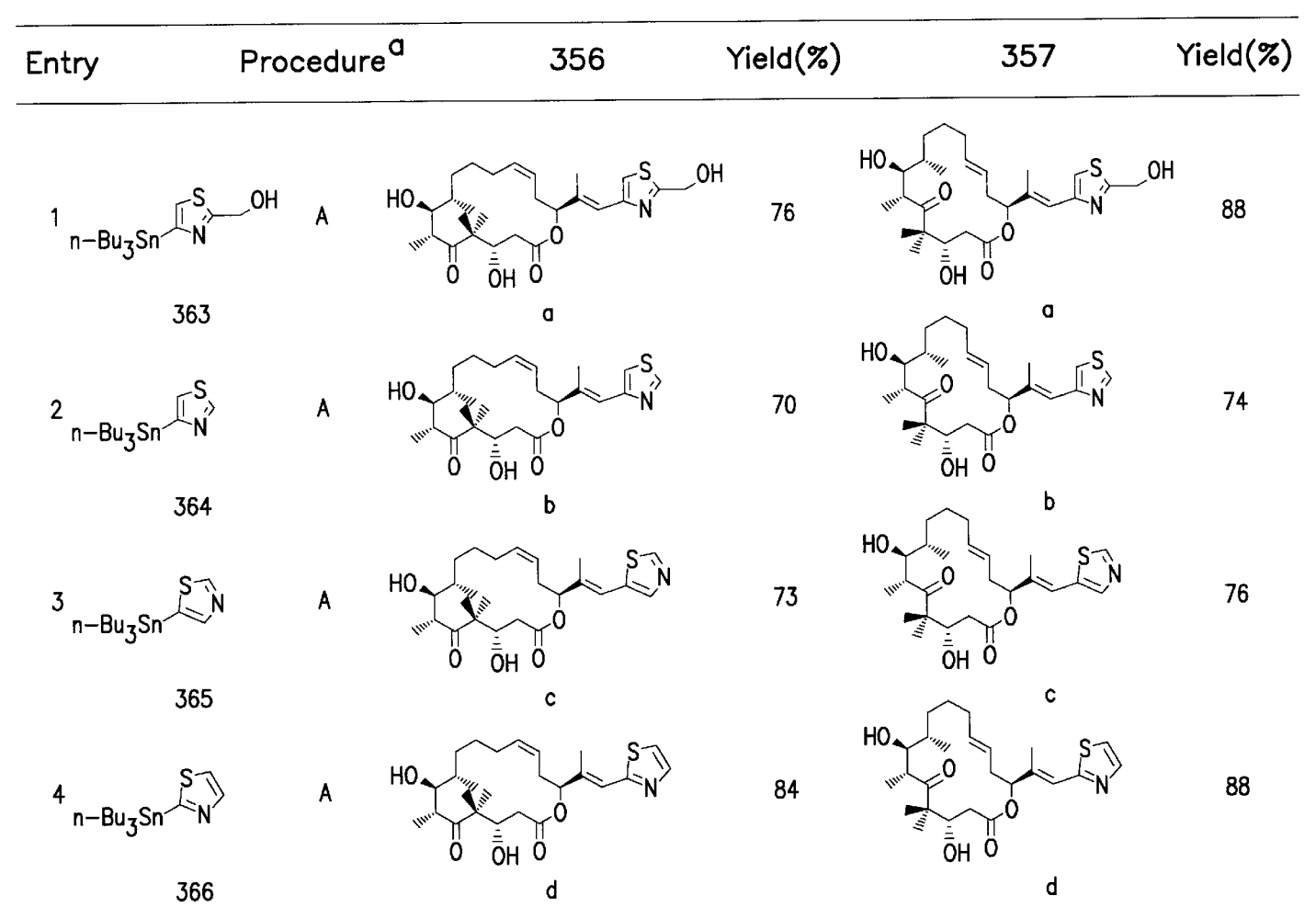
Figure 54B:
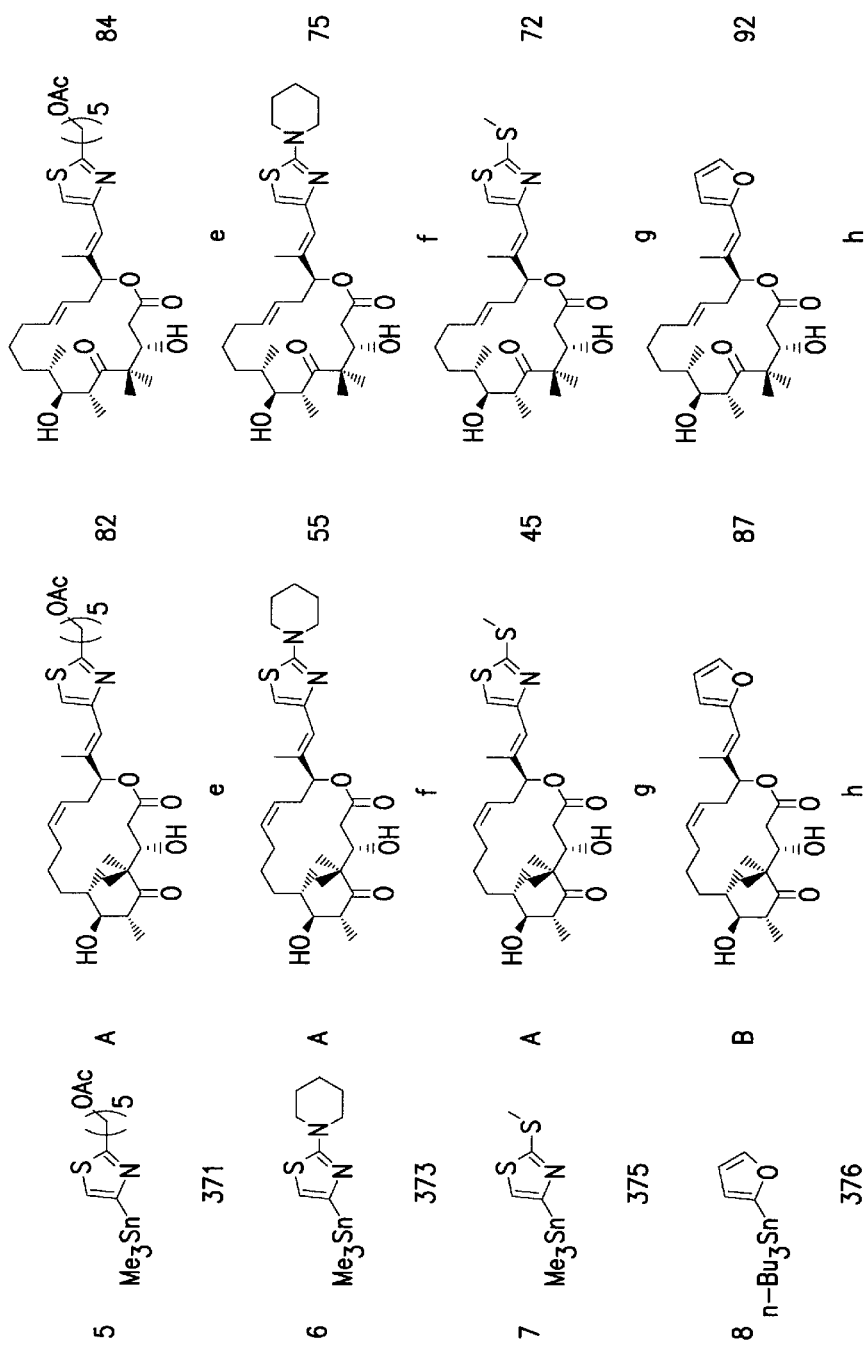

FIG. 54 shows a table of achieved compounds using the noted stannanes. Compound 356 and 357 are stereoisomers of each other wherein 356 is the cis olefin and 357 represents the trans olefin analog with indicated yield.

Figure 55A:
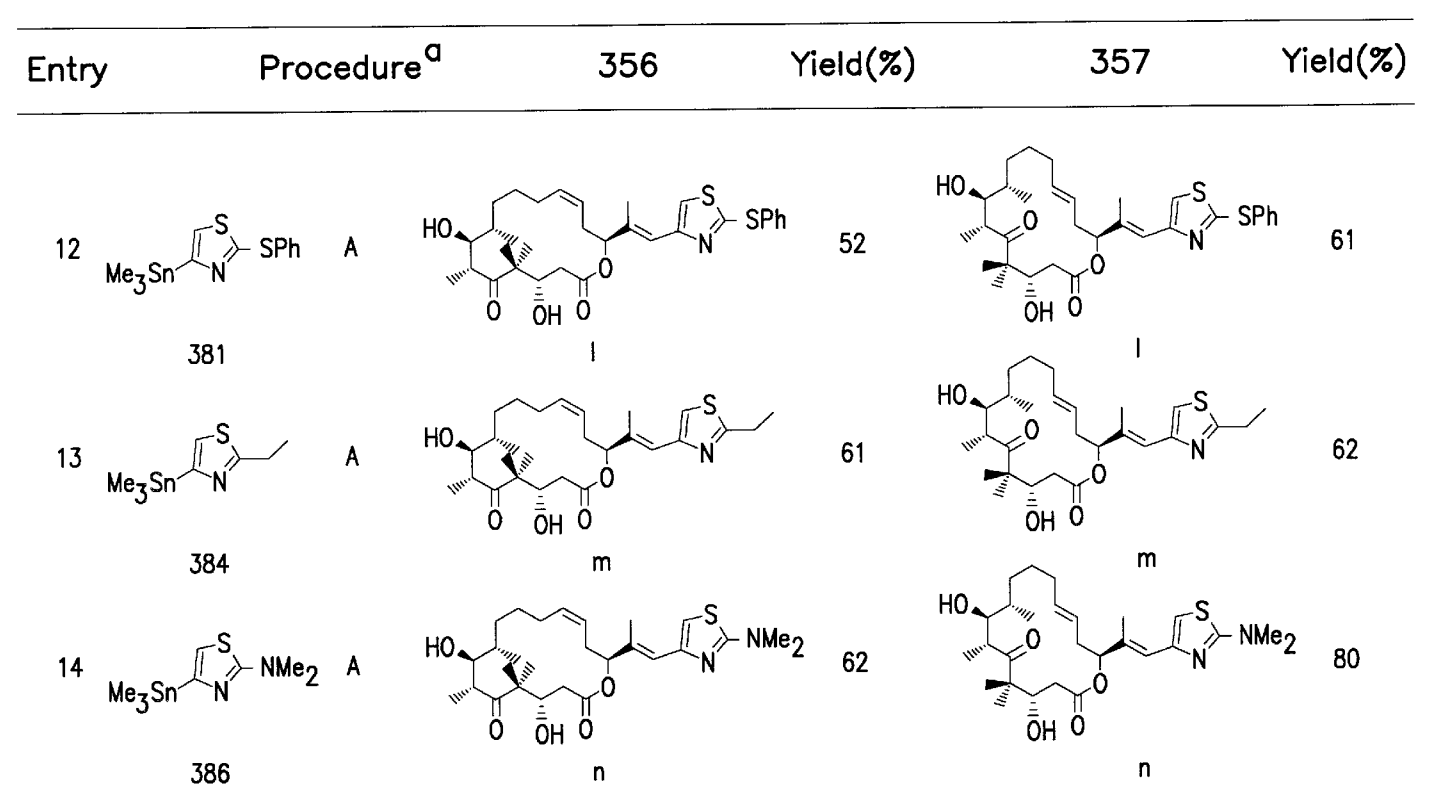
Figure 55B:
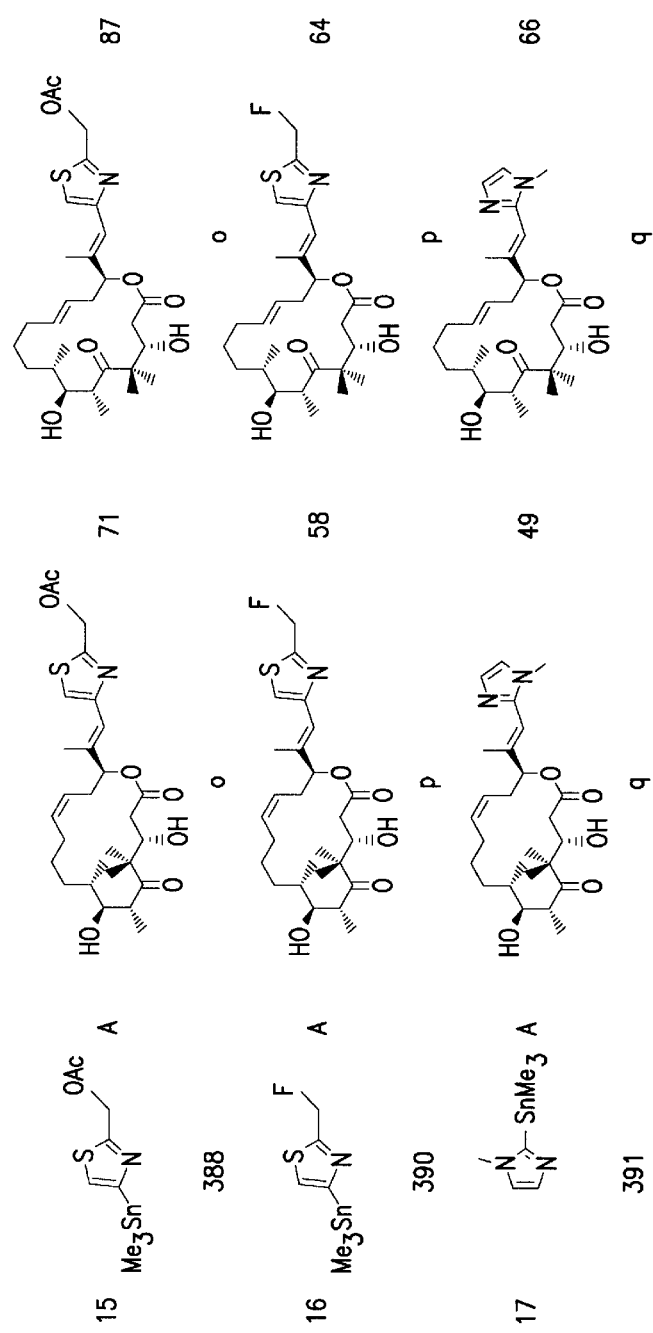

FIG. 55 shows a table of achieved compounds using the noted stannanes. Compound 356 and 357 are stereoisomers of each other wherein 356 is the cis olefin and 357 represents the trans olefin analog with indicated yield.

Figure 56:
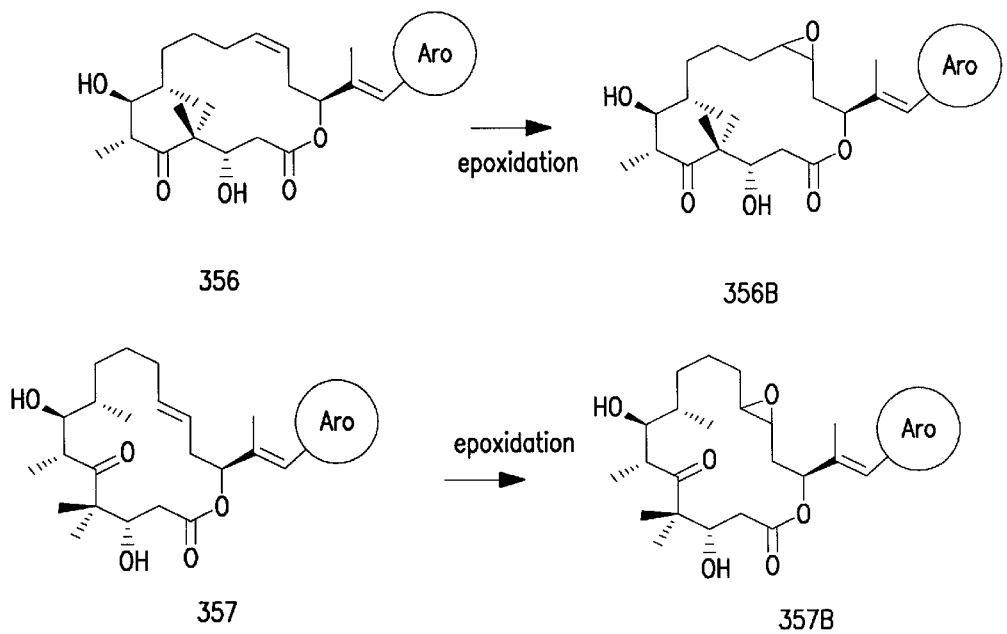

FIG. 56 illustrates the synthesis of epothilone E. Reagents and conditions: (a) 33 equiv of $H_2O_2$, 60 equiv of $CH_3CN$, 9.0 equiv of $KHCO_3$, MeOH, 25 C, 4 h, 65% (based on 50% conversion).

Figure 57:
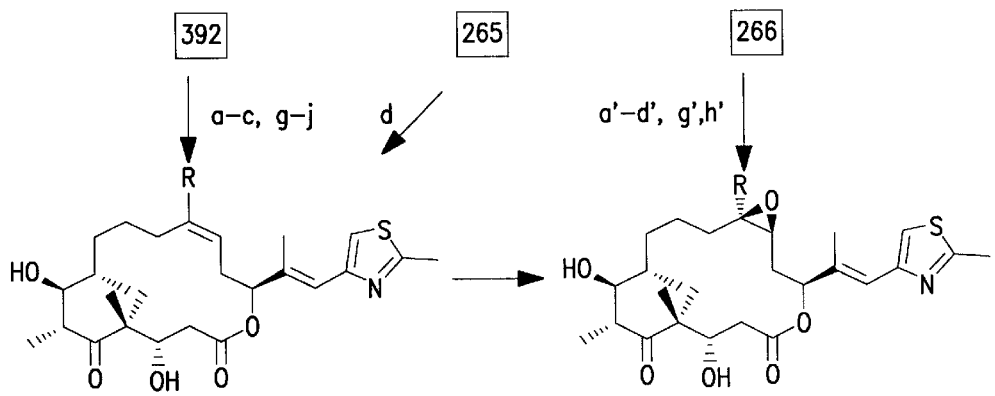

FIG. 57 illustrates the synthesis of 26-hydroxycompounds. Reagents and conditions: (a) 1.3 equiv. of $Ac_2O$, 1.0 equiv. of 4-DMAP, EtOAc, 0° C., 0.5 h, 95%; then 25% HF.pyr. (by volume) in THF, 0→25° C., 24 h, 92%; (b) 3.0 equiv. of pivalcyl chloride, 4.0 equiv. of $Et_3N$, 0.05 equiv. of 4-DMAP, $CH_2Cl_2$, 0° C., 0.5 h, 93%; then desilylation as in (a), 90%; (c) 3.0 equiv. of benzoyl chloride, 4.0 equiv. of $Et_3N$, 0.05 equiv. of 4-DMAP, $CH_2Cl_2$, 0° C., 0.5 h, 85%; then desilylation as in (a), 90%; (d) 5.0 equiv. of $MnO_2$, $Et_2O$, 25° C., 3 h, 85%; (e) 5.0 equiv. of $NaClO_2$, 70 equiv. of 2-methyl-2-butene, 2.5 equiv. of $NaH_2PO_4$, tBuOH:$H_2O$ (5:1), 0° C., 0.5 h, 98%; (f) CH2N2, Et2O, 0° C., 80%; (g) 4.0 equiv. of Ph3P, CCl4, 75° C. 24 h, 85%; then desilylation as in (a), 86%; (h) 1.1 equiv. of NaH, 20 equiv. of MeI, DMF, 0° C., 1 h, 65%; then desilylation as in (a), 89%; (i) 1.1 equiv. of NaH, 20 equiv. of BnBr, DMF, 0→25° C., 1 h, 40%; then desilylation as in (a), 87%; (j) 1.1 equiv. of DAST, $CH_2Cl_2$, −78→25° C., 1 h, 60%; then desilylationas in (a), 85%; (k) 5.0 equiv. of $MnO_2$, $Et_2O$, 25° C., 3 h, 90%; then 2.0 equiv. of $Ph_3P+CH_3Br−$, 2.0 equiv. of LiHMDS. THF, 0° C. 85%; then desilylation as in (a), 85%; (a') 1.1 equiv. of $Ac_2O$, 1.0 equiv. of 4-DMAP, EtOAc, 0° C., 0.5 h, 90%; (b') 3.0 equiv. of pivaloyl chloride, 4.0 equiv. of $Et_3N$, 0.05 equiv. of 4-DMAP, $CH_2Cl_2$, 0° C., 0.5 h, 90%; (c') 1.2 equiv. of benzoyl chloride, 4.0 equiv. of $Et_3N$, 0.05 equiv. of 4-DMAP, $CH_2Cl_2$, 0° C., 0.5 h, 75%; (d') 1.5 equiv. of TEMPO (0.008 M solution in $CH_2Cl_2$), 1.0 equiv. of NaOCl (0.035 M solution in 5% aqueous $NaHCO_3$), 0.1 equiv of KBr (0.2 M aqueous solution), $CH_2Cl_2$, 0° C., 0.5 h, 75%; (e') 5.0 equiv. of $NaClO_2$, 70 equiv. of 2-methyl-2-butene, 2.5 equiv. of $NaH_2PO_4$, tBuOH:H2O (5:1), 0° C., 0.5 h, 95%; (f) $CH_2N_2$, $Et_2O$:EtOAc (1:2), 0° C., 2 h, 90%; (g') 4.0 equiv. of $Ph_3P$, $CH_3CN$:$CCl_4$ (1:3), 25° C., 1 h, 85%; (h') 1.1 equiv. of NaH, 20 equiv. of MeI, DMF, 50%; (i') 1.3 equiv. of TsCl, 2 equiv. of triethylamine, 0.1 equiv. of DMAP, methylene chloride, 0 C, 1 h 85%, then 3 equiv. of NaI, $CH_3C(O)CH_3$, 25 C, 10 h, 85% of 1000i'; (j') 1.1 equiv. of DAST, methylene chloride, −78 to 25° C. 1 h, 65% of 1000j'; (k') 6 equiv. of TMSCl, 10 equiv. of triethylamine, methylene chloride 0 to 25° C., 10 h, 67%, then 2 equiv. of $Ph_3PCH_3Br$, 2.0 equiv. of NaHMDS, THF, 0 to 25° C., 75%, then HF.pyr in pyridine, THF, 0 to 25° C., 3 h, 97% of 1000k'; (l') same as (h'), 55% of 1000l'; Bn=benzyl; DAST=diethylaminosulfur trifluoride; LiHMDS=lithium bis(trimethylsilyl)amide; TEMPO= 2,2,6,6-tetramethyl-1-piperidinyloxy, free radical.

Figure 58A:
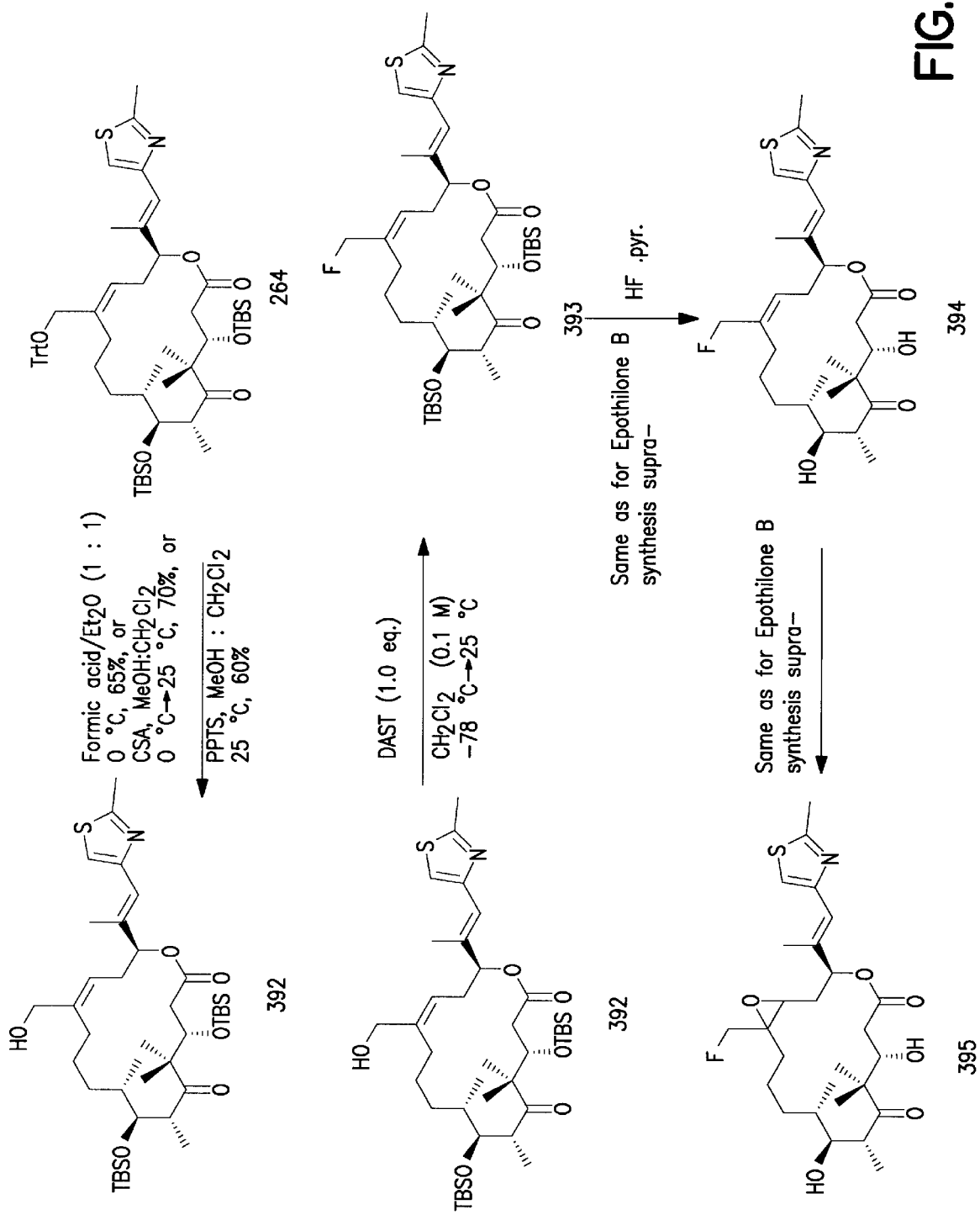
Figure 58B:
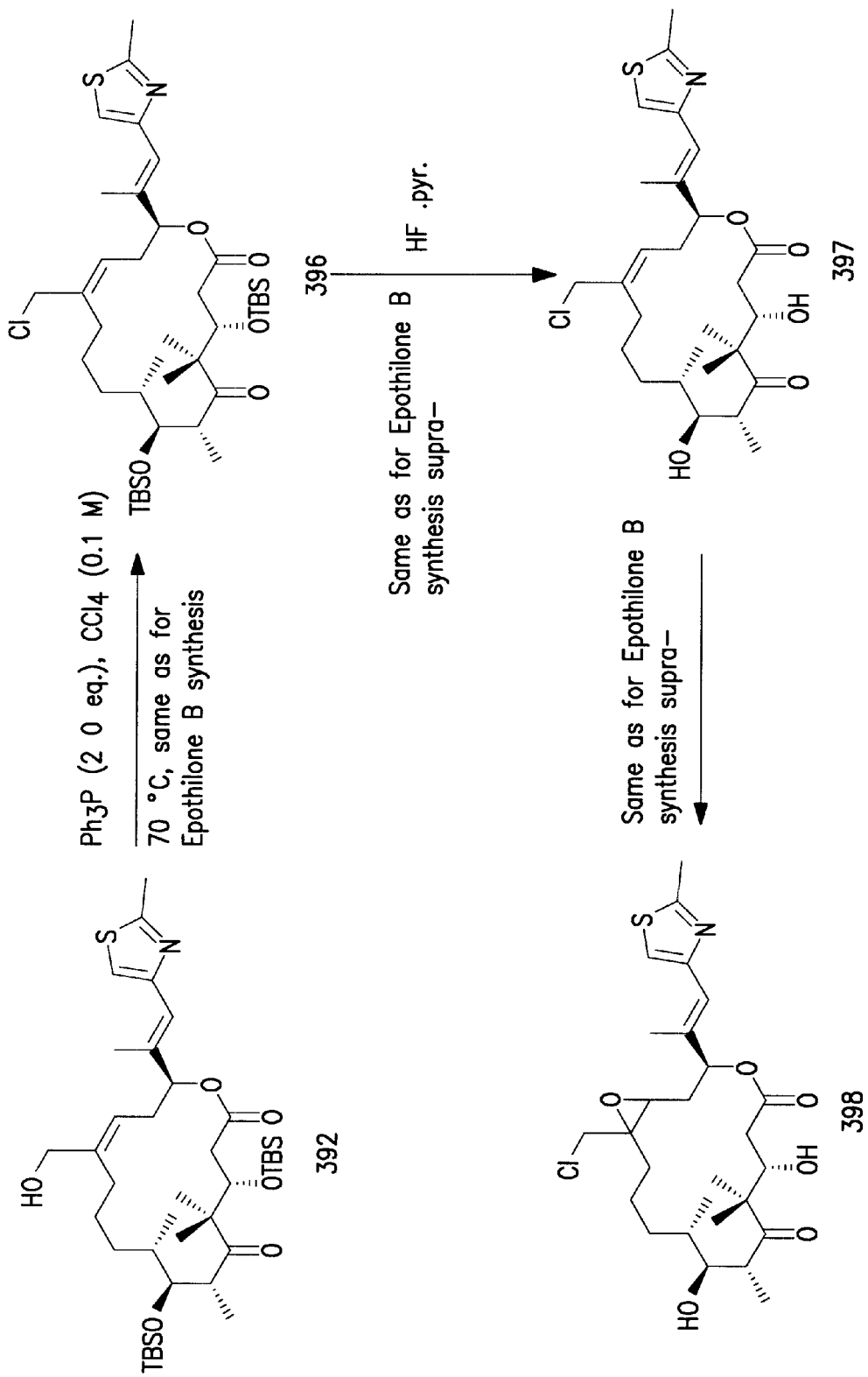

FIG. 58 illustrates synthesis of 26-halogen substituted epothilone analogs.

Figure 59:
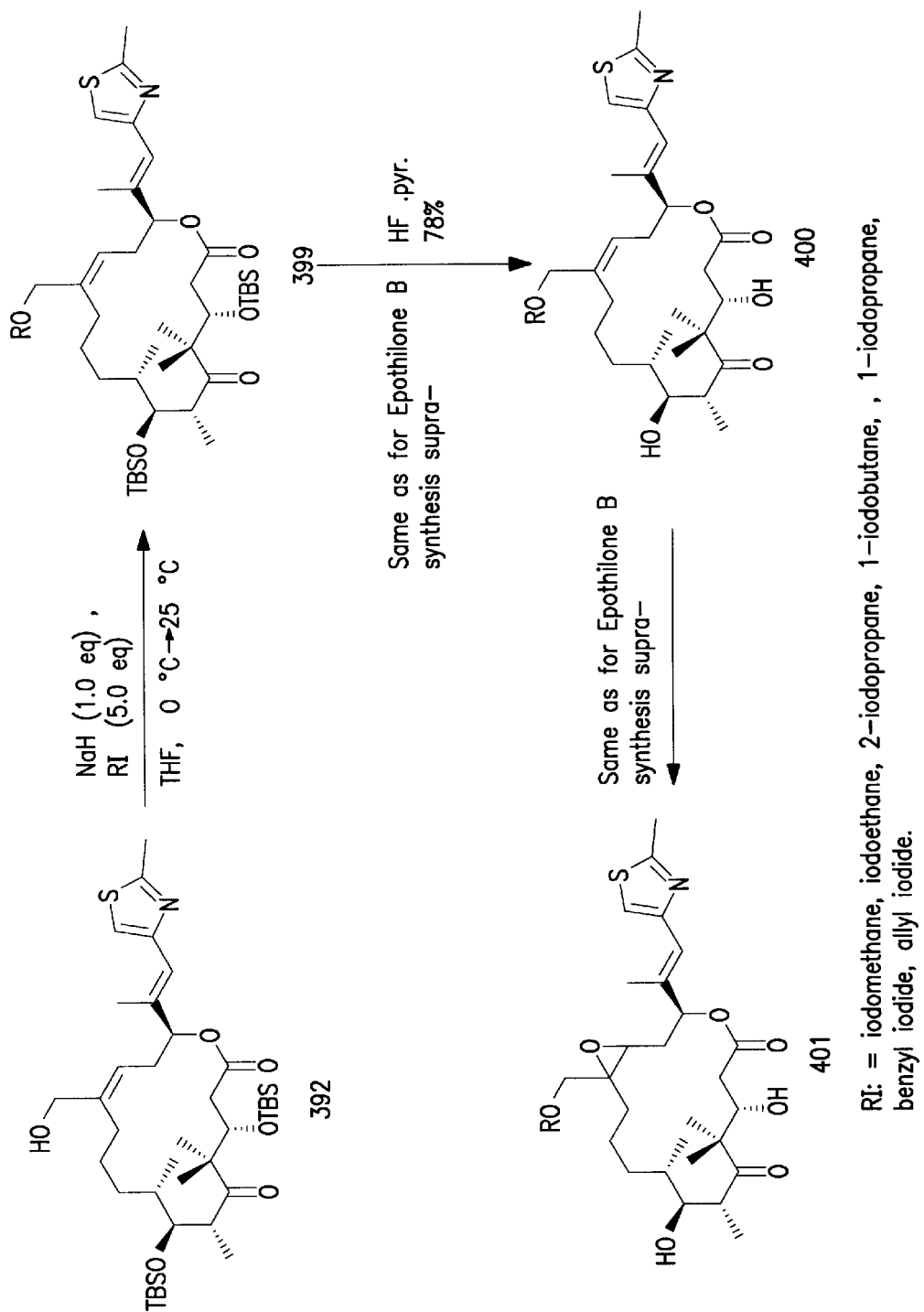

FIG. 59 illustrates synthesis of 26-alkoxy substituted epothilone analogs.

Figure 60A:
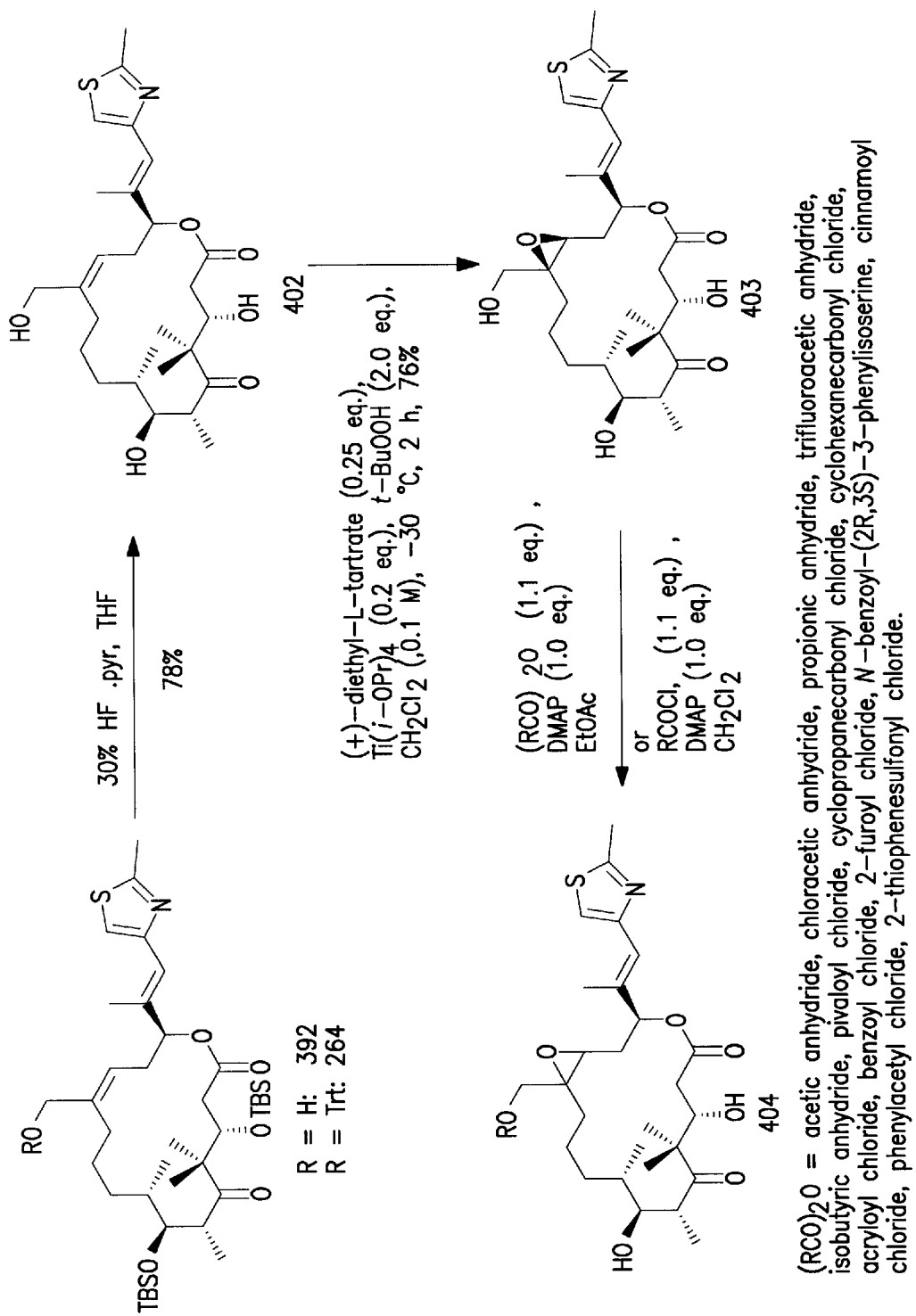
Figure 60B:
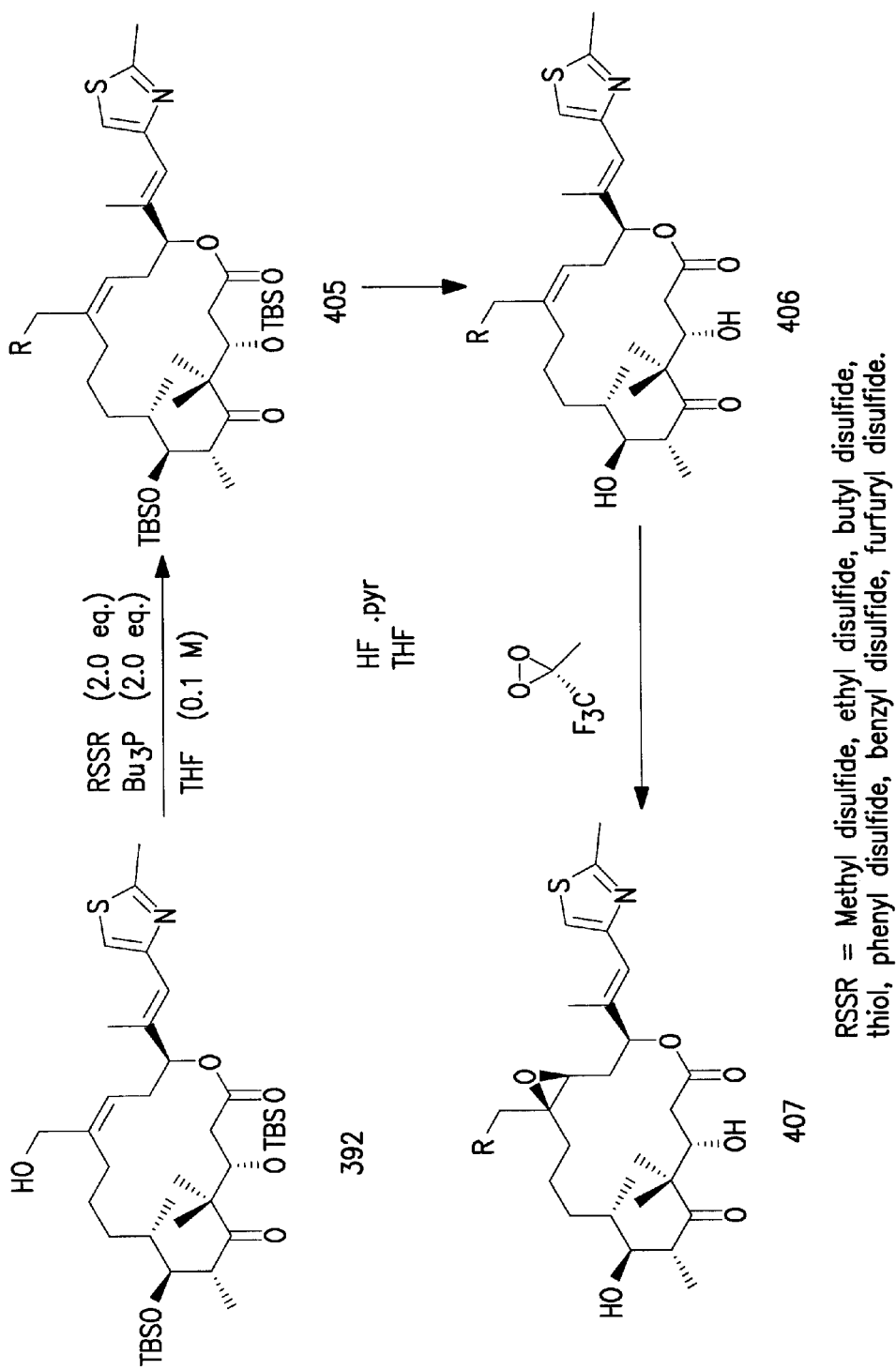

FIG. 60 illustrates synthesis of 26-ester substituted epothilone analogs (top scheme) and 26-thio ether substituted epothilone analogs (bottom scheme).

Figure 61A:
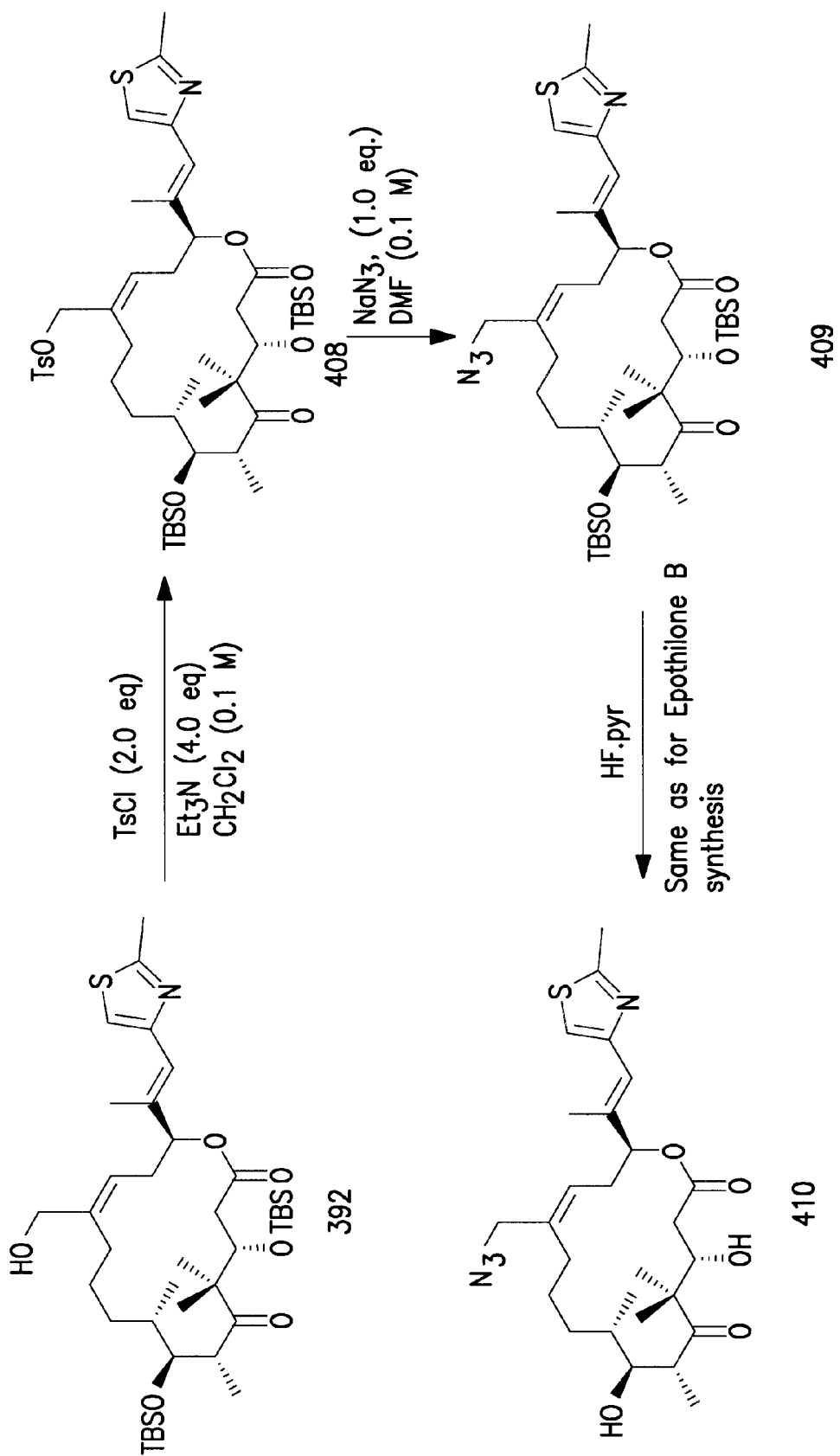

FIG. 61 illustrates synthesis of 25-amine substituted epothilone analogs.

Figure 62:
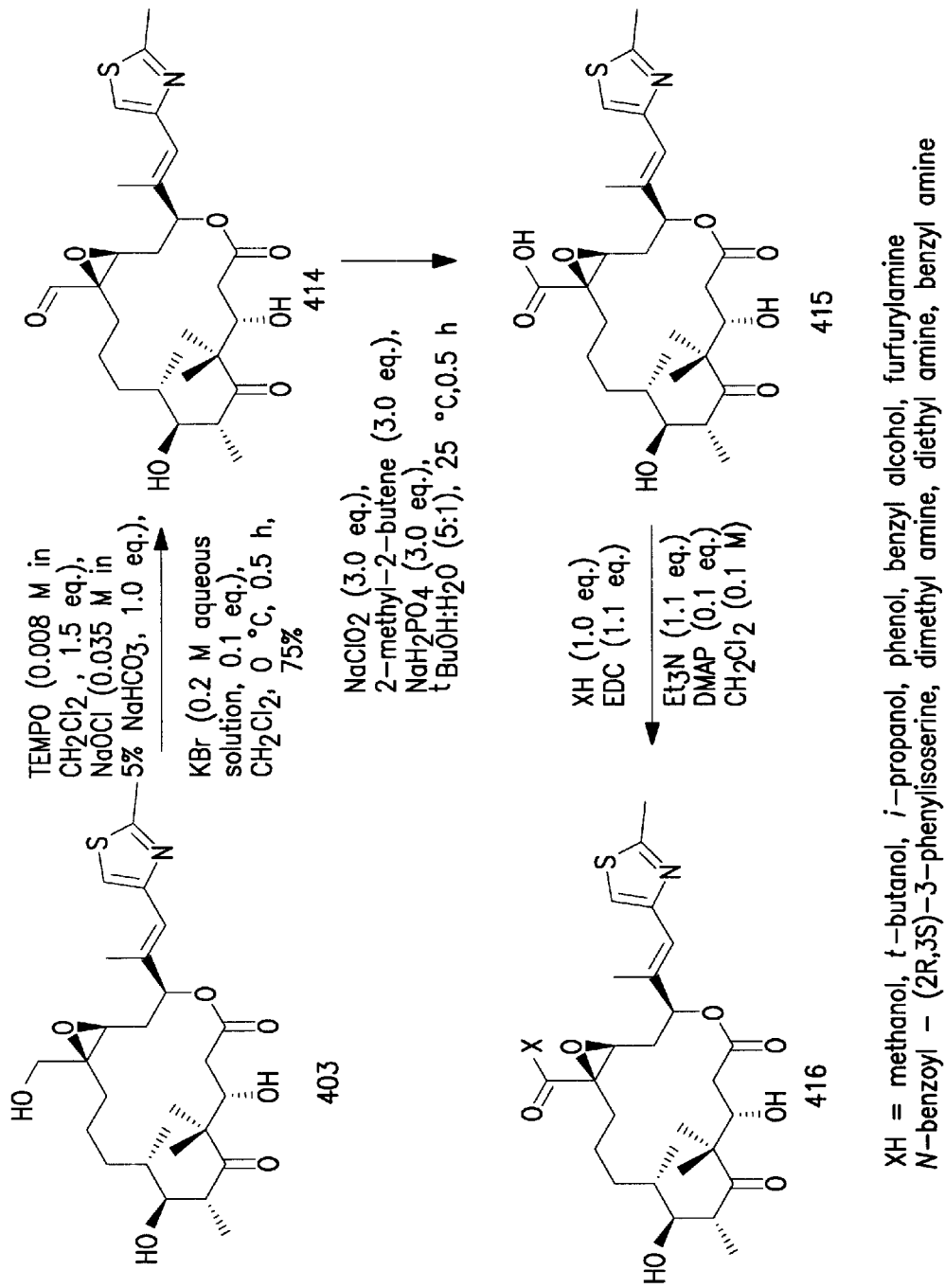

FIG. 62 illustrates synthesis of 26-aldhehyde substituted epothilone analog 414 and 26-acid and ester substituted epothilone analogs 415 and 416.

Figure 63:
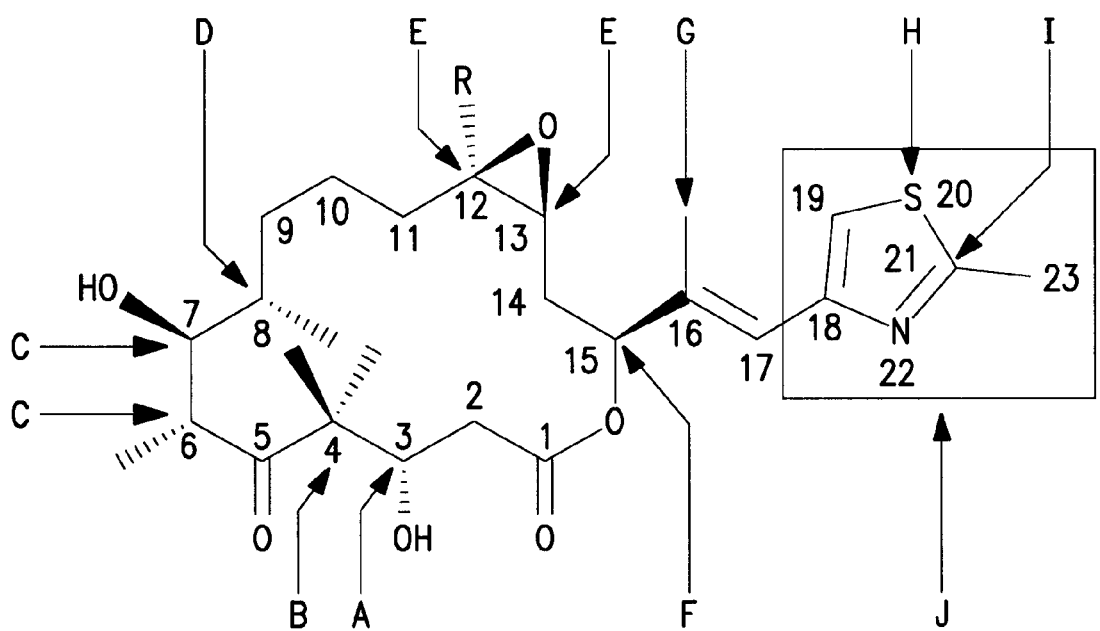

FIG. 63 illustrates epothilone structure activity relationships (tubulin binding assay): A: 3S-stereochemistry important; B: 4,4-ethano group not tolerated; C: 6R,7S-stereochemisty crucial; D: 8S-stereochemistry important, 8,8-dimethyl group not tolerated; E: epoxide not essential for tubulin polymerization activity, but may be important for cytotoxicity; epoxide stereochemistry may be important; R group important; both olefin geometries tolerated; F: 15S-stereochemistry important; G: bulkier group reduces activity; H: oxygen substitution tolerated; I: substitution important; J: heterocycle important.

Figure 64A:
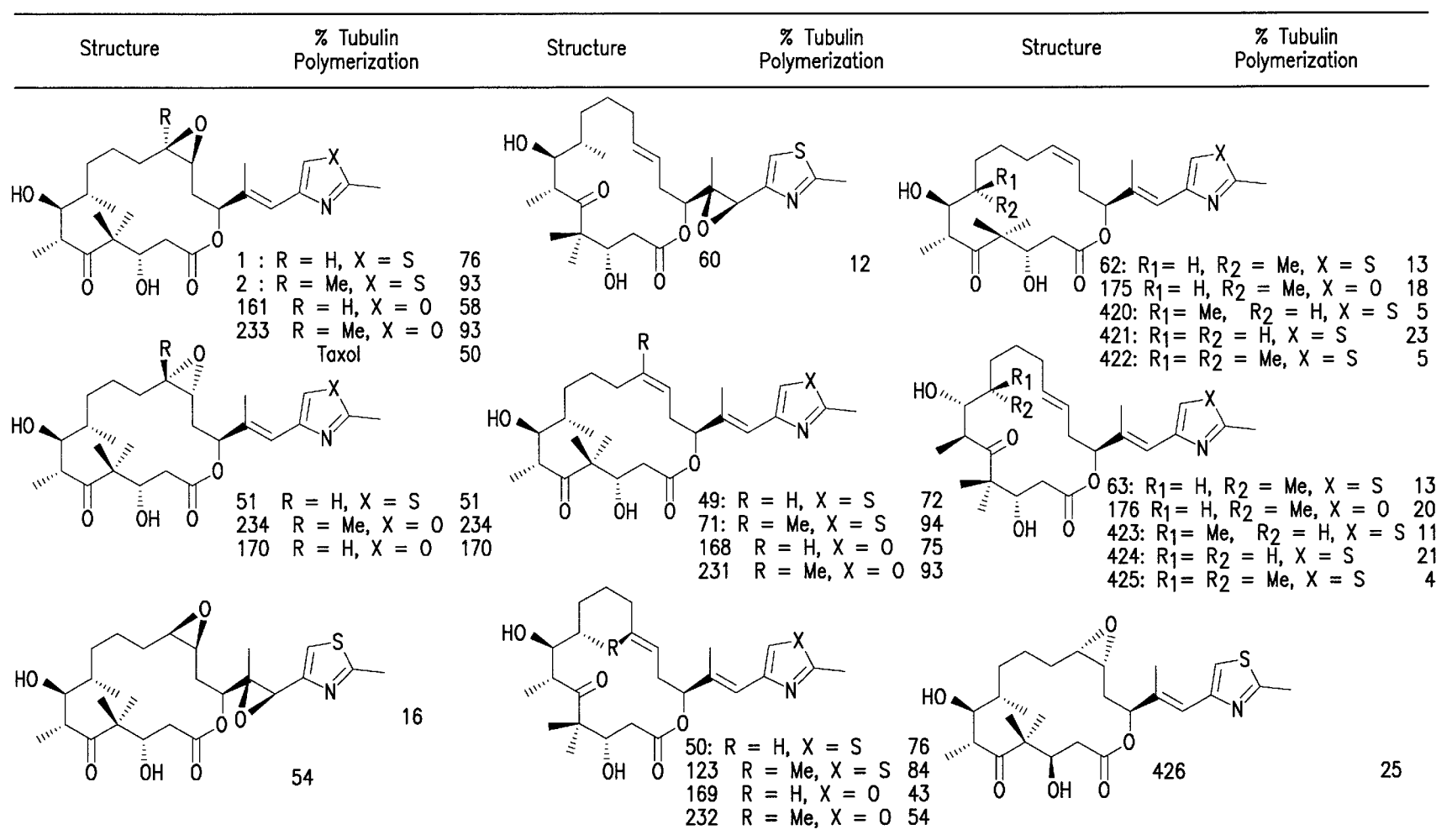
Figure 64B:
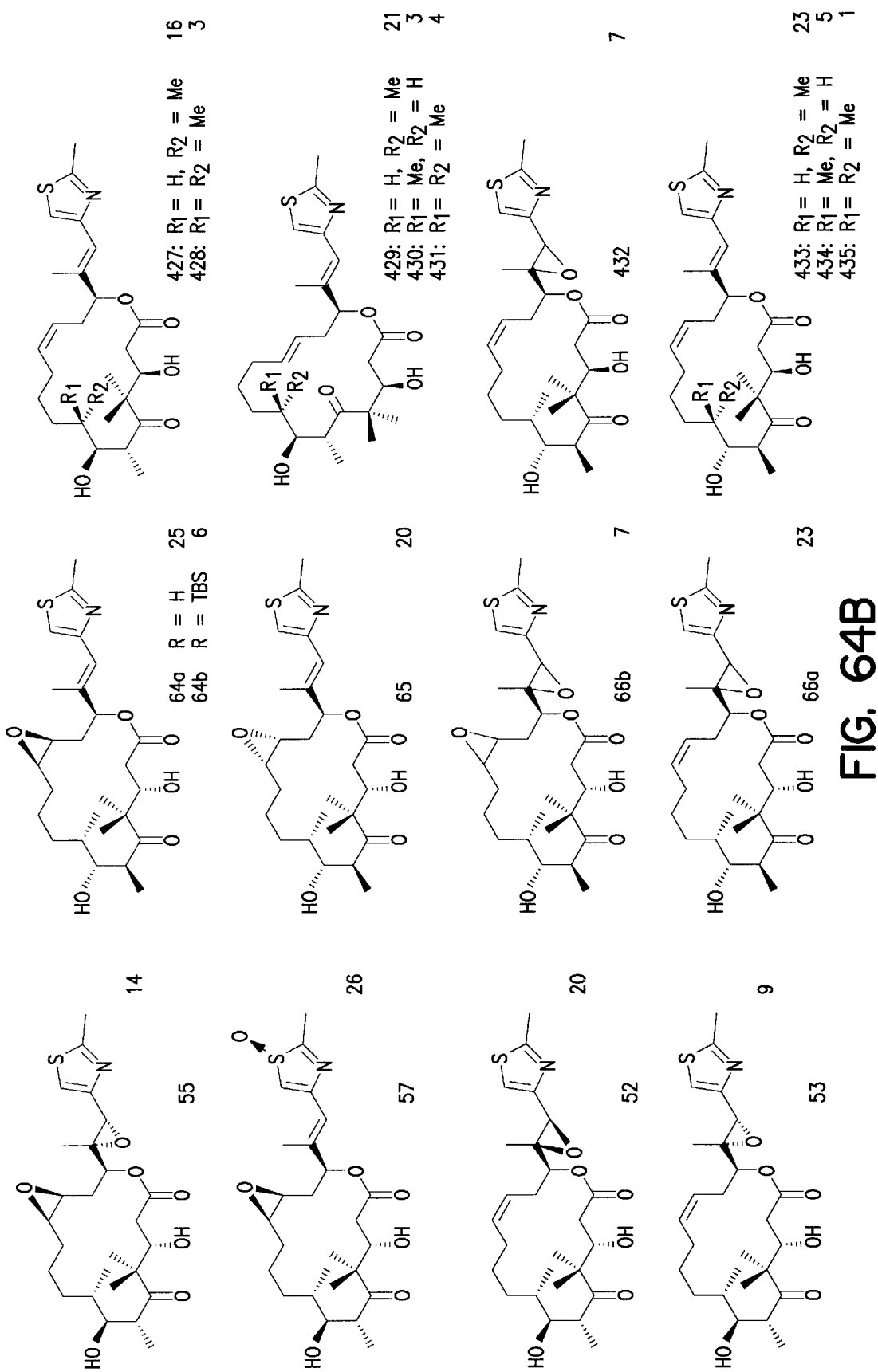
Figure 64C:
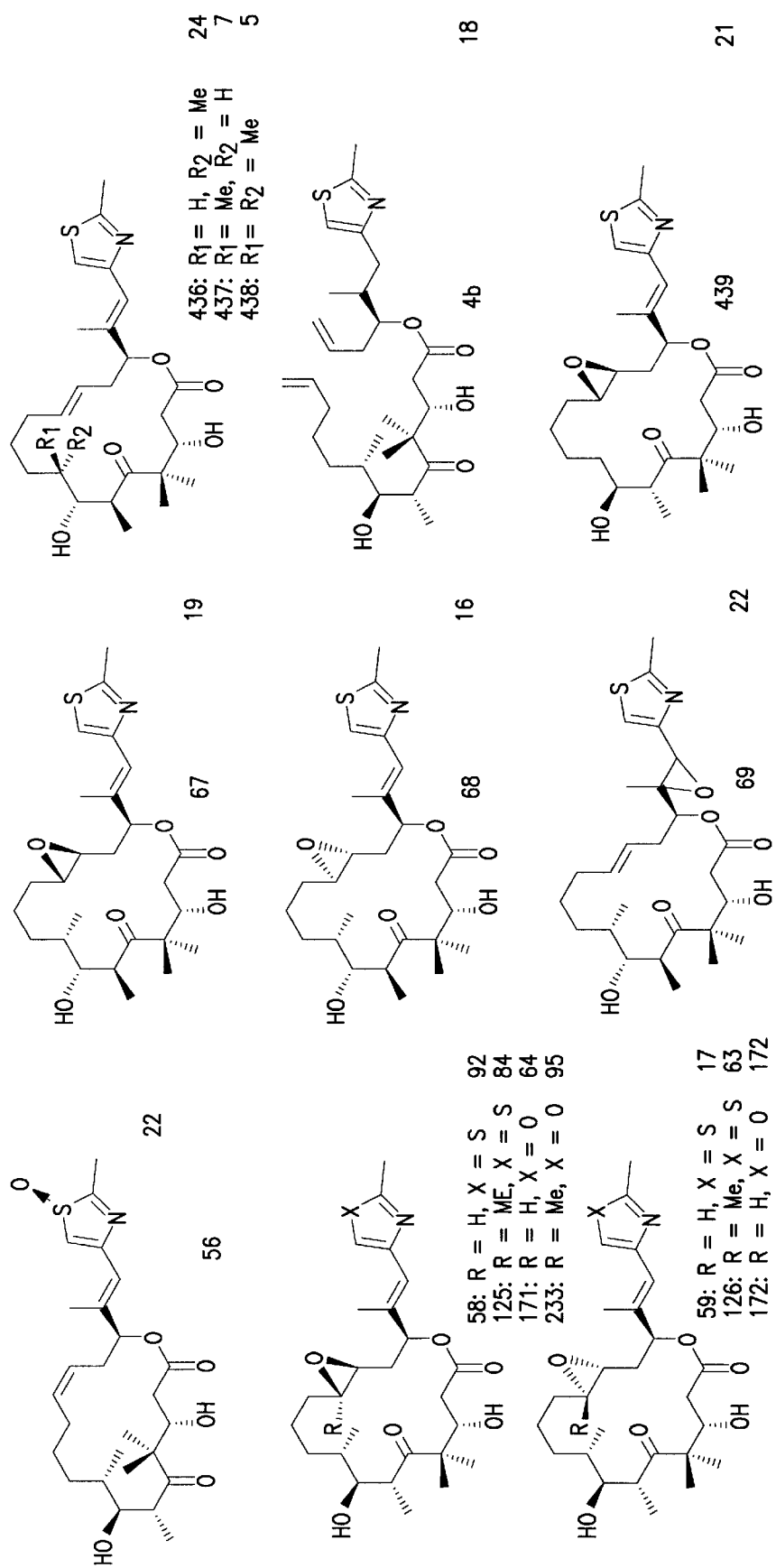

FIG. 64 shows a table of achieved compounds using both metathesis and esterification procedures with noted % tubulin polymerization accomplished via each analog.

Figure 65A:
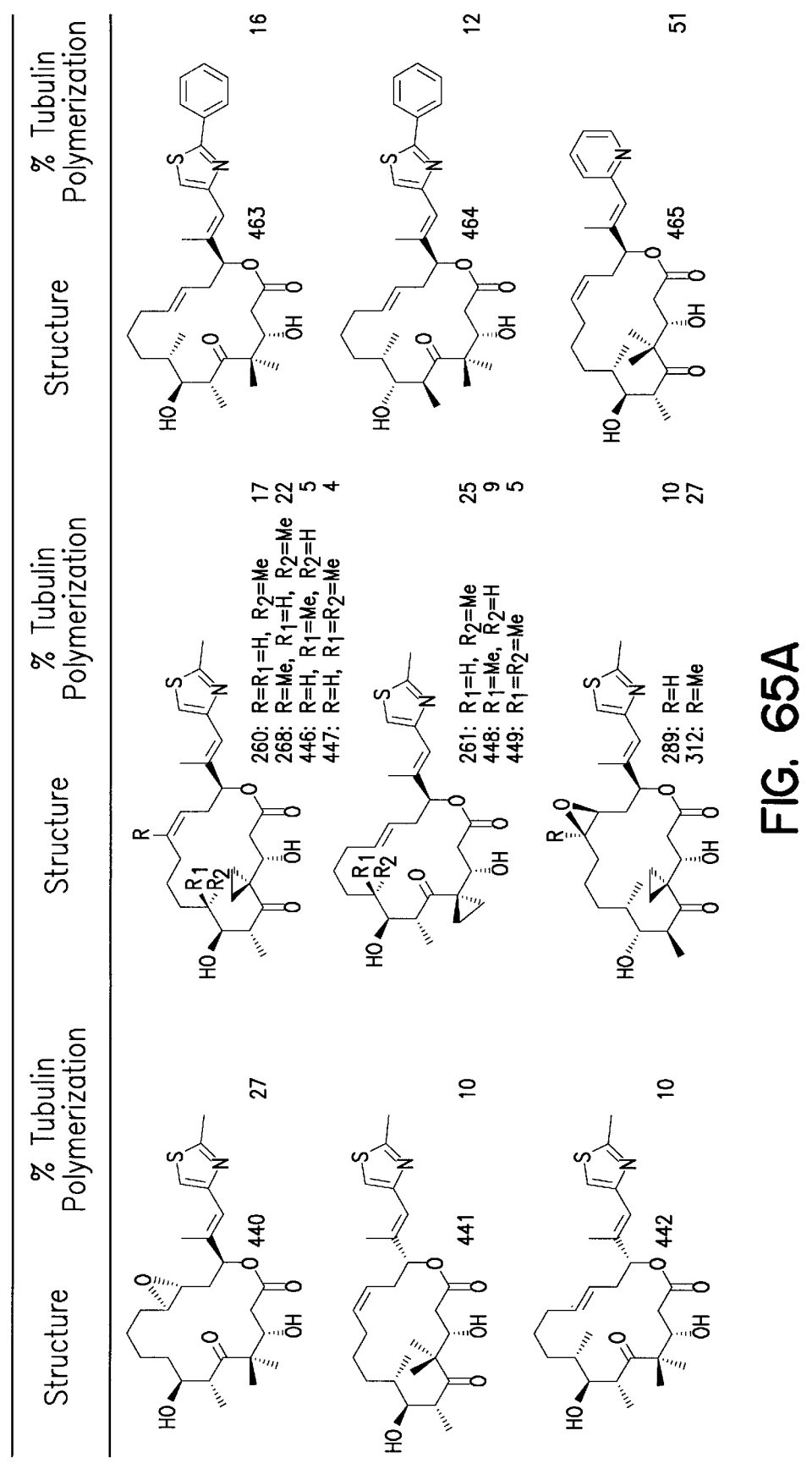
Figure 65B:
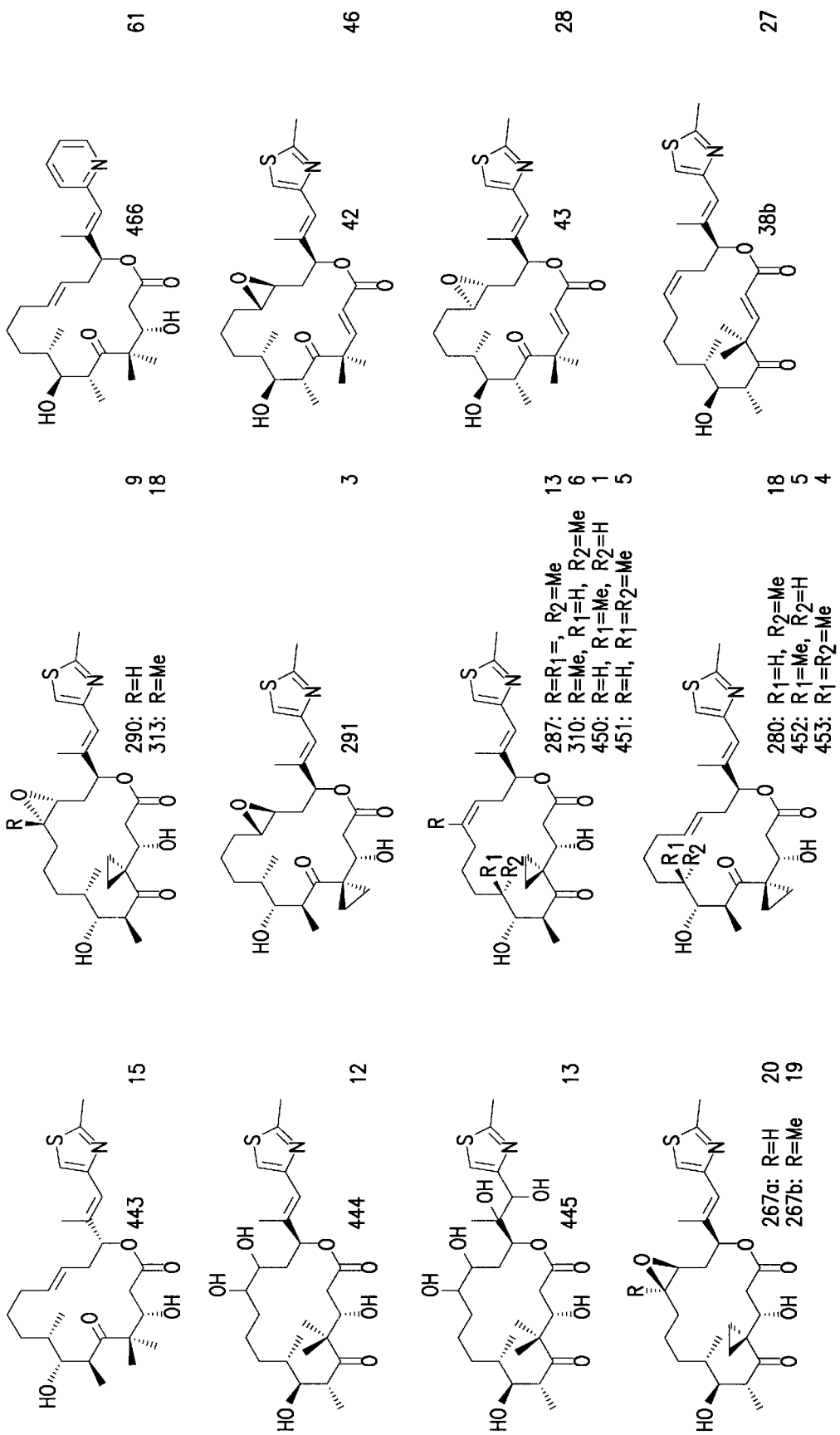
Figure 65C:
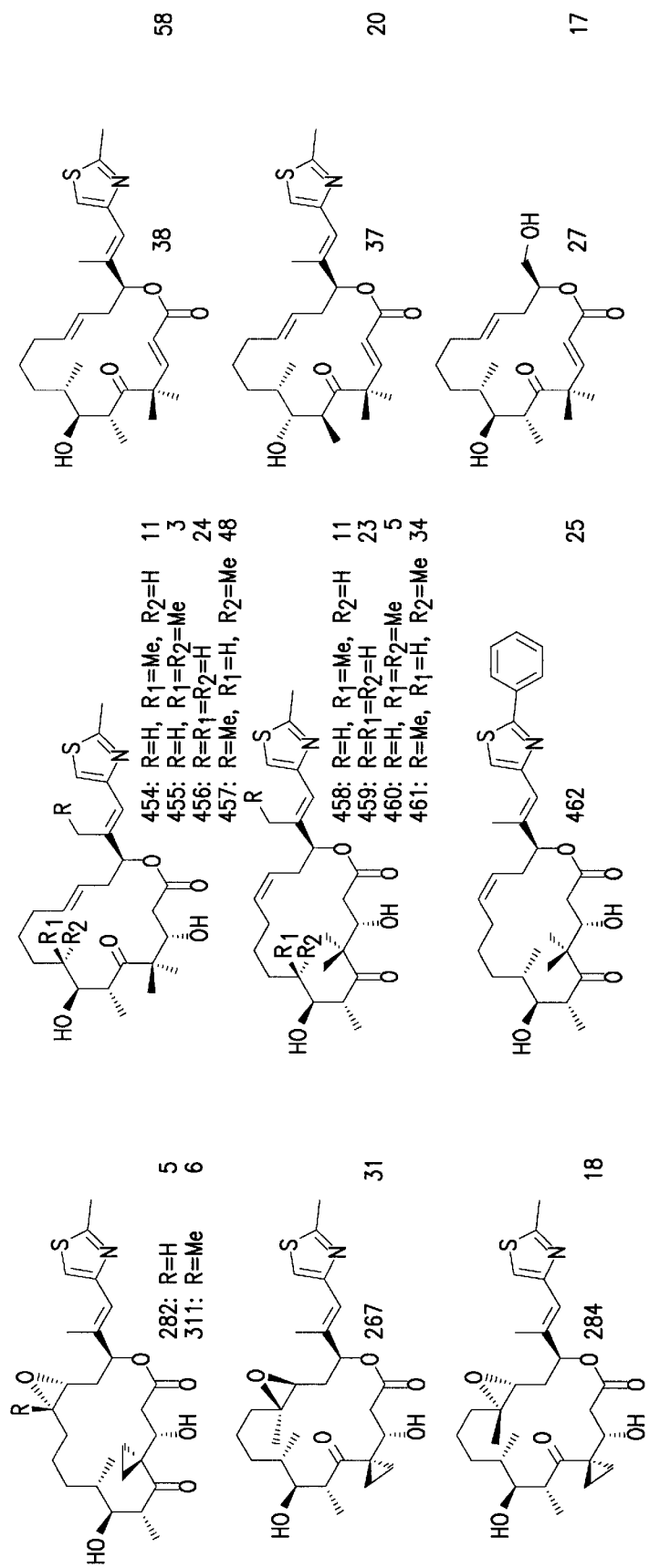

FIG. 65 shows a table of achieved compounds using both metathesis and esterification procedures with noted % tubulin polymerization accomplished via each analog.

FIG. 66 is as shown and noted as follows: [a] From FIGS. 64–65 [b] Assay performed as described vida supra; reaction mixtures contained 10 mM purified tubulin, 0.7 M monosodium glutamate, 5% DMSO and drug; incubation was for 20 min at room temperature and reaction mixtures were centrifuged at 14,000 rpm; supernatant protein concentration was measured and the $EC_{50}$ value is defined as the drug concentration resulting in a 50% reduction in supernatant protein relative to control values; each EC50 value shown is an average obtained in 2–4 independent assays, with standard deviations within 20% of the average. [c] Cell growth was evaluated by measurement of increase in cellular protein. [d] The parental ovarian cell line, derived as a clone of line A2780, was used to generate Taxol-resistant cell lines by incubating the cells with increasing concentrations of Taxol with verapamil; the cells were grown in the presence of drug for 96 h; values shown in the Figure were single determinations, except for those of Taxol, 1 and 2 (average of 6 determinations each); the values for 1 and 2 are averages of data obtained with both synthetic and natural samples (generously provided to E.H. by Merck Research Laboratories), which did not differ significantly. [e] The MCF7 cells were obtained from the National Cancer Institute drug screening program; cells were grown in the presence of drug for 48 h; each value represents an average of two determinations. [f] Relative resistance is defined as the $IC_{50}$ value obtained for the –tubulin mutant line divided by that obtained for the parental cell line.

Figure 67:
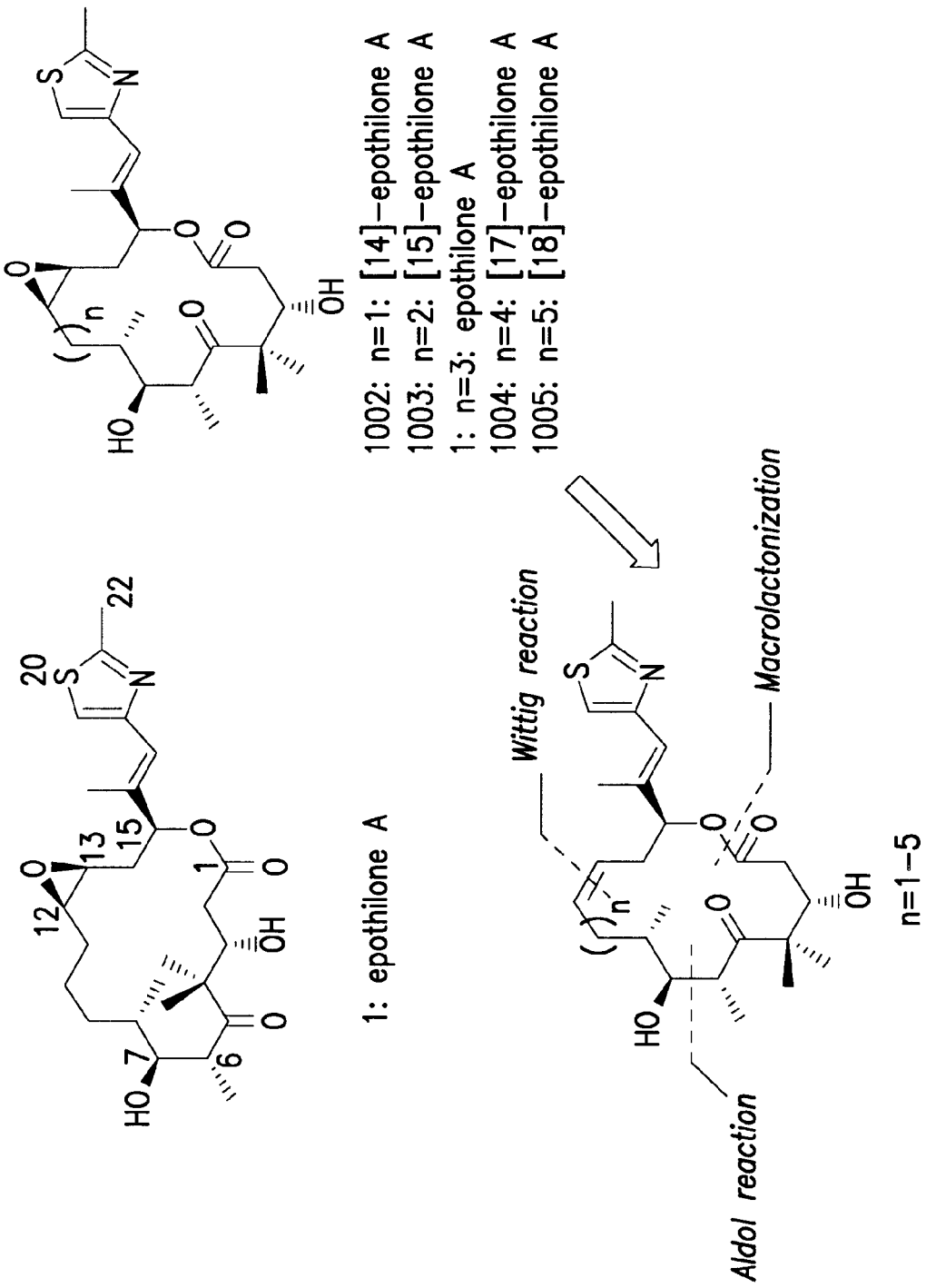

FIG. 67 illustrates the structures and numbering of [n]-epothilones A, where n=1–5.

Figure 68:
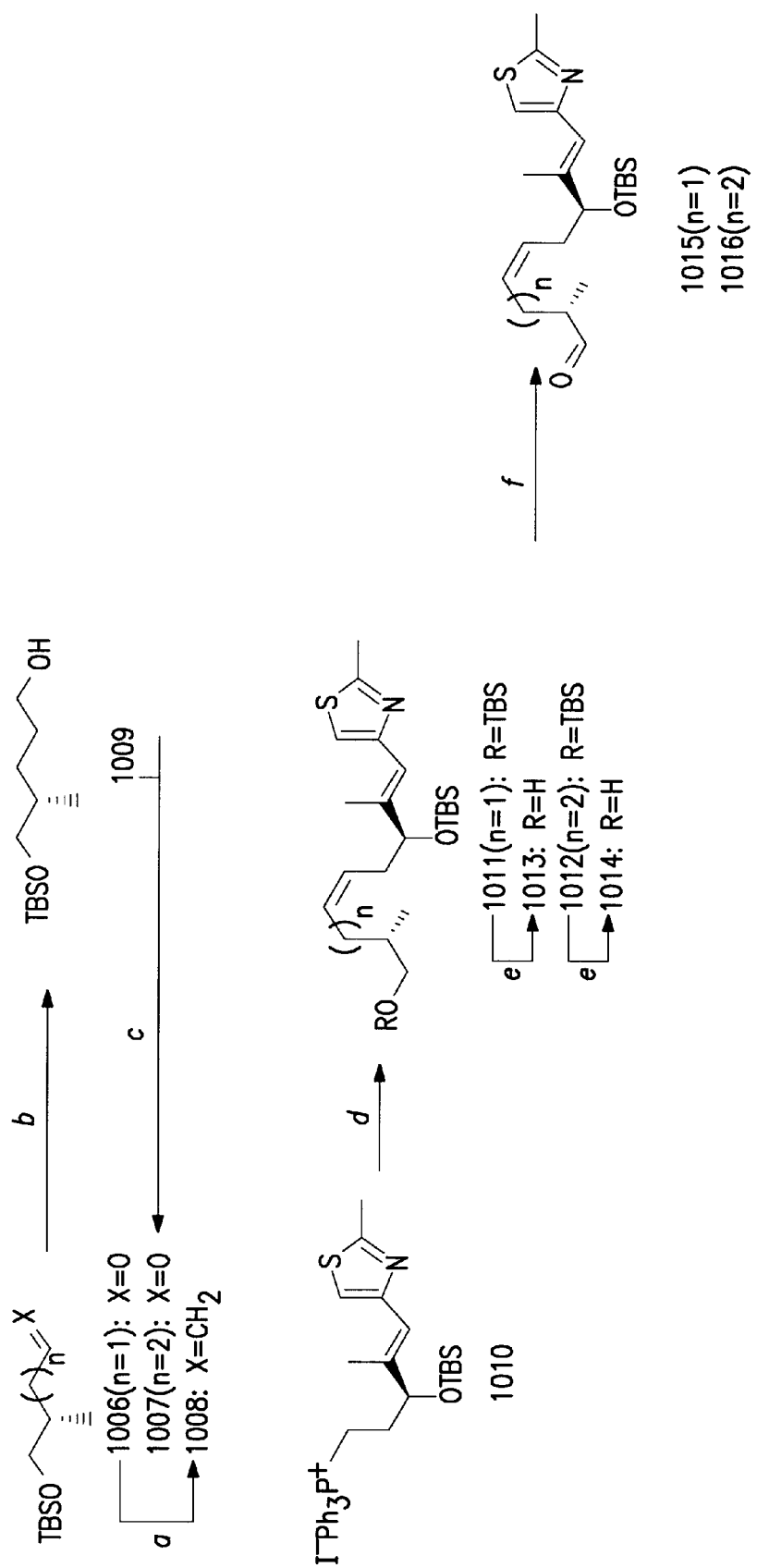

FIG. 68 illustrates the synthesis of aldehydes 1015 and 1016. Reagents and conditions: (a) 2.0 equiv. of $Ph_3P+CH_3$, Br–, 1.98 equiv of NaHMDS, THF, 0° C., 15 min; then 1.0 equiv of 1006 in THF, 0° C., 0.5 h, 95%; (b) 1.5 equiv. of 9-BBN 0.5 M, THF, 25° C., 3 h; then 6 equiv. of 3 N NaOH and 6.0 equiv of 30% $H_2O_2$, 0° C., 1 h, 85%; (c) 2.0 equiv of $(COCl)_2$, 4.0 equiv of DMSO, 6.0 equiv of $Et_3N$, $CH_2Cl_2$, –78 to 0° C., 1.5 h, 98%; (d) 1.2 equiv of 1010, 1.2 equiv of NaHMDS, THF, 0° C., 15 min; then add 1.0 equiv of aldehyde 1006 or 1007, 0° C., 15 min, 77% (Z:E ca 9:1) for 1011 or 83% (Z:E ca 9:1) for 1012; (e) 1.0 equiv of CSA added portionwise over 1 h, $CH_2Cl_2$:MeOH (1:1), 0 to 25° C., 0.5 h, 81% for 1013 and 61% for 1014 (f) 2.0 equiv of $SO_3$.pyr., 10.0 equiv of DMSO, 5.0 equiv of $Et_3N$, $CH_2Cl_2$, 25° C., 0.5 h, 81% for 1015 and 84% for 1016. NaHMDS= sodium bis(trimethylsilyl)amide; 9-BBN=9-borabicyclo [3.3.1]nonane; DMSO=dimethylsulfoxide; CSA 10-camphorsulfonic acid; TBS=tertbutyldimethylsilyl.

Figure 69:
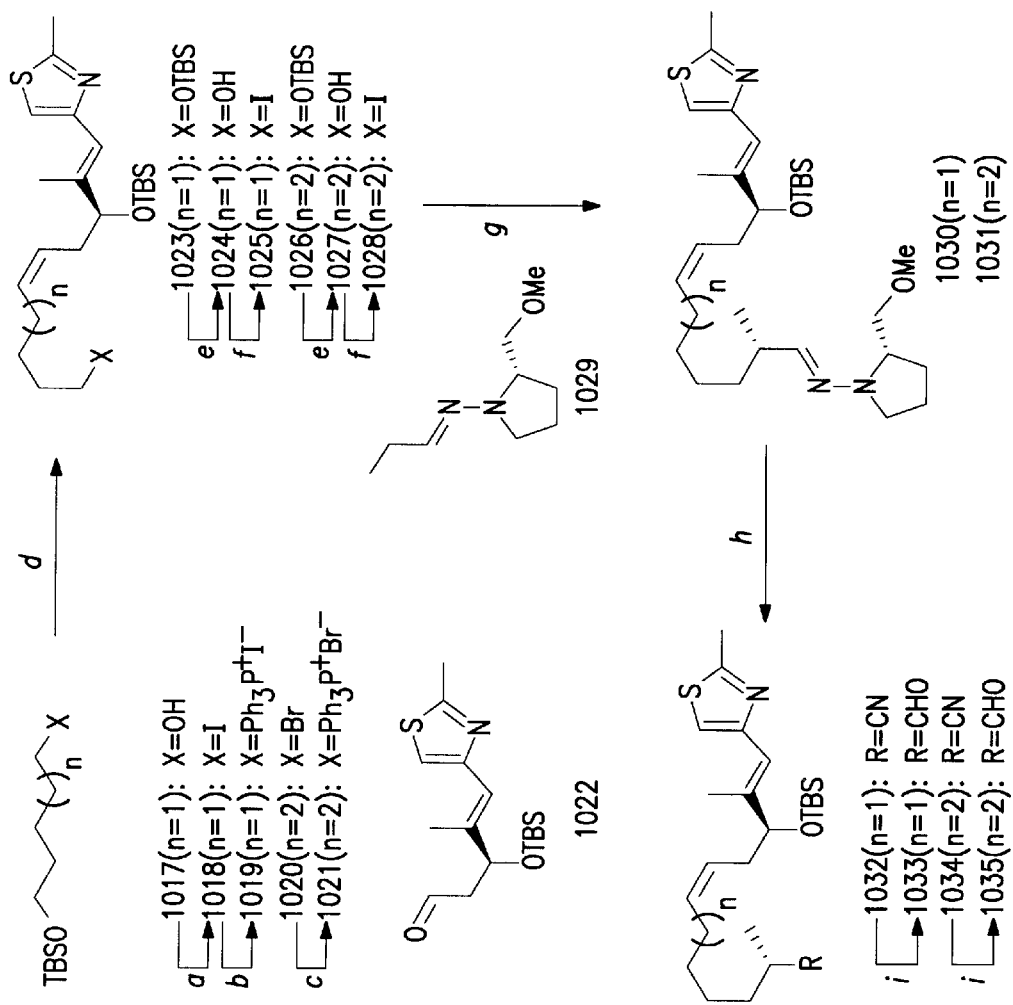

FIG. 69 illustrates the synthesis of aldehydes 1033 and 1035. Reagents and conditions: (a) 1.5 equiv of $I_2$, 3.0 equiv of imidazole, 1.5 equiv of $Ph_3P$, $Et_2O$:MeCN (3:1), 0° C., 0.5 h, 95%; (b) 1.1 equiv of $Ph_3P$, neat, 100° C., 2 h, 97%; (c) 1.5 equiv of $Ph_3P$, neat, 100° C., 7 h, 99%; (d) 1.2 equiv of 1019 or 1021, 1.2 equiv of NaHMDS, THF, 0° C., 15 min; then add 1.0 equiv of aldehyde 1022, 0° C., 15 min, 85% (Z:E ca 9:1) for 1023, 79% (Z:E ca 9:1) for 1026; (e) 1.0 equiv of CSA added portionwise over 1 h, $CH_2Cl_2$:MeOH (1:1), 0 TO 25° C., 3 h, 99% for 1024, 95% for 1027; (f) 1.5 equiv of $I_2$, 3.0 equiv of imidazole, 1.5 equiv of $Ph_3P$, $Et_2O$:MeCN (3:1), 0° C., 0.5 h, 84% for 1025. 98% for 1028; (g) 1.5 equiv of 1029, 1.5 equiv of LDA, THF, 0° C., 16 h; then 1.0 equiv of 1025 or 1028 in THF, –100 TO –20° C., 10 h, 60% for 1030, or 82% for 1031; (h) 2.5 equiv of monoperoxyphthalic acid, magnesium salt (MMPP), MeOH:phosphate buffer pH7 (1:1), 0° C., 1 h, 99% for 32, 96% for 1034; (i) 2.0 equiv DIBAL, toluene, –78° C., 1 h, 90% for 1033, 81% for 1035. LDA=lithium diisopropylamide; DIBAL=diisotutylaluminum hydride.

Figure 70A:
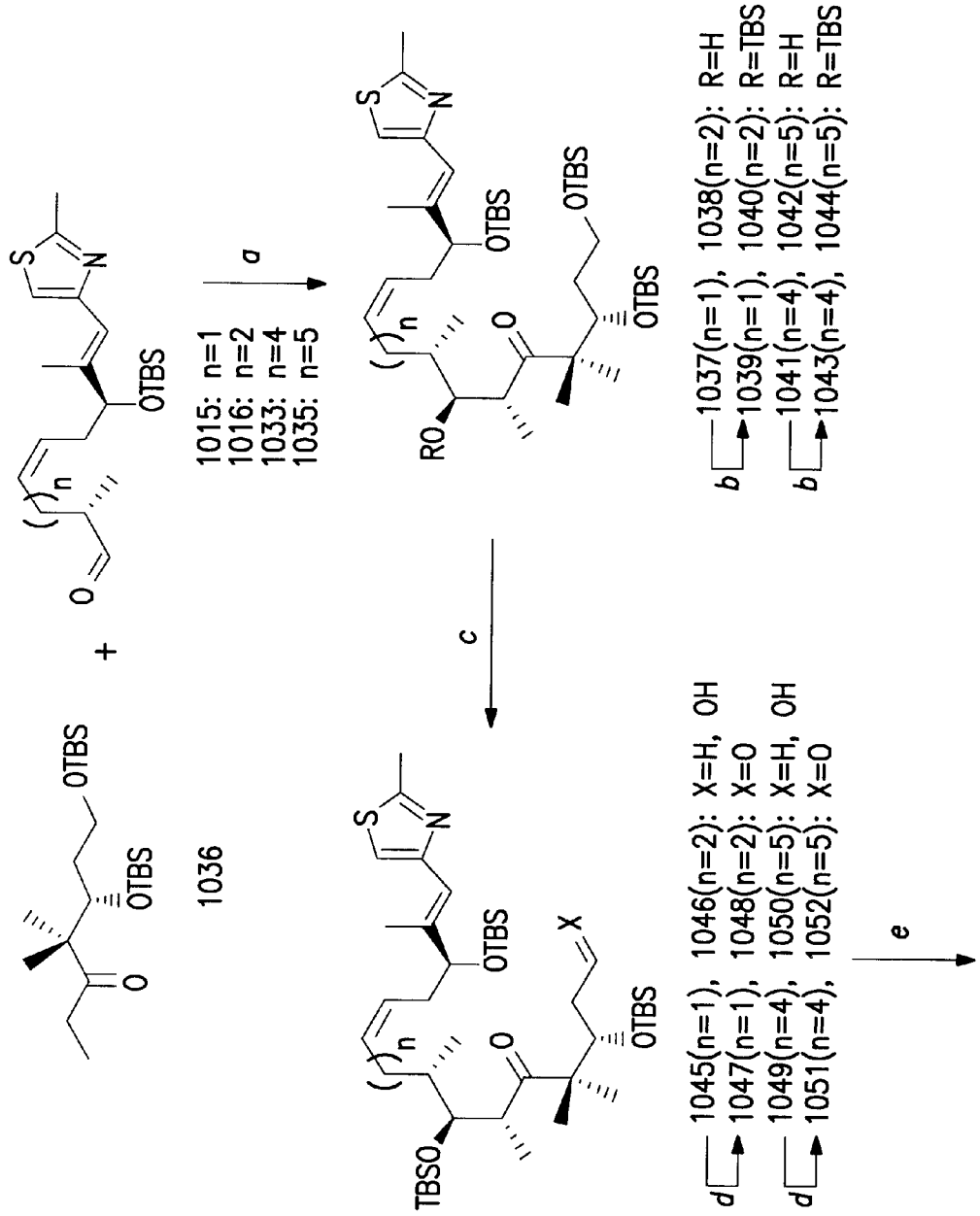
Figure 70B:
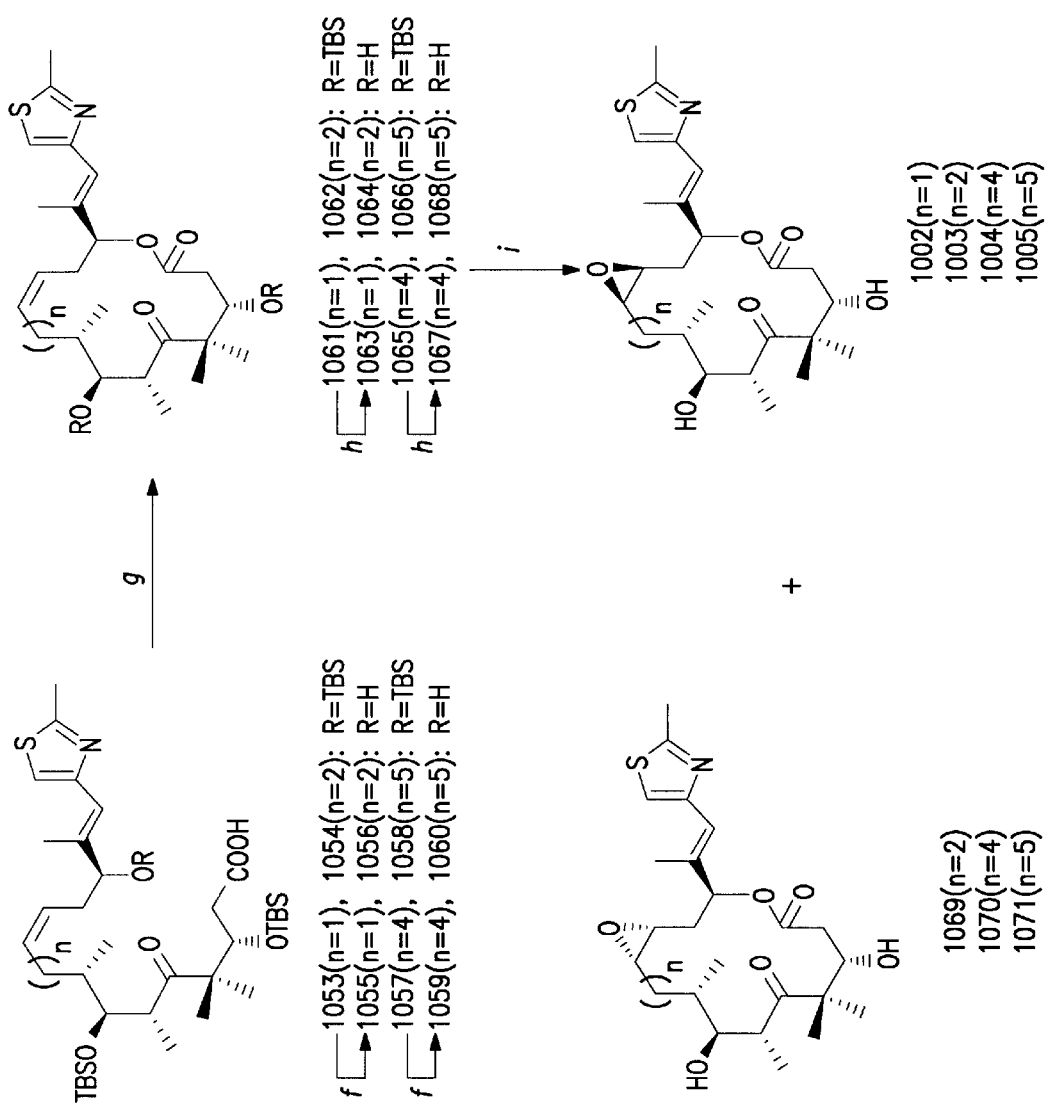

FIG. 70 illustrates the synthesis of epothilone A analogs 1002–1005. Reagents and conditions: (a) 1.2 equiv of LDA, THF, 0° C., 15 min; then 1.2 equiv of 1036 in THF, –78° C., 1 h; then 1.0 equiv of aldehyde (1015, 1016, 1033, 1035) in THF at –78° C., 71% for 1037 (single diastereoisomer), 72% for 1038 and its 6S,7R-diastereoisomer (ca. 4:1 ratio), 77% for 1041 and its 6S,7R-diastereoisomer (ca. 6:1 ratio), 60% for 1042 and its 6S,7R-diastereoisomer (ca. 5:1 ratio); (b) 1.5 equiv of TBSOTf, 2.0 equiv of 2,6-lutidine, methylene chloride, 0° C., 1 h, 94% for 1039, 93% for 1040, 85% for 1043, 95% for 1044; (c) 1.0 equiv of CSA added portionwise over 1 h, methylene chloride:MeOH (1:1), 0° C., 3 h, 77% for 1045, 82% for 1046, 91% for 1049, 83% for 1050; (d) 2.0 equiv of $(COCl)_2$, 4.0 equiv of DMSO, 6.0 equiv of $Et_3N$, $CH_2Cl_2$, –78 to 0° C., 1.5 h, 93% for 1047, 85% for 1048, 99% for 1051, 95% for 1052; (e) 5.0 equiv of $NaClO_2$, 10.0 equiv of 2-methyl-2-butene, 2.5 equiv of $NaH_2PO_4$, tBuOH:$H_2O$ (5:1), 0° C., 1 h, 99% for 1053, 95% for 1054, 99% for 1057, 98% for 1058; (f) 6.0 equiv of TBAF, THF, 25° C., 10 h, 92% for 1055, 77% for 1056, 85% for 1059, 85% for 1060; (g) 2.5 equiv of 2,4,6-trichlorobenzoylchloride, 5.0 equiv of $Et_3N$, THF, 0 to 25° C., 1 h; then slow addition (1 mL/h) to a solution of 2.0 equiv of 4-DMAP in toluene (0.005 M based on hydroxy acid), 70° C., 0.5–8 h, 70% for 1061, 82% for 1062, 73% for 1065, 75% for 1066; (h) 20% HF.pyr (by volume) in THF, 25° C., 24 h, 82% for 1063, 91% for 1064, 86% for 1067, 71% for 1068; (i) methyl(trifluoromethyl)dioxirane, MeCN, 0° C., 54% for 1002 (single diastereoisomer), 35% of 1003 and 35% of 1069 (ca. 1:1 ratio of diastereoisomers), 97% for 1004 and 1070 (ca. 6:1 ratio of diastereoisomers), 53% of 1005 and 26% of 1071 (ca. 2:1 ratio of diastereoisomers). Tf=triflate; TBAF=tetra-n-butylammonium fluoride; 4-DMAP=4-dimethylaminopyridine.

FIG. 71 shows the tublin binding (% tubulin polymerization in the filtration-colorimetric tubulin polymerization assay) and cytotxicity properties (against the parental 1A9, and the Taxol-resistant cell lines PTX10 and PTX22) of a selected number of the synthesized epothilones.

Figure 72:
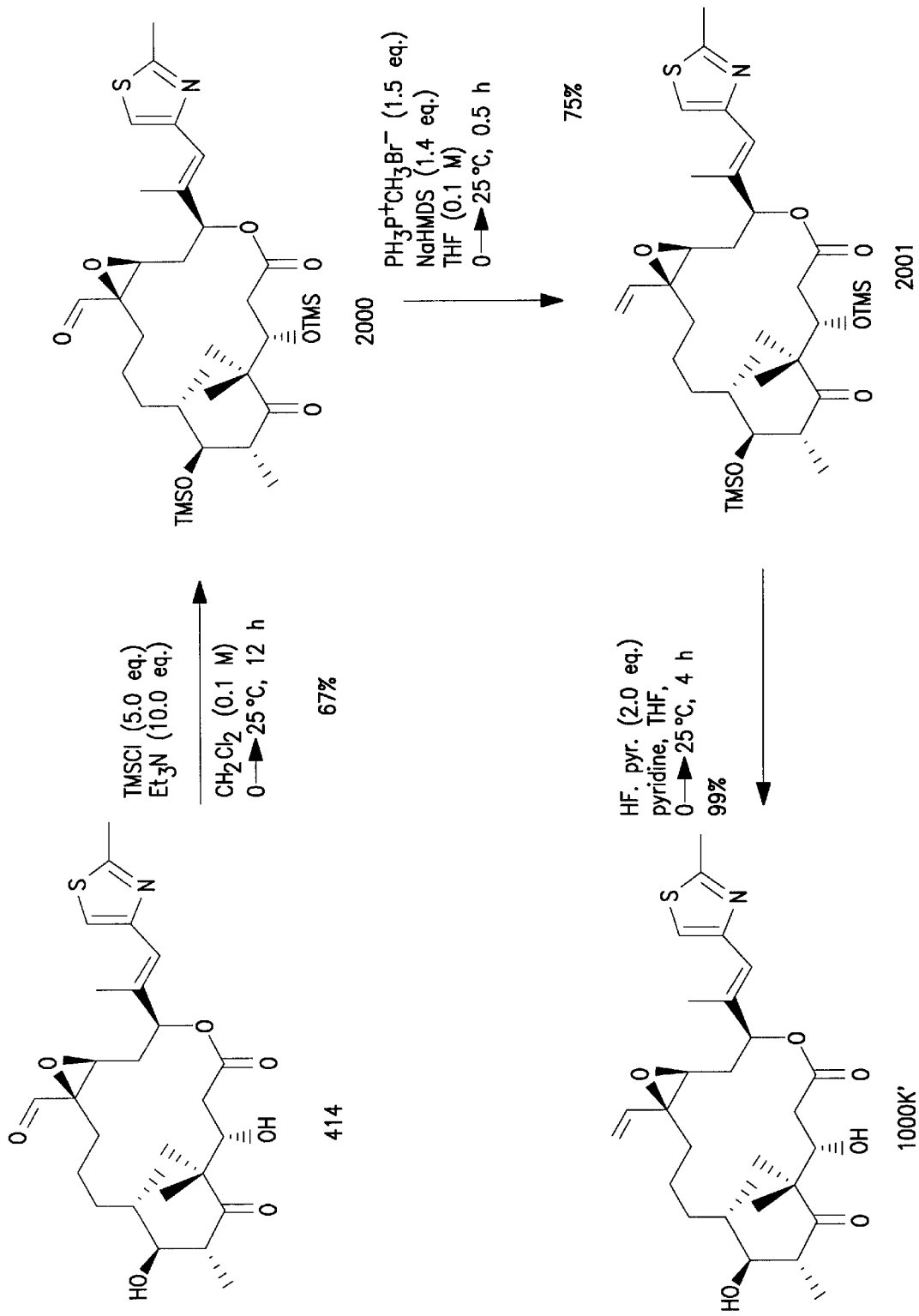

FIG. 72 illustrates the synthesis of $C_{12}$ substituted analog 1000k'.

Figure 73A:
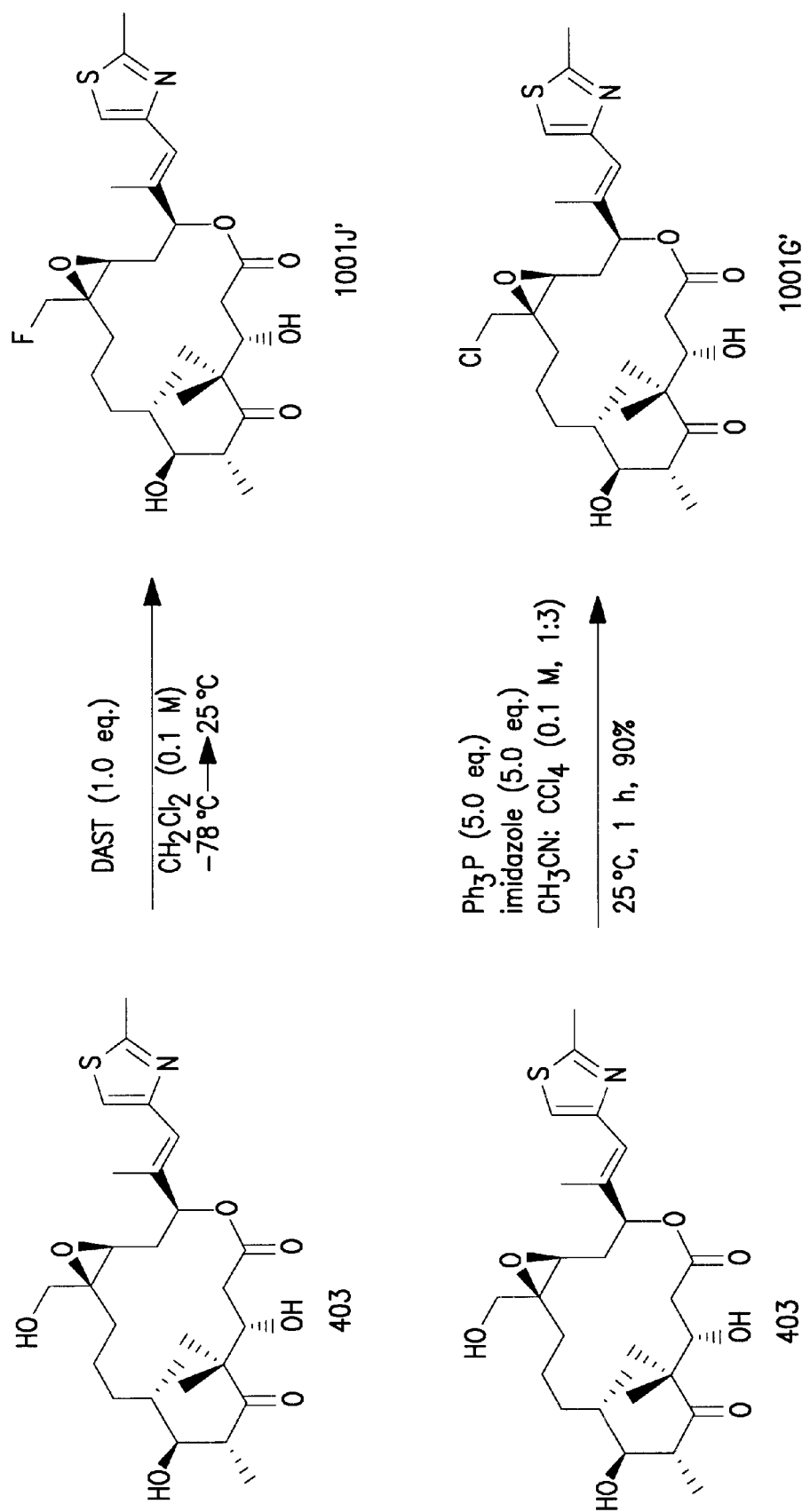
Figure 73B:
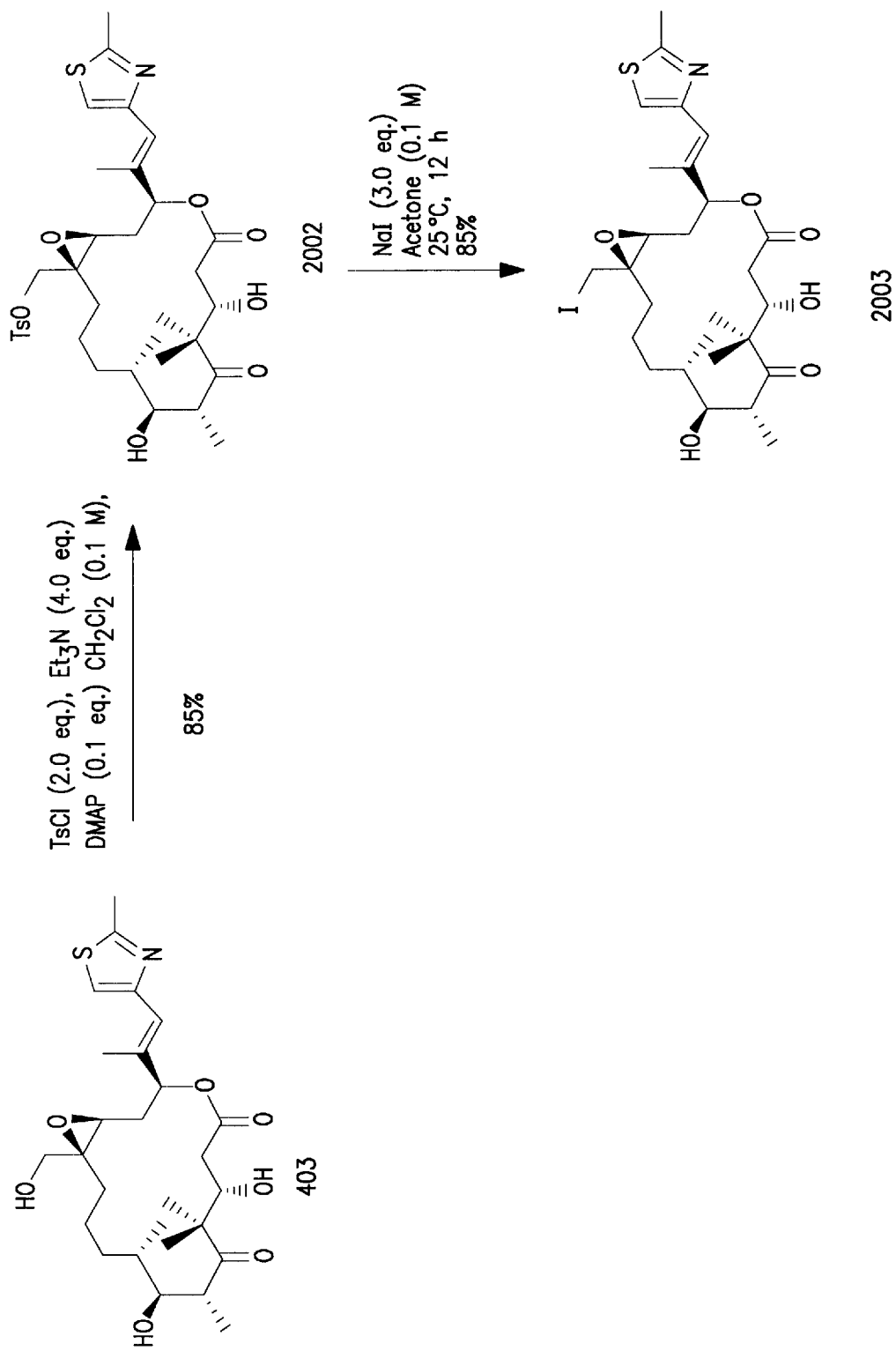

FIG. 73 illustrates the synthesis of $C_{12}$ substituted analog 2003.

Figure 74:
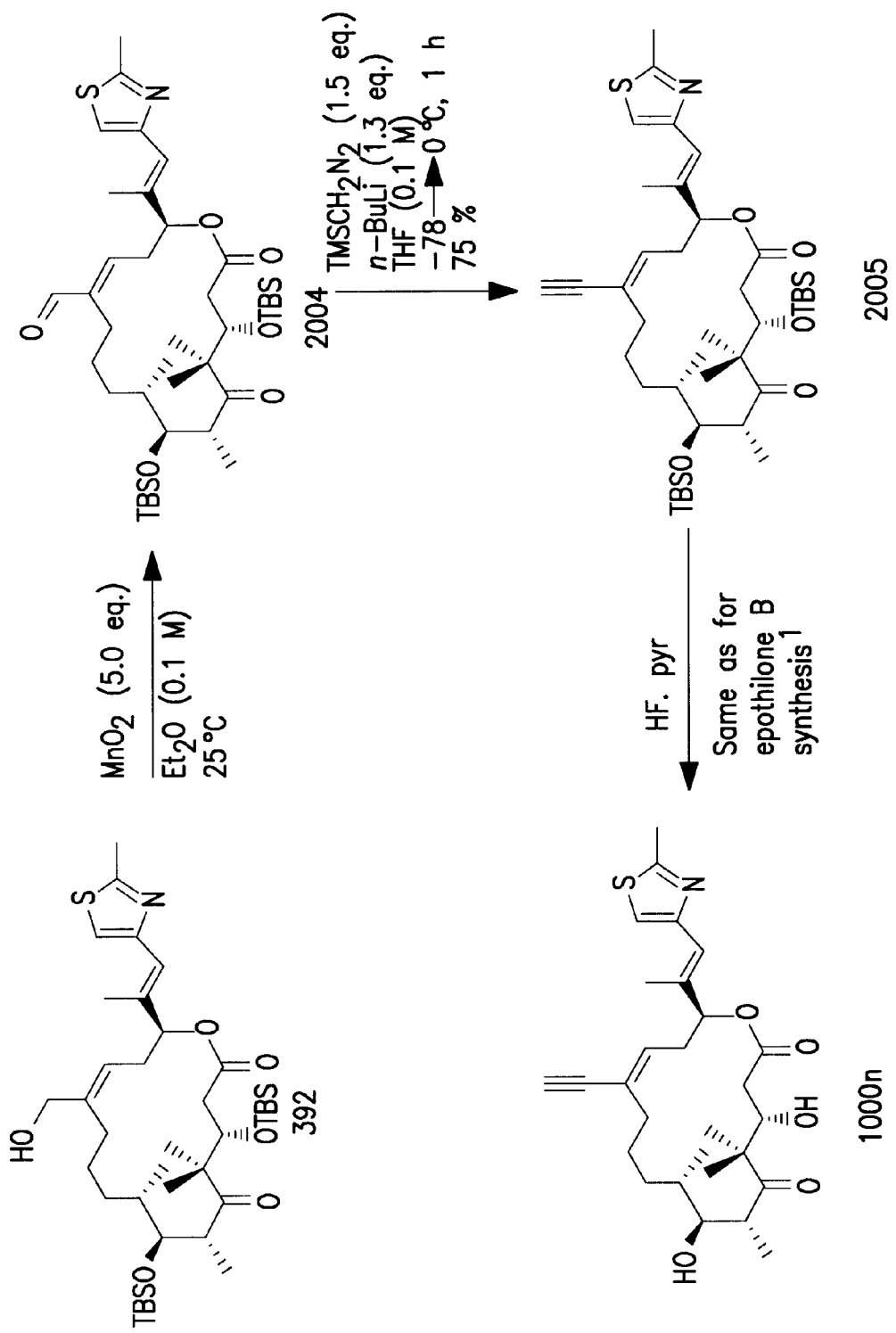

FIG. 74 illustrates the synthesis of $C_{12}$ substituted analog 1000n.

Figure 75:
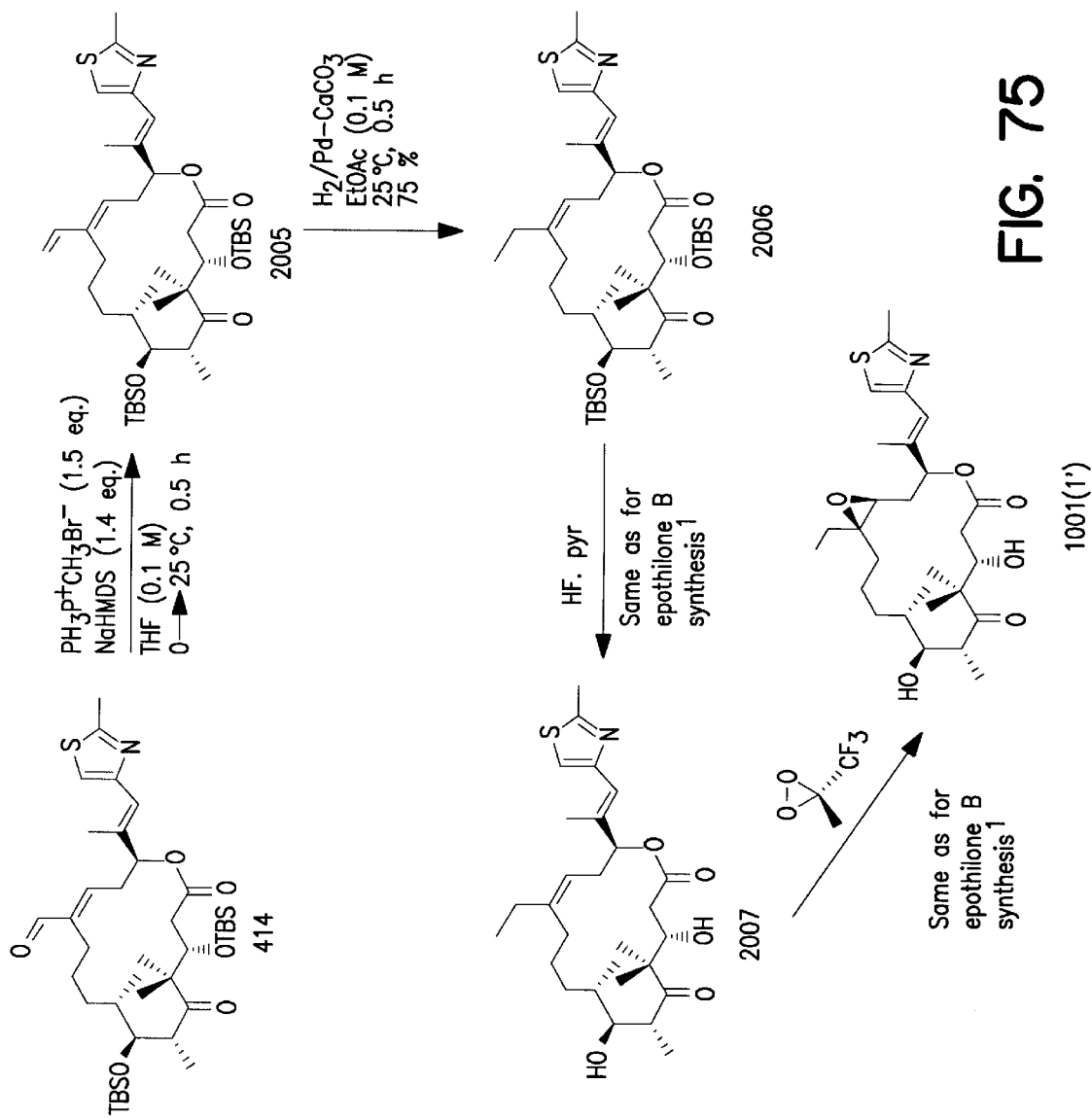

FIG. 75 illustrates the synthesis of $C_{12}$ substituted analog 1001(1'); figure note 1: see FIGS. 1–25.

Figure 76A:
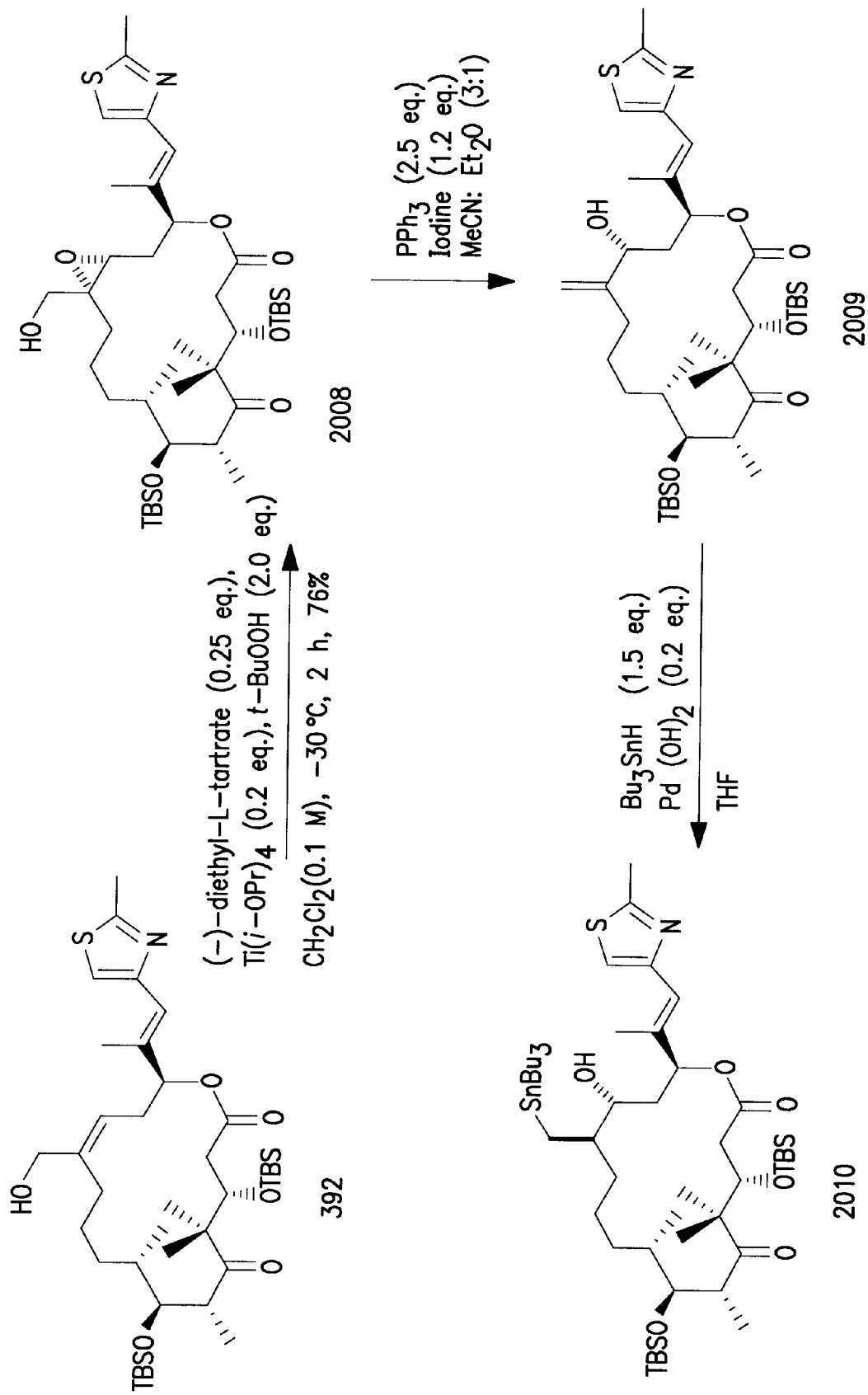
Figure 76B:
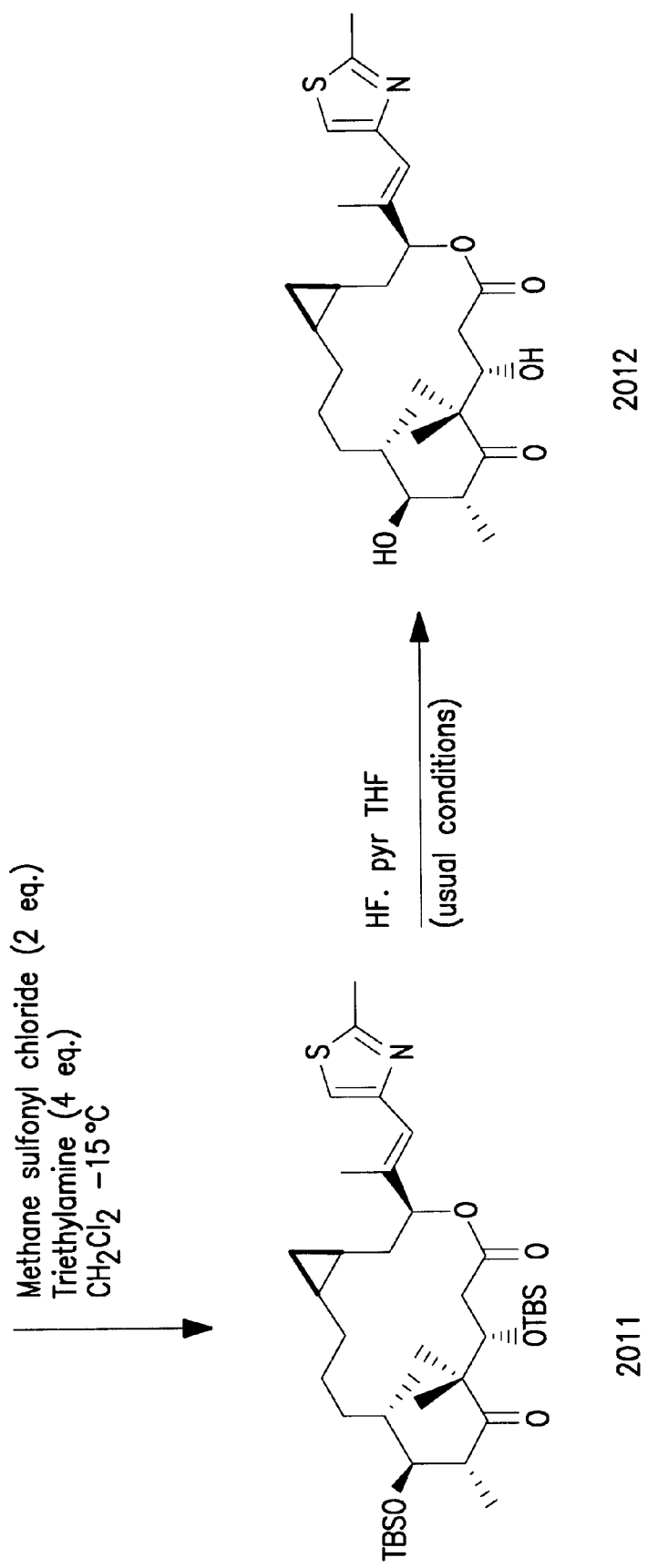

FIG. 76 illustrates the synthesis of cyclopropane epothilone A 2012 starting from advanced $C_{12}$-hydroxy intermediate 392.

DETAILED DESCRIPTION OF THE INVENTION

The invention is especially directed to epothilone analogs and methods for producing such analogs using solid and solution phase chemistries based on approaches used to synthesize epothilones A and B (Nicolaou et al. Angew. Chem. Int. Ed. Engl. 35, 2399–2401 (1996); Nicolaou et al. Angew. Chem. Int. Ed. Engl. 36, 166–168 (1997); Nicolaou et al. Angew. Chem. Int. Ed. Engl., 36, 525–527 (1997)), as well as to intermediates for these epothilones and their synthesis.

The following general definitions are used within the specification and can, where appropriate, be replaced by the more specific definitions mentioned herein:

The prefix "lower" stands for moiety having preferably up to and including 7, preferably up to and including 4, carbon atoms. "Lower alkanoyl" preferably stands for acetyl, or also for propionyl or butyryl.

Where hereinafter compounds of the formula I or intermediates are mentioned, this wording is intended to include both the free forms as well as any salt, where one or more salt-forming groups are present.

Salts of compounds of formula I are especially acid addition salts, salts with bases or, where several salt-forming groups are present, can also be mixed salts or internal salts.

Salts are especially pharmaceutically acceptable salts of compounds of formula I.

Such salts are formed, for example, from compounds of formula I having an acid group, for example a carboxy group, a sulfo group, or a phosphoryl group substituted by one or two hydroxy groups, and are, for example, salts thereof with suitable bases, such as non-toxic metal salts derived from metals of groups Ia, Ib, IIa and IIb of the Periodic Table of the Elements, especially suitable alkali metal salts, for example lithium, sodium or potassium salts, or alkaline earth metal salts, for example magnesium or calcium salts, also zinc salts or ammonium salts, as well as salts formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)-amines, such as N,N-dimethyl-N-(2-hydroxyethyl)-amine or tri-(2-hydroxyethyl)-amine, or N-methyl-D-glucamine, or quaternary ammonium salts, such as tetrabutylammonium salts. The compounds of formula I having a basic group, for example an amino group, can form acid addition salts, for example with inorganic acids, for example hydrohalic acids, such as hydrochloric acid, sulfuric acid or phosphoric acid, or with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, as well as with amino acids, for example the α-amino acids mentioned hereinbefore, especially glutamic acid and aspartic acid, and with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (forming cyclamates) or with other acidic organic compounds, such as ascorbic acid. Compounds of formula I having acid and basic groups can also form internal salts.

For isolation or purification purposes, it is also possible to use pharmaceutically inacceptable salts, for example a perchlorate or picolinate salt.

The invention especially relates to the compounds of the formula (I) as such as described above, or a salt thereof where a salt-forming group is present, except for the compounds of formula I wherein n is 3 (or, in a preferred variant, 1 to 5);

$R_1$ is hydrogen, methyl (preferably lower alkyl), acetyl (preferably lower alkanoyl) or benzoyl (when the group of compounds of formula I is represented in a more preferred version) trialkyl silyl or benzyl;

$R_2$ is methyl;

$R_3$ is methyl;

$R_4$ is hydrogen, methyl (preferably lower alkyl), acetyl (preferably lower alkanoyl) or benzoyl or (when the group of compounds of formula I is represented in a more preferred version) trialkyl silyl or benzyl;

$R_5$ is hydrogen or methyl;

$R_6$ is O or $R_6$ is absent and a is a double bond;

$R_7$ is hydrogen;

$R_8$ is a radical of the formula

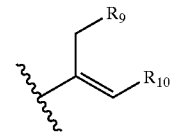

wherein $R_9$ is a radical selected from the group consisting of hydrogen and methyl;

and $R_{10}$ is a radical represented by the formula:

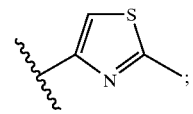

which, as such, are excluded from the scope of the present invention. This is also valid for any subsequent embodiments of the invention mentioning a compound falling under formula I, if required.

In the following, where compounds falling under the definitions of formula (I) given above are present, the invention primarily deals with their use as described above and below; however, the compounds as such which are novel are also comprised.

In the following any moieties such as $R_1$, $R_2$, $R_3$, $R_4$, $R_5$, $R_6$, $R_7$, $R_8$, $R_9$, $R_{10}$, $R_{11}$, $R_{12}$, n, a, b, c, in all intermediates and all compounds falling under the definitions of formula I have the meanings given for a compound of formula I, preferebly the preferred meaning, if not indicated otherwise.

Furthermore, any sequence of reactions may include the removal of protecting groups, e.g. of the protected precursor compounds to yield either epothilone A or epothilone B, according to procedures that are well-known in the art; this deprotection is usually not mentioned, but may be present in all synthesis steps mentioned herein and at all stages.

One aspect of the invention is directed to an epothilone analog represented by formula II,

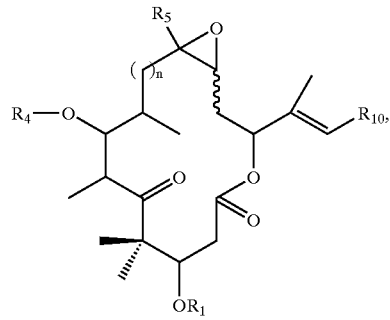

(II)

wherein, in a preferred embodiment, n is one to five, more preferably 3, $R_1$ is a radical selected from the group consisting of hydrogen (preferred), methyl or a protecting group, especially selected from the group consisting of tert-butyldimethylsilyl, trimethylsilyl, acetyl, benzoyl and tert-butoxycarbonyl, $R_4$ is a radical selected from the group consisting of hydrogen, methyl or a protecting group, especially selected from the group consisting of tert-butyldimethylsilyl, trimethylsilyl, acetyl, benzoyl and tert-butoxycarbonyl, $R_5$ is a radical selected from the group consisting of hydrogen, methyl, —CHO, —COOH, —$CO_2$Me, —$CO_2$(tert-butyl), —$CO_2$(isopropyl), —$CO_2$(phenyl), —$CO_2$(benzyl), —CONH(furfuryl), —$CO_2$(N-benzo-(2R,3S)-3-phenylisoserine), —CON(methyl)$_2$, —CON(ethyl)$_2$, —CONH(benzyl), and —$CH_2R_{11}$; or in a broader aspect also from —CH=$CH_2$ and HC≡C—; where $R_{11}$ is a radical selected from the group consisting of —OH, —O-Trityl, —O—($C_1$-$C_6$ alkyl), —O-benzyl, —O-allyl, —O—$COCH_3$, —O—$COCH_2$Cl, —O—$COCH_2CH_3$, —O—$COCF_3$, —O—$COCH(CH_3)_2$, —C—CO—C($CH_3$)$_3$, —O—CO(cyclopropane), —OCO(cyclohexane), —O—$COCH=CH_2$, —O—CO-phenyl, —O-(2-furoyl), —O—(N-benzo-(2R,3S)-3-phenylisoserine), —O-cinnamoyl, —O-(acetyl-phenyl), —O-(2-thiophenesulfonyl), —S—($C_1$-$C_6$ alkyl), —SH, —S-Phenyl, —S-Benzyl, —S-furfuryl, —$NH_2$, —$N_3$, —$NHCOCH_3$, —$NHCOCH_2$Cl, —$NHCOCH_2CH_3$, —$NHCOCF_3$, —$NHCOCH(CH_3)_2$, —NHCO—C($CH_3$)$_3$, —NHCO(cyclopropane), —NHCO(cyclohexane), —$NHCOCH=CH_2$, —NHCO-phenyl, —NH(2-furoyl), —NH—(N-benzo-(2R,3S)-3-phenylisoserine), —NH-(cinnamoyl), —NH-(acetylphenyl), —NH-(2-thiophenesulfonyl), —F, —Cl, —I, and $CH_2CO_2H$; and, in a broader aspect, also from —($C_1$-$C_6$ alkyl) and methyl;

and $R_{10}$ is a radical selected from the group represented by the formulae:

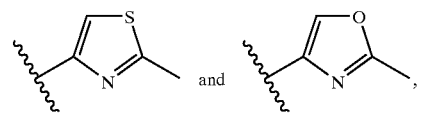

or (in a broader aspect of the invention) from

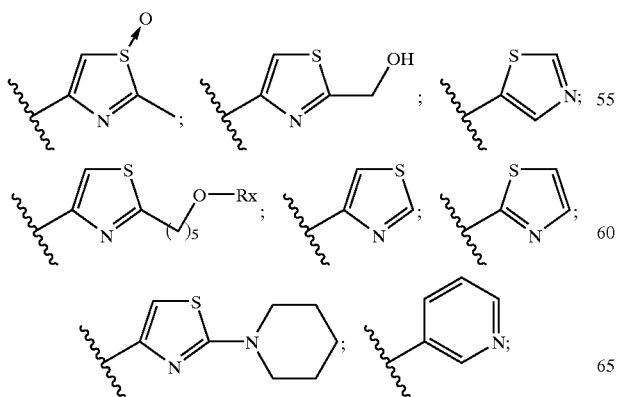

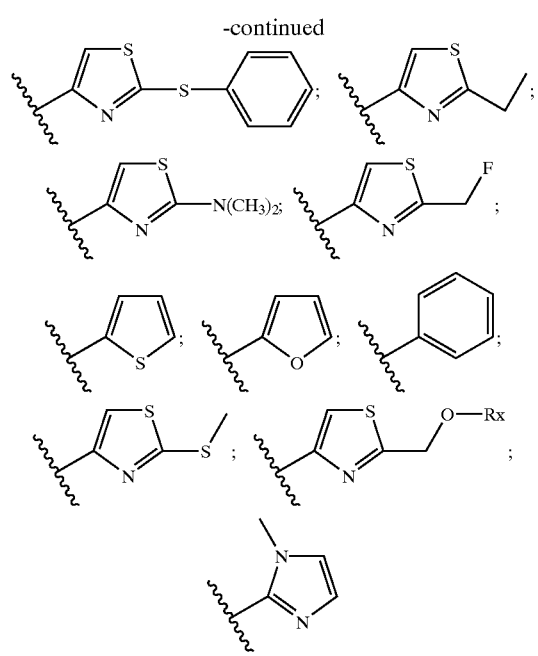

and (in a still broader aspect of the invention)

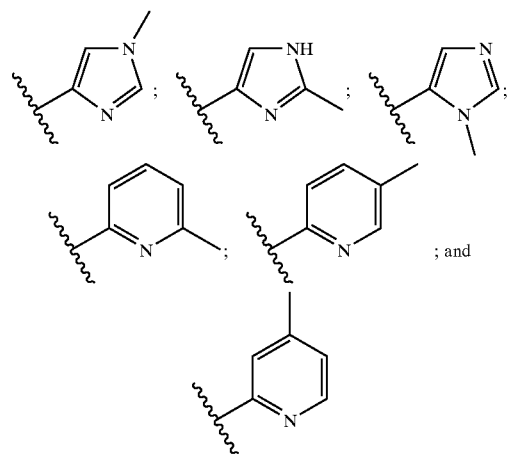

wherein Rx is acyl, especially lower alkanoyl, such as acetyl with the proviso that if $R_5$ is either methyl or hydrogen and $R_{10}$ is represented by the following formula:

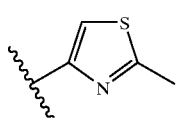

then $R_1$ and $R_4$ cannot simultaneously be hydrogen or methyl or acetyl. Preferred epothilone analogs of this aspect of the invention include a compound represented by the following structures, the substitutents being as defined above:

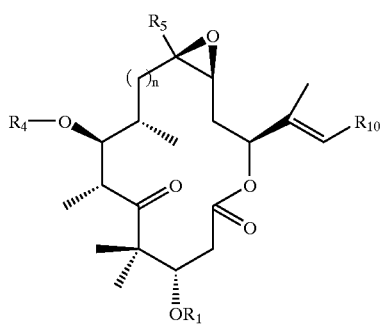

(IIa)

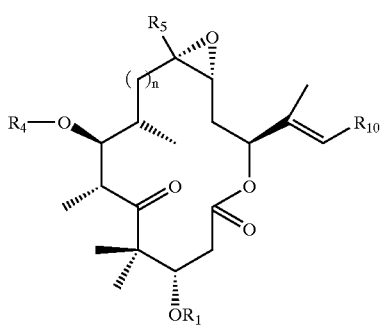

(IIb)

Another aspect of the invention is directed to an epothilone analog represented by the following structure:

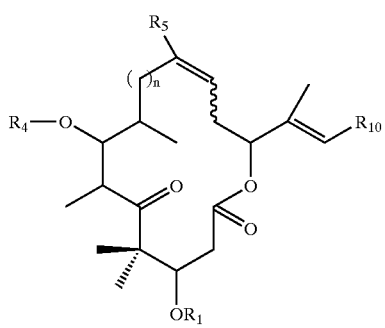

(III)

wherein n preferably is one to five, more preferably 3;

$R_1$ is a radical selected from the group consisting of hydrogen (preferred), methyl or a protecting group, especially selected from the group consisting of tert-butyldimethylsilyl, trimethylsilyl, acetyl, benzoyl and tert-butoxycarbonyl, $R_4$ is a radical selected from the group consisting of hydrogen, methyl or a protecting group, especially selected from the group consisting of tert-butyldimethylsilyl, trimethylsilyl, acetyl, benzoyl and tert-butoxycarbonyl, $R_5$ is a radical selected from the group consisting of hydrogen, methyl, —CHO, —COOH, —$CO_2$Me, —$CO_2$(tert-butyl), —$CO_2$(iso-propyl), —$CO_2$(phenyl), —$CO_2$(benzyl), —CONH(furfuryl), —$CO_2$(N-benzo-(2R,3S)-3-phenylisoserine), —CON(methyl)$_2$, —CON(ethyl)$_2$, —CONH(benzyl), and —$CH_2R_{11}$; or in a broader aspect also from —CH═$CH_2$ and HC≡C—; where $R_{11}$ is a radical selected from the group consisting of —OH, —O-Trityl, —O—($C_1$-$C_6$ alkyl), —O-benzyl, —O-allyl, —O—$COCH_3$, —O—$COCH_2$Cl, —O—$COCH_2CH_3$, —O—$COCF_3$, —O—COCH($CH_3$)$_2$, —O—C($CH_3$)$_3$, —O—CO(cyclopropane), —OCO(cyclohexane), —O—COCH═$CH_2$, —O—CO-phenyl, —O-(2-furoyl), —O—(N-benzo-(2R,3S)-3-phenylisoserine), —O-cinnamoyl, —O-(acetyl-phenyl), —O-(2-thiophenesulfonyl), —S—($C_1$-$C_6$ alkyl), —SH, —S-Phenyl, —S-Benzyl, —S-furfuryl, —$NH_2$, —$N_3$, —$NHCOCH_3$, —$NHCOCH_2$Cl, —$NHCOCH_2CH_3$, —$NHCOCF_3$, —NHCOCH($CH_3$)$_2$, —NHCO—C($CH_3$)$_3$, —NHCO(cyclopropane), —NHCO(cyclohexane), —NHCOCH═$CH_2$, —NHCO-phenyl, —NH(2-furoyl), —NH—(N-benzo-(2R,3S)-3-phenylisoserine), —NH-(cinnamoyl), —NH-(acetylphenyl), —NH-(2-thiophenesulfonyl), —F, —Cl, I, -and $CH_2CO_2$H; and, in a broader aspect, also from —($C_1$-$C_6$ alkyl) and methyl; preferably being —$CH_2$F, —$CH_2$Cl, $CH_2OOCCH_3$, —$CH_2CH_3$ or —CH═$CH_2$ where, at the same time, the double bond with the wavered line is in the cis form;

and $R_{10}$ is a radical selected from the group represented by the formulae:

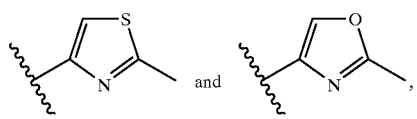

and (in a broader aspect of the invention)

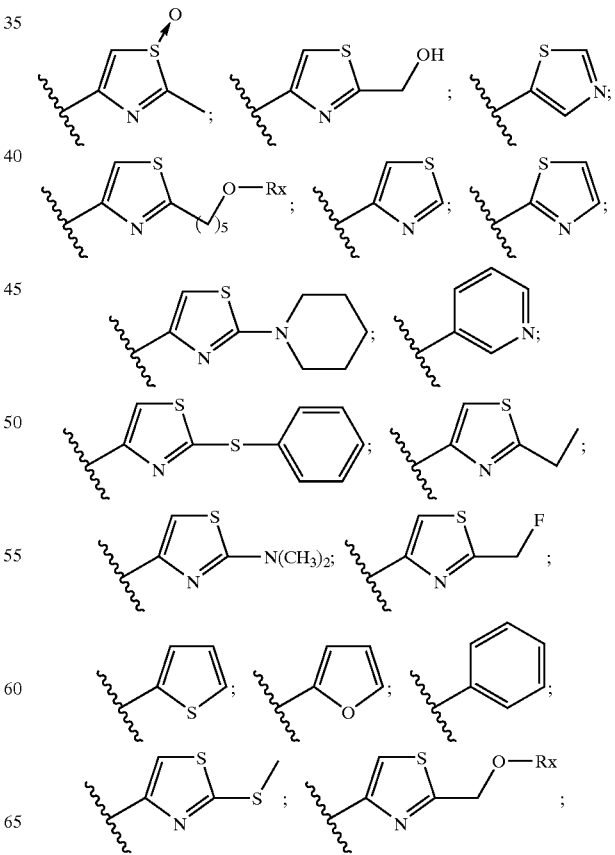

-continued

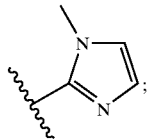

and (in a still broader aspect of the invention)

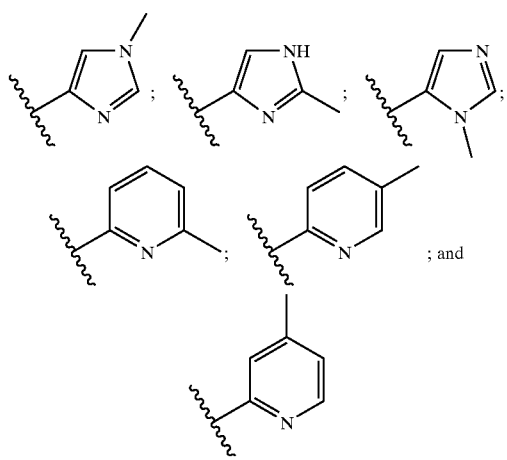

wherein Rx is acyl, especially lower alkanoyl, such as acetyl;

with the proviso that if $R_5$ is either methyl or hydrogen and $R_{10}$ is represented by the following formula:

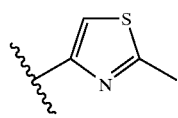

then $R_1$ and $R_4$ cannot simultaneously be hydrogen or methyl or acetyl.

Another aspect of the invention is directed to an epothilone analog represented by the following structure:

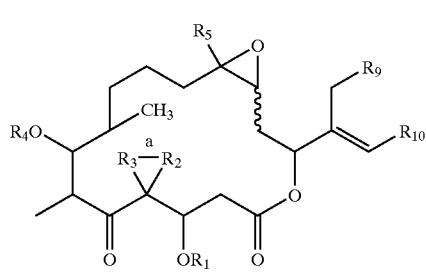

(IV)

wherein $R_1$ is a radical selected from the group consisting of hydrogen (preferred), methyl or a protecting group, especially selected from the group consisting of tert-butyldimethylsilyl, trimethylsilyl, acetyl, benzoyl and tert-butoxycarbonyl, $R_4$ is a radical selected from the group consisting of hydrogen, methyl or a protecting group, especially selected from the group consisting of tert-butyldimethylsilyl, trimethylsilyl, acetyl, benzoyl and tert-butoxycarbonyl, $R_5$ is a radical selected from the group consisting of hydrogen and methyl, $R_{10}$ is a radical selected from the group represented by the formulae:

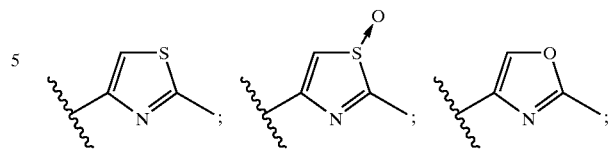

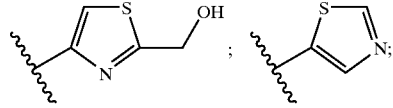

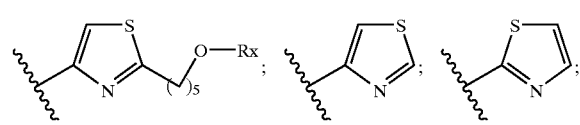

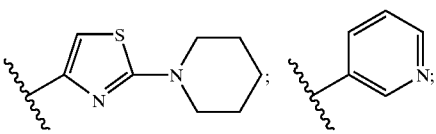

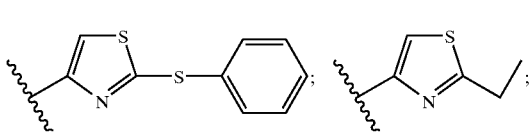

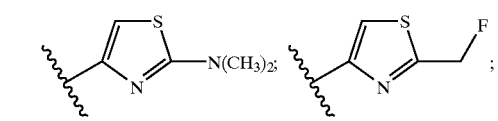

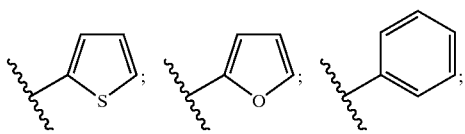

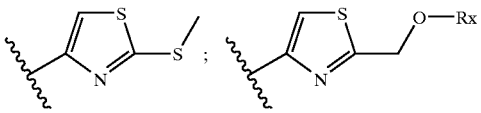

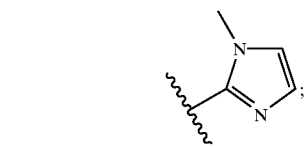

and (in a broader aspect of the invention)

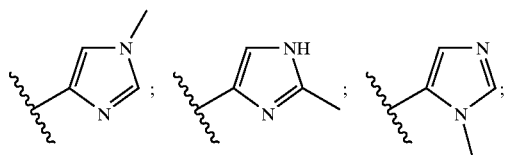

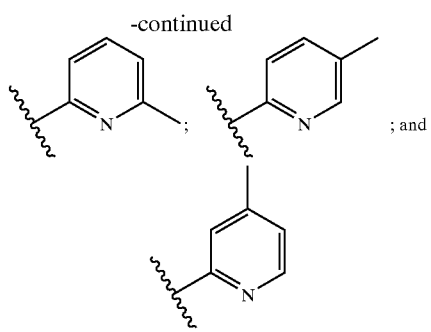

wherein Rx is acyl, especially lower alkanoyl, such as acetyl;

$R_3$ is a radical selected from hydrogen, methylene or methyl; $R_2$ is hydrogen, methylene or methyl; and $R_9$ is hydrogen or methyl; with the following provisos:

If $R_3$ is methylene, then $R_2$ is methylene. If $R_3$ and $R_2$ are methylene, then $R_3$ and $R_2$ are chemically bonded to each other through a single bond "a". If $R_3$ and $R_2$ are hydrogen or methyl, then the single bond "a" is absent. If $R_5$ is methyl or hydrogen and $R_{10}$ is represented by the formula

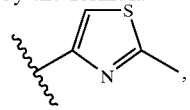

then $R_1$ and $R_4$ cannot simultaneously be hydrogen or methyl or acetyl; in the definition of compounds of formula IV those wherein neither $R_2$ nor $R_3$ are methylene and the bond "a" is absent being especially preferred.

Another aspect of the invention is directed to an epothilone analog represented by the following structure:

(V)

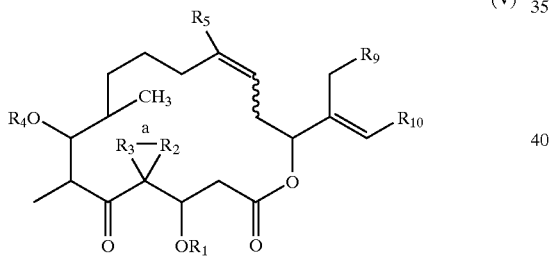

wherein $R_1$, $R_2$, $R_3$, $R_4$, $R_5$, $R_9$, $R_{10}$ and "a" are as defined under formula IV.

Preferred embodiments of the invention include the synthesis of compounds represented by the following structures, as well as novel compounds falling under their formulae:

Another aspect of the invention is directed to a macrolactonization procedure for synthesizing epothilone and epothilone analogs represented by the following structure:

(VI)

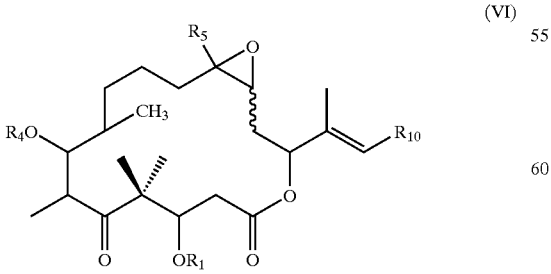

wherein $R_1$ is a radical selected from the group consisting of hydrogen (preferred), methyl or a protecting group, especially selected from the group consisting of tert-butyldimethylsilyl, trimethylsilyl, acetyl, benzoyl and tert-butoxycarbonyl, $R_4$ is a radical selected from the group consisting of hydrogen, methyl or a protecting group, especially selected from the group consisting of tert-butyldimethylsilyl, trimethylsilyl, acetyl, benzoyl and tert-butoxycarbonyl, $R_5$ is a radical selected from the group consisting of hydrogen, methyl, —$CH_2$— OH, —$CH_2Cl$ or —$CH_2CO_2H$, or (further or alternatively to the preceding moieties) is —$CH_2F$, —CH=$CH_2$ or HC≡C—, and $R_{10}$ is a radical selected from the group represented by the formulae:

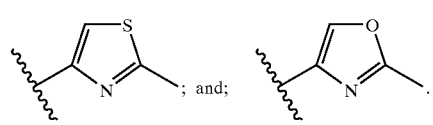

The synthesis can be initiated by condensing a keto acid represented by the following formula:

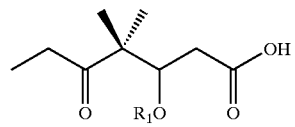

with an aldehyde represented by the following structure:

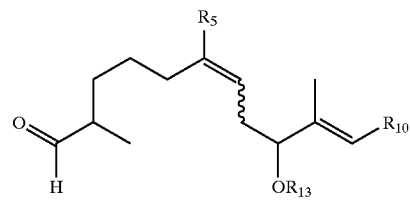

wherein $R_{13}$ is a protecting group, especially tert-butyldimethylsilyl or trimethylsilyl, for producing a carboxylic acid with a free hydroxyl moiety represented by the following structure:

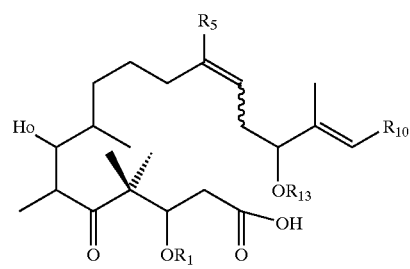

The synthesis is then continued by derivatizing the free hydroxyl moiety of the above carboxylic acid with a derivatizing agent represented by the formula $R_4$—X wherein $R_4$—X is a reactive reagent for introducing a protecting group, especially tert-butyldimethylsilyl chloride, tertbutyldimethylsilyl triflate, trimethylsilyl chloride, trimethylsilyl triflate, methyl sulfate, acetic anhydride, acetic acid, acetyl chloride, benzoic acid, benzoyl chloride, and 2-(tert-butoxycarbonyloxyimino)-2-phenylacetonitrile, or methyl iodide, for producing a protected or derivatized carboxylic acid represented by the following structure:

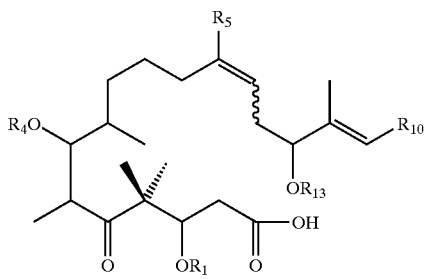

The $R_5$ protected hydroxyl moiety of the above derivatized carboxylic acid is then regioselectively deprotected for producing a hydroxy acid with the following structure

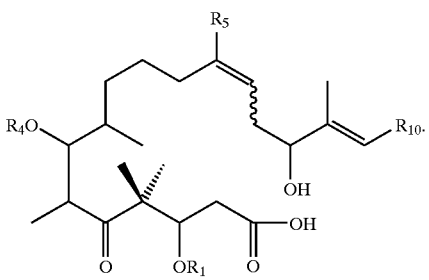

The above hydroxy acid is then macrolactonized for producing a macrolide with the following structure:

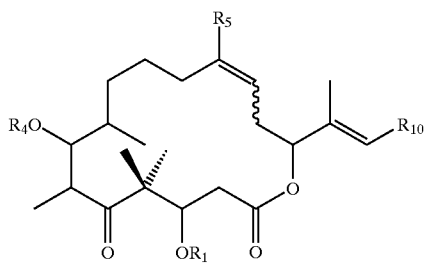

where the moieties in each of the intermediates have the meanings given above under formula VI.

The synthesis is then completed by epoxidizing the above macrolide for producing the epothilone or epothilone analog of the formula VI.

The invention relates to the last two steps of this synthesis (macrolactonization and epoxidation, and, where protecting groups are present, removal of such protecting groups if desired), but in a preferred form to the full synthesis including all steps for the synthesis of a compound of the formula.

A method of synthesis for epothilone B according to this sequence is especially preferred, characterized in that the starting materials with the corresponding substituents are used and, where required, any protecting group or groups is or are removed.

A further mode of the invention is directed to a metathesis approach to synthesizing epothilone and epothilone analogs represented by the following structure:

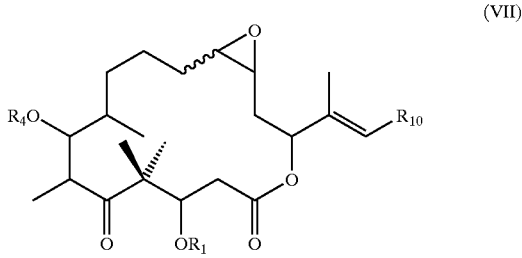

(VII)

wherein $R_1$ is a radical selected from the group consisting of hydrogen (preferred), methyl or a protecting group, especially selected from the group consisting of tert-butyldimethylsilyl, trimethylsilyl, acetyl, benzoyl and tert-butoxycarbonyl, $R_4$ is a radical selected from the group consisting of hydrogen, methyl or a protecting group, especially selected from the group consisting of tert-butyldimethylsilyl, trimethylsilyl, acetyl, benzoyl and tert-butoxycarbonyl, and $R_{10}$ is a radical selected from the group represented by the formulae:

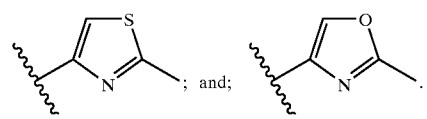

The synthetic protocol is initiated by condensing a keto acid represented by the following structure:

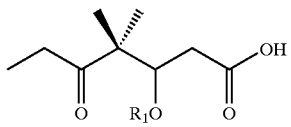

with an aldehyde represented by the following structure:

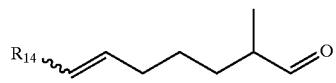

wherein $R_{14}$ is hydrogen or $(CH_2)_m$-(solid phase support) wherein m is a positive integer, for produsing a carboxylic acid with a free hydroxyl moiety reprsented by the following formula:

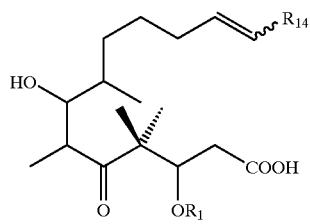

Alternative preferred solid supports include Merrifield resin, PEG-polystyrene, hydroxymethyl polystyrene, formyl polystyrene, aminomethyl polystyrene, and phenolic polystyrene.

The above carboxylic acid is then esterified with a secondary alcohol represented by the following structure:

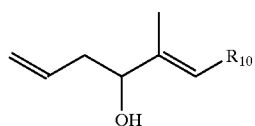

for producing an ester with a free hydroxyl moiety represented by the following formula:

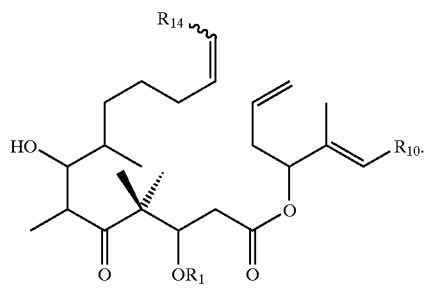

The synthesis is then continued by derivatizing the free hydroxyl moiety of the above ester with a derivatizing agent represented by the formula $R_4$—X wherein $R_4$—X is a reactive agent for introducing a protecting group, preferably tert-butyldimethylsilyl chloride, tert-butyldimethylsilyl triflate, trimethylsilyl chloride, trimethylsilyl triflate, methyl sulfate, acetic anhydride, acetic acid, acetyl chloride, benzoic acid, benzoyl chloride, and 2-(tert-butoxycarbonyloxyimino)-2-phenylacetonitrile, or methyl iodide, for producing a protected or derivatized ester represented by the following structure:

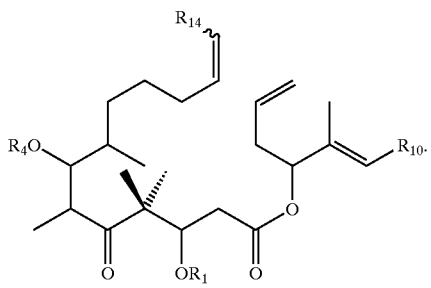

This ester is then metasthesized with an organo-metallic catalyst for producing a macrolide with the following formula:

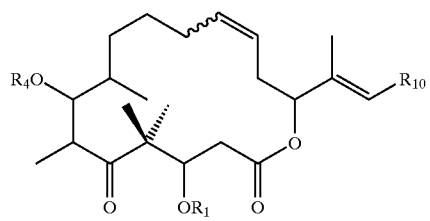

where the moieties in each of the intermediates have the meanings given above under formula VI.

Preferred organo-metallic catalyst include bis(tricyclohexylphosphine)benzylidine ruthenium dichloride and 2,6-diisopropylphenylimido neophylidenemolybdenum bis(hexafluoro-tert-butoxide).

The above macrolide is then epoxidized for producing the epothilone analog of the formula VII.

The invention relates to the last two steps of this synthesis (metathesis and epoxidation, and, where protecting groups are present, removal of such protecting groups if desired), but in a preferred form to the full synthesis including all steps for the synthesis of a compound of the formula VII.

Another embodiment of the invention is directed to a metathesis approach to synthesizing an epothilone or analog represented by the following structure:

(VIII)

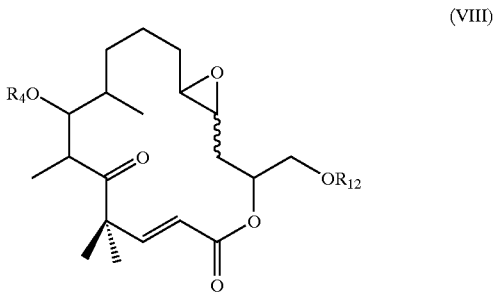

wherein $R_{12}$ is hydrogen (preferred) or methyl, or a protecting group, preferably tert-butyldiphenylsilyl, tert-butyldimethylsilyl, trimethylsilyl, acetyl, benzoyl, tert-butoxycarbonyl, or a radical represented by one of the following formulae:

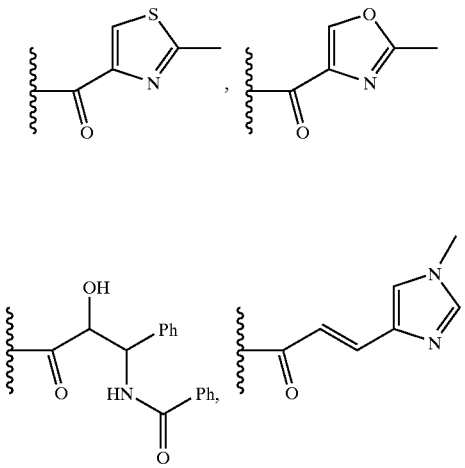

and wherein $R_4$ is hydrogen (preferred), methyl or a protecting group, especially tert-butyldimethylsilyl, trimethylsilyl, acetyl, benzoyl or tert-butoxycarbonyl.

The synthesis is initiated by esterifying a keto acid of the formula

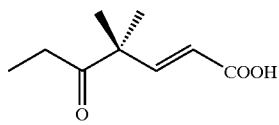

with an alcohol of the formula

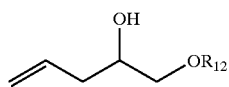

for producing an ester of the formula

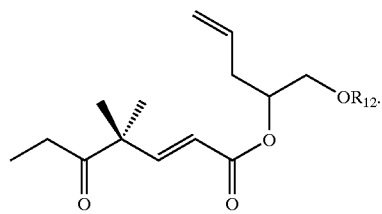

Then, this ester is condensed with an aldehyde of the formula:

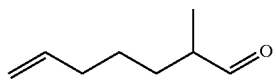

for producing a bis-terminal olefin of the formula:

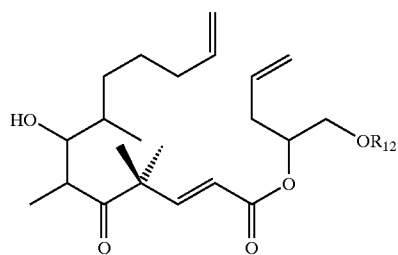

The synthesis is then continued by metathesizing the above bis-terminal olefin with an organo-metallic catalyst for producing a macrlcyclic lactone with a free hydroxyl moiety of the formula:

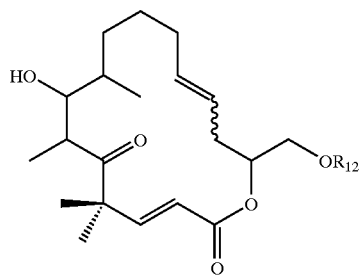

Preferred organo-metallic catalysts include bis(tricyclohexylphosphine)benzylidine ruthenium dichloride, and 2,6-diisopropylphenylimido neophylidenemolybdenum bis(hexafluoro-t-butoxide).

The free hydroxyl of the above macrocyclic lactone is then, if desired, derivatized with a derivatizing agent represented by the formula $R_4$—X wherein $R_4$—X is hydrogen or a reactive agent for introducing a protecting group, preferably tert-butyldimethylsilyl chloride, tert-butyldimethylsilyl triflate, trimethylsilyl chloride, trimethylsilyl triflate, methyl sulfate, acetic anhydride, acetic acid, acetyl chloride, benzoic acid, benzoyl chloride, or 2-(tert-butoxycarbonyloxyimino)-2-phenylacetonitrile, or methyl iodide, for producing a protected or derivatized macrolide with the following structure:

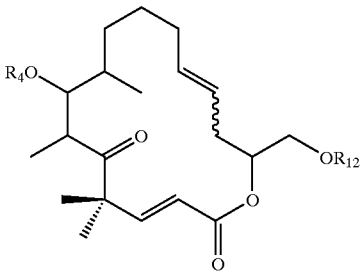

The synthesis is then completed by epoxidizing this protected or derivatized macrolide for producing the epothilone analog of the formula VIII. In all intermediates, the substitutents have the meanings given under formula VIII, if not mentioned otherwise.

The invention relates to the last two or three steps of this synthesis (metathesis; if desired, introduction of a protecting group; and epoxidation, and, where protecting groups are present, removal of such protecting groups if desired), but in a preferred form to the full synthesis including all steps for the synthesis of a compound of the formula VIII.

Another aspect of the invention is directed to a method employing a metathesis approach for synthesizing an epothilone or analog represented by the following structure:

(IX)

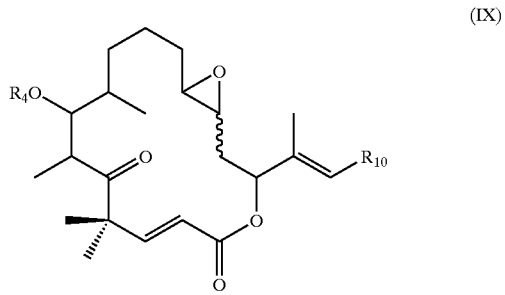

wherein $R_4$ is hydrogen (preferred), methyl or a protecting group, preferably ten butyldimethylsilyl, trimethylsilyl, acetyl, benzoyl or tert-butoxycarbonyl; wherein $R_{10}$ is one of the radicals of the formulae:

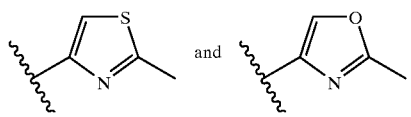

The synthesis is initiated by condensing a keto acid of the formula

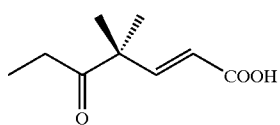

with an aldehyde represented by the formula

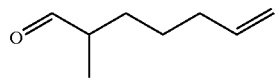

for producing a carboxylic acid with a free hydroxyl moiety of the formula

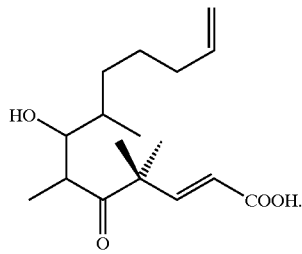

The free hydroxyl moiety of the above carboxylic acid is then derivatized with a derivatizing agent represented by the formula $R_4$—X wherein $R_4$—X is a reactive agent for the introduction of a protecting group, especially tert-butyldimethylsilyl chloride, tert-butyldimethylsilyl triflate, trimethylsilyl chloride, trimethylsilyl triflate, methyl sulfate, acetic anhydride, acetic acid, acetyl chloride, benzoic acid, benzoyl chloride, and 2-(tert-butoxycarbonyloxyimino)-2-phenylacetonitrile, or is methyl iodide, for producing a protected or derivatized carboxylic acid represented by the following structure:

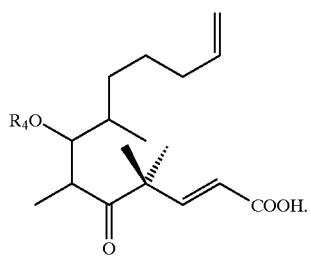

This derivatized carboxylic acid is then reacted with an alcohol of the formula

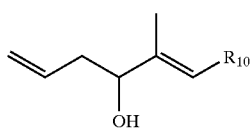

for producing a bis-terminal olefin of the formula

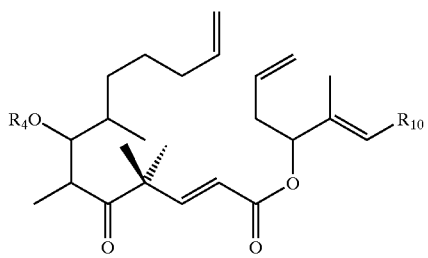

This bis-terminal olefin is then metathesized with an organo-metallic catalyst for producing a macrocyclic lactone with the following structure:

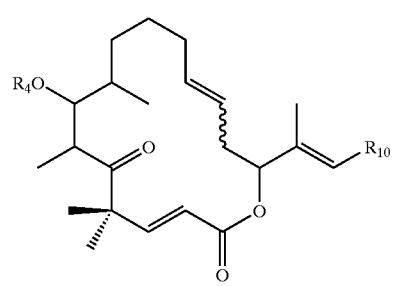

Preferred organo-metallic catalysts include bis (tricyclohexylphosphine)benzylidine ruthenium dichloride, or 2,6-diisopropylphenylimido neophylidenemolybdenum bis(hexafluoro-t-butoxide).

The synthesis is then completed by epoxidizing the above-mentioned macrocyclic lactone for producing the epothilone analog of the formula IX. Any substitutents in the intermediates have the meanings given under formula IX, if not mentioned otherwise.

The invention relates to the last two steps of this synthesis (metathesis and epoxidation, and, where protecting groups are present, removal of such protecting groups if desired), but in a preferred form to the full synthesis including all steps for the synthesis of a compound of the formula IX.

Another (especially preferred) aspect of the invention is directed to a method employing a macrolactonization approach for synthesizing an epothilone or analog of the formula:

(X)

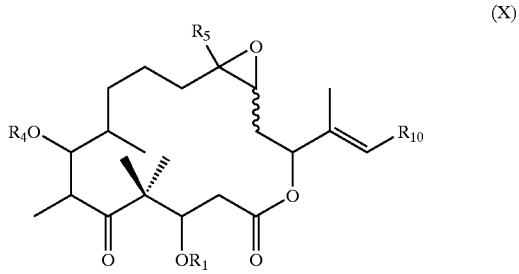

wherein each of $R_1$ and $R_4$ is, independently of the other, hydrogen (preferred), methyl or a protecting group, especially tert-butyldimethylsilyl, trimethylsilyl, acetyl, benzoyl, or tert-butoxycarbonyl; $R_5$ is as defined under formula I, especially hydrogen, methyl, —$CH_2$—OH, —$CH_2Cl$, or —$CH_2CO_2H$, or most especially $CH_2CH_3$, —CH=$CH_2$, —$CH_2OOCCH_3$ or especially —$CH_2F$; and $R_{10}$ is one of the radicals of the formulae

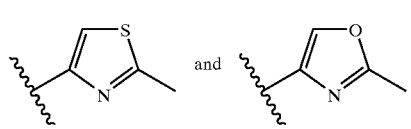

The synthesis is initiated by condensing a ketone of the formula

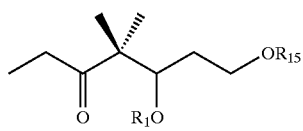

wherein $R_6$ is hydrogen or methyl or a protecting group, especially especially tertbutyldimethylsilyl, trimethylsilyl, tert-butyldiphenylsilyl, triethylsilyl or benzyl; with an aldehyde of the formula

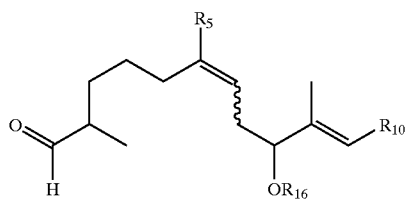

wherein $R_{16}$ is a protecting group, especially tert-butyldimethylsilyl or trimethylsilyl, for producing a β-hydroxy ketone, with a free hydroxyl moiety and a $R_{15}$ protected hydroxyl moiety, of the formula

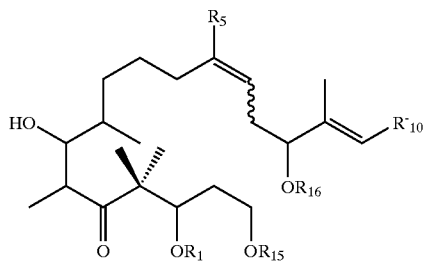

The free hydroxyl moiety of this β-hydroxy ketone is then derivatized with a derivatizing agent $R_4$—X wherein $R_4$—X is a reactive agent for the introduction of a protecting group, especially tert-butyldimethylsilyl chloride, tert-butyldimethylsilyl triflate, trimethylsilyl chloride, trimethylsilyl triflate, acetic anhydride, acetic acid, acetyl chloride, benzoic acid, benzoyl chloride, or 2-(tert-butoxycarbonyloxyimino)-2-phenylacetonitrile, or methyl iodide or methyl sulfate, for producing a protected or derivatized β-hydroxy ketone of the formula

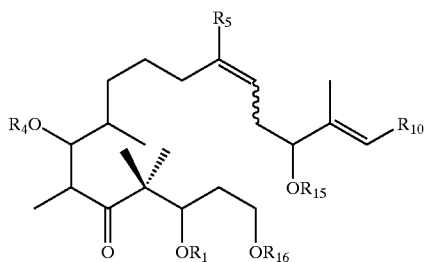

The $R_{15}$ protected hydroxyl moiety of this protected or derivatized β-hydroxy ketone is then regioselectively deprotected for producing a terminal alcohol with the following structure:

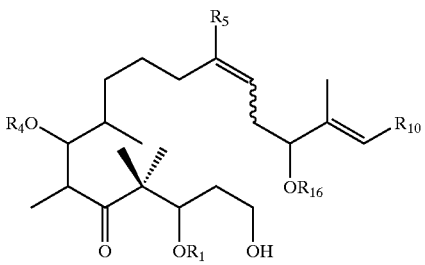

This terminal alcohol is then oxidized for producing a derivatized carboxylic acid with a $R_{16}$ protected hydroxyl moiety of the formula

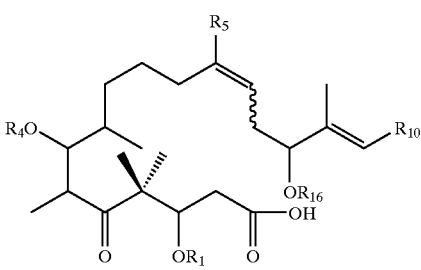

This compound is then deprotected regioselectively by removal of the protecting group $R_{16}$ to yield a hydroxy acid of the formula:

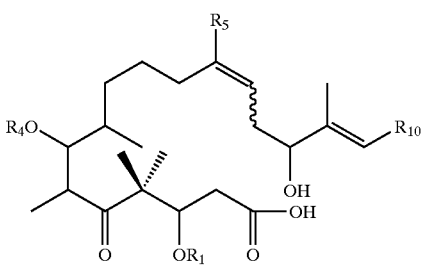

This hydroxy acid is then macrolactonized to yield a macrolide of the formula

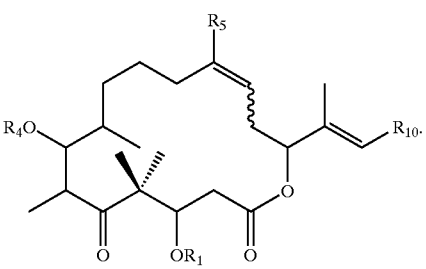

The synthesis is then completed by epoxidizing the above macrolide for producing the epothilone compound of the formula X. Any substitutents in the intermediates have the meanings given under formula X, if not mentioned otherwise.

The invention relates to the last two steps of this synthesis (macrolactonization and epoxidation, and, where protecting groups are present, removal of such protecting groups if desired), but in a preferred form to the full synthesis including all steps for the synthesis of a compound of the formula X.

Preferred is this process for the synthesis of epothilone B, characterized in that the starting materials with the corresponding substituents, where required, in protected form, are used, and any protecting group or groups is or are removed.

Another aspect of the invention is directed to a process for synthesizing an epothilone analog having an epoxide and an aromatic substitutent. In the first step of this process, a first epothilone intermediate and an aromatic stannane are coupled by means of a Stille coupling reaction to produce a second epothilone intermediate. The first epothilone intermediate has a vinyl iodide moiety to which the aromatic stannane is coupled for producing the second epothilone intermediate. Preferred embodiments of the first epothilone intermediate are represented by the following structure:

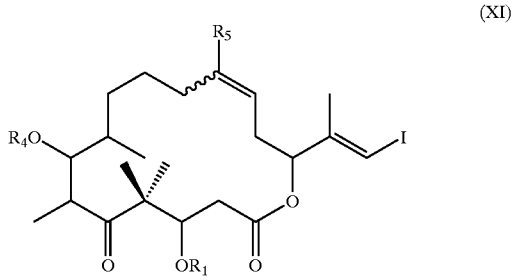

(XI)

In the above structure, $R_5$ is methyl or preferably hydrogen, while $R_1$ and $R_4$ are, each independently of the other, selected from hydrogen (preferred), methyl or a protecting group, especially tert-butyldimethylsilyl, trimethylsilyl, acetyl, benzoyl or tert-butoxycarbonyl.

In a preferred embodiment, the aromatic stannane is a compound represented by one of the following structures:

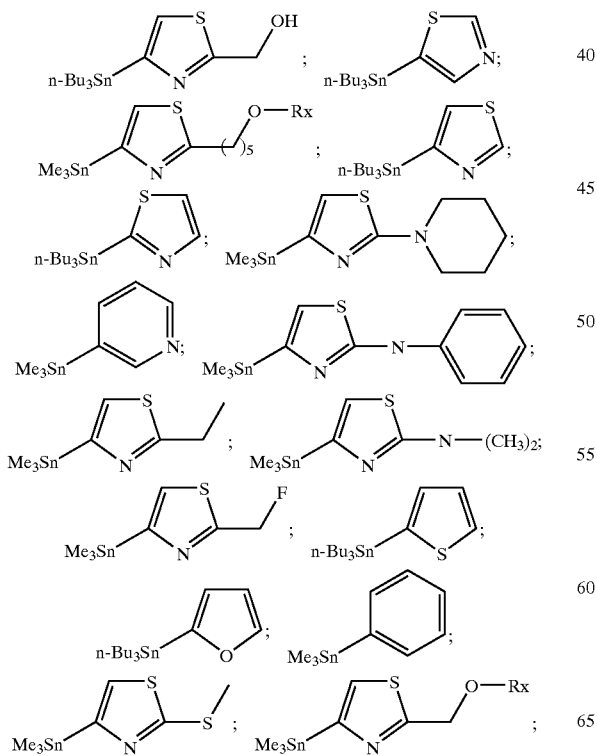

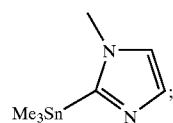

and (in a broader aspect of the invention

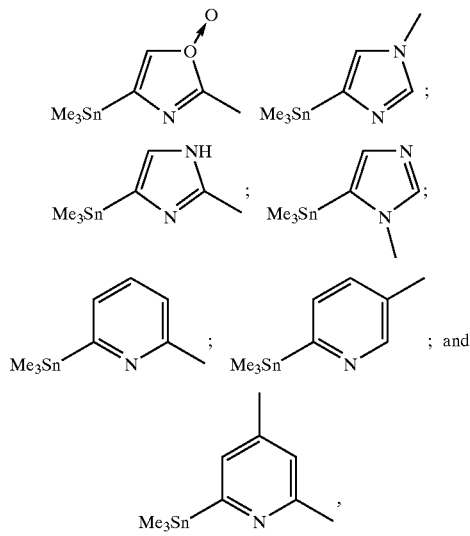

wherein Rx is acyl, especially lower alkanoyl, such as acetyl.

The second epothilone intermediate has the aromatic substitutent and a cis olefin. In a prefered embodiment, the second epothilone intermediate is represented by the following structure:

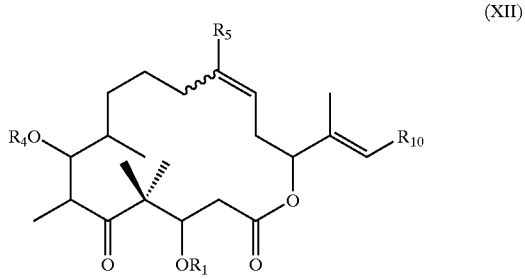

(XII)

wherein $R_{10}$ is a radical represented by any one of the following formulae:

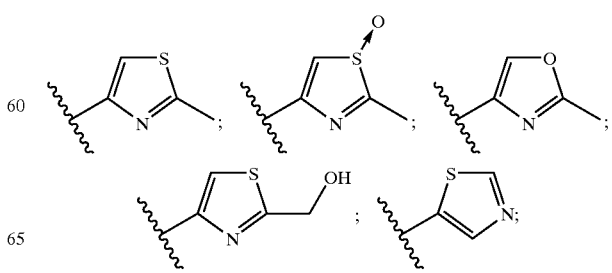

-continued

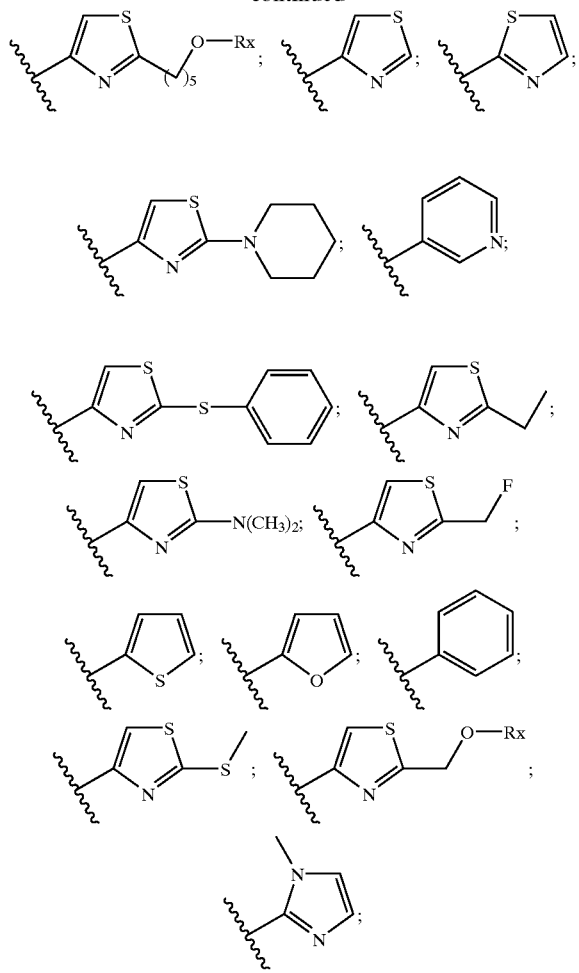

and (in a broader aspect of the invention)

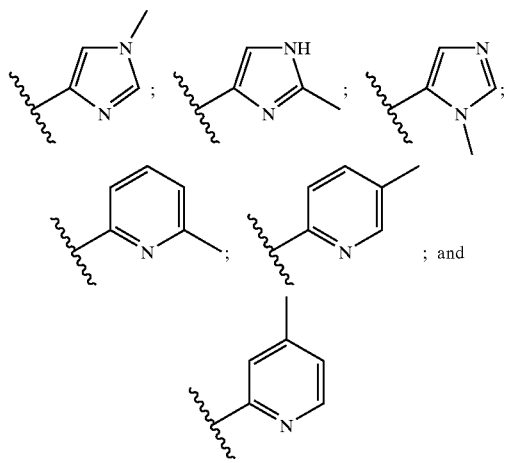

wherein Rx is acyl, especially lower alkanoyl, such as acetyl;

and wherein the other moieties are as defined under formula XI, R$_5$ preferably being hydrogen.

In the second step of this process, the cis olefin of the second epothilone intermediate is epoxidized to produce the epothilone analog. In a preferred embodiment, the epothilone analog is represented by the following structure:

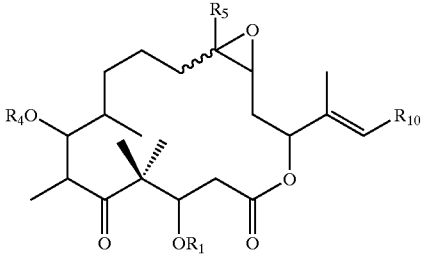

(XIII)

wherein the moieties are as defined for the first and second epothilone intermediate mentioned above; if desired, any protecting group(s) can then be removed.

In a preferred mode of the above-mentioned process for synthesizing an epothilone analog, there are several additional steps that arre performed prior to the Stille coupling. The first of the additional steps involves the condensation of a keto acid represented by the formula

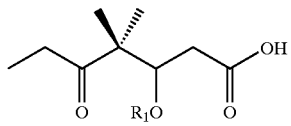

with an aldehyde represented by the following structure:

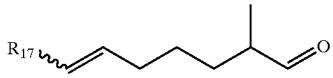

wherein R$_{17}$ is hydrogen of $(CH_2)_m$-(solid phase support) wherein m is a positive integer for producing a carboxylic acid represented by the following structure:

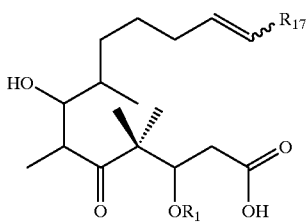

Then, this carboxylic acid is esterified with a secondary alcohol represented by the following structure:

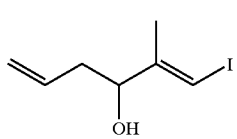

for producing an ester with a free hydroxyl moiety represented by the following formula:

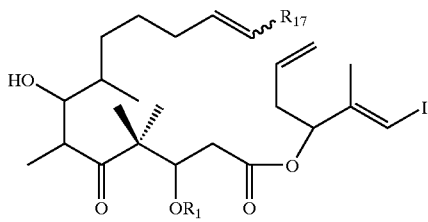

Then, there is an optional step. The free hydroxy of the above ester may be derivatized with a derivatizing agent for introducing e.g. a protecting group or methyl. Preferred derivatizing agents include reactive agents for the introduction of protective groups, especially tert-butyldimethylsilyl chloride, tert-butyldimethylsilyl triflate, trimethylsilyl chloride, trimethylsilyl triflate, acetic anhydride, acetic acid, acetyl chloride, benzoic acid, benzoyl chloride or 2-(tert-butoxycarbonyloxyimino)-2-phenylacetonitrile, or methyl iodide or methyl sulfate, for producing an optionally derivatized ester represented by the formula

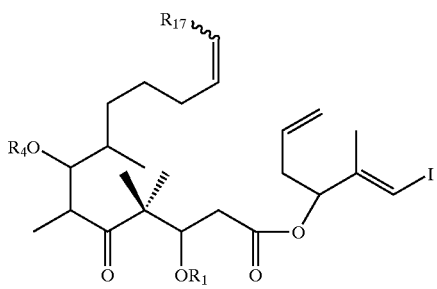

Finally, the above optionally derivatized ester is metathesized with an organo-metallic catalyst (as already mentioned in other cases above) for producing the epothilone analog of the formula XIII.

Another aspect of the invention is directed to the use of each of the above-mentioned metathesis approaches for synthesizing libraries of epothilone analogs. In this mode, a combinatorial approach is employed for synthesizing libraries of epothilone analogs having various combinations of the preferred R group(s).

Further modes of the invention are directed to each of the individual steps of the synthesis processes mentioned hereinabove or hereinbelow.

Especially preferred are the following groups of compounds of the formula I and the intermediates with the corresponding substituents: (a) compounds of the formula I wherein $R_{10}$ is a moiety of the formula

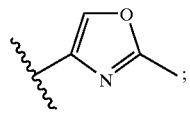

(b) compounds wherein $R_5$ is $CH_2$—F or, in a broader aspect, —$CH_2CH_3$, —$CH_2OOCCH_3$, —$CH$=$CH_2$ or —$CH_2Cl$; (c) n is one; or any combination of the compounds falling under (a) to (c) as far as they are not excluded; especially the compounds of formula I mentioned in the Examples and Figures below that meet one or more of the conditions (a) to (c).

Especially preferred are also compounds 265 and 266 in the Figures, as well as the new synthetic strategies according to FIGS. 34 to 39.

Especially preferred is also any one compound falling under the following definition:
A compound of the formula

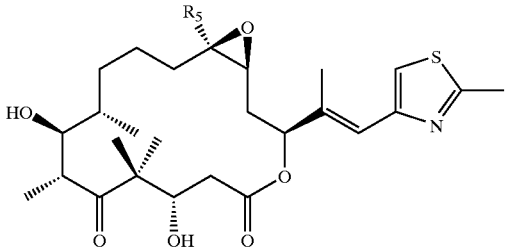

wherein $R_5$ is —$CH_2F$, —$CH_2Cl$, —$CH_2OOCCH_3$, —$CH_2CH_3$ or —$CH$=$CH_2$.

Especially important is also the process according to FIG. 17 for the synthesis of the end product mentioned therein.

As already mentioned, the compounds of formula I have useful pharmacological properties. Especially, they can be used for the treatment of proliferative diseases, such as cancer. One of the many advantages is that the compounds can also be used against proliferative diseases that are drug-resistant. The pharmacological usefulness of the compounds of formula I is especially demonstrated by the test systems mentioned above in the description of the figures; however, other test systems that are known to the man skilled in the art which have been used in the characterisation of Taxol and Epothilones A and B are appropriate as well. Especially, the compounds can be used for the treatment of solid cancers and leukemias, such as colon, breast, lung, prostate and epithelial carcinomas.

The present invention also relates to pharmaceutical compositions which comprise, as the active ingredient, one of the pharmacologically active compounds of the formula I as defined above or below, or a pharmaceutically acceptable salt thereof. Compositions for enteral, in particular oral, and especially for parenteral administration are particularly preferred. The compositions comprise the active ingredient by itself or, preferably, together with a pharmaceutically acceptable carrier. The dosage of the active ingredient depends on the disease to be treated and on the species, age, weight, skin area and individual condition, as well as on the mode of administration.

The pharmaceutical compositions comprise about 5% to about 95% of the active ingredient, single-dose administration forms preferably containing about 20% to about 90% and administration forms which are not single-dosed preferably containing about 5% to about 20% of active ingredient. Dose unit forms, such as coated tablets, tablets or capsules, contain about 0.01 g to about 2 g, preferably about 0.02 g to about 1.0 g, of the active ingredient, in particular 0.02 to 0.6 g.

The present invention also relates to the use of compounds of the formula I for the preparation of pharmaceutical compositions for use against a proliferative disease, for example for the treatment of diseases which respond to enhancers of tubulin polymerization, in particular of the abovementioned diseases.

The pharmaceutical compositions of the present invention are prepared in a manner known per se, for example by means of conventional mixing, granulating, coating, dissolving or lyophilizing processes. Thus, pharmaceutical compositions for oral use can be obtained by combining the active ingredient with one or more solid carriers, granulating a resulting mixture, if appropriate, and processing the mixture or granules, if desired, to tablets or coated-tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, and furthermore binders, such as starches, for example corn, wheat, rice or potato starch, methylcellulose, hydroxypropylmethylcellulose, sodium carboxymethylcellulose and/or polyvinylpyrrolidone, and/or, if desired, disintegrants, such as the abovementioned starches, and furthermore carboxymethyl starch, crosslinked polyvinylpyrrolidone, alginic acid or a salt thereof, such as sodium alginate.

Additional excipients are, in particular, flow conditioners and lubricants, for example silicic acid, talc, stearic acid or salts thereof, such as magnesium stearate or calcium stearate, or derivatives thereof.

Coated-tablet cores can be provided with suitable coatings, if appropriate resistant to gastric juice, the substances used being, inter alia, concentrated sugar solutions, which contain gum arabic, talc, polyvinylpyrrolidone and/or titanium dioxide if appropriate, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated-tablet coatings, for example for identification or characterization of different active ingredient doses.

Pharmaceutical compositions which can be used orally are also dry-filled capsules of gelatin and soft, closed capsules of gelatin and a softener, such as glycerol or sorbitol. The dry-filled capsules can contain the active ingredient in the form of granules, for example mixed with fillers, such as corn starch, binders and/or lubricants, such as talc or magnesium stearate, and if appropriate stabilizers. In soft capsules, the active ingredient is preferably dissolved or suspended in suitable liquid excipients, such as fatty oils or paraffin oil, it also being possible to add stabilizers.

Further oral administration forms are, for example, syrups which are prepared in the customary manner and contain the active ingredient, for example, in suspended form and in a concentration of about 5% to 20%, preferably about 10%, or in a similar concentration which gives a suitable single dose, for example, when 5 or 10 ml are measured out. Further suitable forms are also, for example, pulverulent or liquid concentrates for preparation of shakes, for example in milk. Such concentrates can also be packed in single-dose amounts.

Compositions which are suitable for parenteral administration are, in particular, aqueous solutions of an active ingredient in water-soluble form, for example a water-soluble salt, or aqueous injection suspensions which contain viscosity-increasing substances, for example sodium carboxymethylcellulose, sorbitol and/or dextran, and if appropriate stabilizers. The active ingredient can also be present here in the form of a lyophilisate, if appropriate together with excipients, and can be dissolved by addition of suitable solvents before parenteral administration.

Solutions such as are used, for example, for parenteral administration can also be used as infusion solutions.

The invention also relates to a method (process) for the treatment of the abovementioned disease states in warm-blooded animals, i.e. mammals, and in particular humans, preferably those warm-blooded animals which require such treatment. The compounds of the formula I of the present invention or their pharmaceutical salts, if salt-forming groups are present, are administered for this purpose for prophylaxis or treatment, and are preferably used in the form of pharmaceutical compositions, for example in an amount which is suitable for enhancing tubulin polymerization and is active prophylactically or especially therapeutically against one of the diseases mentioned which respond to such treatment, for example tumours. For a body weight of about 70 kg, a daily dose of about 0.1 g to about 15 g, preferably about 0.2 g to about 5 g, more preferably of about 0.5 to 3 g, of a compound of the formula I is administered here.

The pharmaceutical compositions are preferably those which are suitable for administration to a warm-blooded animal, for example a human, for treatment or prophylaxis of one of the abovementioned diseases and comprise an amount of a compound of the formula I or of a pharmaceutically acceptable salt thereof which is active against said diseases, together with an excipient.

Especially preferred are the final products and intermediates, as well as their salts, where salt-forming groups are present, and the reaction procedures or any parts thereof mentioned in the subsequent examples and in the figures:

The following examples illustrate methods for the total synthesis of epothilone A(1), epothilone B(2), designed analogs and the generation of epothilone libraries. The examples rely inter alia on the olefin metathesis reaction and macrocyclization as a means to form the macrocyclic ring. The disclosed methods promise the discovery of anticancer agents which will be superior to existing ones. The examples represent exemplary conditions which demonstrate the versatility of the methodology and are not meant to be restricted to the modes and compounds or intermediates disclosed.

EXAMPLE 1

Solution Phase Synthesis of Epothilone A and B and analogs Using an Olefin Metathesis Approach (FIGS. 1–10)

A method using the olefin metathesis approach to synthesize epothilone A(1) and several analogs (39–41, 4244, 51–57, 58–60, 64–65, and 67–69) is described (FIGS. 1–10). In this example, we describe the details of our olefin metathesis approach to epothilone A(1) and its application to the synthesis of several of its analogs. Key building blocks 6, 7 and 8 were constructed in optically active form and were coupled and elaborated to olefin metathesis precursor 4 via an aldol reaction and an esterification coupling. Olefin metathesis of compound 4, under the catalytic influence of $RuCl_2(=CHPh)(PCy_3)_2$ catalyst, furnished cis- and trans-cyclic olefins 3 and 48. Epoxidation of 49 gave epothilone A(1) and several analogs, whereas epoxidation of 50 resulted in additional epothilones. Similar elaboration of isomeric as well as simpler intermediates resulted in yet another series of epothilone analogs and model systems.

Figure 2:
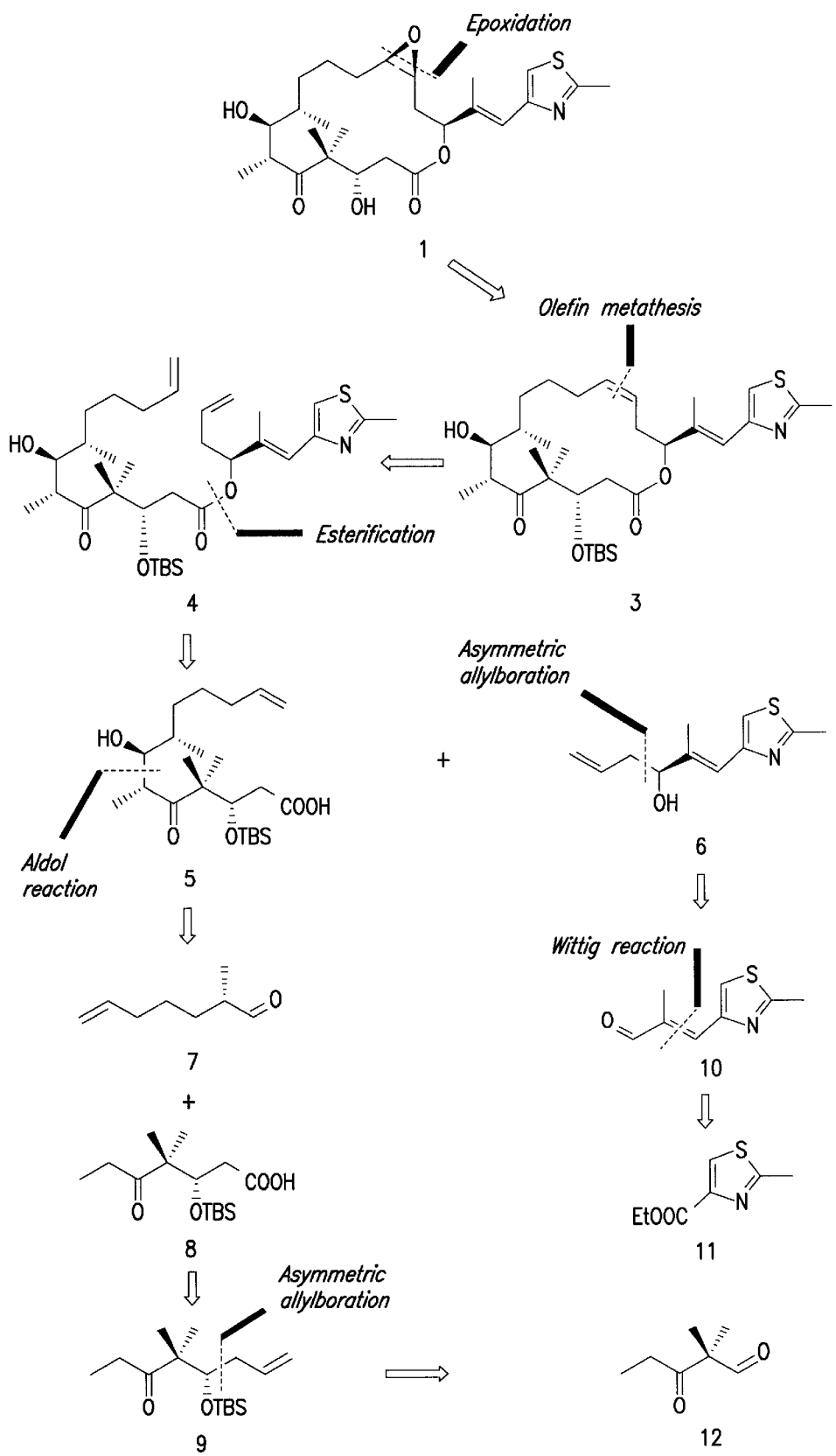
FIG. 2 illustrates the retrosynthetic analysis of the natural product compound epothilone A (1).

A. Retrosynthetic Analysis and Strategy (FIG. 2)

Figure 1:
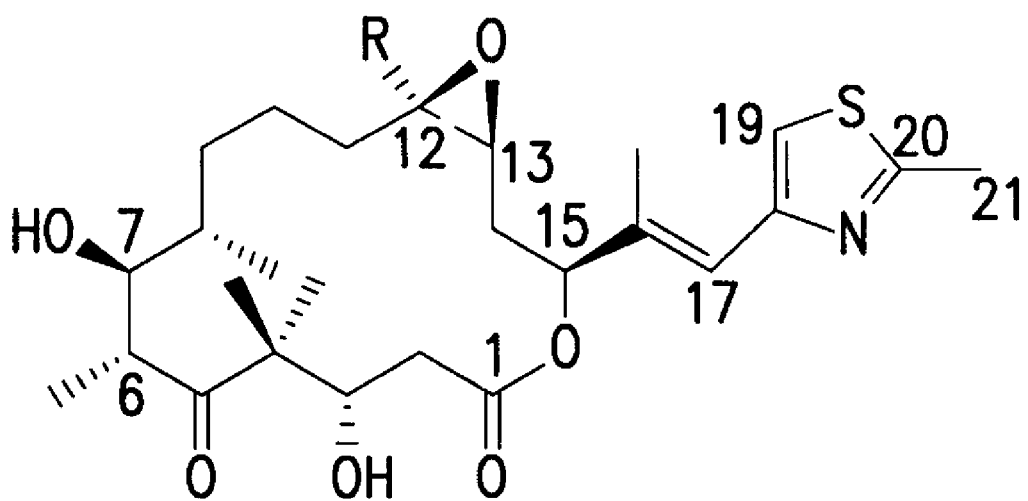
FIG. 1 illustrates the structure and numbering of epothilone A(1) and B(2).

The structure of epothilone A(1) is characterized by a 16-membered macrocyclic lactone carrying a cis-epoxide moiety, two hydroxyl groups, two secondary methyl groups, and a gem dimethyl group, as well as a side-chain consisting of a trisubstituted double bond and a thiazole moiety (FIG. 1). With its seven stereocenters and two geometrical elements, epothilone A(1) presents a considerable challenge as a synthetic target, particularly with regard to stereochemistry and functional group sensitivity. In search for a suitable synthetic strategy, we sought to apply new principles of organic synthesis and, at the same time, retain optimum flexibility for structural diversity and construction of libraries.

In recent years, the olefin metathesis reaction became a powerful tool for organic synthesis (For the development of the olefin metathesis as a ring forming reaction, see: Zuercher et al. J. Am. Chem. Soc. 1996, 118, 6634–6640; Schwab et al. J. Am. Chem. Soc. 1996, 118, 100–110; Grubbs et al. Acc. Chem. Res. 1995, 28, 446–452; Tsuji et al. Tetrahedron Lett. 1980, 21, 2955–2959; Katz et al. Tetrahedron Lett. 1976, 4247–4250; Katz et al. Tetrahedron Lett. 1976, 4241–4254; Katz et al. J. Am. Chem. Soc. 1976, 98, 606–608; Katz et al. Advances in Organomet. Chem. 1977, 16, 283317).

In particular, a number of publications report application of this chemistry to the construction of macrocycles (For a number of applications of the olefin metathesis reaction in medium and large ring synthesis, see: Borer et al. Tetrahedron Lett. 1994, 35, 3191–3194; Clark et al. J. Am. Chem. Soc. 1995, 117, 12364–12365; Houri et al. J. Am. Chem. Soc. 1995, 117, 2943–2944; Fürstner et al. J. Org. Chem. 1996, 61, 3942–3943; Martin et al. Tetrahedron 1996, 52, 7251–7264; Xu et al. J. Am. Chem. Soc. 1996, 118, 10926–10927).

Inspection of the structure of epothilone A(1; FIG. 2) reveals the intriguing possibility of applying the olefin metathesis reaction to bis(terminal) olefin 4 to yield the cis-olefin containing macrocyclic lactone 3, which could be converted to the natural product by simple epoxidation, as retrosynthetically outlined in FIG. 2. Daring as it was, this strategy has the potential of delivering both the cis- and trans-cyclic olefins corresponding to 4 for structural variation. Proceeding with the retrosynthetic analysis, an esterification reaction was identified as a means to allow disconnection of 4 to its components, carboxylic acid 5 and secondary alcohol 6. The aldol moiety in 5 allows the indicated disconnection, defining the aldehyde 7 and keto acid 8 as potential intermediates. Carboxylic acid 8 can then be traced to intermediate 9, whose asymmetric synthesis via allylboration of the known keto aldehyde 12 is straightforward. An asymmetric allylboration can also be envisioned as a means to construct alcohol 6, leading to precursor 10, which can be derived from the known thiazole derivative 11. This retrosynthetic analysis led to a highly convergent and flexible synthetic strategy, the execution of which proved to be highly rewarding in terms of delivering epothilone A(1) and a series of analogs of this naturally occurring substance for biological screening (FIG. 2).

B. Construction of Key Building Blocks and Models as Illustrated in FIGS. 3–6

As a prelude to the total synthesis, a number of building blocks were synthesized and utilized in model studies. Thus, fragments 7, 18a, 18b and 21 (FIG. 3; schemes A–C) were targeted for synthesis. Aldehyde 7 was constructed by two different routes, one of which is summarized in FIG. 3A. Thus, Oppolzer's acylated sultam derivative 13 (Oppolzer et al. Tetrahedron Lett. 1989, 30, 5603–1989; Oppolzer et al. Pure & Appl. Chem. 1990, 62, 1241–1250) was alkylated with 5-iodo-1-pentene in the presence of sodium bis (trimethylsilyl)amide (NaHMDS) to furnish compound 14 as a single diastereoisomer (by $^1$H NMR). Lithium aluminum hydride reduction of 14 gave alcohol 15 in 60% overall yield from sultam 13. Oxidation of 15 with tetrapropylammonium perruthenate(VII) (TPAP) and 4-methylmorpholine-N-oxide (NMO) yielded the desired aldehyde 7 in 95% yield.

Figure 3I:
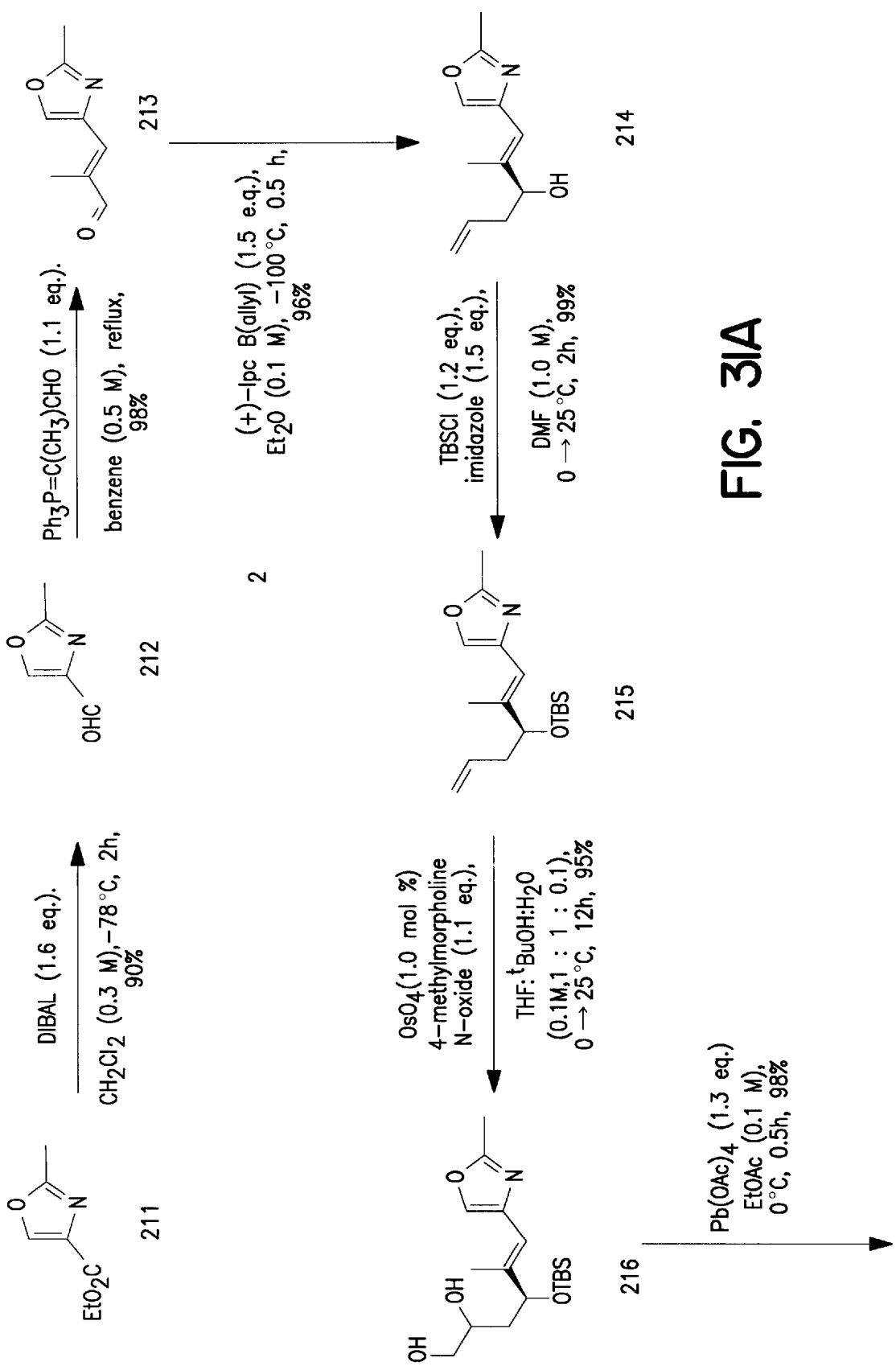
FIG. 3 illustrates the synthesis of 3 building block substrates wherein A) represents the synthesis of aldehyde 7 with reagents and conditions as follows: (a) 1.05 equivalents of NaHMDS, 2.0 equivalents of n-$C_5H_9I$, 3.0 equivalents HMPA, −78 to 25° C., 5 hours; (b)1.1 equivalents of LiAlH$_4$, THF, −78° C., 15 minutes, 60% (2 steps); (c) 1.5 equivalents of NMO, 5 mol % of TPAP, Methylene chloride, 4 Å MS, 25° C., 0.5 hour, 95%. NaHMDS=sodium bis(trimethylsilyl) amide; HMPA=hexamethylphosphoramide, NMO=4-methylmorpholine-N-oxide; TPAP=tetrapropyl ammonium perruthenate; B) represents the synthesis of alcohols 18a and 18b. Reagents and conditions: (a) 1.3 equivalents of TPSCl, 2.0 equivalents of imidazole, DMF, 0 to 25° C., 1.5 hours (90% of 17a, 94% of 17b); (b) 1.25 equivalents of tetravinyltin, 5.0 equivalents of n-BuLi, THF, −78° C., 45 minutes, then 2.5 equivalents of CuCN in THF, −78 to −30° C.; then 17a or 17b in THF, −30° C., 1 hour, 18a (86%), 18b (83%) (TPS=SiPh$_2$tBu); C) represents the synthesis of ketoacid 21. Reagents and conditions: (a) 1.2 equivalents of 19, 1.6 equivalents of NaH, THF, 0→25 C, 1 hour, 99%; (b) CF$_3$COOH:Methylene chloride (1:1), 25 C, 0.5 hour, 99%.
Figure 3I:
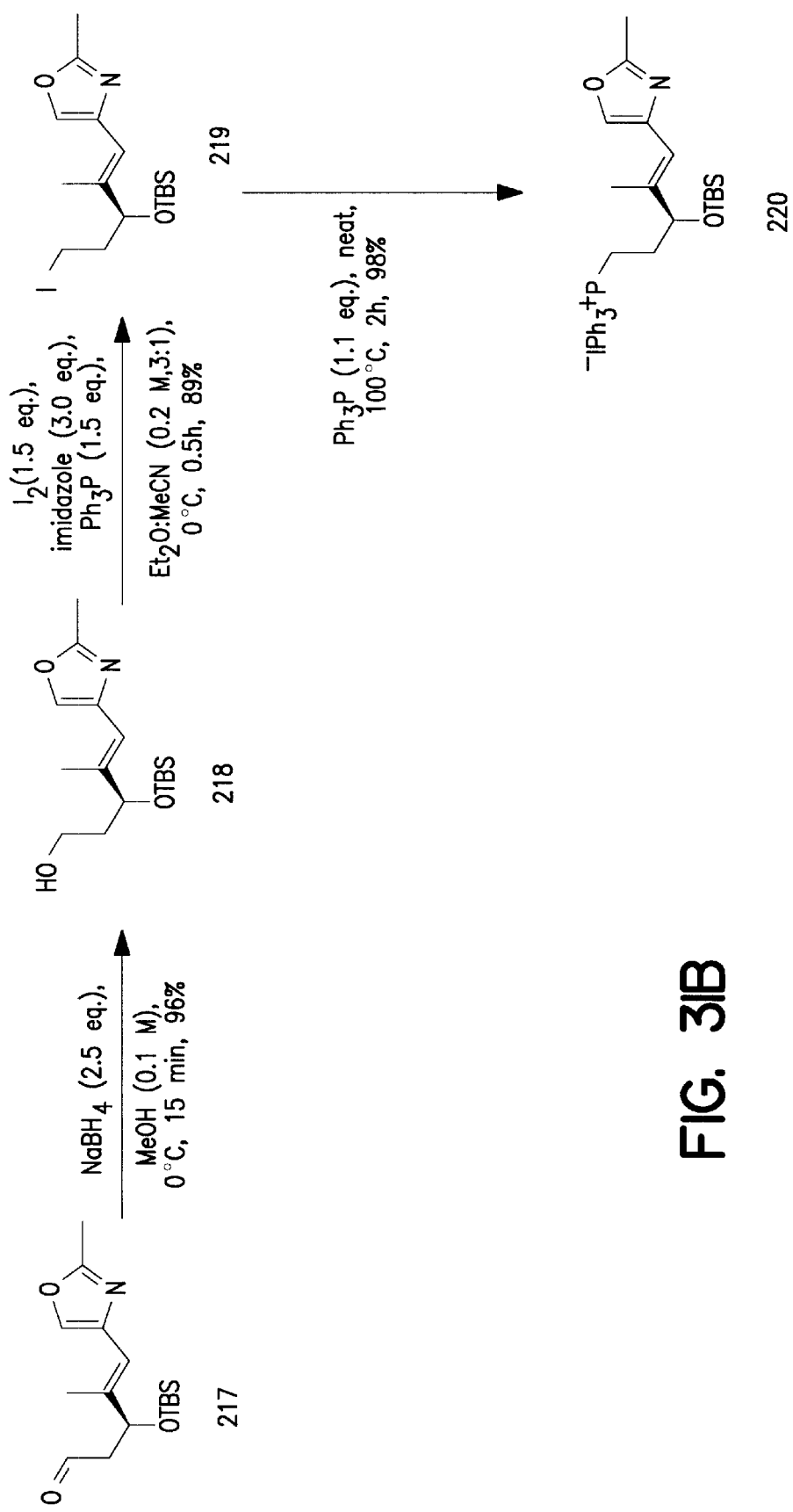

The synthesis of the two antipodal alcohols 18a and 18b is outlined in FIG. 3B. Thus, glycidols 16a and 16b were converted to the corresponding tert-butyldiphenylsilyl ethers (OTPS) 17a (90% yield) and 17b (94% yield), respectively, by a standard procedure (TPSCl, imidazole), and then to 18a (86% yield) and 18b (83% yield) by reaction with the vinyl cuprate reagent derived from copper(I) cyanide and vinyllithium.

FIG. 3C summarizes the synthesis of the third required building block, keto acid 21, starting with the known and readily available keto aldehyde 12 (Inuka et al. J. Org. Chem. 1967, 32, 404–407). Condensation of 12 with the sodium salt of phosphonate 19 produced, β-unsaturated ester 20 in 99% yield. Cleavage of the tertbutyl ester with $CF_3COOH$ in methylene chloride resulted in a 99% yield of carboxylic acid 21.

Figure 4:
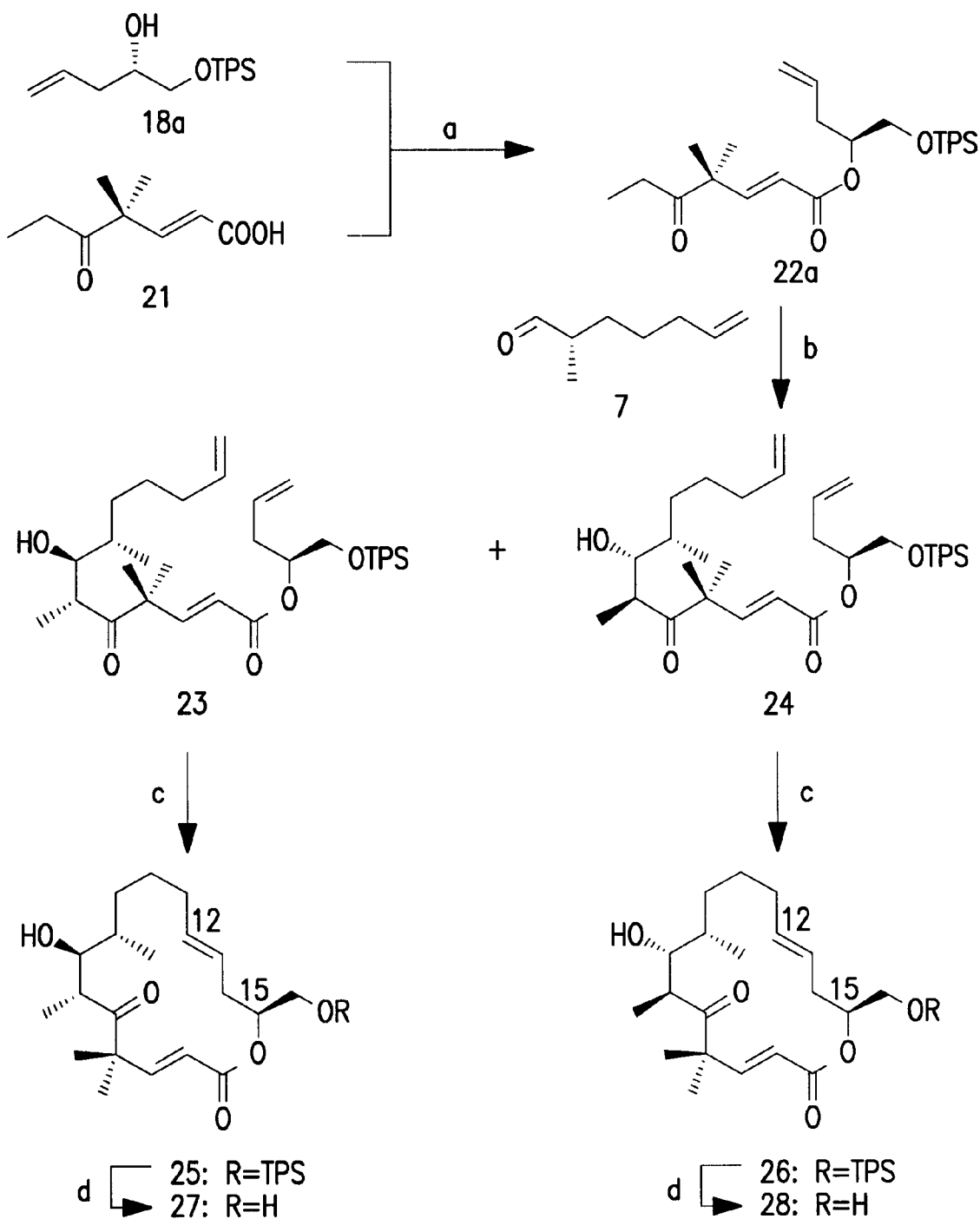
FIG. 4 illustrates the synthesis of the epothilone cyclic framework via olefin metathesis: the 15S series. Reagents and conditions: (a) 1.2 equivalents of EDC, 0.1 equivalent of 4-DMAP, Methylene chloride, 0→25° C., 12 hours, 86%; (b) 21, 1.2 equivalents of LDA, −78 C→−40° C., THF, 45 minutes; then 1.6 equivalents of 7 in THF, −78→−40° C., 0.5 h, 23 (42%), 24 (33%); (c) 0.1 equivalent of RuCl$_2$ (=CHPh)(PCy$_3$)$_2$, methylene chloride, 25° C., 12 hours, 25 (85%), 26 (79%); (d) 2.0 equivalents of TBAF, 5.0 equivalents of AcOH, 25° C., 36 hours, 27 (92%), 28 (95%). DCC=dicyclohexylcarbodiimide, 4-DMAP=4-dimethylaminopyridine, LDA=lithium diisopropylamide.

With the requisite fragments in hand, we turned our attention to a feasibility study of the olefin metathesis strategy. FIG. 4 summarizes the results of our work in this area. Thus, coupling of fragments 18a and 21, mediated by the action of EDC and 4-DMAP, led to ester 22a in 86% yield. Aldol condensation of the lithium enolate of keto ester 22a (generated by the action of LDA) and aldehyde 7 resulted in the formation of aldols 23 and 24 in ca. 4:3 ratio. Chromatographic separation allowed the isolation of pure 23 (42% yield) and 24 (33% yield). The stereochemical assignments of compounds 23 and 24 were based on an X-ray crystallographic analysis of a subsequent intermediate as will be described below. In FIG. 4, exposure of 23 to the $RUCl_2(=CHPh)(PCy_3)_2$ catalyst in methylene chloride solution under high-dilution conditions at 25° C. for 12 hours resulted in clean formation of a single transmacrocyclic olefin (25) ($J_{12,13}$=15.5 Hz) in 85% yield. Similar treatment of 24 generated the diastereomeric trans-olefin 26 ($J_{12,13}$=15.2 Hz) as the sole product in 79% yield. Desilylation of 25 and 26 with TBAF and AcOH in THF at 25° C. gave dihydroxy lactones 27 (92% yield) and 28 (95% yield, mp 128–129 C, EtOAc-hexanes), respectively.

X-ray crystallographic analysis of macrocyclic diol 28 revealed the trans nature of the double bond and defined the stereochemistry of all stereogenic centers. Comparison of the $^1$H NMR spectra of 26 and 28 with those of 25 ($J_{12,13}$=15.5 Hz), 27, 31 ($J_{12,13}$=15.7 Hz) and 32 (vide infra) supported the trans geometry of the double bond generated by the olefin metathesis, and the C6–C7 stereochemistry. Therefore, the original assignment (Nicolaou et al. Angew. Chem. Int. Ed. Engl. 1996, 35, 2399–2401) of the cis geometry for this double bond and the C6–C7 stereochemistry of the aldol products in these model systems should now be revised as shown. Ironically, it was this erroneous, but encouraging assignment that let us to embark on the final plan to synthesize epothilone A by the olefin metathesis approach. As events unfolded (vide infra), the real system produced both the cis- and the trans-cyclic olefins and the metathesis approach turned out to be fruitful.

Figure 5:
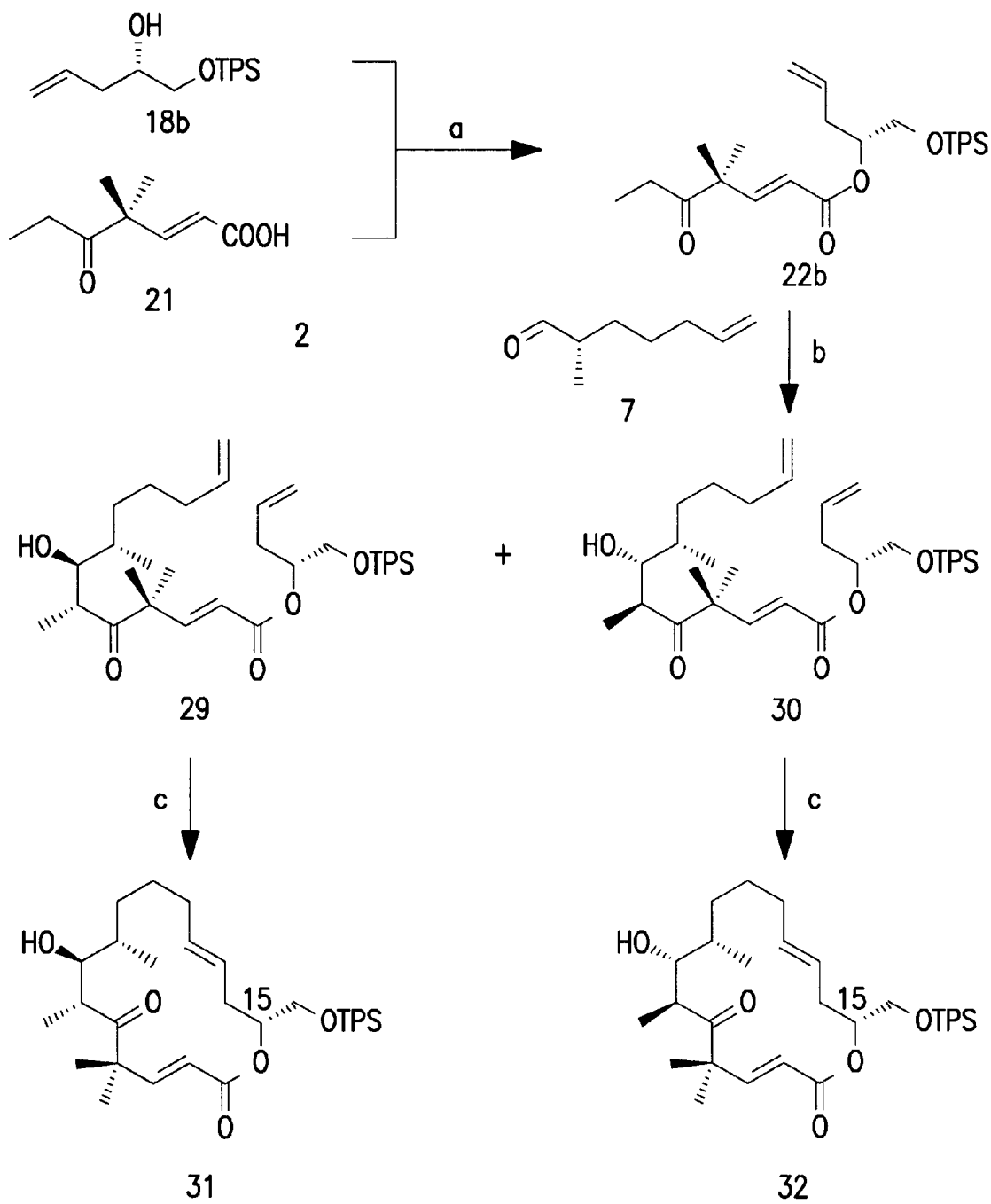
FIG. 5 illustrates the synthesis of the epothilone cyclic framework via olefin metathesis: the 15R series. Reagents and conditions: (a) 1.4 equivalents of DCC, 1.4 equivalents of 4-DMAP, toluene, 25° C., 12 hours, 95%; (b) 21, 1.2 equivalents of LDA, −78° C.→−40° C., THF, 45 minutes; then 1.6 equivalents of 7 in THF, −78→−40° C., 0.5 hour, 29 (54%), 30 (24%); (c) 0.1 equivalent of RuCl$_2$(=CHPh) (PCy$_3$)$_2$, methylene chloride, 25° C., 12 hours, 31 (80%), 32 (81%).

For the purposes of analog synthesis, the 15R fragment 18b was utilized in these studies as well, as shown in FIG. 5. Coupling of 18b and 21 with DCC and 4-DMAP led to a 95% yield of ester 22b, the enantiomer of 22a. LDA-mediated aldol condensation of 22b with aldehyde 7 furnished aldols 29 (54% yield) and 30 (24% yield), which are diastereomeric with 23 and 24 of FIG. 4. Olefin metathesis of 29 and 30 with the $RuCl_2(=CHPh)(PCy_3)_2$ catalyst led to cyclic systems 31 ($J_{12,13}$=15.7 Hz) (80% yield) and 32 ($J_{12,13}$=15.4 Hz) (81% yield), respectively. Compounds 27, 28, 31 and 32 may serve as suitable precursors for the construction of a series of designed epothilones for biological investigations. At this juncture, however, it was considered more urgent to investigate the compatibility of the thiazole side-chain with the conditions of olefin metathesis and epoxidation.

Figure 6A:
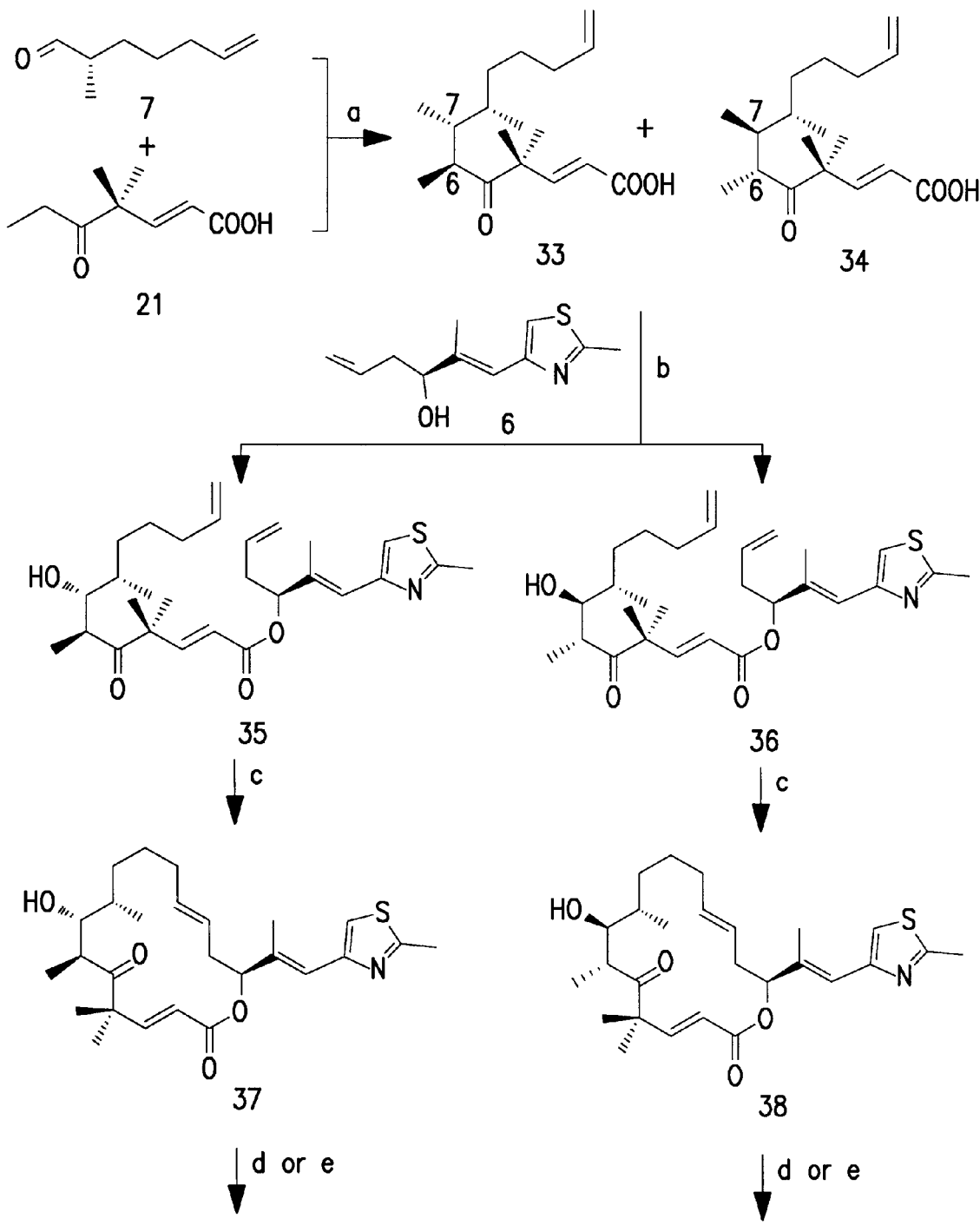
FIG. 6 illustrates the metathesis approach and epoxidation in the presence of thiazole: synthesis of epothilone analogs 39–44. Metathesis and epoxidation in the presence of thiazole: synthesis of epothilone analogs 39–44. Reagents and conditions: (a) 21, 2.3 equivalents of LDA, −78→−30° C., THF, 1.5 hours; then 1.6 equivalents of 7 in THF, −78→−40° C., 1 h (33:34, 2:3); (b) ca 2.0 equivalents of 6, ca 1.2 equivalents of EDC, ca 0.1 equivalent of 4-DMAP, methylene chloride, 0→25° C., 12 hours, 35 (29%), 6 (44%) (2 steps); (c) 0.1 equivalent of RuCl$_2$(=CHPh)(PCy$_3$)$_2$, methylene chloride, 25° C., 12 hours, 7 (86%), 38 (66%); (d) 0.9–1.2 equivalents of mCPBA, CHCl$_3$, −20→0° C., 12 hours, 37→39 (or 40) (40%), 40 (or 39) (25%), 41 (18%); 38→42 (or 43) (22%), 43 (or 42) (11%), 44 (7%); (e) excess of CF$_3$COCH$_3$, 8.0 equivalents of NaHCO$_3$, 5.0 equivalents of Oxone®, CH$_3$CN/Na$_2$EDTA (2:1), 0° C., 37 39 (or 40) (45%), 40 (or 39) (28%); 38–42 (or 43) (60%), 43 (or 42) (15%). MCPBA=meta-chloroperbenzoic acid.
Figure 6B:
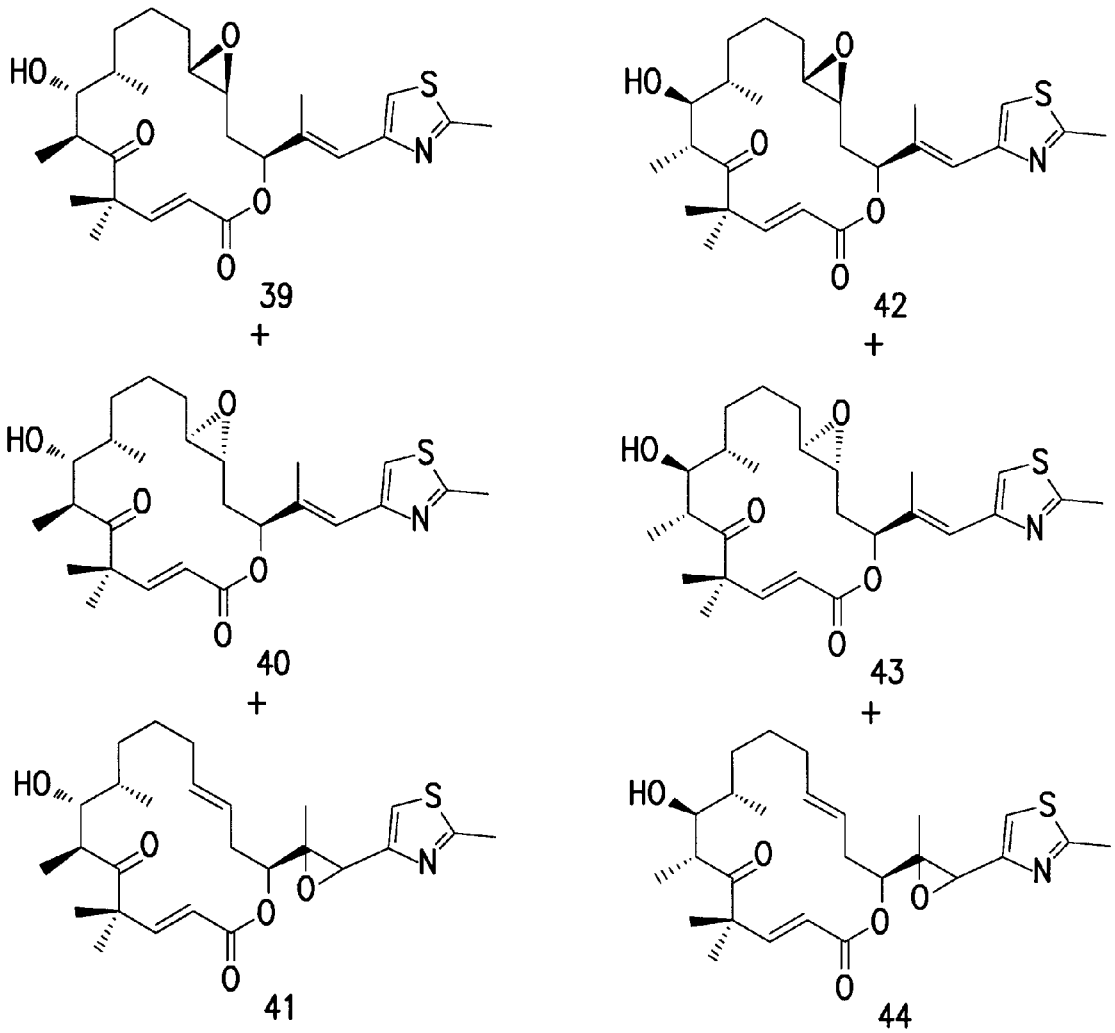
Figure 6I:
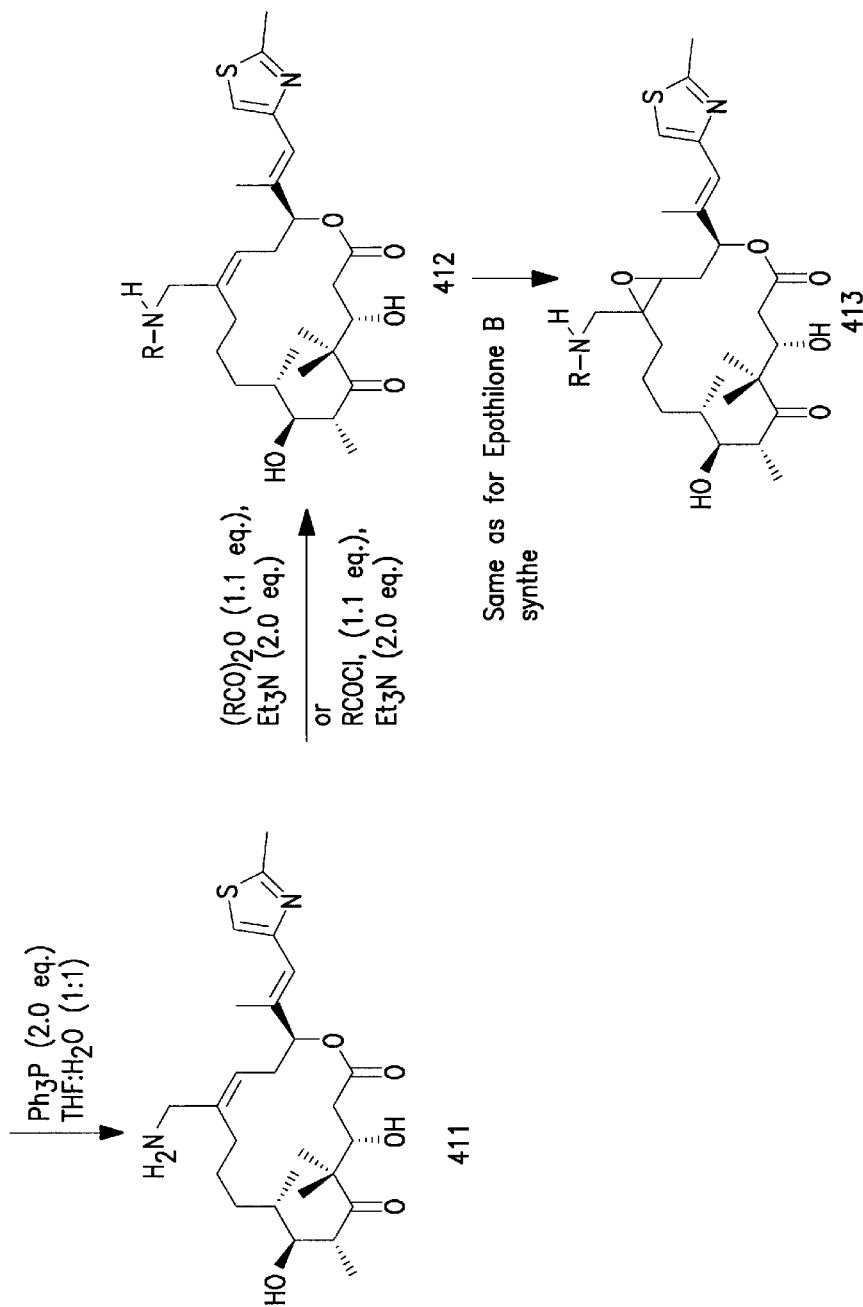

To this end, the chemistry shown in FIG. 6 was studied. The enolate of keto acid 21 (2.3 equivalents of LDA, THF, −78 C) reacted with aldehyde 7 to afford hydroxy acids 33 and 34 as a mixture of C6–C7 (ca 2:3 by $^1$H NMR) in good yield. This mixture was coupled with alcohol 6 in the presence of EDC and 4-DMAP, to afford two diastereomeric esters, 35 and 36 (29% and 44% yield, respectively, for two steps). Both products, 35 and 36 were subjected to the olefin metathesis reaction, and we were delighted to observe a smooth ring closure leading to trans-macrocycles 37 ($J_{12,13}$=15.5 Hz) (86%) and 38 ($J_{12,13}$=15.0 Hz) (66%). With cyclized product 37 and 38 in hand, we then proceeded to demonstrate the feasibility of epoxidizing the C12–C13 double bond in the presence of the sulfur and olefin functionalities in the thiazole side chain. Thus, treatment of both 37 and 38 with 0.9–1.2 equivalents of mCPBA in CHCl$_3$ at 0° C. resulted in the formation of epoxides 39 (or 40) (40%), 40 (or 39) (25%, stereochemistry unassigned), and 41 (18%, stereochemistry unassigned), as well as 42 (or 43) (22%), 43 (or 42) (11%) and 44 (7%) along with some unidentified side products. These results paved the way for the final drive towards epothilone A(1). More recently we found that methyl(trifluoromethyl)dioxirane (Yang et al. J. Org. Chem. 1995, 60, 3887–3889) gives superior results in the epoxidation reactions in regard to regioselectivity and yields. Thus, olefins 37 and 38 were converted to epoxides 39 (or 40) (45%) and 40 (or 39) (28%), and epoxides 42 (or 43) (60%) and 43 (or 42) (15%), respectively. No side-chain epoxidation was observed in either case.

C. Total Synthesis of Epothilone A and Analogs

Figure 7:
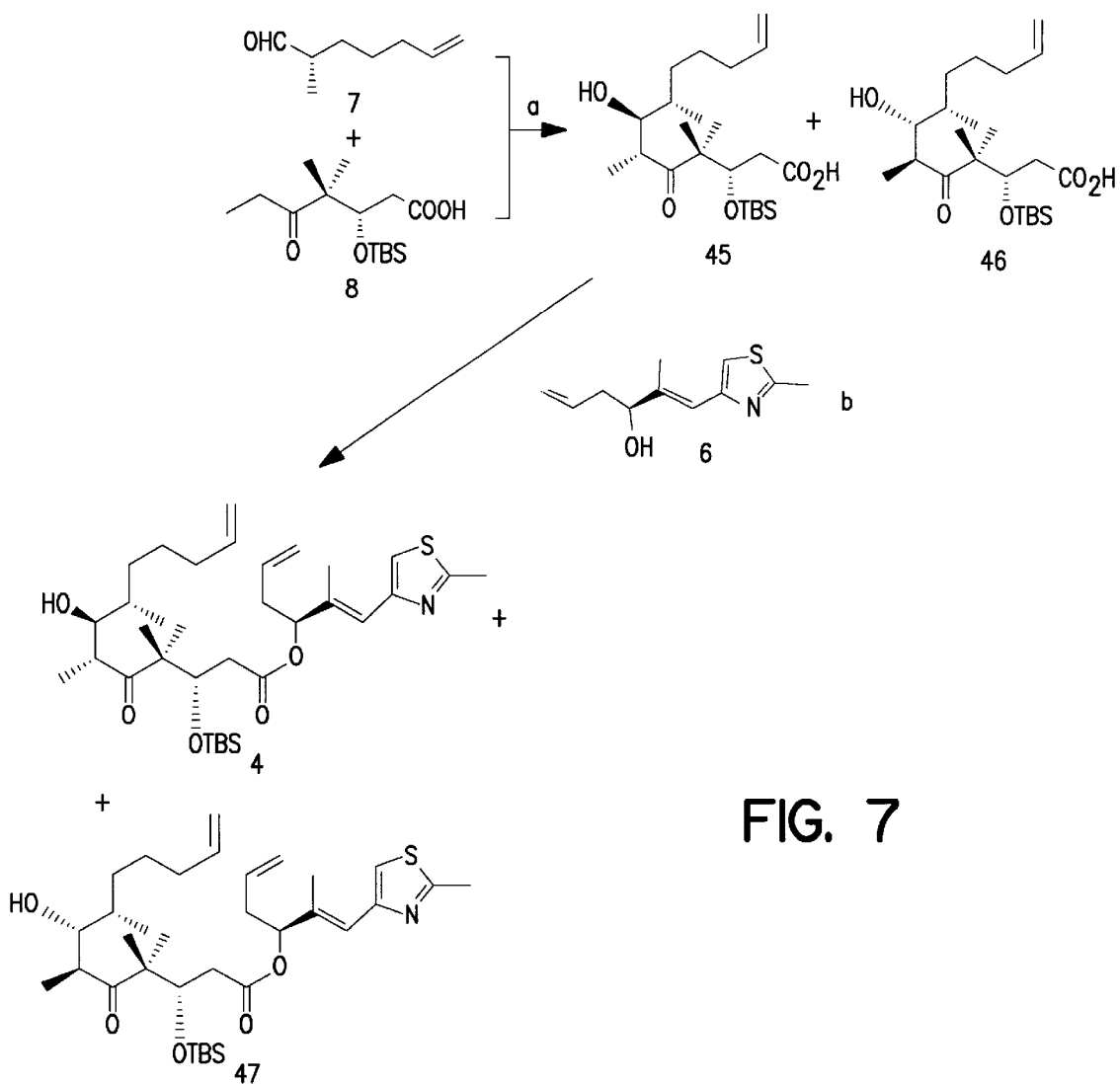
FIG. 7 illustrates the coupling of building blocks 6–8. Reagents and conditions: (a) 8, 2.3 equivalents of LDA, −78→−30° C., THF, 1.5 hours; then 1.6 equivalents of 7 in THF, −78→−40° C., 1 hour (45:46, 3:2); (b) ca 2.0 equivalents of 6, ca 1.2 equivalents of EDC, ca 0.1 equivalent of 4-DMAP, methylene chloride, 0→25° C., 12 hours, 4 (52%), 47 (31%) (2 steps).

Encouraged by the results of the model studies described above, we proceeded to assemble epothilone A(1). FIG. 7 shows the initial stages of the construction beyond the key building blocks 6–8. Thus, aldol condensation of 8 (2.3 equivalents of LDA) with aldehyde 7 afforded diastereomeric products 45 and 46 (ca 3:2 ratio by $^1$H NMR), which were coupled as a mixture with allylic alcohol 6 in the presence of EDC and 4-DMAP, to afford, after chromatographic purification, pure esters 4 (52% overall from 8) and 43 (31% overall from 8).

Figure 8A:
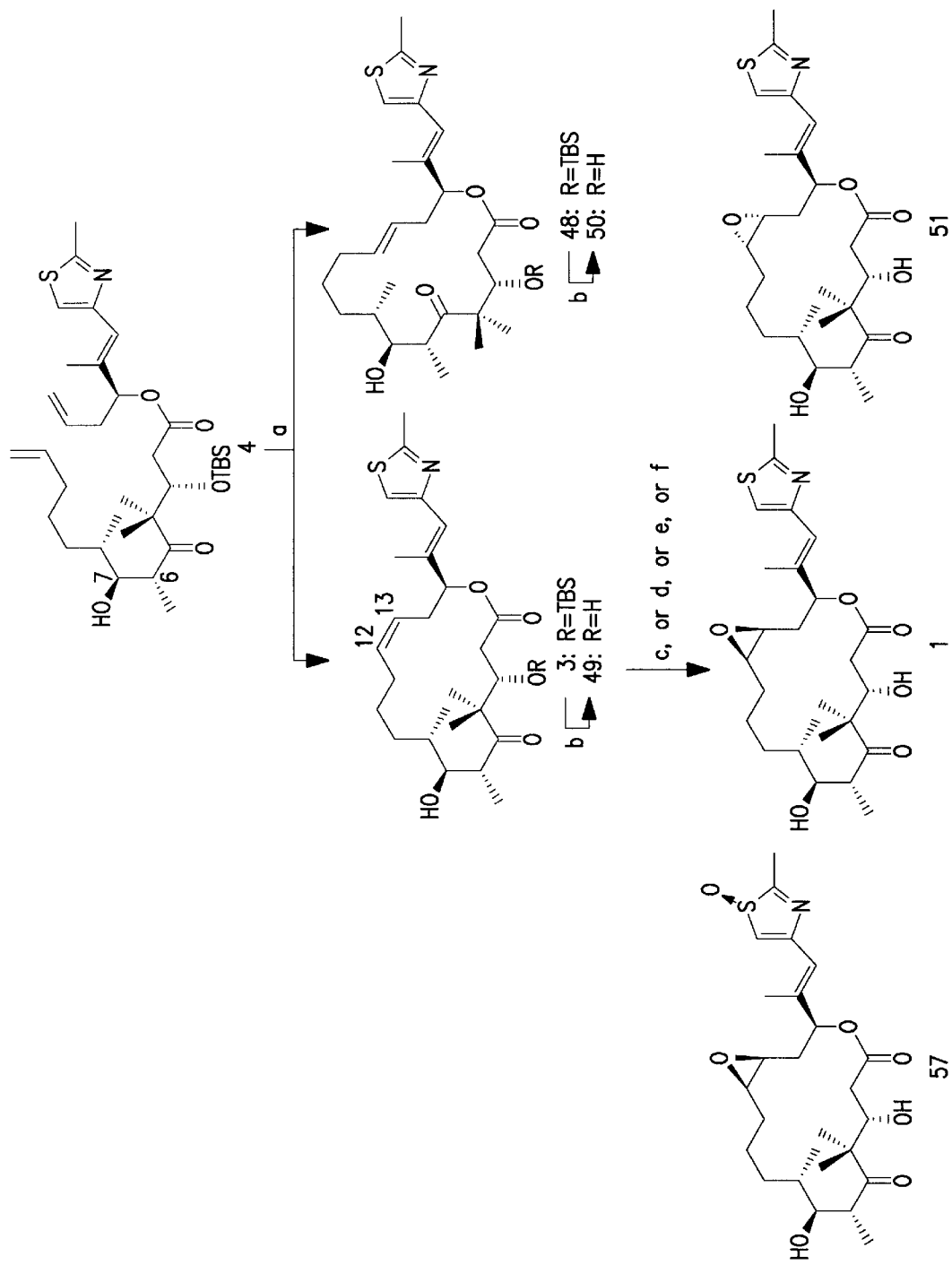
FIG. 8 illustrates the epoxidation of epothilone framework: total synthesis of epothilone A (1) and analogs 51–57. Epoxidation of epothilone framework: total synthesis of epothilone A (1) and analogs 51–57. (a) 0.1 equivalent of RuCl$_2$(=CHPh)(PCy$_3$)$_2$, methylene chloride, 25° C., 20 hours, 3 (46%), 48 (39%); (b) 20% CF$_3$COOH in methylene chloride, 0° C., 3 h, 3→49 (90%); 48→50 (92%); (c) 0.8–1.2 equivalents of mCPBA, CHCl$_3$, −20→0° C., 12 h, 49→1 (35%), 51 (13%), 52 (or 53) (9% ), 53 (or 52) (7%), 54 (or 55) (5%), 55 (or 54) (5%); 1→54 (or 55) (35%%), 55 (or 54) (33%), 57 (6%); (d) 1.3–2.0 equivalents of mCPBA, CHCl$_3$, −20→0° C., 12 hours, 1 (15%), 51 (10%), 52 (or 53) (10%), 53 (or 52) (8%), 54 (or 55) (8%), 55 (or 54) (7%), 56 (5%), 57 (5%); (e) 1.0 equivalent of dimethyidioxiran CH$_2$Cl$_2$/acetone, 0 C, 1 (50%), 51 (15%), 52 (or 53) (5%), 53 (or 52) (5%); (f) excess of CF$_3$COCH$_3$, 8.0 equivalents of NaHCO$_3$, 5.0 equivalents of Oxone®, CH$_3$CN/Na$_2$EDTA (2:1), 0 C, 1 (62%), 51 (13%).
Figure 8B:
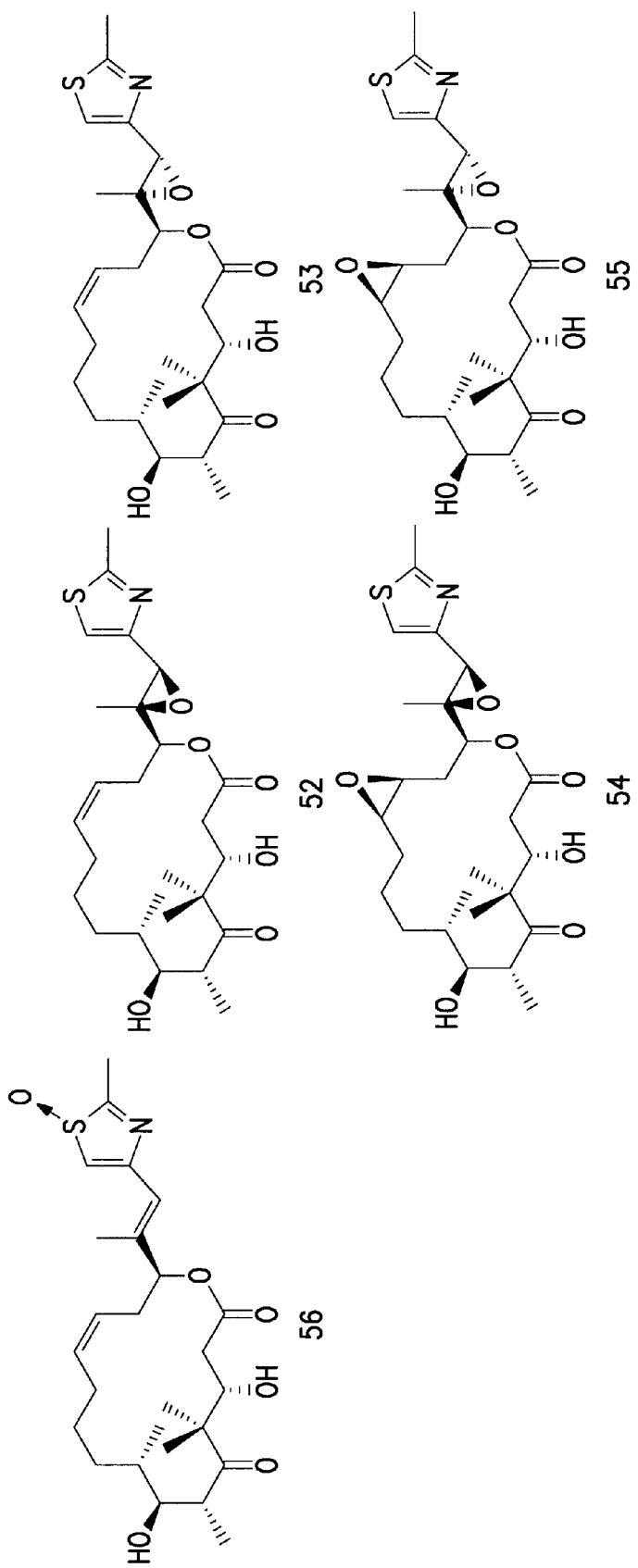

The olefin metathesis reaction of 4 (6R,7S stereochemistry as proven by conversion to epothilone A) proceeded smoothly in the presence of the RuCl$_2$(=CHPh)(PCy$_3$)$_2$ catalyst, as shown in FIG. 8, to afford cyclic systems 8 ($J_{12,13}$=10.5 Hz) (46%) and 48 ($J_{12,13}$=15.0 Hz) (39%). The silyl ethers from 3 and 48 were removed by exposure to CF$_3$COOH in methylene chloride, affording dihydroxy compounds 49 (90% yield) and 50 (92% yield), respectively.

The cis-olefin 49 was converted to epothilone A(1) by the action of mCPBA (0.8–1.2 equivalents) in a reaction that, in addition to 1 (35% yield), produced the isomeric epoxides 51 (13% yield), 52 (or 53) (9% yield, stereochemistry unassigned) and 53 (or 52) (7% yield, stereochemistry unassigned), as well as bis(epoxides) 54 (or 55) and 55 (or 54) (10% total yield, stereochemistry unassigned). Reaction of olefin 49 with excess mCPBA (1.3–2.0 equivalents) gave a different product distribution: 1 (15%), 51 (10%), 52 (or 53) (10%), 53 (or 52) (8%), 54 (or 55) (8%), 55 (or 54) (7%), 56 (5%), and 57 (5%). The action of dimethyldioxirane (Murray et al. J. Org. Chem. 1985, 50, 2847–2853) (Methylene chloride, 0 C) on 49 gave mainly 1 (50%) and 51 (15%), together with small amounts of 53 (or 54) and 54 (or 53) (10% total yield).

However, we found that the preferred procedure for this epoxidation was the one employing methyl(trifluoromethyl)dioxirane (CH$_3$CN, Na$_2$EDTA, NaHCO$_3$, Oxone®, 0 C; Yang et al. J. Org. Chem. 1995, 60, 3887–3889), a method that furnished epothilone A(1) in 62% yield, together with smaller amount of its -epoxide epimer 51 (13% yield). Chromatographically purified synthetic epothilone A(1) exhibited identical properties to those of an authentic sample (TLC, HPLC, [ ]$_D$, IR, $^1$H and $^{13}$C NMR, and Mass spec). Further, epoxidation of pure 1 with mCPBA (0.8–1.1 equivalents) resulted in the formation of bis (epoxides) 54 (or 55) (35%) and 55 (or 54) (32%) along with sulfoxide 57 (6%), confirming the C12–C13 stereochemical assignments shown in FIG. 8. Under similar conditions, -isomeric epoxide 51 was recovered unreacted.

Figure 9:
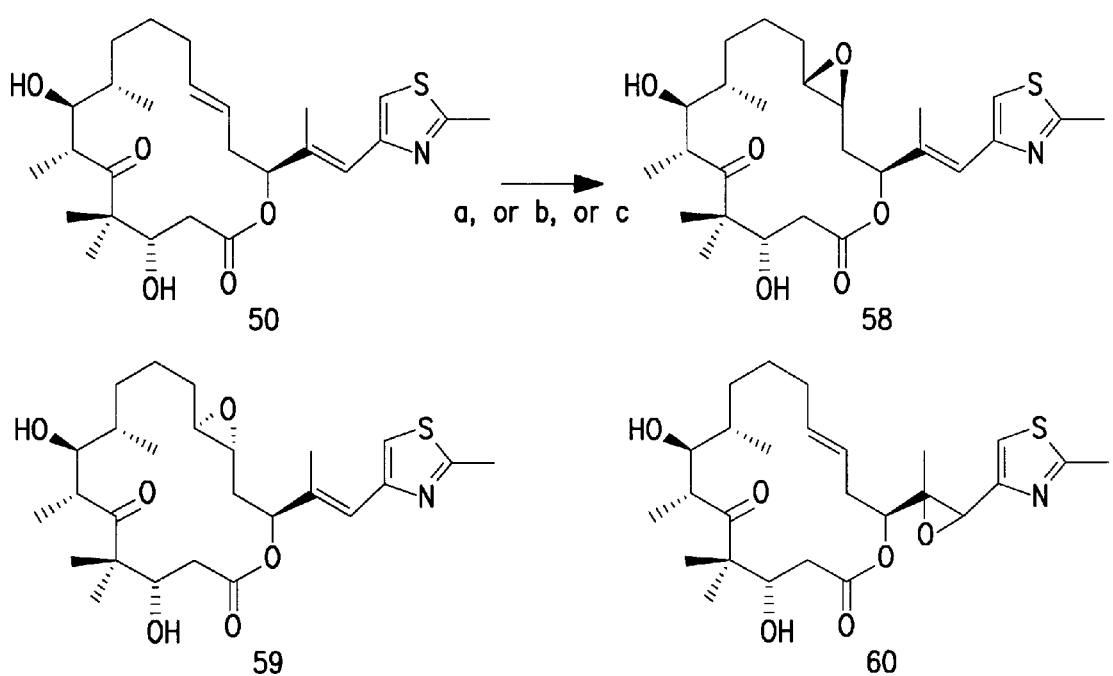
FIG. 9 illustrates the synthesis of epothilones 58–60. Reagents and conditions: (a) 0.9–1.3 equivalents of mCPBA, CHCl$_3$, −20 to 0° C., 12 hours, 58 (or 59) (5%), 59 (or 58) (5%), 60 (60%); (b) 1.0 equivalent of dimethyldioxirane, methylene chloride/acetone, 0° C., 58 (or 59) (10%), 59 (or 58) (10%), 60 (40%); (c) excess of CF$_3$COCH$_3$, 8.0 equivalents of NaHCO$_3$, 5.0 equivalents of Oxone®, MeCN/Na$_2$EDTA (2:1), 0 C, 58 (or 59) (45%), 59 (or 58) (35%).

The trans-olefinic compound 50 gave rise to another series of epothilones A (58–60) as shown in FIG. 9. Thus, epoxidation of 50 with 1.0 equivalent of mCPBA furnished compounds 58 (or 59) (5%, stereochemistry unassigned), 59 (or 58) (5%, stereochemistry unassigned) and 60 (60%, stereochemistry unassigned). Similarly, epoxidation of 50 with 1.0 equivalent of dimethyldioxirane resulted in the formation of 58 (or 59) (10%), 59 (or 58) (10%) and 60 (40%). Interestingly, however, the action of methyl (trifluoro-methyl)dioxirane led only to 58 (or 59) (45%) and 59 (or 58) (35%) in a much cleaner fashion.

Figure 10A:
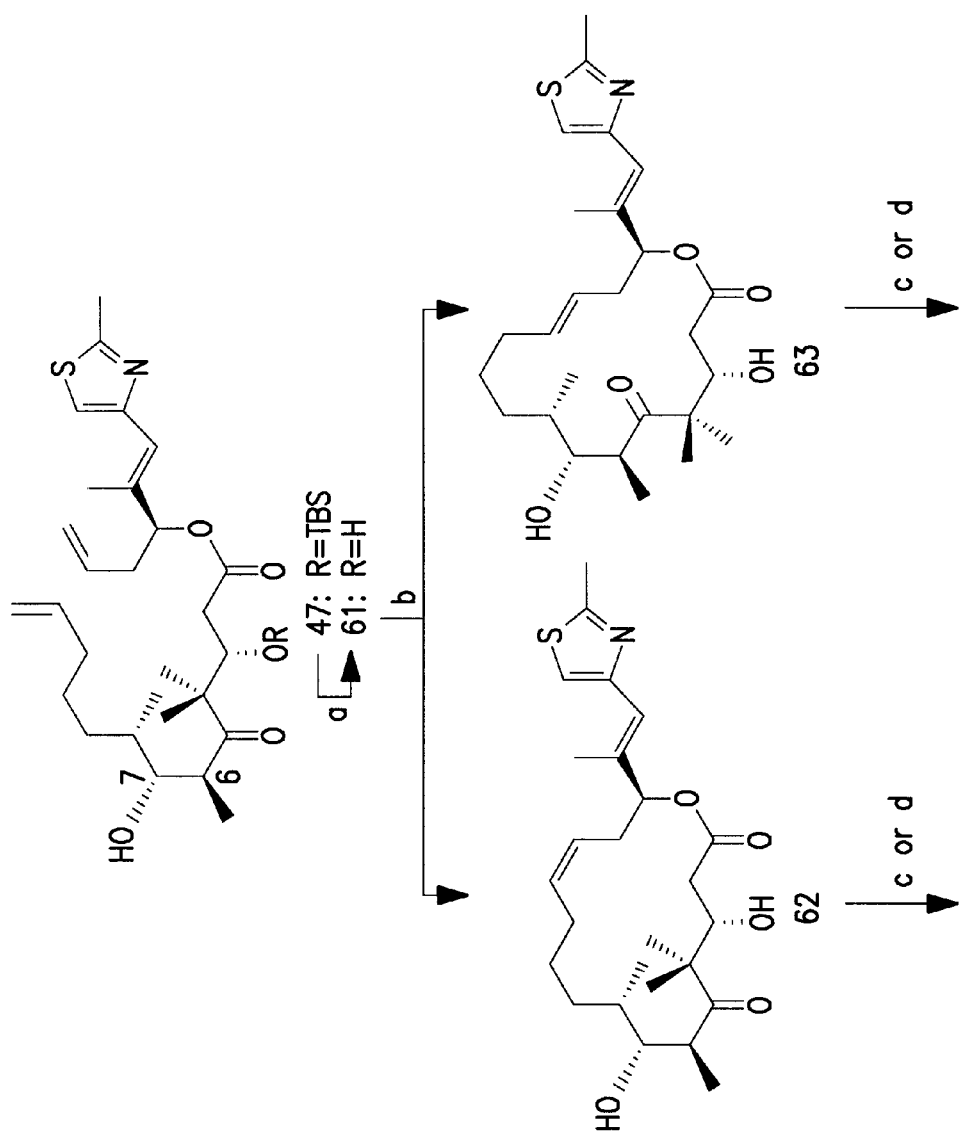
FIG. 10 illustrates the synthesis of epothilones 64–69. (a) 20% CF$_3$COOH in methylene chloride, 0° C., 3 h, 90%; (b) 0.1 equivalent of RuCl$_2$(=CHPh)(PCy$_3$)$_2$, methylene chloride, 25° C., 20 h, 62 (20%), 63 (69%); (c) 0.8–1.2 equivalents of mCPBA, CHCl$_3$, −20→0° C., 12 hours, 62→64 (or 65) (25%), 65 (or 64) (23%); 63 4 67 (or 68) (24%), 68 (or 67) (19%), 69 (31%); (d) excess of CF$_3$COCH$_3$, 8.0 equivalents of NaHCO$_3$, 5.0 equivalents of Oxone®, CH$_3$CN/Na$_2$EDTA (2:1), 0 C, 62→64 (or 65) (58%), 65 (or 64) (29%); 63→67 (or 68) (44%), 68 (or 67) (21%).
Figure 10B:
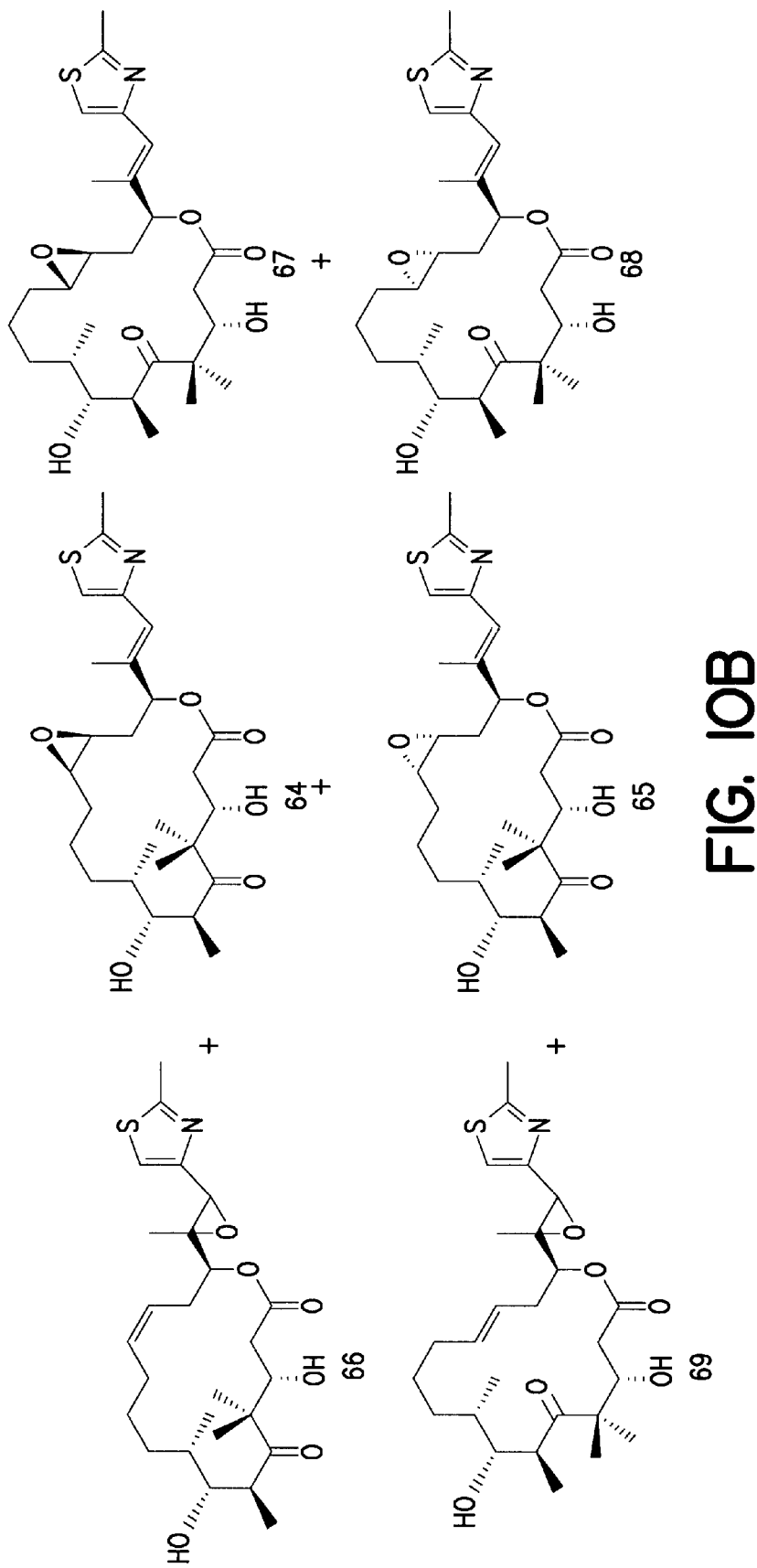

In order to expand the epothilone A library, we utilized the 6S,7R-stereoisomer 61 (obtained from 47 by CF$_3$COOH-induced desilylation in 90% yield) in the olefin metathesis reaction, to afford cyclic compounds 62 ($J_{12,13}$=9.8 Hz) (20%) and 63 ($J_{12,13}$=15.0 Hz) (69%) (FIG. 10). Epoxidation of the dihydroxy macrocyclic compound 62 with mCPBA (0.8–1.2 equivalents) in CHCl$_3$ at −20 to 0° C. gave isomeric epoxides 64 (or 65) (25%) and 65 (or 64) (23%). Side-chain epoxide 66 was not isolated in this case. Similarly, diol 63 furnished 67 (or 68) (24%), 68 (or 67) (19%), and 69 (31%) under the same reaction conditions. The stereochemistry of epothilones 64–69 remains unassigned. Again, epoxidation of compounds 62 and 63 using methyl(trifluoromethyl) dioxirane resulted in epoxides 64 (or 65) (58%) and 65 (or 64) (29%), and in epoxides 67 (or 68) (44%) and 68 (or 67) (21%), respectively, in a cleaner fashion (FIG. 10).

In example 1, we illustrate methods culminating in the total synthesis of epothilone A(1) and of analogs by an olefin metathesis approach. Furthermore, besides defining the scope and limitations of this new methodology in total synthesis, the methods provide a series of epothilone A analogs for biological investigations and further chemical explorations. The high convergence and relative simplicity of the chemistry involved in this construction make this strategy amenable to combinatorial synthesis for the generation of large libraries of these structures, as illustrated in a later example.

EXAMPLE 2

Solution Phase Synthesis of Epothilone A and B and Analogs Using a Macrolactonization Approach as Illustrated in FIGS. 11–19

In this example, we illustrate methods for the total synthesis of both epothilones A(1) and B (2) and of a number of analogs using our macrolactonization strategy (Nicolaou Angew. Chem. Int. Ed. Engl. 1997, 36, 525–527). The reported strategy relies on a macrolactonization approach and features selective epoxidation of the macrocycle double bond in precursors 70 and 71 (FIG. 1), respectively, as well as high convergency and flexibility. Building blocks 76–79 and 82 were constructed by asymmetric processes and coupled via Wittig, aldol, and macrolactonization reactions to afford the basic skeleton of epothilones and that of several of their analogs by a relatively short route. The utilization of intermediate 81, obtained via a stereoselective Wittig reaction and its Enders coupling to SAMP hydrazone 80 (FIG. 17), in combination with a stereoselective aldol reaction with the modified substrate 136 (FIG. 19) improved the stereoselectivity and efficiency of the total synthesis of these new and highly potent microtubule binding antitumor agents.

A. Retrosynthetic Analysis

Figure 11A:
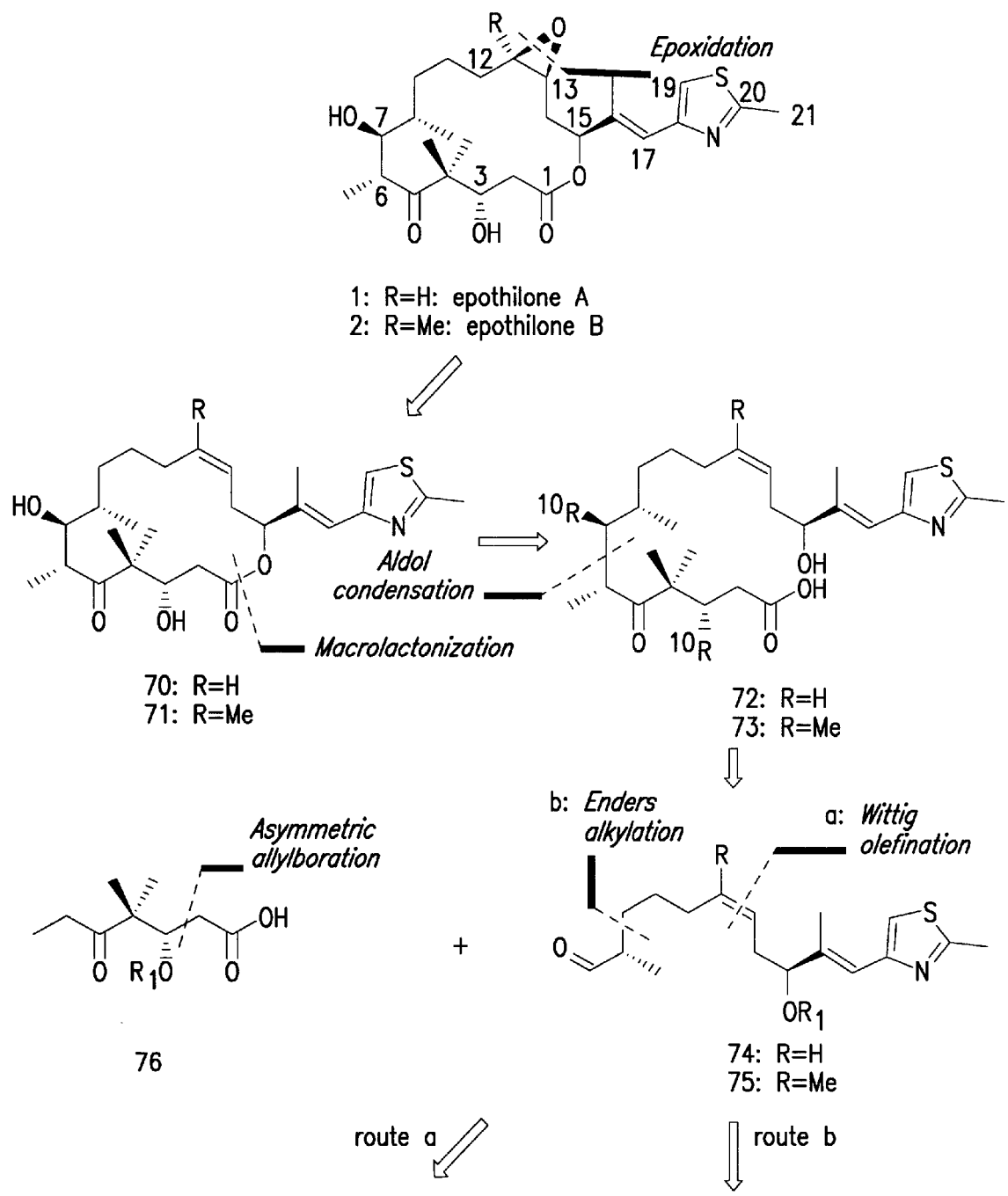
FIG. 11 illustrates the molecular structures and retrosynthetic analysis of epothilones A(1) and B(2) using the macrolactonization approach.

FIG. 11 outlines the macrolactonization-based retrosynthetic analysis of epothilones A(1) and B(2). Thus, retrosynthetic removal of the epoxide oxygen from 1 and 2 reveals the corresponding Z-olefins, 70 and 71, as potential precursors, respectively. The second major retrosynthetic step along this route is the disconnection of the macrocyclic ring at the lactone site, leading to hydroxy acids 72 and 73 as possible key intermediates. Moving further along the retrosynthetic path, an aldol-type disconnection allows the generation of keto acid 76 as a common intermediate, and aldehydes 74 and 75 as reasonable building blocks for 72 and 73, respectively. Keto acid 76 can be envisioned to arise from an asymmetric allylboration of the corresponding aldehyde, followed by appropriate elaboration of the terminal olefin. The larger intermediates, 74 and 75, can be disconnected by two slightly different ways. The first disconnection (route a) involves a retro-Wittig type reaction accompanied by a number of functional group interchanges, leading to compounds 77, 78 and 79. The second disconnection, specifically sought for its potential to address the geometry issue of the trisubstituted double bond of epothilone B(2) (route b), involves: (i) a retro-Enders alkylation, leading to hydrazone 80 and iodide 81; and (ii) a retro-Wittig type disconnection of the latter intermediate (81) to reveal aldehyde 82 and stabilized ylide 83 as potential building segments. An asymmetric allylboration of 82 then points to Brown's chiral allylborane, and an aldehyde carrying the required thiazole moiety as potential starting points.

B. Total Synthesis

Figure 12A:
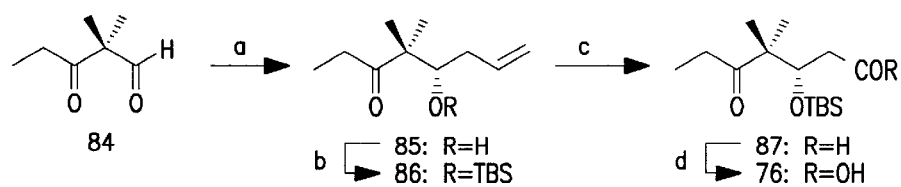
FIG. 12 illustrates the synthesis of 2 building block substrates wherein A) represents the synthesis of keto acid 76. Reagents and conditions: (a) 1.2 equivalents of (+)-Ipc$_2$B(allyl), Et$_2$O, −100° C., 0.5 hour, 74% (ee>98% by Mosher ester analysis); (b) 1.1 equivalents TBSOTf, 1.2 equivalents of 2,6-lutidine, methylene chloride, 25° C., 98%; (c) O$_3$, methylene chloride, −78° C., 0.5 hour; then 1.2 equivalents Ph$_3$P, −78→25° C., 1 hour, 90%; (d) 3.0 equivalents of NaClO$_2$, 4.0 equivalents of 2-methyl-2-butene, 1.5 equivalents of NaH$_2$PO$_4$, tBuOH:H$_2$O (5:1), 25° C., 2 hours, 93%; B) represents the synthesis of phosphonium salt 79 and aldehyde 82. Reagents and conditions: (a) 1.6 equivalents of DIBAL, methylene chloride, −78° C., 2 hours, 90%; (b) Ph$_3$P=C(CH$_3$)CHO, benzene, reflux, 98%; (c) 1.5 equivalents of (+)-Ipc$_2$B(allyl), Et$_2$O, −100° C., 0.5 hour, 96% (ee>97% by Mosher ester analysis); (d) 1.2 equivalents TBSCl, 1.5 equivalents of imidazole, DMF, 0→25° C., 2 hours, 99%; (e) i. 1.0 mol % OsO$_4$, 1.1 equivalents of 4-methylmorpholine N-oxide (NMO), THF:tBuOH:H$_2$O (1:1:0.1), 0→25° C., 12 hours, 95%; ii. 1.3 equivalents of Pb(OAc)$_4$, EtOAc, 0° C., 0.5 h, 98%; (f) 2.5 equivalents of NaBH$_4$, MeOH, 0° C., 15 minutes, 96%; (g) 1.5 equivalents of I$_2$, 3.0 equivalents of imidazole, 1.5 equivalents of Ph$_3$P, Et$_2$O:MeCN (3:1), 0° C., 0.5 hour, 89%; g. 1.1 equivalents Ph$_3$P, neat, 100° C., 2 hours, 98%.
Figure 12B:
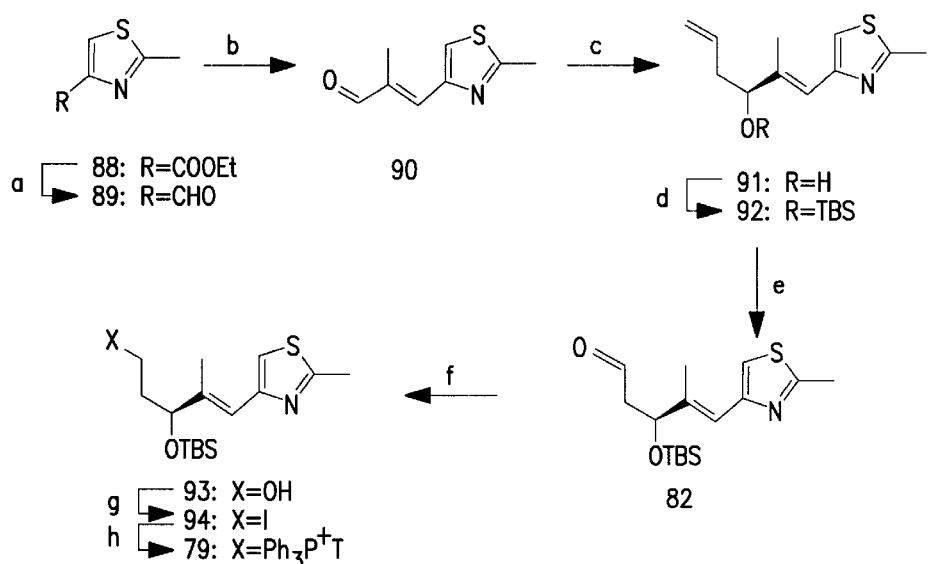

1. Construction of Building Blocks (FIGS. 12–13):

The strategy derived from the retrosynthetic analysis discussed above (FIG. 1), required building blocks 76–79, 82, and related compounds. Their construction in optically active form proceeded as follows. FIG. 12 summarizes the synthesis of keto acid 76 starting with the known keto aldehyde 84. Thus, addition of (+)-Ipc$_2$B(allyl) to 84 in ether at −100° C. resulted in the formation of enantiomerically enriched alcohol 85 (74% yield, ee>98% by Mosher ester determination). Silylation of 85 with tert-butyldimethylsilyl triflate (TBSOTf) furnished, in 98% yield, silyl ether 86. The conversion of terminal olefin 86 to carboxylic acid 76 was carried out in two steps: (i) ozonolysis in methylene chloride at −78° C. followed by exposure to Ph$_3$P to give aldehyde 87 (90% yield); and (ii) oxidation of 87 with NaClO$_2$ in the presence of 2-methyl-2-butene and NaH$_2$PO$_4$ in tBuOH-H$_2$O (5:1) (93% yield).

The synthesis of the thiazole-containing fragments 82 and 79 was accomplished as shown in FIG. 12. Thus, the known thiazole derivative 88 was reduced with DIBAL (1.6 equivalents, methylene chloride, −78° C.) to aldehyde 89 (90% yield), which reacted with the appropriate stabilized ylide [Ph$_3$P=C(Me)CHO] in benzene at 80° C. to afford the required (E)-, β-unsaturated-aldehyde 90 in 98% yield. Addition of (+)-Ipc$_2$B(allyl) to 90 in ether/pentane at −100° C. gave allylic alcohol 91 in 96% yield (>97% ee by Mosher ester analysis). Protection of the hydroxyl group in 91 as a TBS ether (TBSCl, imid., DMF, 99% yield), followed by chemoselective dihydroxylation (OsO$_4$ cat., NMO) of the terminal olefin (95% yield) and Pb(OAc)$_4$ cleavage of the resulting diol (98% yield), furnished aldehyde 82 via intermediate 92. Finally, NaBH$_4$ reduction of 82 (96% yield), followed by iodination (I$_2$, imidazole, Ph$_3$P, 89% yield) and phosphonium salt formation (Ph$_3$P, neat, 98% yield) gave the requisite fragment 79 via the intermediacy of alcohol 93 and iodide 94.

Figure 13:
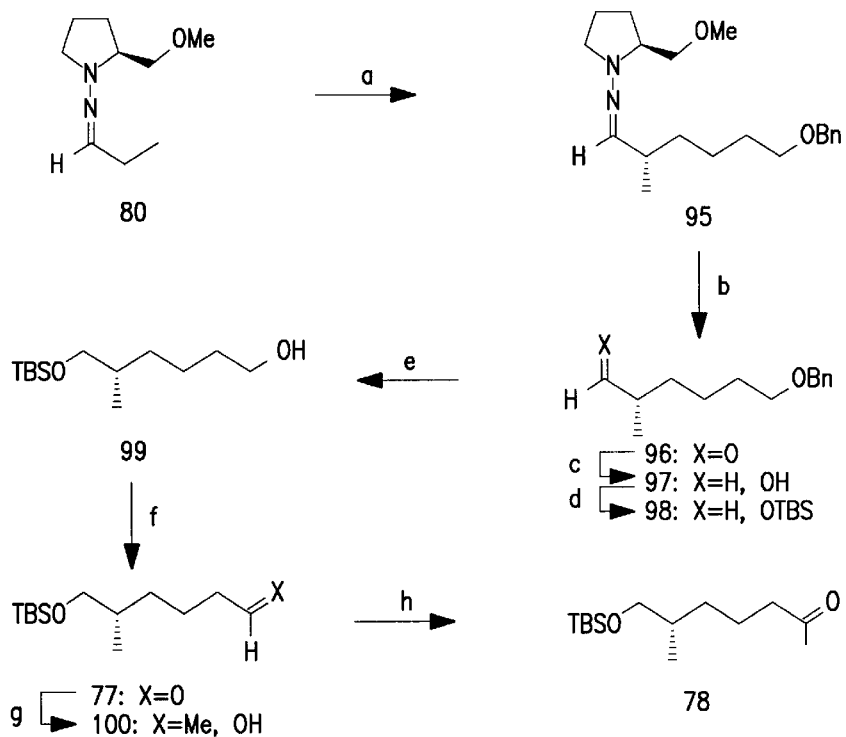
FIG. 13 illustrates the synthesis of aldehyde 77 and ketone 78. Reagents and conditions: (a) 1.1 equivalents of LDA, THF, 0° C., 8 hours; then 1.5 equivalents of 4-iodo-1-benzyloxybutane in THF, at −100→0° C., 6 h, 92% (de>98% by $^1$H NMR); (b) O$_3$, methylene chloride, −78° C., 77% or MeI, 60° C., 5 hours; then 3 N aq HCl, n-pentane, 25° C., 1 hour, 86%; (c) 3.0 equivalents of NaBH$_4$, MeOH, 0° C., 15 minutes, 98%; (d) 1.5 equivalents of TBSCl, 2.0 equivalents of Et$_3$N, methylene chloride, 0→25° C., 12 hours, 95%; (e) H$_2$, Pd(OH)$_2$ cat., THF, 50 psi, 25° C., 15 minutes, 95%; (f) 2.0 equivalents of (COCl)$_2$, 4.0 equivalents of DMSO, 6.0 equivalents of Et$_3$N, methylene chloride, −78→0° C., 1.5 hours, 98%; (g) 1.5 equivalents of MeMgBr, THF, 0° C., 15 minutes, 84%; (h) 1.5 equivalents of NMO, 0.05 equivalent of tetra-i-propylammonium perruthenate (TPAP), 4 Å MS, Methylene chloride, 25° C., 45 min, 96%.

The construction of aldehyde 77 and ketone 78 proceeded from SAMP hydrazone 80 as shown in FIG. 13. Thus, reaction of propionaldehyde with SAMP, furnished 80, which upon sequential treatment with LDA (THF, 0° C.) and 4-iodo-1-benzyloxybutane (THF, −100 to 0° C.) led to compound 95 in 92% yield and >98% de ($^1$H NMR). Cleavage of the hydrazone moiety by exposure to ozone (methylene chloride, −78° C., 77% yield), or by treatment with MeI at 60° C. followed by acidic workup (aq HCl, 86% yield), followed by NaBH$_4$ reduction of the resulting aldehyde (96), furnished alcohol 97 in 98% yield. The latter compound (97) was then silylated with TBSCl in methylene chloride in the presence of Et$_3$N and 4-DMAP to afford silyl ether 93 in 95% yield. Cleavage of the benzyl ether in 98 by hydrogenolysis [H$_2$, Pd(OH)$_2$ cat., THF, 50 psi], gave primary alcohol 99 (95% yield), which was smoothly oxidized to the desired aldehyde 77 under Swern conditions [(COCl)$_2$, DMSO, Et$_3$N, 98% yield]. Addition of MeMgBr to 77 proceeded in 84% yield, and was followed by TPAP-NMO oxidation of the resulting secondary alcohol (100) to give the other required building block, ketone 78, in 96% yield (FIG. 13).

With the appropriate building blocks at hand the convergent approach to epothilones A(1) and B(2) could now enter its second phase.

2. Total Synthesis of Epothilones A as Illustrated in FIG. 14

Figure 14:
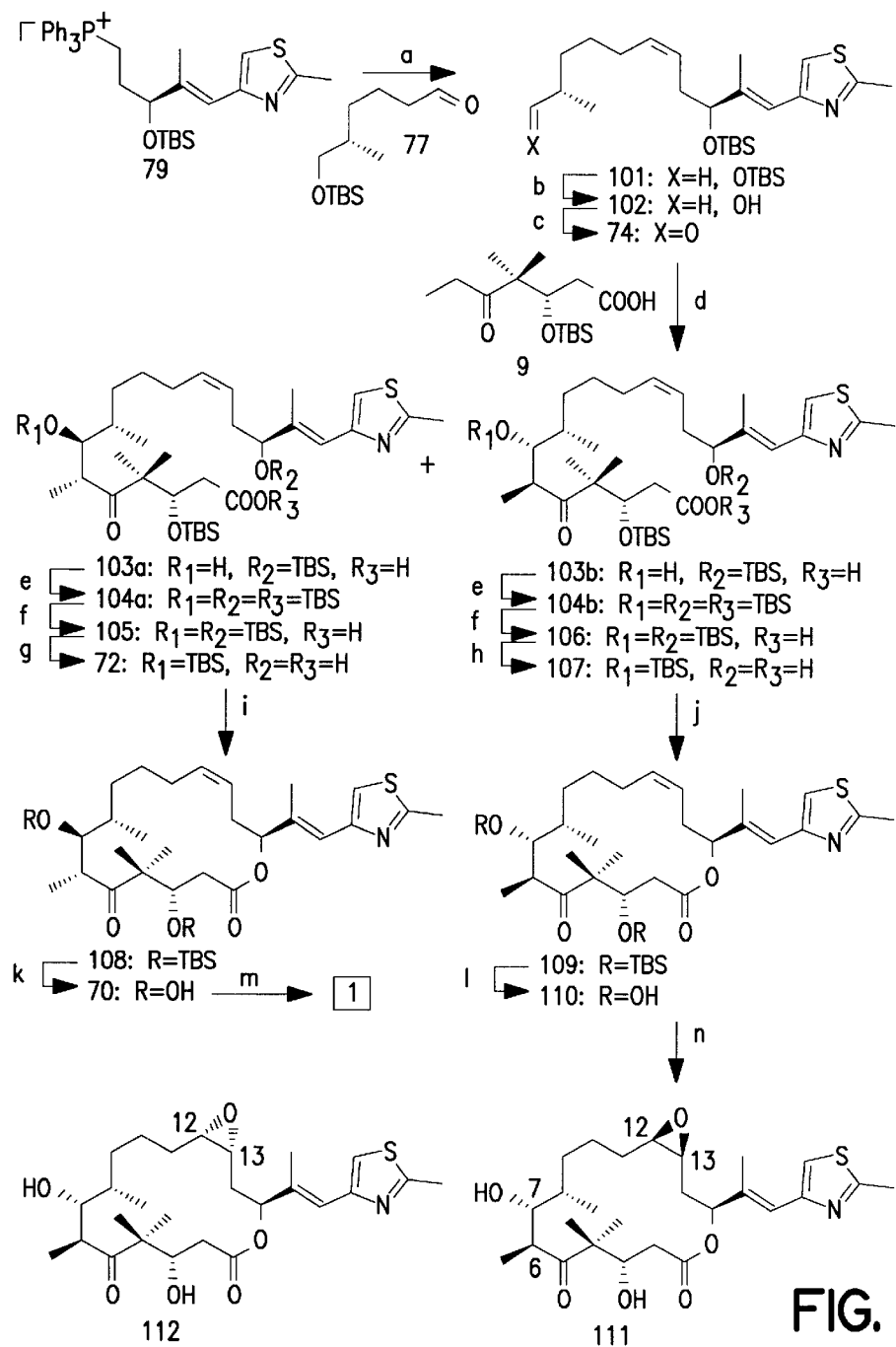
FIG. 14 illustrates the total synthesis of epothilone A (1) and its 6S,7R-diastereoisomers (111 and 112). Reagents and conditions: (a) 1.2 equivalents of 79, 1.2 equivalents of NaHMDS, THF, 0° C., 15 minutes, then add 1.0 equivalent of aldehyde 77, 0° C., 15 min, 77% (Z:E ca. 9:1); (b) 1.0 equivalent of CSA portionwise over 1 hour, methylene chloride:MeOH (1:1), 0→25° C., 0.5 hour, 86%; (c) 2.0 equivalents of SO$_3$.pyr., 10.0 equivalents of DMSO, 5.0 equivalents of Et$_3$N, methylene chloride, 25° C., 0.5 hour, 94%; (d) 3.0 equivalents of LDA, THF, 0° C., 15 minutes; then 1.2 equivalents of 76 in THF, −78→−40° C., 0.5 hour; then 1.0 equivalent of 74 in THF at −78° C., high yield of 103a and its 6S,7R-diastereoisomer 103b (ca. 1:1 ratio); (e) 3.0 equivalents of TBSOTf, 5.0 equivalents of 2,6-lutidine, Methylene chloride, 0° C., 2 hours; (f) 2.0 equivalents of K$_2$CO$_3$, MeOH, 25° C., 15 min, 31% of 105 and 30% of 6S,7R-diastereoisomer 106 from 74; (g) 6.0 equivalents of TBAF, THF, 25° C., 8 hours, 78%; (h) same as g, 82%; (i) 5.0 equivalents of 2,4,6-trichlorobenzoylchloride, 6.0 equivalents of Et$_3$N, THF, 25° C., 15 minutes; then add to a solution of 10.0 equivalents of 4-DMAP in toluene (0.002 M based on 72), 25° C., 0.5 hour, 90%; (j) same as i, 85%; (k) 20% CF$_3$COOH (by volume) in methylene chloride, 0° C., 1 hour, 92%; (l) same as k, 95%; (m) methyl (trifluoromethyl)dioxirane, MeCN, 0° C., 75% (ca 5:1 ratio of diastereoisomers); (n) same as m, 87% (111:112 ca 2:1 ratio of diastereoisomers, tentative stereochemistry).
Figure 15:
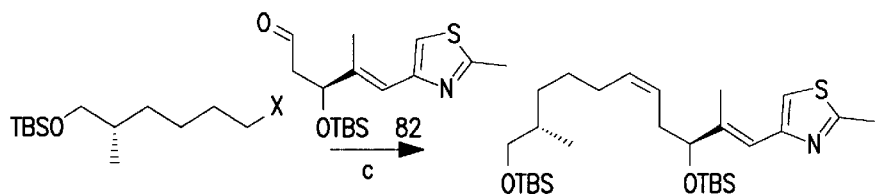
FIG. 15 illustrates the synthesis of compound 101. Reagents and conditions: (a) 1.5 equivalents of I$_2$, 3.0 equivalents of imidazole, 1.5 equivalents of Ph$_3$P, Et$_2$O:MeCN (3:1), 0° C., 0.5 hour, 91%; (b) 1.1 equivalents Ph$_3$P, neat, 100° C., 2 hours, 91%; (c) 1.2 equivalents of 114, 1.2 equivalents of NaHMDS, THF, 0° C., 15 minutes; then add 1.0 equivalent of aldehyde 82, 0° C., 15 minutes, 69% (Z:E ca 9:1).

The couplings of building blocks 76, 77 and 79 and the total synthesis of epothilone A(1) and its 6S,7R-diastereoisomers (111 and 112) are shown in FIG. 14. Thus, generation of the ylide from phosphonium salt 79 with sodium bis(trimethylsilyl)amide (NaHMDS), followed by reaction with aldehyde 77 resulted in the formation of the desired Z-olefin 101 ($J_{12,13}$=10.8 Hz, obtained from decoupling experiments) as the predominant product in 77% yield, [Z:E ca 9:1; the minor isomer (E) was removed chromatographically in subsequent steps]. Parenthetically, key intermediate 101 was also prepared by Wittig coupling of phosphonium salt 114 and aldehyde 82 in a reversal of the reacting functionalities of the two fragments as shown in FIG. 15. Thus, alcohol 99 was directly converted to iodide 113 by the action of I$_2$, imidazole, and Ph$_3$P (91% yield), and then to phosphonium salt 114 by heating with Ph$_3$P (triphenylphosphine) (91% yield). Generation of the ylide from 114 with equimolar amounts of NaHMDS in THF, followed by reaction with aldehyde 82 yielded Z-olefin 101 in 69% and in ca 9:1 ratio with its E-isomer.

Returning to FIG. 14, selective desilylation of the primary hydroxyl group from 101, was achieved by the action of camphorsulfonic acid (CSA) in MeOH:Methylene chloride (1:1), leading to hydroxy compound 102 in 86% yield. Oxidation of 102 to aldehyde 74 was then carried out using SO$_3$pyr., DMSO and Et$_3$N (94% yield). With the availability of 74, we were then in a position to investigate its aldol condensation with keto acid 76. It was found that the optimum conditions for this coupling reaction required generation of the dilithioderivative of 76 (1.2 equivalents) with 3.0 equivalents of lithium diisopropylamide (LDA) in THF (−78 to −40° C.), followed by addition of aldehyde 74 (1.0 equivalent), resulting in the formation of a mixture of the desired product 103a and its 6S,7R-diastereoisomer 103b in ca 1:1 ratio and in high yield. Despite the lack of stereoselectivity in this reaction, the result was welcome at least with regard to the prospect it provided for the construction of the 6S,7R-diastereoisomer of epothilones A and B. This mixture was then carried through to the stage of carboxylic acids 105 and 106 (FIG. 14), where it was chromatographically separated to its components. Thus, exposure of 103a/103b to excess of TBSOTf and 2,6-lutidine furnished a mixture of tetra-silylated products 104a/104b, which was then briefly treated with $K_2CO_3$ in $MeOH_2$ to afford, after silica gel flash or preparative layer chromatography, carboxylic acids 105 (31% overall yield from 7) and 106 (30% overall yield from 74) (105: Rf=0.61; 39: Rf=0.70, silica gel, 5% MeOH in Methylene chloride). The indicated stereochemistry at C7 and C6 in compounds 105 and 106 was assigned later and was based on the successful conversion of 105 to epothilone A(1) as described below.

At this stage, it was necessary to selectively remove the TBS group from the allylic hydroxyl group of 105, so as to allow macrolactonization of the seco-acid substrate (72). This goal was achieved by treatment of 38 with tetra-n-butylammonium fluoride (TBAF) in THF at 25° C., generating the desired hydroxy acid 72 in 78% yield. The key macrolactonization reaction of 72 was carried out using the Yamaguchi method (2,4,6-trichlorobenzoyl chloride, $Et_3N$, 4-DMAP) at 25° C., affording compound 108 in 90% yield. Removal of both TBS groups from 108 ($CF_3COOH$, Methylene chloride, 0° C.) furnished diol 70 in 92% yield. Finally, treatment of 70 with methyl(trifluoromethyl) dioxirane led cleanly to epothilone A(1) (62% yield) and its -epoxide epimer (13% yield). Synthetic epothilone A(1) was chromatographically purified (preparative thin layer chromatography, silica gel) and exhibited identical properties to those of an authentic sample (TLC, HPLC, [ ]D, IR, $^1H$ and $^{13}C$ NMR and HRMS).

A similar sequence was followed for the synthesis of the 6S,7R-diastereoisomers 111 and 112 of epothilone A(1) from compound 106 (FIG. 14) via intermediates 107 (82% yield from 106), 109 (85% yield from 107), and 110 (95% yield from 109). Epothilone 111 was obtained as the major product, together with its -epoxide epimer 112 (87% total yield, ca 2:1 ratio) from olefinic precursor 110 by methyl (trifluoromethyl)dioxirane epoxidation.

Figure 16:
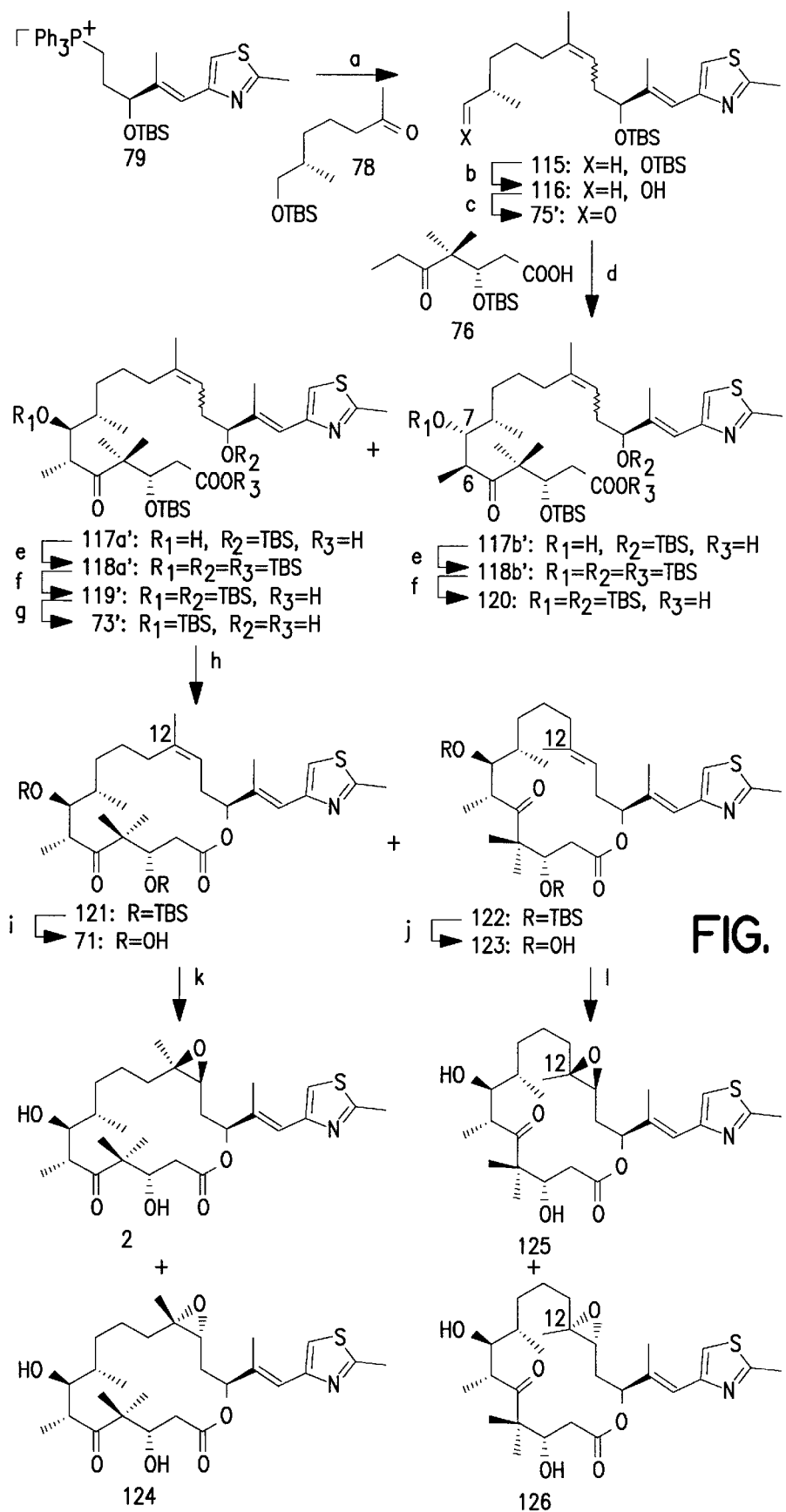
FIG. 16 illustrates the total synthesis of epothilone B(2) and analogs. Reagents and conditions: (a) 1.5 equivalents of 79, 1.5 equivalents of NaHMDS, THF, 0° C., 15 minutes, then add 1.0 equivalent of ketone 78, −20° C., 12 hours, 73%

3. Total Synthesis of Epothilones B (FIG. 16)

The first approach to epothilone B(2) was designed with the aim of delivering, not only the natural substance, but also its 12S-diastereoisomer 125 (FIG. 16), which in turn required the generation of both 12Z- and 12E-olefins. To this end, the ylide generated from phosphonium salt 79 with equimolar amounts of NaHMDS in THF, was reacted with ketone 78 to afford a mixture of Z- and E-olefins 115 (ca 1:1 ratio) in 73% total yield. This mixture was carried through the sequence to the stage of carboxylic acids 119 and 120 (see FIG. 16 for details), which were chromatographically separable. Carboxylic acid 120 (mixture of geometrical isomers) with the wrong stereochemistry at C6 and C7 (6S,7R) was abandoned at this stage, whereas the mixture of Z- and E-isomers 119 with the correct stereochemistry at C6 and C7 (6R,7S) was taken to the macrolactone stage (compounds 121 and 122) via hydroxy acid 6', by: (i) selective desilylation of the C15 hydroxyl group (TBAF, THF, 75% yield); and (ii) Yamaguchi cyclization (37% yield of 121, plus 40% of 122). Deprotection of bis(silylether) 121 by treatment with $CF_3COOH$ in methylene chloride afforded diol 71 in 91% yield. Finally, epoxidation of 71 with mCPBA in benzene at 3° C. gave epothilone B(2), together with its α-epoxide epimer 124 in 66% total yield and ca 5:1 ratio ($^1H$ NMR) while the use of dimethyidioxirane, gave 2 and 124 in 75% total yield in the same ratio (ca 5:1 in favor of 2). Epoxidation of 71 with methyl(trifluoromethyl) dioxirane in $CH_3CN$ at 0° C. improved the yield of epothilone B(2) and its -epimer 124 to 85%, but did not significantly change the diastereoselectivity of the reaction. Epothilone B(2) was purified by silica gel preparative layer chromatography and exhibited identical properties (TLC, HPLC, [ ]$_D$, IR, H and $^{13}C$ NMR, and HRMS) with those of an authentic sample.

By the same sequence, and in similar yields, the macrocycle 122 containing the E-endocyclic double bond (FIG. 16), was converted to the 12S-epimeric epothilone B 125 and its—epoxy epimer 126 via dihydroxy macrocyclic compound 123 (epoxidation with methyl(trifluoromethyl) dioxirane).

In order to improve the efficiency of the route to epothilone B(2), a more stereoselective total synthesis was devised and executed as follows. FIG. 17 addresses the stereoselective construction of intermediate 75 with the 12Z-geometry. Thus, condensation of the stabilized ylide 83 (obtained from 4-bromo-1-butene by: (i) phosphonium salt formation; (ii) anion formation with NaHMDS; and (iii) quenching with MeOC(O)Cl) with aldehyde 82 proceeded smoothly to afford olefinic compound 127 in 95% yield and as a single isomer. Reduction of the methyl ester in 127 with DIBAL resulted in the formation of allylic alcohol 128 (98% yield), which was deoxygenated by first reacting it with $Ph_3P—CCl_4$, and thence with $LiEt_3BH$, to afford the desired trisubstituted 12Z-olefin 130, via chloride 129, in 82% overall yield. The latter compound 130 was regioselectively hydroborated with 9-BBN and converted to the primary alcohol 131 (91%), which was then treated with $I_2$-imidazole-$Ph_3P$ to afford iodide 81 (92% yield). This iodide was then used in an Enders alkylation reaction with SAMP hydrazone 80 to give compound 132 as a single isomer ($^1H$ NMR) and in 70% yield. Treatment of hydrazone 132 with monoperoxyphthalic acid magnesium salt (MMPP) in MeOH:phosphate pH 7 buffer (1:1) resulted in clean conversion to nitrile 133 (80% yield), which formed aldehyde 75 (82% yield) upon exposure to DIBAL at −78° C. in toluene solution.

The homogeneous aldehyde 75 was converted to epothilone B(2) by the sequence depicted in FIG. 18. Thus, condensation of the dianion of 76 with 75 as before (FIG. 16), produced two diastereoisomers, 117a (6R,7S stereoisomer) and 117b (6S,7R stereoisomer) in high yield, and in ca 1.3:1.0 ratio (117a:117b). This mixture was carried through the indicated sequence to carboxylic acids 119 (32% overall yield from 75) and 119 (28% overall yield from 75), which were separated by silica gel preparative layer or flash column chromatography and taken individually further along the sequence as described for the corresponding stereoisomeric mixtures shown in FIG. 16. Thus, 119 was selectively deprotected with TBAF to afford hydroxy acid 73 (73% yield), which was then cyclized to macrolactone 121 in 77% yield by the Yamaguchi method. The conversion of 121 to epothilone B(2) and its -epoxide epimer 119 has already been described above (FIG. 16).

In an effort to improve the diastereoselectivity of the aldol condensation between C1–C6 and C7–C15 fragments, the following chemistry was explored (FIG. 19). Thus, ketone 136 (prepared from ketone 87, FIG. 12, by selective reduction, followed by silylation) was converted to its enolate with stoichiometric amounts of LDA and reacted with aldehyde 75 (Z-isomer), affording coupling products 137 and 138 in 85% total yield and ca 3:1 ratio, with the desired compound 137 predominating as proven by its conversion to 119 and epothilone B(2). Thus, chromatographic purification (silica gel, 20% ether in hexanes) led to 137, which was efficiently transformed to the previously synthesized intermediate 119 (FIG. 18) as follows. The newly generated hydroxyl group in 137 was silylated with TBSOTf-2,6-lutidine to furnish 139 (96% yield), which was then selectively desilylated at the primary position by the mild action of camphorsulfonic acid (CSA) in MeOH-Methylene chloride, leading to 140 (85%). Finally, sequential oxidation of the primary alcohol with $(COCl)_2$-DMSO-$Et_3N$ (95% yield) and $NaClO_2$—$NaH_2PO_4$ (90% yield) led to hydroxy acid 119 via aldehyde 141. The conversion of 119 to 2 has already been described above (FIG. 18). This sequence represents a stereoselective and highly efficient synthesis of epothilone B(2) and opens the way for the construction of further analogs within this important family of microtubule binding agents.

The chemistry described in this example defines a concise methodology for the construction of epothilones A(1) and B(2) based on a macrolactonization strategy, and which enjoys convergency and flexibility for structural diversity. The methodology is not limited to epothilones A(1) and B(2), but can be extended to numerous intermediates and structural analogs included herein. In addition, the resultant analogs will play a crucial role in elucidating structure-activity relationships of these new substances and in determining their relevance to cancer chemotherapy. Binding assays, vida infra, have demonstrated that compounds 70, 71, 123 and 125 show binding affinities to microtubules comparable to those of epothilones A(1), B(2), and Taxol™.

EXAMPLE 3

Solid Phase Synthesis of the Epothilones as Illustrated in FIGS. 20–21 and FIGS. 49–50

In this example, we demonstrate the first solid phase synthesis of epothilone A(1) and the total synthesis of epothilone B(2), the generation of a small epothilone library, and the identification of a synthetic epothilone that interacts with tubulin more potently than epothilones A(1) and B(2) and Taxol (FIGS. 20–24 and FIGS. 49–50). The solid phase construction of 1 may herald a new era of natural products synthesis and, together with the solution phase synthesis of 2, paves the way for the generation of large combinatorial libraries of these important molecules for biological screening.

The strategy for the solid phase synthesis of epothilone A(1) was based on the retrosynthetic analysis indicated in FIG. 20 (Nicolaou et al. Angew. Chem. Int. Ed. Engl. 35, 2399–2401 (1996); Yang et al. Angew. Chem. Int. Ed. Engl. 36, 166–168 (1997)). Thus, it was anticipated that the three requisite fragments (143–145), one on a solid support (145), would be coupled together sequentially through an aldol reaction, an esterification reaction, and an olefin metathesis reaction, the latter simultaneously cyclizing and liberating the product from the solid support (144+145+143 leads to 142 which leads to 141; FIG. 20). A simple desilylation and epoxidation reaction would then complete the total synthesis of epothilone A(1) and analogues thereof (141 leads to 1; FIG. 20). The outlook for obtaining two products at each of the aldol, metathesis, and epoxidation steps was considered advantageous for the purposes of library generation.

As illustrated in FIG. 21, Merrifield resin (146) was converted to phosphonium salt 147 in >90% yield by sequential reaction with: (i) 1,4-butanediol-NaH-n-$Bu_4NI$ catalyst; (ii) $Ph_3P$-iodine-imidazole; and (iii) $Ph_3P$. Preferred alternative resins, other than the Merrifield resin, employable in this procedure include PEG-polystyrene, hydroxymethyl polystyrene, formyl polystyrene, aminomethyl polystyrene and phenolic polystyrene. Ylide 148 generated from 147 by the action of NaHMDS in THF:DMSO at 25° C., reacted with aldehyde 149 at 0° C. to form olefinic compound 150 in >70% yield. The geometry of the double bond in 150 was tentatively assigned as Z, but its geometry was neither rigorously determined nor did it matter for our purposes. Desilylation of 150 with HF.pyr., followed by Swern oxidation of the resulting primary alcohol furnished aldehyde 145 in high yield (>95%). The aldol condensation of the polymer-bound aldehyde 145 with the dianion derived from keto acid 144 in the presence of $ZnCl_2$ in THF gave a mixture of diastereoisomers (ca 90% yield, ca 1:1 ratio). Finally, introduction of the heterocyclic segment 143 onto the growing substrate was achieved by esterification, leading to the required precursor 152 in ca 80% yield. Exposure of 152 to $RuCl_2$(=CHPh)($PCy_3$)$_2$ catalyst (153) in methylene chloride at 25° C. released from the resin olefinic compounds 154–156 and 141 (52% total yield, 154:155:156:141 ca 3:3:1:3 as determined by HPLC). Compounds 154–156 and 141 could be separated either by HPLC or by preparative layer silica gel chromatography, and the two with the correct C6–C7 stereochemistry (e.g. 155 and 141) were desilylated by exposure to TFA to afford epothilone precursors 157 (92%) and 158 (90%), respectively. Epoxidation of 157 and 158 with trifluoro(methyl)dioxirane then furnished epothilone A(1, 70%) and its diastereoisomer 159 (45%), respectively. The -epoxy isomers of 1 and 159 were also obtained in these epoxidation reactions. Pure synthetic epothilone A(1) exhibited identical properties (TLC, [ ]$_D$, $^1H$ and $^{13}C$ NMR, IR and HRMS) to those of an authentic sample (FIG. 21).

The solid phase synthesis of epothilone A(1) described herein (FIGS. 20–24 and FIGS. 49–50) represents a new concept for the total synthesis of natural products, traces a highly efficient pathway to the naturally occurring epothilones, and opens the way for the generation of large combinatorial epothilone libraries. The biological results demonstrate that more potent microtubule binding analogues than the parent epothilones can be obtained (e.g. compound 71; biological results vida infra) by chemical synthesis. Furthermore, our findings point to lipophilic substituents rather than the epoxide moiety as important elements for binding activity.

The epothilone library (FIGS. 24–25) was designed without a methyl group at C-8 (the necessity of this methyl group for biological activity will be tested first, through the synthesis of 8-nor epothilone A prior to undertaking the construction of this library) for simplicity. The C1–C5 fragment is varied as outlined in FIGS. 24–25, whereas the stereochemistry at C-6, C-7, C-12 and C-15 is deliberately varied to multiply the number of compounds by two for each center. In addition, groups R1, R3 and R4 also vary. The requisite building blocks (boxes, lower part of FIGS. 24–25) are known in the prior art and synthesized by standard methods; solid support is prepared from polystyrene as shown in FIGS. 24–25. The enolates of the corresponding ketoacids are generated by the action of LDA and the aldol products are derivatized with $R_3$ and condensed with 165 to afford 166. Palladium catalyzed coupling of 166 with specific aromatic stannanes, followed by olefin metathesis, form the macroring and simultaneously release the substrate from the solid support. The remaining two steps are carried out in solution. The epoxidation is carried out using a solid phase-bound peracid or dimethyloxirane, (for minimal work-up procedures) and the desilylation step is conveniently achieved by HF.pyr in methylene chloride. The final products are generally pure enough for characterization and biological assay (or they can, if necessary, be purified by HPLC) and their numbers may vary from hundreds to thousands (see description of figures section for FIG. 25 for a calculation of such a library).

EXAMPLE 4

Total Synthesis of Epoxalones A and Epoxalone Analogs as Illustrated in FIGS. 24–39

In this example, we report the total synthesis of a novel series of designed epothilones with an oxygen instead of a sulfur atom at position 20 (see FIG. 24). The name epoxalones (ep for epoxide, oxa for oxazole, one for ketone; cf epothilone: ep for epoxide, thi for thiazole, one for ketone) is proposed for this new class of compounds. These compounds represent a preferred embodiment of the invention.

The synthesis of the epoxalone A series was based on our olefin metathesis strategy towards epothilone A(1). This highly convergent and flexible sequence led to the construction of compounds 161, 168, 169, 170, 171, 172, 175, 176, 177, 178, 179, and 180 in rapid fashion starting with building blocks 7, 8 and 163 (FIG. 25). Thus, asymmetric allylboration of aldehyde 162 (obtained via the procedure by Kende et al. Tetrahedron Lett. 1995, 36, 4741–4744) with Brown's (+)-Ipc$_2$B(allyl) in Et$_2$O-pentane at –100° C. furnished compound 163 in 91% yield and >98% ee. This alcohol was esterified with the mixture of carboxylic acids 45 and 46 (ca. 5:3 ratio) obtained by aldol condensation of fragments 8 and 7 to afford compounds 164 and 165 as a ca. 5:3 mixture (82% total yield). Chromatographic separation (flash column, silica gel, 20% EtOAc in hexanes) of this mixture gave pure diastereoisomers 164 and 165.

Subjection of precursor 164 (possessing the correct C6–C7 stereochemistry) to the olefin metathesis reaction [RuCl$_2$(=CHPh)(PCy$_3$)$_2$, CH$_2$Cl$_2$, 25° C.] resulted in the formation of cyclic olefins 166 (40% yield) and 167 (29% yield) which were chromatographically separated (flash column, silica gel, 20% EtOAc in hexanes, 1:1) (FIG. 26). Exposure of 166 to 20% trifluoroacetic acid in CH$_2$Cl$_2$ at 25° C. furnished diol 168 in 89% yield. Similar treatment of 167 led to 169 (95% yield). Epoxidation of 168 with methyl (trifluoromethyl)dioxirane furnished epoxides 161 (34% yield) and 170 (15% yield) which were separated by preparative layer chromatography (silica gel, 75% EtOAc in hexanes). Similar treatment of 169 led to epoxides 171 (25%) and 172 (20%) (as illustrated in FIG. 26).

A parallel sequence starting with diastereoisomer 165 led to the 6S,7R series of epoxalones 175–180 as summarized in FIG. 27.

The synthesized compounds (161, 168, 169, 170, 171, 172, 175, 176, 177, 178, 179, and 180) were tested for their tubulin assembly properties using the Filtration-Colorimetric Assay (outlined vida infra) at 20 mM concentrations at 30° C. and with pure tubulin. The most potent ones (161, 168, 169, 171 and 172) were then assayed at 0.1, 1.0, 2.0, 3.0, 4.0 and 5.0 mM concentrations under the same conditions leading to the plots shown in FIG. 28. Thus, both epoxalones 161 and 171 were found to be more potent than Taxol in inducing tubulin polymerization, whereas compounds 168, 169 and 172 showed comparable or slighlty less potencies than Taxol. The high potency of the trans-epoxide epoxalone 171 is perhaps the most striking observation in these studies and holds true for the corresponding trans-epoxides of epothilones A and B.

The implementation of the macrolactonization strategy towards the oxazole series of epothilones B proceeded along a similar path developed for the corresponding thiazole series of epothilones. FIG. 31 shows the stereoselective construction of the requisite aldehyde 217 and phosphonium salt 220 starting with the readily available oxazole derivative 213. Thus, asymmetric addition of (+)-Ipc$_2$B(allyl) to aldehyde 213 (see FIG. 31), as described in the preceding section gave alcohol 214. Silylation of 214 with TBSCl (for abbreviations, see description of figures) and imidazole gave 99% yield of silylether 215. Selective dihydroxylation of the terminal olefin in 215 employing the Upjohn procedure (NMO-OsO$_4$ cat.), followed by NaIO$_4$ cleavage of the resulting diol led to aldehyde 217 in excellent yield (93%). Reduction of the aldehyde group in 217 with NaBH$_4$ (99% yield) followed by exposure to Ph$_3$P-I$_2$-imidazole furnished iodide 219 (87% yield) via primary alcohol 218. Finally, heating of 219 with Ph$_3$P at 100° C. gave phosphonium salt 220 in 90% yield. In order to obtain both the 12E- and 12Z-isomers of epothilone B analogs, we initially undertook the non-stereoselective synthesis depicted in FIGS. 32 and 33 in which the first step involves a Wittig reaction, yielding a 1:1 mixture of geometrical isomers. Thus, generation of the ylide from phosphonium salt 220 by the action of NaHMDS in THF at –20° C., followed by addition of ketone 221, furnished compound 222 in 68% yield as a 1:1 mixture of E:Z isomers. Preparation of the desired aldehyde 224 from 222 required selective desilylation of the primary hydroxyl group (CSA, CH$_2$Cl$_2$-MeOH, 0 to 25° C., 92% yield) and oxidation of the resulting alcohol (223) with SO$_3$.pyr.-DMSO-Et$_3$N (98% yield). The condensation of aldehyde 224 (mixture of 12E- and 12Z-geometrical isomers, FIGS. 2 32 and 33) with the anion derived from ketone (LDA, THF) proceeded smoothly at –78° C. to afford a mixture of diastereomeric aldols 226 and 227 (ca 4:1 ratio) in 73% combined yield. Chromatographic separation (silica, preparative layer) led to pure 2226 and 227, each consisting of E- and Z- geometrical isomers (ca. 1:1). Only the 6R,7S diastereoisomer 226 (less polar mixture of D12,13 geometrical isomers) was taken forward (polarity and comparison with the natural series was used as a guide to choose the desired 6R,7S-diastereoisomer at this stage). The geometrical isomers were separated after the macrolactonization reaction (vide infra).

The next task in the synthesis was to prepare hydroxyacid (FIG. 33). To this end, the hydroxy group in 226 was silylated (TBSOTf-2,6-lutidine, 96%) to afford tris (silylether) and then selectively deprotected at the primary position by exposure to CSA in MeOH:CH$_2$Cl$_2$ at 0 to 25° C. leading to 228 (85% yield). A stepwise protocol was used to oxidize primary alcohol to the desired carboxylic acid: (i) (COCl)$_2$-DMSO-Et$_3$N, –78 to 0° C., yielding aldehyde (94% yield); and (ii) NaClO$_2$-2-methyl-2-butene, NaH$_2$PO$_4$, furnishing acid (99% yield). Selective desilylation at the allylic position with TBAF in THF then gave hydroxyacid in 78% yield.

Yamaguchi macrolactonization of hydroxyacid as in the natural series (2,4,6-trichlorobenzoylchloride-Et$_3$N-4-DMAP, high dilution, 25° C.), followed by preparative thin layer chromatography (silica, 20% ether/hexanes) led to lactones 229 (Rf=0.24, 35%) and 230 (Rf=0.20, 42%). The identity of 229 was proven by comparison with an authentic sample prepared by a stereoselective route. Deprotection of 229 and 230 was carried out with HF.pyr. in THF at 25° C.

and furnished diols 231 (62% yield) and 232 (82% yield), respectively. Finally, epoxidation of 231 and 232 with mCPBA in $CHCl_3$ at 0° C. furnished the corresponding α- and β-epoxides (2+30, 40% total yield, ca 5:1 ratio, and 31+32, 45% total yield, ca 6:1 ratio). The stereochemical assignments shown in FIG. 33 for these compounds are tentative and are exclusively based on comparisons with the series related to natural epothilone B.

A stereoselective synthesis of the D12,13-series of the oxazole-containing epothilones (231, 233 and 234) was also developed and is shown in Schemes 33, 34 and 35. Thus, the desired geometry of the D12,13 position was fixed by condensation of the stabilized ylide (FIG. 34) with aldehyde 217 (benzene, D), a reaction that led to 90% yield of compound 237. Subsequent reduction of the ester group of 237 (DIBAL, CH2Cl2, −78° C., 99% yield), chlorination ($Ph_3P$, $CCl_4$, D, 81%), and further reduction ($LiEt_3BH$, THF, 0° C., 97% yield) furnished intermediate 240 via allylic alcohol 238 and chloride 239. Selective hydroboration of 240 at the terminal olefin site was achieved by the use of 9-BBN, and after oxidative work up, primary alcohol 241 was obtained in 92% yield. Conversion of 241 to iodide 242 was subsequently carried out by the standard $I_2$-imidazole-$Ph_3P$ procedure (89% yield). The iodide 242 was then used to alkylate the SAMP hydrazone (LDA, THF, −100 to −20° C.), furnishing hydrazone 243 in 70% yield. The latter compound (243) was then transformed sequentially to nitrile 244 (MMPP, MeOH-phosphate buffer pH 7, 0° C., 46% yield), and thence to aldehyde 224 (DIBAL, toluene, −78° C., 84% yield).

The aldol condensation of the lithioderivative of the ketone with stereochemically homogeneous aldehyde 224 (FIG. 35) proceeded in a similar fashion to the case of the E:Z mixture described above, leading to pure compounds 245 and 246. After chromatographic separation, the pure 6R,7S-diastereoisomer 245 [tentative assignment of stereochemistry based on polarity (less polar) and comparison to the natural series] was taken through the sequence, and on to the final products 233 as detailed in FIG. 35.

EXAMPLE 5

The 4,4-Ethano Series of Epothilone A Analogs

A. Olefin Metathesis Approach as Illustrated in FIGS. 40–48

Applying the olefin metathesis approach to epothilones, we have synthesized a series of cyclopropane containing epothilone A analogs. These compounds considerably enrich the known epothilone libraries in terms of molecular diversity and numbers. Biological investigations with these analogs established useful structure-activity relationships within this important class of compounds. Interestingly, while the oxazole series of compounds exhibited comparable tubulin polymerization activity and cytotoxicity to the corresponding thiazole series, the 4,4-ethano-epothilones proved inactive. These results underscore the importance of conformational precision in these compounds for biological action.

Following the same retrosynthetic rationale as the one outlined above for the oxazole analogs, the 4,4-ethano epothilone A was analyzed as shown in FIG. 40. This time, the analysis led to building blocks 271, 7 and 272. The latter compound (272) was easily traced to β-ketoester 275 via intermediates 273 and 274. The forward construction of 267 and its congeners proceeded as follows.

We began with the synthesis of cyclopropyl-ketoacid 31 (FIG. 41). Thus, reaction of 1,2-dibromoethane with ethyl propionylacetate (275) in the presence of $K_2CO_3$ at ambient temperature resulted in the formation of cyclopropyl ketoester 276 (60% yield). Reduction of the ester- and keto-groups with $LiAlH_4$ (93% yield) followed by Swern oxidation of the resulting diol [$(COCl)_2$; DMSO; $Et_3N$] furnished ketoaldehyde 274 in 64% yield. Chemo- and stereoselective addition of (+)-$Ipc_2B$(allyl) to aldehyde 274 (>85% ee by Mosher ester analysis), followed by silylation (TBSOTf; 2,6-lutidine) of the generated secondary alcohol, gave silyl ether 273. Finally, cleavage of the terminal olefin in 273 with $NaIO_4$ in the presence of catalytic amounts of $RuCl_3 \cdot H_2O$ in MeCN—$H_2O$—$CCl_4$ (2:3:2) at 25° C. yielded the desired ketoacid 272 in 43% overall yield from cyclopropyl ketoaldehyde 274.

The dianion of ketoacid 272 (LDA in THF at −30° C.) reacted with aldehyde 7 to form aldols 270 and 277 in ca. 2:3 (ratio by $^1H$ NMR) (FIG. 42). The coupling of the mixture of 270 and 277 with fragment 271 was facilitated by EDC and 4-DMAP and the resulting hydroxyesters were chromatographically separated to afford pure 269 (15%) and 278 (36%). Ring closure of advanced intermediate 269 and epoxidation of the desilylated cyclic diols are shown in FIG. 43. Thus, stirring of 269 with $RuCl_2(=CHPh)(PCy_3)_2$ catalyst in $CH_2Cl_2$ at 25° C. followed by chromatographic separation (silica gel, preparative thin layer) furnished cis- and trans-olefins 268 (37% yield) and 279 (35% yield), respectively. The corresponding diols 280 (65% yield) and 281 (62% yield) were obtained by treating the respective silyl ethers with 25% HF.pyr. in THF at ambient temperature. Finally, epoxidation of 280 with methyl (trifluoromethyl)dioxirane gave epoxides 267 (or 282) (50% yield) and 282 (or 267) (29% yield), whereas similar treatment of 281 furnished 283 (or 284) (11% yield) and 284 (or 283) (31% yield). The stereochemistry of epoxides 267, 282–4 is unassigned. The other aldol product, compound 278, was processed in a similar way as described above for 269, furnishing the 4,4-ethano-epothilone A analogs 287–292 as shown in FIG. 44. Again, the stereochemical details of these compounds remain unassigned.

B. Macrolactonization Approach

The 4,4-ethano analogs of epothilones B were designed in order to test the tolerance of the receptor site for the substitution of the gem-dimethyl group of the natural substance. As the retrosynthetic analysis of FIG. 45 succinctly shows, the requisite fragments for the synthesis of the designed 4,4-ethano-epothilone B (267) and its relatives, are defined as fragments 75 and 294. The synthesis of building block 294 was described in conjuction with the stereoselective total synthesis of epothilone B, whereas that of building block 294 is shown in FIG. 46.

Thus, the ketocyclopropane derivative 273 (FIG. 46), described in the preceding section was subjected to ozonolysis and subsequent reduction with $Ph_3P$ to afford aldehyde 295 in 90% yield. Further reduction [$LiAl(OtBu)_3H$, THF, −78° C], followed by silylation of the resulting primary alcohol 296 (TBSCl, $Et_3N$, 4-DMAP) furnished ketocyclopropane fragment 294 in 83% overall yield.

FIG. 47 details the coupling of fragments 294 and 75 and the assembly of a series of 4,4-ethano-epothilone B analogs. Thus, generation of the lithium enolate of ketone 294 with LDA in THF at −78° C. to −60° C., followed by addition of aldehyde 75 resulted in the formation of aldols 297 and 298 in ca 1:2 ratio and 71% total yield. Stereochemical assignments were based on a X-ray crystallographic analysis of a subsequent intermediate, and will be discussed below. The difference in the ratio of aldol products between fragments 298 (ca 1:2, FIG. 47) and 297 (ca 4:1, see FIG. 36) is rather striking, and it may have its origin in the effect of the cyclopropane ring on the transition state of the reaction. The two diastereomeric aldol products 297 and 298 were chromatographically separated (silica, flash column chromatography) and processed separately in order to obtain both the 6S,7R and 6R,7S series of compounds.

Thus, stereoisomer 297 (FIG. 47) was silylated with TBSOTf and 2,6-lutidine affording tris(silylether) 299 in 92% yield, and then exposed to the action of CSA in CH2Cl2:MeOH at 0 to 25° C. to give hydroxy bis(silylether) 301 (74% yield) in which only the primary hydroxyl group was liberated. Stepwise oxidation of 301 with: (i) $(COCl)_2$, DMSO, $Et_3N$, −78 to 0° C., 96% yield, and (ii) $NaClO_2$, 2-methyl-2-butene, $NaH_2PO_4$, 91% yield, gave sequentially aldehyde 303 and carboxylic acid 305. Selective desilylation of 305 with TBAF in THF at 25° C. furnished the desired hydroxyacid 293 in 62% yield.

The intended macrolactonization of 293 was accomplished by the Yamaguchi method (2,4,6-trichlorobenzoylchloride, $Et_3N$, 4-DMAP, toluene, 25° C., high dilution), furnishing compound 308 in 70% yield. Exposure of 308 to HF.pyr. in THF at 25° C. resulted in the removal of both silyl groups, leading to diol 268 in 92% yield. Finally, epoxidation of 268 with (trifluoromethyl) methyldioxirane in MeCN resulted in the formation of epothilone B analogs 267 and 311 in ca 8:1 ratio (by 1H NMR) and 86% total yield. Preparative thin layer chromatography (silica, 5% MeOH in $CH_2Cl_2$) gave pure epothilone B analogs 267 and 312.

The same chemistry was performed with diastereoisomer 298 (FIG. 47) leading to epothilone B analogs 310, 312 and 313 via intermediates in similar yields to those described for 297. The latter compound (309) crystallized as long needles from MeOH-EtOH (mp. 157° C.) and provided for X-ray crystallographic analysis which revealed its stereochemical structure (see ORTEP drawing in FIG. 48).

EXAMPLE 6

Solid Phase Synthesis of Designed Epothilone Analogs Based on Combinatorial Approach, Tubulin Assembly Properties of Compounds and Cytotoxic Actions Against Tumor Cell Lines as Illustrated in FIGS. 49–50 and FIGS. 63–66

In this example, we illustrate (a) the solid phase synthesis of several epothilone A analogs based on a combinatorial approach; (b) the tubulin assembly properties of an extensive library of compounds; and (c) the cytotoxic actions against breast and ovarian carcinoma cells (including a number of Taxol-resistant tumor cell lines) of a selected number of these designed epothilones. The results provide comprehensive information on structure-activity relationships of epothilones and set the foundation for their further development. The structures of epothilones are amenable to modification by changing the configuration of certain stereocenters, the geometry of the double bonds, the size of the rings, and the nature of their substituents. Our synthetic strategies towards these molecules were, therefore, designed on the premise of modifying these elements so as to reach optimum molecular diversity and obtain a maximum number of library members. FIG. 64 includes the structures of an epothilone library obtained by solution and solid phase combinatorial methods as described vide supra. Biological screening of these compounds was expected to lead to the establishment of sufficient structure-activity relationships to allow the next phase of the program, the design, synthesis and identification of potential drug candidates, to proceed along a narrower track.

The strategy for the construction of a library of epothilone A analogs was based on our epothilone A and an established variation of solid phase synthesis using Radiofrequency Encoded Combinatorial (REC™) chemistry (Nicolaou et al. Angew. Chem. 1995, 107, 2476–2479; Angew. Chem. Int. Ed. Engl. 1995, 34, 2289–2291; Moran et al. J. Am. Chem. Soc. 1995, 117, 10787–10788). FIG. 50 summarizes the synthesis of a library of 12,13-desoxyepothilones A from the three key fragments generically denoted as 330, 331 and 332. Thus, SMART Microreactors™ containing Merrifield resin were smoothly converted to Microreactors 148 by chain extension and phosphonium salt formation as outlined in FIG. 50 (the reported combinatorial chemistry was performed using MicroKans™, while a single MicroTube™0 was utilized to synthesize a set of four epothilones A (i.e. 422, 425, 455 and 460, FIGS. 64 and 65)). Phosphonium salt resin 148 was then sorted according to the radiofrequency tag and treated with NaHMDS to generate the corresponding ylides which were reacted with the aldehydes 330. The SMART Microreactors 333 were pooled for washing and subsequent deprotection and oxidation to obtain the polymer-bound aldehydes 335. Further sorting and treatment with the dianion of the ketoacids 331 provided the polymer bound carboxylic acids 336 as a mixture of diastereoisomers. Resorting and esterification with alcohols 332 afforded dienes 337. The SMART Microreactors were separately treated with $RuCl_2(=CHPh)(PCy_3)_2$ catalyst to simultaneously effect cyclization via olefin metathesis, and cleavage of the products, leading to products as mixtures of four 12,13-desoxyepothilones A (339, 340, 341, 342). Each mixture was identified and subjected to preparative thin-layer chromatography to provide pure compounds, which were individually deprotected by treatment with TFA in dichloromethane and then epoxidized accordingly.

The epothilone library (FIG. 64) was screened for induction of tubulin assembly with 5 mM compound at 37° C. Previously tested compounds (in FIG. 64) were re-evaluated for comparative purposes. Most analogs were subjected to more detailed investigation in cytotoxicity assays with human ovarian and breast cancer cells, including Taxol-resistant lines, and a quantitative tubulin assembly assay that differentiates between potent taxoid compounds (FIG. 65). It soon became apparent that compounds with assembly values below 40% in the screen yielded high $EC_{50}$ values in the quantitative assay and had little inhibitory effect on cell growth (only positive results shown in FIG. 65).

A standard glutamate assay tested the hypothesis that taxoids more active than Taxol in tubulin assembly would also be more cytotoxic, and this was validated with over fifty analogs. With the epothilones, however, the quantitative assay was less successful. A low glutamate concentration resulted in a high false negative rate in predicting cytotoxicity, while higher glutamate concentrations (e.g. 0.7 M, FIG. 65) were comparable to the screening assay in identifying cytotoxic analogs. If "significant" cytotoxicity is defined as an $IC_{50}$ value below 10 nM, we identified nine analogs with activity against the breast and ovarian lines (161, 234, 48, 125, 171, 233, 126, 172, 71, and 231). With the screening assay, there were no false negatives, but there were seven false positives (agents with limited cytotoxicity yielding >40% polymerization) among examined compounds. With the glutamate assay, the same results were obtained. The nine cytotoxic analogs had $EC_{50}$ values of 3.3–13 mM, but an additional nine agents had $EC_{50}$ values of 6.0–17 mM.

Two Taxol-resistant lines were generated from the 1A9 ovarian cells, and resistance resulted from mutations in the M40 gene, which codes for a highly expressed $b_I$ isotype in the parental and resistant cell lines. The altered amino acids were residue 270 in the 1A9PTX10 line (Phe→Val) and 364 in 1A9PTX22 (Al→Thr). This agreed with other observations that the Taxol binding site is on β-tubulin. In preliminary results reported with 1 (vida supra) and several analogs that 1A9PTX22 cells retained nearly complete sensitivity to epothilones, while 1A9PTX10 cells remained partially resistant to the drugs. These findings have been confirmed (FIG. 65). The relative resistance observed with 1A9PTX22 cells was 27-fold with Taxol and 1.0–2.7-fold with the eleven cytotoxic epothilones. With 1A9PTX10 cells, relative resistance was 23-fold with Taxol and 3.5–9.1-fold with the epothilones. The Taxol and epothilone binding sites could overlap, since 1 and 2 are competitive inhibitors of Taxol binding to tubulin polymer. If one assumes that $Phe_{270}$ and $Ala_{364}$ interact directly with Taxol, the results with the resistant cells suggest that $Phe_{270}$ is more important than $Ala_{364}$ in the interaction of epothilones at the Taxol binding site.

The data shown in FIGS. 64 and 65, together with previously reported results, revealed important information regarding structure-activity relationships for in vitro tubulin polymerization and cytotoxicity, and lead to several conclusions. That the macrocycle is important was confirmed by the lack of significant tubulin polymerization activity of the open chain olefin metathesis precursor 4b. Inversion of the 3-OH stereochemistry resulted in reduced tubulin polymerization potency. Interestingly, however, α,β-unsaturated lactones (e.g. 42 and 38) retained significant tubulin assembly properties (FIG. 65) suggesting a conformational, rather than a direct binding effect, for this hydroxyl group. Neither 42 nor 38, however, exhibited significant cytotoxicity indicating an additional role for the 3-OH group. Substitution of the 4-gem-dimethyl with a 4,4-ethano moiety (e.g. 267a and 267b) resulted in loss of tubulin polymerization activity in all cases, pointing to the crucial importance of a proper conformation of epothilones for biological activity. Apparently the partial $sp^2$ character and the accompanied widening of the C3-C4-C5 angle introduced intolerable conformational changes within the macrocycle for effective interaction with tubulin. Another clear requirement for tubulin polymerization activity was the (6R,7S) stereochemistry as revealed by the failure of all (6S,7R) stereoisomers to induce tubulin polymerization at significant concentrations (e.g. 64, 425, 432–438, 443, 289, 312, 290, 313, 287, 319, 450–451, 464, and 37, FIGS. 64–65). Interesting, also, was the notable decrease in interaction with tubulin upon inversion of the C8 methyl group (e.g. 458 vs 49), introduction of a gem-dimethyl group at C8 (460 49 and 455 vs 50), and removal of the C8 methyl group (e.g. 459 vs 49 and 456 vs 49 and 439 vs 58).

The importance of the natural stereochemistry (12S,13R) for the epoxide was demonstrated by the general trend of the unnatural 12R,13S epoxides to exhibit lower activities in inducing tubulin assembly. Most interestingly, both the cis and trans olefins corresponding to epothilones A and B were active in the tubulin assembly assays, and the activities of the cis olefins were comparable to those of the natural substances. However, we found that the cis and, especially, the trans olefins were significantly less cytotoxic than the naturally occurring epoxides (49 and 50 vs 1, 71 and 123 vs 2). Moreover, both the α- and β-epoxides derived from the 12,13 E-olefinic precursors exhibited considerable ability to induce tubulin assembly and inhibit cell growth (58, 171 and 172 vs 1, 125 and 126 vs 2; in fact, compound 125 appears to be the most cytotoxic analog from those shown in FIG. 64).

The C12-methyl group consistently bestowed higher potency to all epothilones studied as compared to the C12-des-methyl counterparts (e.g. 2 vs 1 and 233 vs 161), with the exception of compounds 55 and 57 where comparable results were obtained. Inversion of configuration at C15 led to loss of ability to induce tubulin polymerization (141 vs 49, 346 vs 50). Replacement of the C16-methyl with an ethyl group also reduced activity in the tubulin assay (461 vs 49, 457 vs 50) suggesting that the methyl group may play a role in maintaining the planar conformation of the side-chain. The inactivity of the C16–C17 epoxides further supports this conclusion. The epothilone pharmacophore tolerated some heterocycle modifications. Thus, a number of oxazole derivatives exhibited activity comparable to the corresponding thiazoles. Furthermore, replacement of the thiazole with a 2-pyridyl moiety led only to a slight decrease in activity in the tubulin assays, whereas substitution of the C23-methyl with a phenyl group yielded inactive compounds). FIG. 63 summarizes graphically the structure-activity relationships within the epothilone family of compounds as derived from these and previous studies.

The reported work demonstrates the power of interfacing combinatorial chemistry with chemical biology as facilitated by solid phase synthesis, REC chemistry and modern biological assays. Furthermore, this research should facilitate the process of drug discovery and development in the area of cancer chemotherapy.

EXAMPLE 7

Total Synthesis of Epothilone E and Side-Chain Epothilone Analogs via the Stille Coupling Reaction as Illustrated in FIGS. 51–56

In this example we report the first total synthesis of the naturally occurring epothilone E (FIG. 51) via an olefin metathesis reaction to form the macrocycle and a Stille coupling to construct the side chain. In addition, the developed strategy was applied to the synthesis of a library of analogs containing a variety of aromatic systems in place of the 2-methylthiazole moiety of natural epothilone A (see FIGS. 54–55).

FIG. 51 outlines, in retrosynthetic format, the highly convergent metathesis-Stille strategy towards epothilone E and the analogs shown in FIGS. 54–55. The utilization of a common advanced intermediate gives this Stille strategy a distinct advantage in delivering rapidly a plethora of side-chain modified epothilone analogs for biological screening.

The epothilones shown in FIGS. 54–55 were constructed as summarized in FIG. 52. Thus, alcohol 350, prepared in 91% yield by addition of (+)-allyidiisopinocampheyl borane [Icp2B(allyl)] to aldehyde 349, was coupled with carboxylic acid 348 (mixture of C6–C7 diastereoisomers in ca. 3:2 ratio in favor of 348) with DCC and 4-DMAP to afford ester 351 (49% yield, after chromatographic separation from its C6–C7 diastereoisomer). Exposure of 351 to catalytic amounts of $RuCl_2(=CHPh)(PCy_3)_2$ in $CH_2Cl_2$ at ambient temperature resulted in a mixture of cis and transcyclic olefins which were chromatographically separated on silica gel followed by desilylation leading to diols 354 (84%) and 355 (85%), respectively.

The required stannanes were either commercially available, synthesized according to literature procedures or by the sequences shown in FIG. 53. For the synthesis of epothilone E, dibromide 358 was selectively metallated with n-BuLi and then reacted, in the presence of HMPA, with dimethylformamide (DMF) to afford after $NaBH_4$ reduction alcohol 360 in 63% overall yield. Protection of 360 as a silyl ether (TBSCl, imidazole, 96% yield) followed by a second metallation (n-BuLi) and exposure to n-Bu$_3$SnCl (85% yield) furnished after desilylation (TBAF, 95% yield) stannane 363. The synthesis of stannane 371 required: (i) Sonogashira coupling of dibromide 356 with 4-pentyn-1-ol [(Pd(PPh$_3$)$_4$-CuI, i-Pr$_2$NH, 70° C., 83% yield] (ii) chemoselective hydrogenation of the triple bond (cat. PtO$_2$-H$_2$, 100% yield); and (iii) reaction with Me$_3$SnSnMe$_3$-cat. Pd(PPh$_3$)$_3$ (toluene, 100° C., 93% yield). Stannane 373 was prepared from dibromide 358 by reaction with piperidine (60° C., 100% yield), followed by palladium-catalyzed coupling with Me$_3$SnSnMe$_3$ [Pd(PPh$_3$)$_4$, toluene, 80° C., 100% yield]. Similarly, 375 was obtained from 358 by reaction with NaSMe (EtOH, 25° C., 94% yield) followed by exposure to cat. Pd(PPh$_3$)$_4$ and Me$_3$SnSnMe$_3$ (toluene, 80° C., 100%).

Attachment of the aromatic moieties to the macrocyclic framework of vinyl iodides 354 and 355 was performed with the aromatic stannanes shown in FIGS. 54–55 under palladium-catalyzed Stille-type conditions A [Pd(PPh$_3$)$_4$, toluene, 100° C.] or B [Pd(CN)$_2$Cl$_2$, DMF, 25° C.]. FIGS. 54–55 include a selection of the synthesized epothilone A analogs, the coupling method, and the obtained yields.

Epothilone E (356b, FIG. 56) was synthesized from its desoxy analog 356a (FIG. 54) by epoxidation with H$_2$O$_2$-KHCO$_3$—CH$_3$CN in methanol as shown in FIG. 56 (65% yield, based on 50% conversion). Synthetic 356b exhibited identical $^1$H and $^{13}$C NMR spectra to those of the natural substance.

Epothilone E (356b) exhibited 52% tubulin polymerization as compared to 76% for epothilone A, 98% for epothilone B and 50% for Taxol in the filtration-colorimetric tubulin polymerization assay.

EXAMPLE 8

Construction of 26-Substituted Epothilones as Illustrated in FIGS. 57–62

In this example, a series of 26-substituted epothilones has been constructed by total synthesis involving a selective Wittig olefination, an aldol reaction, and a macrolactonization as key steps.

The approach to the C26-modified epothilones B, follows the same path as that developed for epothilone B (vida supra), and involved the following steps: (a) a stereoselective Wittig olefination; (b) an aldol condensation; and (c) a macrolactonization (see FIGS. 57–62).

With large quantities of the allylic alcohol 392 (FIG. 58) at our disposal, our immediate task was the selection of a suitable group for the protection of the primary hydroxyl functionality at C26. A triphenylmethyl (trityl) group was judged to be most useful for this purpose, and indeed served admirably throughout the course of the synthesis. Thus, the key C7–C22 aldehyde fragment 257 was synthesized from 251 as shown in FIG. 37. Protection of 251 as a trityl ether (trityl chloride, 4-DMAP, DMF) furnished 252 in 99% yield. Regioselective hydroboration employing 9-BBN, and an ensuing basic hydrogen peroxide work-up led to primary alcohol 253 in 94% yield, which was converted to iodide 254 by the action of Ph$_3$P, iodine and imidazole in the mixed solvent system of MeCN:Et2O (3:1, 90% yield). Stereoselective alkylation of SAMP hydrazone via its lithio derivative (LDA, THF, –78 to 0° C.), with iodide 254 (–100 to –20° C., 94% yield, based on ca. 70% conversion) led to hydrazone 255. The transformation of 255 to nitrile 256 proceeded smoothly under the influence of MMPP (91% yield), and reduction of the latter with DIBAL in toluene at –78° C. provided the key aldehyde 257 in excellent yield (97%).

The coupling of the C1–C6 ketone fragment with aldehyde 257 via a syn-selective aldol reaction (LDA, –78° C.) as shown in FIG. 38 furnished compound 258 along with its (6S,7R)-diastereoisomer (85% total yield, ca. 3:1 ratio in favor of 13). Chromatographic purification (silica gel, 20% Et$_2$O in hexanes), followed by silylation (TBSOTf, 2,6-lutidine, methylene chloride, 0° C., 92% yield) gave tetra (silyl) ether 259. The use of buffered pyridinium hydrofluoride in THF (alternatively CSA in methylene chloride/methanol) permitted selective desilylation of the primary TBS group (74% yield), which was sequentially oxidized to aldehyde 261 [(COCl)$_2$, DMSO, Et$_3$N], and thence to carboxylic acid 262 (NaClO$_2$, 99%). Selective desilylation at C15 was achieved by the use of TBAF in THF providing the seco-acid 263 in 89% yield. The latter compound was in turn subjected to the macrolactonization conditions described by Yamaguchi allowing isolation of the lactone 264 in 75% yield. Exposure of 264 to pyridinium hydrofluoride in THF promoted concomitant removal of both the silyl groups and the trityl moiety, leading to triol 265 in 78% yield. Alternatively, treatment of 264 with camphorsulfonic acid in MeOH and methylene chloride resulted in the selective removal of the trityl group, giving 265 in 70% yield. Sharpless asymmetric epoxidation of 265 then gave 26-hydroxyepothilone B (266) in 76% yield and as a single diastereoisomer (as judged by both TLC and 1H NMR analysis) (FIGS. 38–39).

The ready availability of the above compound 266 and intermediates facilitated rapid access to a number of 26-substituted epothilones. As indicated in FIGS. 57–62, allylic alcohol 392 was converted, in high yield, to the corresponding esters 1000a–c (see FIG. 57 description of figures for explanation of steps) by reaction with the corresponding acid anhydride or chloride under basic conditions followed by desilylation. MnO$_2$ oxidation of 265 proved highly efficient, providing α,β-unsaturated aldehyde 1000d (step d in 85% yield. Further oxidation of 1000d with NaClO$_2$ led to carboxylic acid 1000e (step e) (98%) which was converted to methyl ester 1000f (step f) by treatment with CH$_2$N$_2$ (80%). Methylation (NaH—MeI) and benzylation (NaH-PhCH$_2$Br) of 266, followed by desilylation afforded methoxy and benzyloxy compounds 1000h, and 1000i, respectively. Halogenation (DAST or CCl$_4$-Ph$_3$P), followed by desilylation, led to chloride 397 or 398 (as epoxide) (73% overall yield) or fluoride 395 (51% overall yield). The aldehyde obtained from MnO$_2$ oxidation of 403 (90%) was subjected to Wittig methylenation (85%) furnishing, after desilylation (85%), terminal olefin 1000k'. Similar chemistry was employed for the preparation of epothilones 1000a–n and 1000a'–l', 395, 398, 401, 404, 407, 413 and 415 as shown in FIGS. 57–62 and 72–75.

EXAMPLE 9

Construction of 14-, 15-, 17- and 18-Membered Ring Relatives of Epothilone A as Illustrated in FIGS. 67–70

This example describes the construction of 14-, 15-, 17- and 18-membered ring relatives of epothilone A and their desoxy counterparts have been obtained by total synthesis and biologically evaluated for their tubulin polymerization properties as shown in FIGS. 67–70.

This example reveals considerable structural distortions inherent in the [14]-, [15]- and [17]-membered ring epothilones, whereas the overall shape of [18]-epothilone A remained relatively unchanged as compared to natural epothilone A ([16]-epothilone A), heightening expectations for biological activity of the latter compound, if not for the others.

The charted route projected epoxidation of the C12–C13 double bond of the macrocycle as the final step and a convergent assembly of the epothilone skeleton via a Wittig reaction, an aldol condensation, and a macrolactonization. This strategy required fragments 1006, 1007 and 1010— FIGS. 67–70 (made exactly as similar analogs described vida supra) or the construction of the key intermediates 1015 and 1016 (FIGS. 67–70) needed for the 14- and 15-membered rings. A slightly different strategy for the synthesis of key building blocks 1033 and 1035 needed for the 17- and 18-membered rings was adopted requiring fragments 1019, 1021 and 1022 FIGS. 67–70 (made exactly as similar analogs described above).

Aldehyde 1006 (FIG. 68) was available via a literature procedure (Eguchi et al. J. Chem. Soc. Chem; Commun. 1994, 137–138) and served a precursor for the second required aldehyde, 7. Thus, olefination of 1006, hydroboration of the resulting olefin, and oxidation of the resulting primary alcohol 1009 furnished the desired aldehyde 1007 in excellent overall yield (see FIG. 68). Each of these two aldehydes (1006 and 1007) was condensed separately with the ylide derived from phosphonium salt 1010 (NaHMDS, THF) to afford the corresponding Z-olefins [1011 (77%) and 1012 (83%)] as the major geometrical isomer in each case (ca. 9:1 ratio). The silyl group was then selectively removed from the primary hydroxyl group by the action of CSA leading to alcohols 1013 (81%) and 1014 (61%). Finally, oxidation of 1013 and 1014 with $SO_3$.pyr. (DMSO-Et3N) led to the targeted intermediates 1015 and 1016 in 81 and 84% yield, respectively.

The reverse ylide-aldehyde condensation approach shown in FIG. 69 was utilized for the construction of advanced intermediates 1033 and 1035. Thus, alcohol 1017 was converted to iodide 1018 by treatment with $Ph_3P$-$I_2$-imidazole (95%) and thence to phosphonium salt 1019 by heating with $Ph_3P$ (neat, 100° C., 97%). A similar sequence was used to prepare phosphonium salt 1021 from the bromide 1020 as the intermediate. The ylides derived from 1019 and 1021 (NaHMDS, THF) reacted with aldehyde 1022 to produce Z-olefins 1023 and 1026 in 85 and 79% yields, respectively, as the major isomer (ca. 9:1 Z:E ratio).

Each product, 1023 and 1026, was selectively desilylated at the primary position with CSA, furnishing alcohols 1024 (99%) and 1027 (95%), respectively, and then converted to the corresponding iodides 1025 (84%) and 1028 (98%) by exposure to $Ph_3P$-$I_2$-imidazole.

The iodides 1025 and 1028 were used to alkylate SAMP hydrazone 1029 according to the method of Enders, furnishing compounds 1030 and 1031 in 60 and 82% yield, respectively. Each hydrazone (1030 and 1031) was converted to the corresponding nitrile (1032, 99% and 1034, 96%) by reaction with MMPP, and then to the desired aldehydes 1033 (90%) and 1035 (81%) by DIBAL reduction.

FIG. 70 shows the coupling of the C1–C6 segment 1036 with fragments 1015, 1016, 1033 and 1035 and the elaboration of the products to the targeted epothilones. All synthesis described in this example are carried out with identical conditions and amounts as that of epothilone A and B. Thus, the enolate generated from ketone 1036 (LDA, THF, −78° C.) reacted smoothly with aldehydes 1015, 1016, 1033 and 1035, affording compounds 1037 (71%), 1038 (72%), 1041 (77%) and 1042 (60%) as the aldol products together with their 6S,7R-diastereoisomers (see FIG. 70 for individual yields) which were removed by silica gel chromatography. These compounds were then silylated (TBSOTf-2,6-lutitine) leading to tetra(silyl)ethers 1039, 1040, 1043 and 1044 in 85–95% yield. Selective removal of the silyl group from the primary position with CSA led to alcohols 1045, 1046, 1049 and 1050 which were oxidized to the corresponding aldehydes (1047, 1048, 1051 and 1052) under Swern conditions [$(COCl)_2$-DMSO-$Et_3N$] in 85–99% yield. Further oxidation to the desired carboxylic acids (1053, 1054, 1057 and 1058) was achieved by reaction with $NaClO_2$ (95–98% yield). The carboxylic acids were then selectively desilylated at C-15 by the action of TBAF producing hydroxyacids 1055, 1056, 1059 and 1060 in 77–92% yield. Ring closure of 1055, 1056, 1059 and 1060 was accomplished by the Yamaguchi method as exactly described for epothilones A and B, furnishing macrocyclic lactones 1061, 1062, 1065 and 1066 in yields ranging from 70–82% (see FIG. 70). The silyl ethers were removed from 1061, 1062, 1065 and 1066 by exposure to HF.pyr. in THF, leading to [14]-, [15]-, [17]- and [18]-desoxyepothilones 1063, 1064, 1067 and 1068 (71–91% yield).

Epoxidation of [14]-desoxyepothilone A (1063) with methyl(trifluoromethyl)dioxirane gave [14]-epothilone A (1002) essentially as a single product (52% yield), whereas epoxidation of the [15]-desoxyepothilone A (1064) under the same conditions led to a mixture of [15]-epothilone A (1003 or 1069) and its diastereomeric epoxide 1069 (or 1003) (70% yield, ca. 1:1 ratio). The [17]-membered ring 1067 furnished a 6:1 ratio of diastereomeric epoxides (97% combined yield) and the [18]-membered ring led to a ca. 2:1 ratio of products (79% total yield). In all cases, the isomeric epoxides were chromatographically separated but their stereochemical identities remain presently unassigned.

Preliminary biological investigations with these compounds revealed significant tubulin polymerization activity for [18]-desoxyepothilone A (1068) (40% as compared to 72% for epothilone A and 53% for Taxol), but relatively weak activity for the two epimeric [18]-epothilones A (1005 and 1071) and for all [14]-, [15]- and [17]-epothilones A (1063, 1064, 1067, 1002–1004, 1069 and 1070) in the filtration-colorimetric tubulin assay. These results provide further support for the limited tolerance of the epothilone pharmacophore and its highly specific binding to the tubulin receptor. Further biological studies with 1068 and related compounds are made in analogy.

EXAMPLE 10

Biological Evaluation of Synthesized Compounds as Tabulated in FIGS. 23, 28, and 64–66

We have carried out microtubule assays following literature procedures and evaluated synthesized compounds for their ability to form and stabilize microtubules. Cytotoxicity studies have also been carried out in our laboratories and preliminary data is disclosed vida infra.

The synthesized epothilones were tested for their action on tubulin assembly using purified tubulin with an assay developed to amplify differences between compounds more active than Taxol. As demonstrated in FIG. 22, both epothilone B(2) ($EC_{50}$=4.0±1 mM) and its progenitor 71 ($EC_{50}$=3.3±0.2 mM) were significantly more active than Taxol ($EC_{50}$=15.0±2 mM) and epothilone A(1) (EC50= 14.0±0.4 mM), whereas compounds 125, 158 and 123 were less effective than Taxol (Lin et al. Cancer Chemother. Pharmacol. 38, 136–140 (1996); Rogan et al. Science 244, 994–996 (1984)).

As shown in FIG. 23, cytotoxicity experiments with 1A9, 1A9PTX10 (β-tubulin mutant), 1A9PTX22 (β-tubulin mutant) and A2780AD cell lines revealed a number of interesting results (FIG. 23). Thus, despite its high potency in the tubulin assembly assay, compound 71 did not display the potent cytotoxicity of 2 against 1A9 cells, being similar to 1 and Taxol. These data suggest that while the C12–C13 epoxide is not required for the epothilone-tubulin interaction, it may play an important role in localizing the agent to its target within the cell. Like the naturally occurring epothilones 1 and 2, analogue 71 showed significant activity against the MDR line A2780AD and the altered β-tubulin-expressing cell lines 1A9PTX10 and 1A9PTX22, suggesting, perhaps, different contact points for the epothilones and Taxol with tubulin (i.e. stronger binding of epothilones around residue 364 than around 270 relative to taxoids).

See example 6 (above) for further discussion about analogs which possess strong tubulin binding properties and that which posess potent cytotoxic action against tumor cell lines.

Colorimetric Cytotoxicity Assay for Anticancer-Drug Screening

The calorimetric cytotoxicity assay used was adapted from Skehan et al (*Journal of National Cancer Inst* 82:1107–1112, 19901). The procedure provides a rapid, sensitive, and inexpensive method for measuring the cellular protein content of adherent and suspension cultures in 96-well microtiter plates. The method is suitable for ordinary laboratory purposes and for very large-scale applications, such as the National Cancer Institute's disease-oriented in vitro anticancer-drug discovery screen, which requires the use of several million culture wells per year.

In particular, cultures fixed with trichloroacetic acid were stained for 30 minutes with 0.4% (wt/vol) sulforhodamine B (SRB) dissolved in 1% acetic acid. Unbound dye was removed by four washes with 1% acetic acid, and protein-bound dye was extracted with 10 mM unbuffered Tris base [tris(hydroxymethyl)aminomethane] for determination of optical density in a computer-interfaced, 96-well microtiter plate reader. The SRB assay results were linear with the number of cells and with values for cellular protein measured by both the Lowry and Bradford assays at densities ranging from sparse subconfluence to multilayered supra-confluence. The signal-to-noise ratio at 564 nm was approximately 1.5 with 1,000 cells per well. The sensitivity of the SRB assay compared favorably with sensitivities of several fluorescence assays and was superior to those of both the Lowry and Bradford assays and to those of 20 other visible dyes.

The SRB assay provides a calorimetric end point that is nondestructive, indefinitely stable, and visible to the naked eye. It provides a sensitive measure of drug-induced cytotoxicity, is useful in quantitating clonogenicity, and is well suited to high-volume, automated drug screening. SRB fluoresces strongly with laser excitation at 488 nm and can be measured quantitatively at the single-cell level by static fluorescence cytometry (Skehan et al (*Journal of National Cancer Inst* 82:1107–1112, 19901)).

Filtration Colorimetric Assay

Microtubule protein (0.25 ml of 1 mg/ml) was placed into an assay tube and 2.5 µl of the test compound were added. The sample was mixed and incubated at 37° C. for 30 minutes. Sample (150 µl) was transferred to a well in a 96-well Millipore Multiscreen Durapore hydrophilic 0.22 µm pore size filtration plate which had previously been washed with 200 µl of MEM buffer under vacuum. The well was then washed with 200 l of MEM buffer.

To stain the trapped protein on the plate, 50 µl amido black solution [0.1% naphthol blue black (Sigma)/45% methanol/10% acetic acid] were added to the filter for 2 minutes; then the vacuum was reapplied. Two additions of 200 µl amido black destain solution (90% methanol/2% acetic acid) were added to remove unbound dye. The signal was quantitated by the method of Schaffner and Weissmann et al. *Anal. Biochem.*, 56 502–514, 1973 as follows:

200 µl of elution solution (25 mM NaOH-0.05 mm EDTA-50% ethanol) were added to the well and the solution was mixed with a pipet after 5 minutes. Following a 10-minutes incubation at room temperature, 150 µl of the elution solution were transferred to the well of a 96-well plate and the absorbance was measured on a Molecular Devices Microplate Reader.

Synthetic Protocals

All reactions were carried out under an argon atmosphere with dry, freshly distilled solvents under anhydrous conditions, unless otherwise noted. Tetrahydrofuran (THF), toluene and ethyl ether (ether) were distilled from sodium-benzophenone, and methylene chloride from calcium hydride. Anhydrous solvents were also obtained by passing them through commercially available alumina column. Yields refer to chromatographically and spectroscopically ($^1$H NMR) homogeneous materials, unless otherwise stated. Reagents were purchased at highest commercial quality and used without further purification unless otherwise stated. Reactions were monitored by thin layer chromatography carried out on 0.25 mm E. Merck silica gel plates (60F-254) using UV light as visualizing agent and 7% ethanolic phosphomolybdic acid or p-anisaldehyde solution and heat as developing agents. E. Merck silica gel (60, particle size 0.040–0.063 mm) was used for flash column chromatography. Preparative thin-layer chromatography (PTLC) separations were carried out on 0.25, 0.50 or 1 mm E. Merck silica gel plates (60F-254). NMR spectra were recorded on Bruker AMX-600 or AMX-500 instruments and calibrated using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. Optical rotations were recorded on a Perkin-Elmer 241 polarimeter. High resolution mass spectra (HRMS) were recorded on a VG ZAB-ZSE mass spectrometer under fast atom bombardment (FAB) conditions with NBA as the matrix. Melting points (mp) are uncorrected and were recorded on a Thomas Hoover Unimelt capillary melting point apparatus.

Synthesis of Aldehyde 7 as illustrated in FIG. 3A. A solution of sodium bis(trimethylsilyl)amide (NaHMDS, 236 mL, 1 M in THF, 1.05 equiv) was added over 30 min at −78° C. to a solution of N-acylsultam 13 (synthesized according to Oppolzer et al. Tetrahedron Lett. 11989, 30, 5603–1989; Oppolzer, W. Pure & Appl. Chem. 1990, 62, 1241–1250) (61.0 g, 0.225 mol) in THF (1.1 L, 0.2 M). After stirring the resulting sodium enolate solution at −78° C. for 1 hour, freshly distilled 5-iodo-1-pentene (58 mL, 0.45 mol, 2.0 equiv) in hexamethylphosphoramide (HMPA, 117 mL, 0.675 mol, 3.0 equiv) was added. The reaction mixture was allowed to slowly warm to 25° C., quenched with water (1.5 L) and extracted with ether (3×500 mL). Drying (MgSO4) and evaporation of the solvents gave crude sultam 14 (76.3 g), which was used without further purification. A pure sample of 14 was obtained by preparative thin layer chromatography (250 mm silica gel plate, 10% EtOAc in hexanes). Step 2. (Reductive Cleavage of Sultam 14). A solution of crude sultam 14 (76.0 g, 0.224 mol) in ether (200 mL) was added to a stirred suspension of lithium aluminum hydride (LAH, 9.84 g, 0.246 mol, 1.1 equiv) in diethylether (ether) (900 mL) at −78° C. The reaction mixture was stirred at −78° C. for 15 min, quenched by addition of water (9.8 mL) and warmed to 0° C. Sequential addition of 15% aqueous sodium hydroxide solution (9.8 mL) and water (29.4 mL) was followed by warming the reaction mixture to 25° C. After stirring for 5 h, the aluminum salts were removed by filtration through ceiite, the filtrate was dried (MgSO4) and the solvent was removed by distillation under atmospheric pressure. Vacuum distillation (bp. 85° C./8 mm Hg) furnished pure alcohol 15 as a colorless oil (17.1 g, 60% from sultam). Step 3: To a solution of alcohol 15 (0.768 g, 6.0 mmol) in methylene chloride (30 mL, 0.2 M) were added powdered 4 Å molecular sieves (1.54 g), 4-methylmorpholine N-oxide (NMO, 1.06 g, 9.0 mmol, 1.5 equiv) and tetrapropylammonium perruthenate TPAP, 0.105 g, 0.3 mmol, 0.05 equiv) at room temperature. After stirring for 30 min, the disappearance of starting material was indicated by TLC. Celite was added (1.54 g) and the suspension was filtered through silica gel and eluted with methylene chloride. The solvent was carefully distilled off under atmospheric pressure to yield aldehyde 7 (0.721 g, 95%) as colorless oil.

Synthesis of Alcohol 18a as illustrated in FIG. 3B. (Silylation of alcohol 16a). Alcohol 16a (5.0 g, 0.068 mol; glycidol; Aldrich/Sigma) was dissolved in DMF (70 mL, 1.0 M), the solution was cooled to 0° C. and imidazole (9.2 g, 0.135 mol, 2.0 equiv) was added. After stirring for 10 min, tert-butylchlorodiphenylsilane (TPSCl, 24 mL, 0.088 mol, 1.3 equiv) was added and the reaction mixture was allowed to stir for 30 min at 0° C. and for 1 h at 25° C. Ether (70 mL) was added, followed by saturated aqueous NaHCO3 solution (70 mL). The organic phase was separated and the aqueous layer was extracted with ether (50 mL), washed with water (2×120 mL) and with saturated aqueous NaCl solution (120 mL). The organic extract was dried (MgSO4), filtered through celite, and the solvents were removed under reduced pressure. Flash column chromatography (silica gel, 5% EtOAc in hexanes) provided silyl ether 17a (18.9 g, 90%). Step 2. Silylation of alcohol 16b. Following the procedure described for the synthesis of silyl ether 17a, alcohol 16b (5.0 g, 0.068 mol; Aldrich/Sigma) in DMF (70 mL, 1.0 M) was treated with imidazole (9.2 g, 0.135 mol, 2.0 equiv) and tert-butylchlorodiphenylsilane (24 mL, 0.088 mol, 1.3 equiv) to yield silyl ether 17b (19.8 g, 94%). Rf=0.28 (5% EtOAc in hexanes). Step 3. Opening of Epoxide 17a with Vinylcuprate. To a solution of tetravinyltin (3.02 mL, 16.6 mmol, 1.25 equiv) in THF (44 mL) was added n-butyllithium (41.5 mL, 1.6 M in hexanes, 5.0 equiv) at −78° C. and the reaction mixture was stirred for 45 min. The resulting solution of vinyllithium was transferred via cannula to a solution of azeotropically dried (2×5 mL toluene) copper(I) cyanide (2.97 g, 33.2 mmol, 2.5 equiv) in THF (44 mL) at −78° C., and the mixture was allowed to warm to −30° C. Epoxide 17a (4.14 g, 13.3 mmol) in THF (44 mL) was transferred via cannula to this vinyl cuprate solution, and the mixture was stirred at −30° C. for 1 h. The reaction mixture was quenched with saturated aqueous NH4Cl solution (150 mL), filtered through celite, extracted with ether (2×100 mL) and dried (MgSO4). After removal of the solvents under reduced pressure, flash column chromatography (silica gel, 3% EtOAc in hexanes) furnished alcohol 18a.

Synthesis of Alcohol 18b as illustrated in FIG. 3B. Opening of Epoxide 17b with Vinylcuprate. Following the procedure described for the synthesis of alcohol 18a, epoxide 17b (1.97 g, 6.3 mmol, starting from commerically available 16b in lieu of 16a) yielded alcohol 18b (1.78 g, 83%).

Synthesis of Keto Acid 21 as illustrated in FIG. 3C. Homer-Wadsworth-Emmons Reaction of Aldehyde 12 with Phosphonate 19. A solution of phosphonate 19 (23.6 g, 94 mmol, 1.2 equiv; Aldrich) in THF (100 mL) was transferred via cannula to a suspension of sodium hydride (60% dispersion in mineral oil, 5.0 g, 125 mmol, 1.6 equiv) in THF (200 mL) at 25° C. After stirring for 15 min, the reaction mixture was cooled to 0° C., and a solution of aldehyde 12 (10.0 g, 78 mmol; synthesized according to Inuka, T., and Yoshizawa, R. J. Org. Chem. 1967, 32, 404–407) in THF (20 mL) was added via cannula and the ice-bath was removed. After 1 h at 25° C., TLC indicated the disappearance of aldehyde 12. The mixture was then separated between water (320 mL) and hexanes (100 mL). The aqueous layer was extracted with hexanes (100 mL) and the combined organic layers were successively washed with water (200 mL) and saturated aqueous NaCl solution (200 mL). Drying (MgSO4), concentration under reduced pressure and purification by flash column chromatography (silica gel, 10% EtOAc in hexanes) yielded keto ester 20 (17.4 g, 99%) as a yellow oil. Step 2. Hydrolysis of Keto Ester 20. Keto ester 20 (17.4 g, 77 mmol) in methylene chloride (39 mL, 2 M) was treated with trifluoroacetic acid (TFA, 39 mL, 2 M) at 25° C. Within 30 minutes TLC indicated disappearance of the ester. The mixture was concentrated under reduced pressure, dissolved in saturated aqueous NaHCO3 solution (20 mL) and washed with ether (2×20 mL). The aqueous phase was then acidified to pH~2 with 4 N HCl, saturated with NaCl, and extracted with EtOAc (6×20 mL). The organic layer was dried (MgSO4) and concentrated under reduced pressure to give pure keto acid 21 (13.0 g, 99%) as a clear oil, which solidified on standing.

Synthesis of Dienes 23 and 24 as illustrated in FIG. 4. EDC Coupling of Alcohol 18a with Keto Acid 21. A solution of keto acid 21 (2.43 g, 14.3 mmol, 1.2 equiv), 4-(dimethylamino)pyridine (4-DMAP, 0.145 g, 1.2 mmol, 0.1 equiv) and alcohol 18a (4.048 g, 11.9 mmol, 1.0 equiv) in methylene chloride (40 mL, 0.3 M) was cooled to 0° C. and then treated with 1-ethyl-(3-dimethylaminopropyl)-3-carbodiimide hydrochloride (EDC, 2.74 g, 14.3 mmol, 1.2 equiv). The reaction mixture was stirred at 0° C. for 2 h and then at 25° C. for 12 h. The solution was concentrated to dryness in vacuo, and the residue was taken up in EtOAc (10 mL) and water (10 mL). The organic layer was separated, washed with saturated NH4Cl solution (10 mL) and water (10 mL) and dried (MgSO4). Evaporation of the solvents followed by flash column chromatography (silica gel, 4% EtOAc in hexanes) resulted in pure keto ester 22a (5.037 g, 86%). Step B. Aldol Condensation of Ester 22a with Aldehyde 7. A solution of keto ester 22a (1.79 g, 3.63 mmol, 1.0 equiv) in THF (15 mL) was added via cannula to a freshly prepared solution of lithium diisopropylamide [LDA; formed by addition of n-BuLi (2.83 mL, 1.6 M solution in hexanes, 4.58 mmol, 1.25 equiv) to a solution of diisopropylamine (0.61 mL, 4.36 mmol, 1.2 equiv) in THF (30 mL) at −10° C. and stirring for 30 min] at −78° C. After 15 min the reaction mixture was allowed to warm to −40° C. and was stirred for 45 min. The reaction mixture was cooled to −78° C. and a solution of aldehyde 7 (0.740 g, 5.8 mmol, 1.6 equiv) in THF (15 mL) was added dropwise. The resulting mixture was stirred for 15 min, then warmed to −40° C. for 30 min, cooled back to −78° C. and then quenched by slow addition of saturated aqueous NH4Cl solution (10 mL). The reaction mixture was warmed to 25° C., diluted with EtOAc (10 mL) and the aqueous phase was extracted with EtOAc (3×10 mL). The combined organic layers were dried (MgSO4), concentrated under reduced pressure and subjected to flash chromatographic purification (silica gel, 5 K 20% EtOAc in hexanes) to afford a mixture of aldol products 23 (926 mg, 42%) and 24 (724 mg, 33%), along with unreacted starting keto ester 22a (178 mg, 10%).

Synthesis of Hydroxy Lactone 25 as illustrated in FIG. 4. Olefin Metathesis of Diene 23. To a solution of diene 23 (0.186 g, 0.3 mmol) in methylene chloride (100 mL, 0.003 M) was added (RuCl$_2$(=CHPh)(PCy$_3$)$_2$ (=bis(tricyclohexylphosphine)benzylidine ruthenium dichloride) 25 mg, 0.03 mol, 0.1 equiv; available from Aldrich) and the reaction mixture was allowed to stir at 25° C. for 12 h. After the completion of the reaction was established by TLC, the solvent was removed under reduced pressure and the crude product was purified by flash chromatography (silica gel, 30% EtOAc in hexanes) to give trans-hydroxy lactone 25 (151 mg, 85%).

Synthesis of Hydroxy Lactone 26 as illustrated in FIG. 4. Olefin Metathesis of Diene 24. Following the procedure described above for the synthesis of hydroxy lactone 25, a solution of diene 24 (0.197 g, 0.32 mmol) in methylene chloride (100 mL, 0.003 M) was treated with RuCl$_2$(=CHPh)(PCy$_3$)$_2$ (26 mg, 0.032 mol, 0.1 equiv), to produce, after flash chromatography (silica gel, 18 K 25% EtOAc in hexanes), trans-hydroxy lactone 26 (150 mg, 79%).

Synthesis of Diol 27 as illustrated in FIG. 4. Desilylation of TPS Ether 25. A solution of TPS ether 25 (145 mg, 0.23 mmol) in THF (4.7 mL, 0.05 M) was treated with glacial acetic acid (70 mL, 1.15 mmol, 5.0 equiv) and tetrabutylammonium fluoride (TBAF, 490 mL, 1 M solution in THF, 0.46 mmol, 2.0 equiv) at 25° C. After stirring for 36 h, no starting material was detected by TLC and the reaction mixture was quenched by addition of saturated aqueous NH$_4$Cl (10 mL). Extractions with ether (3×10 mL), drying (MgSO$_4$) and concentration was followed by flash chromatographic purification (silica gel, 50% EtOAc in hexanes) to provide diol 27 (78 mg, 92%).

Synthesis of Diol 28 as illustrated in FIG. 4. Desilylation of TPS Ether 26: In accordance with the procedure describing the desilylation of TPS ether 25 using a solution of TPS ether 26 (31 mg, 0.05 mmol) in THF (1.0 mL, 0.05 M).

Synthesis of Ester 22b as illustrated in FIG. 5. Compound 22b was synthesized according to the procedure as described above for Ester 22a using 18b instead of 18a.

Synthesis of dienes 29 and 30 as illustrated in FIG. 5. Compounds 29 and 30 were synthesized according to the procedure as described above for 23 and 24 using 22b instead of 22a.

Synthesis of Hydroxy Lactone 31 as illustrated in FIG. 5. Compound 31 was synthesized according to the procedure as described via supra for 25 and 26 using 29 instead of 23.

Synthesis of Hydroxy Lactone 32 as illustrated in FIG. 5. Compound 31 was synthesized according to the procedure as described via supra for 25 and 26 using 30 instead of 24.

Synthesis of Hydroxy Acids 33 and 34 as illustrated in FIG. 6. Aldol Condensation of Acid 21 with Aldehyde 7. A solution of keto acid 21 (752 mg, 4.42 mmol, 1.0 equiv) in THF (22 mL) was added dropwise at −78° C. to a freshly prepared solution of LDA [formed by addition of n-BuLi (6.49 mL, 1.6 M solution in hexanes, 10.4 mmol, 2.35 equiv) to a solution of diisopropylamine (1.43 mL, 10.2 mmol, 2.3 equiv) in THF (44 mL) at −10° C. and stirring for 30 min]. After stirring for 15 min the reaction mixture was allowed to warm to −30° C. and stirred at that temperature for 1.5 h. The reaction mixture was cooled back to −78° C. and a solution of aldehyde 7 (0.891 g, 7.07 mmol, 1.6 equiv) in THF (22 mL) was added via cannula. The resulting mixture was stirred for 15 min at −78° C., then warmed to −40° C. and stirred for 1 h, cooled to −78° C. and quenched by slow addition of saturated aqueous NH$_4$Cl (10 mL) solution. The reaction mixture was warmed to 0° C., and acetic acid (1.26 mL, 22.1 mmol, 5.0 equiv) was added, followed by warming to 25° C. Extractions with EtOAc (6×15 mL), filtration through a short plug of silica gel and concentration afforded, in high yield, a mixture of aldol products 33 and 34 along with unreacted starting acid 21 in a 35:50:15 ratio (1H NMR). This crude material was used without further purification.

Synthesis of Esters 35 and 36 as illustrated in FIG. 6. EDC Coupling of Alcohol 6 with Keto Acids 33 and 34. By analogy to the procedure described above for the synthesis of ester 22a, a solution of keto acids 33 and 34 (1.034 g crude), 4-dimethylaminopyridine (4-DMAP, 43 mg, 0.35 mmol), and alcohol 6 (1.1 g, 5.24 mmol; synthesized as compound 91 (see above); eg. alcohol 6 as shown in FIG. 6 is the same compound as compound 91 as shown in FIG. 12) in methylene chloride (4 mL) was treated with 1-ethyl-(3-dimethylaminopropyl)-3-carbodiimide hydrochloride (EDC, 1.00 g, 5.24 mmol) to provide, after column chromatography (silica gel, 20% EtOAc in hexanes), ester 35 (0.567 g, 29% from keto acid 21) and ester 36 (0.863 g, 44% from keto acid 21).

Synthesis of Hydroxy Lactone 37 as illustrated in FIG. 6. Olefin Metathesis of Diene 35. A solution of diene 35 (58 mg, 0.12 mmol) in methylene chloride (129 mL, 0.001 M) was treated with bis(tricyclohexylphosphine)benzylidine ruthenium dichloride ((RuCl$_2$(=CHPh)(PCy$_3$)$_2$, 10 mg, 0.0012 mmol, 0.1 equiv; Aldrich), in accordance with the procedure described for the synthesis of hydroxy lactone 25, to furnish, after column chromatography (silica gel, 15% EtOAc in hexanes) hydroxy lactone 37 (48 mg, 86%).

Synthesis of Hydroxy Lactone 38 as illustrated in FIG. 6. Compound 38 was synthesized according to the procedure as described via supra for 35 using 36 instead of 35.

Synthesis of Epothilones 39, 40 and 41 as illustrated in FIG. 6. Epoxidation of trans-Hydroxy Lactone 37. Procedure A: A solution of trans-hydroxy lactone 37 (20 mg, 0.06 mmol) in CHCl$_3$ (1 mL, 0.06 M) was treated with meta-chloroperbenzoic acid (mCPBA, 57–86%, 15 mg, 0.05–0.07 mol, 0.9–1.2 equiv) at −20° C., and the reaction mixture was allowed to warm up to 0° C. After 12 h, disappearance of starting material was detected by TLC, and the reaction mixture was then washed with saturated aqueous NaHCO$_3$ solution (2 mL) and the aqueous phase was extracted with EtOAc (3×2 mL). The combined organic layer was dried (MgSO4), filtered and concentrated. Purification by preparative thin layer chromatography (250 mm silica gel plate, 30% EtOAc in hexanes) furnished epothilones 39 (or 40) (12 mg, 40%), 40 (or 39) (7.5 mg, 25%) and 41 (5.4 mg, 18%). Procedure B: To a solution of trans-hydroxy lactone 37 (32 mg, 0.07 mmol) in acetonitrile (1.0 mL) was added a 0.0004 M aqueous solution of disodium salt of ethylenediaminetetraacetic acid (Na$_2$EDTA, 0.5 mL) and the reaction mixture was cooled to 0° C. Excess of 1,1,1-trifluoroacetone (0.2 mL) was added, followed by a portionwise addition of Oxone® (200 mg, 0.35 mmol, 5.0 equiv) and NaHCO$_3$ (50 mg, 0.56 mmol, 8.0 equiv) with stirring, until the disappearance of starting material was detected by TLC. The reaction mixture was then treated with excess dimethyl sulfide (150 mL) and water (1.0 mL) and then extracted with EtOAc (4×2 mL). The combined organic layer was dried (MgSO$_4$), filtered, and concentrated. Purification by preparative thin layer chromatography (250 mm silica gel plate, 70% EtOAc in hexanes) provided a mixture of diastereomeric epoxides, epoxide 39 (or 40) (15 mg, 45%) and α-isomeric epoxide 40 (or 39) (9.2 mg, 28%).

Synthesis of Epothilones 42, 43 and 44 as illustrated in FIG. 6. Compounds 42, 43, and 44 were synthesized according to the procedure as described above for 39, 40 and 41 using 38 instead of 37.

Synthesis of Hydroxy Keto Acids 45 and 46 as illustrated in FIG. 7. Compounds 45, and 46 were synthesized according to the procedure as described above for 33 and 34 using 8 instead of 21.

Synthesis of Hydroxy Esters 4 and 47 as illustrated in FIG. 7. Compounds 4 and 47 were synthesized according to the procedure as described above for 35 and 36 using 45 and 46 instead of 33 and 34.

Synthesis of Hydroxy Lactones 3 and 48 as illustrated in FIG. 8. Cyclization of Diene 42 via Olefin Metathesis was performed using conditions as described for the conversion of 23 to 25 above substituting 4 in lieu of 23 to form 3 and 48.

Synthesis of cis-Dihydroxy Lactones 49 and 50 as illustrated in FIG. 8. Desilylation of Compound 3 and 48: Compounds 49 and 50 were synthesized according to the procedure as described above for 28 and 28 using 3 and 48 instead of 25 and 26.

Synthesis of Epothilones A(1) and 51–57 as illustrated in FIG. 8. Epoxidation of cis-Dihydroxy Lactone 49. Procedure A: A solution of cis-dihydroxy lactone 49 (24 mg, 0.05 mmol) in CHCl$_3$ (4.0 mL) was reacted with meta-chloroperbenzoic acid (mCPBA, 57–86%, 13.0 mg, 0.04–0.06 mmol, 0.8–1.2 equiv), at −20 to 0° C., according to the procedure described for the epoxidation of 37, resulting in the isolation of epothilone A(1) (8.6 mg, 35%), its isomeric α-epoxide 51 (2.8 mg, 13%), and compounds 52 (or 53) (1.6 mg, 9%), 53 (or 52) (1.5 mg, 7%), 54 (or 55) (1.0 mg, 5%), and 55 (or 54) (1.0 mg, 5%) (stereochemistry unassigned for 52 and 53 and for 54 and 55), after two consecutive preparative thin layer chromatographic purifications (250 mm silica gel plate, 5% MeOH in methylene chloride and 70% EtOAc in hexanes). Procedure B: To a solution of cis-dihydroxy lactone 49 (15 mg, 0.03 mmol) in methylene chloride (1.0 mL) at 0° C. was added dropwise a solution of dimethyidioxirane in acetone (ca 0.1 M, 0.3 mL, ca 1.0 equiv) until no starting lactone was detectable by TLC. The solution was then concentrated in vacuo and the crude product was subjected to two consecutive preparative thin layer chromatographic purifications (250 mm silica gel plate, 5% MeOH in methylene chloride and 70% EtOAc in hexanes), to obtain pure epothilone A(1) (7.4 mg, 50%), its isomeric α-epoxide 51 (2.3 mg, 15%), and epothilones 52 (or 53) (0.8 mg, 5%) and 53 (or 52) (0.8 mg, 5%) (stereochemistry unassigned for 52 and 53. Procedure C: As described in procedure B for the epoxidation of trans-hydroxy lactone 37, cis-dihydroxy lactone 49 (10.0 mg, 0.02 mmol) in MeCN (200 mL) was treated with a 0.0004 M aqueous solution of disodium salt of ethylenediaminetetraacetic acid (Na$_2$EDTA, 120 mL), excess 1,1,1-trifluoroacetone (100 mL), Oxone® (61 mg, 0.10 mmol, 5.0 equiv) and NaHCO$_3$ (14 mg, 0.16 mmol, 8.0 equiv), to yield, after purification by preparative thin layer chromatography (250 mm silica gel plate, ether), a mixture of diastereomeric epoxides, epothilones A(1) (6.4 mg, 62%) and α-isomeric epoxide 51 (1.3 mg, 13%). Procedure D: A solution of cis-dihydroxy lactone 49 (18 mg, 0.037 mmol) in CHCl$_3$ (1.0 mL) was treated with meta-chloroperbenzoic acid (mCPBA, 57–86%, 15 mg, 0.049–0.074 mmol, 1.3–2.0 equiv), according to the procedure described for the epoxidation of 37, furnishing compounds 1 (2.7 mg, 15%), 51 (1.8 mg, 10%), 52 (or 53) (1.8 mg, 10%), 53 (or mg, 8%), 54 (or 55) (1.4 mg, 8%), 55 (or 54) (1.26 mg, 7%), 56 (0.9 mg, 5%), and 57 (0.9 mg, 5%) (stereochemistry unassigned for 52–57), after two consecutive preparative thin layer chromatographic purifications (250 mm silica gel plate, 5% MeOH in methylene chloride and 70% EtOAc in hexanes). Epothilone A(1).

Synthesis of Compounds 54, 55, and 57 as illustrated in FIG. 8. Oxidation of Epothilone A(1) with mCPBA. A solution of epothilone A(1) (3.0 mg, 0.006 mmol) in CHCl$_3$ (120 mL, 0.05 M) was reacted with meta-chloroperbenzoic acid (mCPBA, 57–86%, 1.1 mg, 0.0023–0.0032 mmol, 0.8–1.1 equiv; Aldrich), at −20 to 0° C., according to the procedure described for the epoxidation of 37, resulting in the formation of bis(epoxides) 54 (or 55) (1.1 mg, 35%) and 55 (or 54) (1.0 mg, 32%) along with sulfoxide 57 (0.2 mg, 6%).

Synthesis of Epothilones 58–60 as illustrated in FIG. 9. Synthesis was the same as for 1 with the following substitutions: (a) 0.9–1.3 equivalents of mCPBA, CHCl$_3$, −20→0° C., 12 hours, 58 (or 59) (5%), 59 (or 58) (5%), 60 (60%); (b) 1.0 equivalent of dimethyidioxiran methylene chloride/ acetone, 0° C., 58 (or 59) (10%), 59 (or 58) (10%), 60 (40%); (c) excess of CF$_3$COCH$_3$, 8.0 equivalents of NaHCO$_3$, 5.0 equivalents of Oxone®, MeCN/Na$_2$EDTA (2:1), 0° C., 58 (or 59) (45%), 59 (or 58) (35%).

Synthesis of Dihydroxy Ester 61 as illustrated in FIG. 10. Synthesis was the same as for 49 and 50 with the following substitutions: use 47 in lieu of 3 and 48.

Synthesis of Dihydroxy Lactones 62 and 63 as illustrated in FIG. 10. Olefin Metathesis of Dihydroxy Ester 61. Same metathesis procedure as used in FIG. 8 converting 4 to 3 and 48, using instead 61 to form 62 and 63.

Synthesis of Epothilones 64–69 as illustrated in FIG. 10. Compounds 64–69 were synthesized according to the procedure as described above for 1 (FIG. 8) using 62 or 63 instead of 1.

Synthesis of Alcohol 85 as illustrated in FIG. 12. Allylboration of Keto Aldehyde 84. Aldehyde 84 (16.0 g, 0.125 mol; Inuka, T.; Yoshizawa, R. J. Org. Chem. 1967, 32, 404–407) was dissolved in ether (400 mL) and cooled to −100° C. To this solution was added (+)-diisopinocampheylallylborane (800 mL, 0.15 M in pentane, 0.125 mol, 1.0 equiv) by cannulation during 45 min. [(+)-Diisopinocampheylallylborane in pentane is prepared by the adaptation of the standard methods reported by Brown]. After the addition was complete, the mixture was stirred at the same temperature for 30 min. Methanol (20 mL) was added at −100° C., and the reaction mixture was allowed to reach room temperature. To this solution was added saturated aqueous NaHCO$_3$ solution (200 mL), followed by H$_2$O$_2$ (80 mL of 50% solution in H$_2$O), and the reaction mixture was allowed to stir at room temperature for 12 h. The reaction mixture was extracted.

Synthesis of Ketone 86 as illustrated in FIG. 12. Silylation of Alcohol 85. Compound 86 was synthesized according to the procedure as described via supra for 17a using TBSOTf and 84 instead of 17a and TPSCl.

Synthesis of Keto Aldehyde 87 as illustrated in FIG. 12. Ozonolysis of Ketone 86. Alkene 86 (2.84 g, 10 mmol) was dissolved in methylene chloride (25 mL) and the solution was cooled to −78° C. Oxygen was bubbled through for 2 min after which time ozone was passed through until the reaction mixture adopted a blue color (ca 30 min). The solution was then purged with oxygen for 2 min at −78° C. (disappearance of blue color) and $Ph_3P$ (3.16 g, 12.0 mmol, 1.2 equiv) was added. The cooling bath was removed and the reaction mixture was allowed to reach room temperature and stirred for an additional 1 h. The solvent was removed, under reduced pressure and the mixture was purified by flash column chromatography (silica gel, 25% ether in hexanes) to provide pure keto aldehyde 87 (2.57 g, 90%).

Synthesis of Keto Acid 76 as illustrated in FIG. 12. Oxidation of Keto Aldehyde 87. Aldehyde 87 (2.86 g, 10 mmol), tBuOH (50 mL), isobutylene (20 mL, 2 M solution in THF, 40 mmol, 4.0 equiv), $H_2O$ (10 mL), $NaClO_2$ (2.71 g, 30.0 mmol, 3.0 equiv) and $NaH_2PO_4$ (1.80 g, 15.0 mmol, 1.5 equiv) were combined and stirred at room temperature for 4 h. The reaction mixture was concentrated under reduced pressure and the residue was subjected to flash column chromatography (silica gel, 50% ether in hexanes) to produce pure keto acid 76 (2.81 g, 93%). Rf=0.12 (silica gel, 20% ether in hexanes).

Synthesis of Aldehyde 89 as illustrated in FIG. 12. Reduction of Ester 88. Ethyl ester 88 (52.5 g, 0.306 mol; Aldrich) was dissolved in methylene chloride (1 L) and cooled to −78° C. DIBAL (490.0 mL, 1 M solution in methylene chloride, 0.4896 mol, 1.6 equiv) was added dropwise via a cannula while the temperature of the reaction mixture was maintained at −78° C. After the addition was complete, the reaction mixture was stirred at the same temperature until its completion was verified by TLC (ca 1 h). Methanol (100 mL) was added at −78° C. and was followed by addition of EtOAc (1 L) and saturated aqueous $NH_4Cl$ solution (300 mL). The quenched reaction mixture was allowed to warm up to room temperature and stirred for 12 h. The organic layer was separated, and the aqueous phase was extracted with EtOAc (3×200 mL). The combined organic phase was dried over $MgSO_4$, filtered, and concentrated under reduced pressure. Flash column chromatography (silica gel, 10 to 90% ether in hexanes) furnished the desired aldehyde 89 (33.6 g, 90%): Rf=0.68 (silica gel, ether).

Synthesis of Aldehyde 90 as illustrated in FIG. 12. Aromatic aldehyde 89 (31.1 g, 0.245 mol) was dissolved in benzene (500 mL) and 2-(triphenylphosphoranilidene)-propionaldehyde (90.0 g, 0.282 mol, 1.15 equiv) was added. The reaction mixture was heated at reflux until the reaction was complete as judged by TLC (ca 2 h). Evaporation of the solvent under reduced pressure, followed by flash column chromatography (10 to 90% ether in hexanes) produced the desired aldehyde 90 (40.08 g, 98%).

Synthesis of Alcohol 91 as illustrated in FIG. 12. Allylboration of Aldehyde 90. Aldehyde 90(20.0 g, 0.120 mol) was dissolved in anhydrous ether (400 mL) and the solution was cooled to −100° C. (+)-Diisopinocampheylallyl borane (1.5 equiv in pentane, prepared from 60.0 g of (−)-Ipc2BOMe and 1.0 equiv of allyl magnesium bromide according to the method described for the synthesis of alcohol 85), was added dropwise under vigorous stirring, and the reaction mixture was allowed to stir for 1 h at the same temperature. Methanol (40 mL) was added at −100° C., and the reaction mixture was allowed to warm up to room temperature. Amino ethanol (72.43 mL, 1.2 mol, 10.0 equiv) was added and stirring was continued for 15 h. The work-up procedure was completed by the addition of a saturated aqueous $NH_4Cl$ solution (200 mL), extraction with EtOAc (4×100 mL) and drying of the combined organic layers with $MgSO_4$. Filtration, followed by evaporation of the solvents under reduced pressure and flash column chromatography (silica gel, 35% ether in hexanes for several fractions until all the boron complexes were removed; then 70% ether in hexanes) provided alcohol 91 (24.09 g, 96%): Rf=0.37 (60% ether in hexanes).

Synthesis of Compound 92 as illustrated in FIG. 12. Silylation of Alcohol 91. Alcohol 91 (7.0 g, 0.033 mol) was dissolved in DMF (35 mL, 1.0 M), the solution was cooled to 0° C. and imidazole (3.5 g, 0.050 mol, 1.5 equiv) was added. After stirring for 5 min, tert-butyldimethylsilyl chloride (6.02 g, 0.040 mol, 1.2 equiv) was added portionwise and the reaction mixture was allowed to stir at 0° C. for 45 min, and then at 25° C. for 2.5 h, after which time no starting alcohol was detected by TLC. Methanol (2 mL) was added at 0° C. and the solvent was removed under reduced pressure. Ether (100 mL) was added, followed by saturated aqueous $NH_4Cl$ solution (20 mL), the organic phase was separated and the aqueous phase was extracted with ether (2×20 mL). The combined organic solution was dried ($MgSO_4$), filtered over celite and the solvents were removed under reduced pressure. Flash column chromatography (silica gel, 10 to 20% ether in hexanes) provided pure 92 (10.8 g, 990%).

Synthesis of Aldehyde 82 as illustrated in FIG. 12. Dihydroxylation of Olefin 92 and 1,2 Glycol Cleavage. Olefin 92 (16.7 g, 51.6 mmol) was dissolved in THF/tBuOH (1:1, 500 mL) and $H_2O$ (50 mL). 4-Methylmorpholine N-oxide (NMO) (7.3 g, 61.9 mmol, 1.2 equiv) was added at 0° C., followed by $OsO_4$ (5.2 mL, solution in tBuOH 1.0 mol %, 2.5% by weight). The mixture was vigorously stirred for 2.5 h at 0° C. and then for 12 h at 25° C. After completion of the reaction, $Na_2SO_3$ (5.0 g) was added at 0° C., followed by $H_2O$ (100 mL). Stirring was continued for another 30 min and then ether (1 L) was added, followed by saturated aqueous NaCl solution (2×100 mL). The organic phase was separated and the aqueous phase was extracted with ether (2×100 mL). The combined organic extracts were dried (MgSO4), filtered, and the solvents were removed under reduced pressure. Flash column chromatography (silica gel, ether to EtOAc) provided 17.54 g (95%) of the expected 1,2-diol as a 1:1 mixture of diastereoisomers.

The diol obtained from 92 as described above (5.2 g, 14.5 mmol) was dissolved in EtOAc (150 mL) and cooled to 0° C. Pb(OAc)4 (8.1 g, 95% purity, 18.3 mmol, 1.2 equiv) was then added portionwise over 10 min, and the mixture was vigorously stirred for 15 min at 0° C. After completion of the reaction, the mixture was filtered through silica gel and washed with 60% ether in hexanes. The solvents were then removed under reduced pressure providing pure aldehyde 82 (4.7 g, 98%).

Synthesis of Alcohol 93 as illustrated in FIG. 12. Reduction of Aldehyde 82. A solution of aldehyde 82 (440 mg, 1.35 mmol) in MeOH (13 mL) was treated with $NaBH_4$ (74 mg, 2.0 mmol, 1.5 equiv) at 0° C. for 15 min. The solution was diluted with ether (100 mL) and then saturated aqueous NH4Cl solution (5 mL) was carefully added. The organic phase was washed with brine (10 mL), dried (MgSO4) and concentrated. Flash column chromatography (silica gel, 60% ether in hexanes) gave alcohol 93 (425 mg, 96%) as a colorless oil. 26: Rf=0.52 (silica gel, 60% ether in hexanes).

Synthesis of Iodide 94 as illustrated in FIG. 12. Iodination of Alcohol 93. A solution of alcohol 93 (14.0 g, 42.7 mmol) in ether: MeCN (3:1, 250 mL) was cooled to 0° C. Imidazole (8.7 g, 128.1 mmol, 3.0 equiv), $Ph_3P$ (16.8 g, 64.1 mmol, 1.5 equiv), and iodine (16.3 g, 64.1 mmol, 1.5 equiv) were sequentially added and the mixture was stirred for 0.5 h at 0° C. A saturated aqueous solution of $Na_2S_2O_3$ (50 mL) was added, followed by the addition of ether (600 mL). The organic phase was washed with brine (50 mL), dried (MgSO4), and the solvents were removed under vacuum. Flash column chromatography (silica gel, 15% ether in hexanes) gave pure iodide 94 (16.6 g, 89%) as a colorless oil.

Synthesis of Phosphonium Salt 79 as illustrated in FIG. 12. A mixture of iodide 94 (16.5g, 37.7 mmol) and $Ph_3P$ (10.9 g, 41.5 mmol, 1.1 equiv) was heated neat at 100° C. for 2 h. Purification by flash column chromatography (silica gel, methylene chloride; then 7% MeOH in methylene chloride) provided phosphonium salt 79 (25.9 g, 98%) as a white solid: Rf=0.50 (silica gel, 7% MeOH in methylene chloride).

Synthesis of Hydrazone 95 as illustrated in FIG. 13. Alkylation of Hydrazone 80. Hydrazone 80 (20.0 g, 117.0 mmol, 1.0 equiv), dissolved in THF (80 mL), was added to a freshly prepared solution of LDA [19.75 mL of diisopropylamine (141.0 mmol, 1.2 equiv was added to a solution of 88.1 mL of 1.6 M solution of n-BuLi in hexanes (141 mmol, 1.2 equiv) in 160 mL of THF at 0° C] at 0° C. After stirring at this temperature for 8 h, the resulting yellow solution was cooled to −100° C., and a solution of 4-iodo-1-benzyloxybutane (36.0 g, 124.0 mmol, 1.2 equiv) in THF (40 mL) was added dropwise over a period of 30 min. The mixture was allowed to warm to room temperature over 8 h, and was then poured into saturated aqueous $NH_4Cl$ solution (40 mL) and extracted with ether (3×200 mL). The combined organic extracts were dried ($MgSO_4$), filtered and evaporated. Purification by flash column chromatography on silica gel (20% ether in hexanes) provided hydrazone 95 as a yellow oil (35.8 g, 92%, de>98% by 1H NMR).

Synthesis of Aldehyde 96 as illustrated in FIG. 13. Cleavage of Hydrazone 95. Procedure A: A solution of hydrazone 95 (13.0 g, 39.1 mmol) in methylene chloride (50 mL) was treated with ozone at −78° C. until the solution turned blue-green. The solution was purged with oxygen for 2 min at −78° C., allowed to warm to room temperature, and then concentrated. The crude mixture so obtained was purified by flash column chromatography (silica gel, 10% ether in hexanes) to give aldehyde 96 (6.6 g, 77%) as a colorless oil. Procedure B: A solution of hydrazone 95 (30 g, 90.3 mmol) in MeI (100 mL) was heated at 60° C. After 5 h, the reaction was complete (TLC), and the mixture was concentrated. The resulting crude product was suspended in n-pentane (360 mL) and was treated with 3 N aqueous HCl (360 mL). The two-phase system was vigorously stirred for 1 h, and the aqueous phase was extracted with n-pentane (3×200 mL). The combined organic solution was dried (MgSO4), concentrated and purified by flash column chromatography (silica gel, 10% ether in hexanes) to give 96 (17.1 g, 86%): Rf=0.49 (silica gel, 50% ether in hexanes).

Synthesis of Alcohol 97 as illustrated in FIG. 13. Reduction of Aldehyde 96. A solution of aldehyde 96 (17.0 g, 77.0 mmol) in MeOH (200 mL) was treated with $NaBH_4$ (8.6 g, 228 mmol, 3.0 equiv) at 0° C. for 15 min. The solution was then diluted with ether (400 mL) and saturated aqueous $NH_4Cl$ solution (50 mL) was carefully added. The organic phase was washed with brine (50 mL), dried ($MgSO_4$), and concentrated. The crude product was purified by flash column chromatography (silica gel, 40% ether in hexanes) to give alcohol 97 (16.8 g, 98%) as a colorless oil.

Synthesis of Silyl Ether 98 as illustrated in FIG. 13. Silylation of Alcohol 97. Alcohol 97 (17.0 g, 76.0 mmol) was dissolved in methylene chloride (350 mL), the solution was cooled to 0° C. and $Et_3N$ (21.2 mL, 152.0 mmol, 2.0 equiv) and 4-DMAP (185 mg, 1.52 mmol, 0.05 equiv) were added. After stirring for 5 min, tert-butyldimethylsilyl chloride (17.3 g, 115 mmol, 1.5 equiv) was added portionwise, and the reaction mixture was allowed to stir at 0° C. for 2 h, and then at 25° C. for 10 h. Methanol (20 mL) was added at 0° C. and the solvents were removed under reduced pressure. Ether (200 mL) and saturated aqueous $NH_4Cl$ solution (30 mL) were sequentially added, and the organic phase was separated. The aqueous phase was extracted with ether (2×100 mL) and the combined organic layer was dried ($MgSO_4$), filtered and concentrated under reduced pressure. Purification by flash column chromatography (silica gel, 5% ether in hexanes) provided pure silyl ether 98 (24.4 g, 95%).

Synthesis of Alcohol 99 as illustrated in FIG. 13. Hydrogenolysis of Benzyl Ether 98. To a solution of benzyl ether 98 (21.0 g, 62.5 mmol) in THF (200 mL) was added 10% $Pd(OH)_2/C$ (1.0 g). The reaction was allowed to proceed under an atmosphere of $H_2$ at a pressure of 50 psi and at 25° C. (Parr hydrogenetor apparatus). After 15 min, no starting benzyl ether was detected by TLC, and the mixture was filtered through celite. The clear solution was concentrated under reduced pressure and the resulting crude product was purified by flash column chromatography (silica gel, 40% ether in hexanes) to give alcohol 99 (14.7 g, 95%) as a colorless oil.

Synthesis of Aldehyde 77 as illustrated in FIG. 13. Oxidation of Alcohol 99. To a solution of oxalyl chloride (5.6 mL, 65.0 mmol, 2.0 equiv) in methylene chloride (250 mL) was added dropwise DMSO (9.2 mL, 130 mmol, 4.0 equiv) at −78° C. After stirring for 15 min, a solution of alcohol 99 (8.0 g, 32.0 mmol, 1.0 equiv) in methylene chloride (50 mL) was added dropwise at −78° C. over a 15 min period. The solution was stirred for further 30 min at −78° C., and $Et_3N$ (27.1 mL, 194 mmol, 6.0 equiv) was added at the same temperature. The reaction mixture was allowed to warm to 0° C. over 30 min and then ether (400 mL) was added, followed by saturated aqueous $NH_4Cl$ solution (100 mL). The organic phase was separated, and the aqueous phase was extracted with ether (2×300 mL). The combined organic solution was dried ($MgSO_4$), filtered and concentrated under reduced pressure. Purification by flash column chromatography (silica gel, 20% ether in hexanes) provided aldehyde 77 (7.9 g, 98%) as a colorless oil.

Synthesis of Alcohol 100 as illustrated in FIG. 13. To a cold (0° C.) solution of aldehyde 77 (7.8 g, 32.0 mmol) in THF (300 mL) was slowly added MeMgBr (1.0 M solution in THF, 48.0 mL, 48.0 mmol, 1.5 equiv). The reaction mixture was stirred for 15 min at 0° C. and then it was diluted with ether (500 mL) and quenched by carefull addition of saturated aqueous $NH_4Cl$ solution (100 mL). The organic phase was washed with brine (100 mL), dried ($MgSO_4$), and concentrated. The crude product so obtained was purified by flash column chromatography (silica gel, 30% ether in hexanes) to give alcohol 100 (7.0 g, 84%) as a colorless oil.

Synthesis of Ketone 78 as illustrated in FIG. 13. Oxidation of Alcohol 100. To a solution of alcohol 100 (7.0 g, 27.0 mmol) in methylene chloride (250 mL) was added molecular sieves (4 Å, 6.0 g), 4-methylmorpholine-N-oxide (NMO) (4.73 g, 40.0 mmol, 1.5 equiv) and tetrapropylammonium perruthenate (TPAP) (189 mg, 0.54 mmol, 0.02 equiv) at room temperature. After stirring for 45 min (depletion of starting material, TLC), the reaction mixture was filtered through celite, and the solvent was removed under reduced pressure. The crude product was purified by flash column chromatography (silica gel, 20% ether in hexanes) to give ketone 78 (6.6 g, 96%) as a colorless oil.

Synthesis of Iodide 113 as illustrated in FIG. 15. Iodination of Alcohol 99. A solution of alcohol 99 (3.8 g, 15.0 mmol) in ether:MeCN 3:1 (150 mL) was cooled to 0° C. Imidazole (3.1 g, 45.0 mmol, 3.0 equiv), $Ph_3P$ (5.9 g, 22.5 mmol, 1.5 equiv) and iodine (5.7 g, 22.5 mmol, 1.5 equiv) were sequentially added and the reaction mixture was stirred at 0° C. for 0.5 h. A saturated aqueous solution of $Na_2S_2O_3$ (200 mL) was added followed with ether (200 mL). The organic phase was washed with brine (200 mL), dried (MgSO4), and the solvents were removed under vacuum. The crude product was purified by flash column chromatography (silica gel, 10% ether in hexanes) to give pure iodide 113 (4.9 g, 91%) as a colorless oil.

Synthesis of Phosphonium Salt 114 as illustrated in FIG. 15. A mixture of iodide 113 (4.7 g, 13.1 mmol) and Ph3P (3.8 g, 14.4 mmol, 1.1 equiv) was heated neat at 100° C. for 2 h. Purification by flash column chromatography (silica gel, Methylene chloride to 7% MeOH in methylene chloride) provided phosphonium salt 114 (7.4 g, 91%) as a white solid: Rf=0.42 (silica gel, 5% MeOH in Methylene chloride). Synthesis of Olefin 101 as illustrated in FIG. 15. Method A. From Phosphonium Salt 79 and Aldehyde 77. Phosphonium salt 79 (13.60 g, 19.4 mmol, 1.2 equiv) was dissolved in THF (80 mL, 0.2 M) and the solution was cooled to 0° C. Sodium hexamethyldisilylamide (NaHMDS, 19.4 mL, 19.4 mmol, 1.0 M solution in THF, 1.2 equiv) was slowly added and the resulting mixture was stirred for 15 min before aldehyde 77 (3.96 g, 16.2 mmol, 1.0 equiv, in 10 mL of THF) was added at the same temperature. Stirring was continued for another 15 min at 0° C. and then, the reaction mixture was quenched with saturated aqueous $NH_4Cl$ solution (25 mL). Ether (250 mL) was added and the organic phase was separated and washed with brine (2×40 mL), dried ($MgSO_4$) and concentrated under vacuo. The crude product was purified by flash column chromatography (silica gel, 10% ether in hexane) to afford olefin 34 (6.70 g, 77%) as a mixture of Z- and E-isomers (ca 9:1 by 1H NMR). Method B. From Phosphonium Salt 114 and Aldehyde 82. Phosphonium salt 114 (7.40 g, 11.96 mmol, 1.2 equiv) was dissolved in THF (120 mL, 0.1 M) and the solution was cooled to 0° C. Sodium hexamethyldisilylamide (NaHMDS, 11.96 mL, 11.96 mmol, 1.0 M solution in THF, 1.2 equiv) was slowly added at the same temperature and the resulting mixture was stirred for 15 min, before aldehyde 82 (3.20 g, 9.83 mmol, 1.0 equiv, in 20 mL of THF; vida 1supra) was slowly added. Stirring was continued for another 15 min at 0° C. and then the mixture was quenched with saturated aqueous $NH_4Cl$ solution (150 mL). Ether (200 mL) was added and the organic phase was separated and washed with brine (2×150 mL), dried ($MgSO_4$) and concentrated under reduced pressure to afford the crude product. Flash column chromatography (silica gel, 10% ether in hexane) furnished olefin 101 (3.65 g, 69% yield) as a mixture of Z- and E-isomers (ca 9:1 by 1H NMR).

Synthesis of alcohol 102 as illustrated in FIG. 14. Compound 101 (1.77 g, 3.29 mmol) was dissolved in methylene chloride: MeOH (1:1, 66 mL) and the solution was cooled to 0° C. and CSA (764 mg, 3.29 mmol, 1.0 equiv) was added over a 5 min period. The mixture was stirred for 30 min at 0° C., and then for 1 h at 25° C. $Et_3N$ (2.0 mL) was added, and the solvents were removed under reduced pressure. Flash column chromatography (silica gel, 50% ether in hexanes) furnished the desired alcohol 35 (1.2 g, 86%).

Synthesis of Aldehyde 74 as illustrated in FIG. 14. Oxidation of Alcohol 102. Alcohol 102 (1.9 g, 4.5 mmol) was dissolved in methylene chloride (45 mL, 0.1 M). DMSO (13.5 mL), $Et_3N$ (3.0 mL, 22.4 mmol, 5.0 equiv) and $SO_3$·pyr (1.43 g, 8.98 mmol, 2.0 equiv) were added at 25° C. and the resulting mixture was stirred for 30 min. Saturated aqueous $NH_4Cl$ solution (100 mL) and ether (200 mL) were added sequentially. The organic phase was washed with brine (2×30 mL), dried ($MgSO_4$) and the solvents were removed under reduced pressure. Flash column chromatography (silica gel, 30% ether in hexanes) furnished aldehyde 74 (1.79 g, 94%).

Synthesis of compounds 105 and 106 as illustrated in FIG. 14: Aldol Reaction of Keto Acid 76 with Aldehyde 74. A solution of keto acid 76 (1.52 g, 5.10 mmol, 1.2 equiv; synthesized vida supra) in THF (10 mL) was added dropwise to a freshly prepared solution of LDA [diisopropylamine (1.78 mL, 12.78 mmol) was added to n-BuLi (7.95 mL, 1.6 M solution in hexanes, 12.78 mmol) in 20 mL of THF at 0° C.] at −78° C. After stirring for 15 min, the solution was allowed to warm to −40° C., and after 0.5 h at that temperature it was recooled to −78° C. A solution of aldehyde 74 (1.79 g, 4.24 mmol, 1.0 equiv) was added dropwise and the resulting mixture was stirred for 15 min, and then quenched at −78° C. by slow addition of saturated aqueous $NH_4Cl$ solution (20 mL). The reaction mixture was warmed to 0° C., and AcOH (2.03 mL, 26.84 mmol, 6.3 equiv) was added, followed by addition of EtOAc (50 mL). The organic layer was separated and the aqueous phase was extracted with EtOAc (3×25 mL). The combined organic solution was dried over $MgSO_4$ and concentrated under vacuum to afford a mixture of aldol products 103a:103b in a ca 1:1 ratio (1H NMR) and unreacted keto acid 76. The mixture was dissolved in methylene chloride (50 mL) and treated, at 0° C., with 2,6-lutidine (3.2 mL, 27.36 mmol) and tert-butyldimethylsilyl trifluoromethanesulfonate (4.2 mL, 18.24 mmol). After stirring for 2 h (complete reaction by TLC), aqueous HCl (20 mL, 10% solution) was added and the resulting biphasic mixture was separated. The aqueous phase was extracted with methylene chloride (3×20 mL) and the combined organic solution was washed with brine (50 mL), dried ($MgSO_4$) and concentrated under reduced pressure to give a mixture of the tetra-tert-butyldimethylsilyl ethers 104a and 104b. The crude product was dissolved in MeOH (50 mL) and $K_2CO_3$ (1.40 g, 10.20 mmol) was added at 25° C. The reaction mixture was vigorously stirred for 15 min, and then filtered. The residue was washed with MeOH (20 mL) and the solution was acidified with ion exchange resin (DOWEX 50WX8-200) to pH 4–5, and filtered again. The solvent was removed under reduced pressure and the resulting residue was dissolved in EtOAc (50 mL) and washed with saturated aqueous $NH_4Cl$ solution (50 mL). The aqueous phase was extracted with EtOAc (4×25 mL) and the combined organic solution was dried ($MgSO_4$), filtered and concentrated to furnish a mixture of carboxylic acids 105, 106 and 76. Purification by preparative thin layer chromatography (silica gel, 5% MeOH in methylene chloride), gave pure acids 105 (1.1 g, 31% from 7) and 106 (1.0 g, 30% from 7) as colorless oils.

Synthesis of Hydroxy Acid 72 as illustrated in FIG. 14. Selective Desilylation of tris(Silyl) Ether 105. A solution of tris(silyl) ether 105 (300 mg, 0.36 mmol) in THF (7.0 mL)

at 25° C. was treated with TBAF (2.2 mL, 1 M solution in THF, 2.2 mmol, 6.0 equiv). After stirring for 8 h, the reaction mixture was diluted with EtOAc (10 mL) and washed with aqueous HCl (10 mL, 1 N solution). The aqueous solution was extracted with EtOAc (4×10 mL) and the combined organic phase was washed with brine (10 mL), dried (MgSO$_4$) and concentrated. The crude mixture was purified by flash column chromatography (silica gel, 5% MeOH in methylene chloride) to provide hydroxy acid 72 (203 mg, 78%) as a yellow oil: Rf=0.40 (silica gel, 5% MeOH in methylene chloride).

Synthesis of Hydroxy Acid 107 as illustrated in FIG. 14. Selective Desilylation of tris(Silyl) Ether 106. Carboxylic acid 106 (150 mg, 0.18 mmol) was converted to hydroxy acid 107 (107 mg, 82%) according to the procedure described above for 72.

Synthesis of Lactone 108 as illustrated in FIG. 14. Macrolactonization of Hydroxy Acid 72. A solution of hydroxy acid 72 (200 mg, 0.28 mmol) in THF (4 mL) was treated at 0° C. with Et$_3$N (0.23 mL, 1.68 mmol, 6.0 equiv) and 2,4,6-trichlorobenzoyl chloride (0.22 mL, 1.40 mmol, 5.0 equiv). The reaction mixture was stirred at 0° C. for 15 min, and then added to a solution of 4-DMAP (342 mg, 2.80 mmol, 10.0 equiv) in toluene (140 mL) at 25° C. and stirred at that temperature for 0.5 h. The reaction mixture was concentrated under reduced pressure to a small volume and filtered through silica gel. The residue was washed with 40% ether in hexanes, and the resulting solution was concentrated. Purification by flash column chromatography (silica gel, 2% MeOH in methylene chloride) furnished lactone 108 (178 mg, 90%) as a colorless oil.

Synthesis of Lactone 109 as illustrated in FIG. 14. Macrolactonization of Hydroxy Acid 107. The cyclization of hydroxy acid 107 (100 mg, 0.14 mmol) was carried out exactly as described for 108 above and yielded lactone 109 (84 mg, 85%) as a colorless oil. Synthesis of Dihydroxy Lactone 70 and 110 as illustrated in FIG. 14. To lactone 108 (50 mg, 0.071 mmol), cooled to −20° C., was added a freshly prepared 20% (v/v) CF$_3$COOH solution in methylene chloride (400 mL). The reaction mixture was allowed to reach 0° C. and was stirred for 1 h at that temperature. The solvents were evaporated under reduced pressure and the crude product was purified by preparative thin layer chromatography (silica gel, 6% MeOH in methylene chloride) to afford pure dihydroxy lactone 70 (31 mg, 92%); 110 is prepared in a likewise manner as shown in FIG. 14.

Synthesis of 6S,7R-Epothilones 111 and 112 as illustrated in FIG. 14. Synthesized according to the procedure as described via supra for 1 using 70 or 110 instead of 1.

Synthesis of Olefinic Compound 115 as illustrated in FIG. 16. Phosphonium salt 79 (9.0 g, 12.93 mmol, 1.5 equiv; vida supra) was dissolved in THF (90 mL) and the solution was cooled to 0° C. Sodium bis(trimethylsilyl)amide (NaHMDS, 1.0 M solution in THF, 12.84 mL, 12.84 mmol, 1.48 equiv) was slowly added and the resulting mixture was stirred at 0° C. for 15 min. The reaction mixture was then cooled to −20° C. before ketone 78 (2.23 g, 8.62 mmol, 1.0 equiv) in THF (10 mL) was added and the reaction mixture was stirred at the same temperature for 12 h. Saturated aqueous NH$_4$Cl solution (50 mL) was added and the mixture was extracted with ether (200 mL). The organic phase was washed with brine (2×100 mL), dried (MgSO$_4$) and concentrated to afford, after flash column chromatography (silica gel, 2% ether in hexanes), olefins 115 (3.8 g, 73%, Z:E ca. 1:1 by 1H NMR).

Synthesis of Hydroxy Olefins 116 as illustrated in FIG. 16. Desilylation of Silylether 115. Silylether 115 (3.80 g, 6.88 mmol) was dissolved in methylene chloride:MeOH (1:1, 70 mL) and the solution was cooled to 0° C. prior to addition of CSA (1.68 g, 7.23 mmol, 1.05 equiv) during a 5 min period. The resulting mixture was stirred for 30 min at 0° C., and then for 1 h at 25° C. Et$_3$N (1.57 mL, 7.23 mmol, 1.05 equiv) was added, and the solvents were removed under reduced pressure. Flash column chromatography (silica gel, 50% ether in hexanes) furnished pure hydroxy compound 116 (2.9 g, 97%).

Synthesis of Epothilone B(2) and analogs as illustrated in FIG. 16. Synthesized according to the procedure as described above as shown in FIG. 14 for 111 and 112 using 71 or 123 instead of 110.

Synthesis of Aldehyde 75 as illustrated in FIG. 17. Synthesized in a similar manner according to the procedure as described for 101 via supra as shown in FIG. 15 using a different order of substrate addition; see conditions in description of Figures.

Synthesis of Lactone 121, 71, 2, 124 and 135 as illustrated in FIG. 18. Synthesized according to the procedure as described above as shown in FIG. 16 using 75 instead of 75'; see conditions in description of Figures.

Synthesis of Carboxylic Acid 119 as illustrated in FIG. 19. Synthesized according to the procedure as described above as shown in FIG. 16 using 136 instead of 75'; see conditions in description of Figures.

Synthesis of of aldehyde 149 as illustrated in FIG. 21 Synthesized according to the procedure as described above as shown in FIG. 13 for 77; see conditions in description of Figures.

Synthesis of phosphonium resin 147 as illustrated in FIG. 21. Step 1) Alkylation of Merrifield Resin: A solution of 1,4-butanediol (7.18 g, 80.0 mmol, 5.0 equiv.) in DMF (600 mL) was cooled to 0° C. and sodium hydride (60%, 3.20 g, 80.0 mmol, 5.0 equiv.) was added. The reaction mixture was stirred at 0° C. for 2 h and Merrifield resin (40.0 g, 16.0 mmol, 1.0 equiv.) followed by n-Bu4NI (0.58 g, 1.60 mmol, 0.1 equiv.) were added. The reaction mixture was stirred at 23° C. for 20 h, then poured into a frit, and the polymer was washed with MeOH (2×500 mL), DMF (500 ml), H2O at 80° C. (500 mL), DMF (500 ml), MeOH (500 mL), CH$_2$Cl$_2$ (500 mL), Et$_2$O (2×300 mL). The resin was dried under high vacuum to a constant weight of 40.8 g.

Step 2) Conversion of alcohol resin. A suspension of resin from above step 1 (40.8 g, 16.0 mmol, 1.0 equiv.) in CH$_2$Cl$_2$ (700 mL) at 23° C. was treated with Ph$_3$P (20.9 g, 80.0 mmol, 5.0 equiv.), imidazole (6.46 g, 80.0 mmol, 5.0 equiv.) and iodine (16.0 g, 64.0 mmol, 4.0 equiv.). The reaction mixture was stirred at 23° C. for 3 h, then poured into a frit, and the polymer was washed with CH$_2$Cl$_2$ (500 mL), MeOH (500 mL), CH$_2$Cl$_2$ (500 mL), MeOH (500 mL), CH$_2$Cl$_2$ (500 mL), Et$_2$O (2×300 mL). The resin was dried under high vacuum to a constant weight of 42.6 g.

Step 3) Reaction of iodo resin formed in step 2 with Ph$_3$P. A suspension of iodo resin (42.6 g, 16.0 mmol, 1.0 equiv.) in DMF (200 mL) at 23° C. was treated with Ph$_3$P (41.9 g, 160 mmol, 10 equiv.). The reaction mixture was stirred at 90° C. for 12 h, then poured into a frit, and the polymer was washed with DMF at 80° C. (3×500 mL), CH$_2$Cl$_2$ (500 mL), DMF (500 mL), Et$_2$O (3×500 mL). The resin was dried under high vacuum to a constant weight of 46.61 g.

Synthesis of Ylide resin 148 as illustrated in FIG. 21 Deprotonation of Phosphonim resin 147: A suspension of resin 147 (15.0 g, 5.11 mmol, 1.0 equiv.) in a mixture of DMSO (50 mL) THF (35 mL) at 23° C. was treated with a 1 M solution of NaHMDS in THF (15.3 mL, 15.3 mmol, 3.0 equiv.). The reaction mixture was stirred at 23° C. for 12 h, then canulated into a Schlenk frit, and the polymer was washed under argon with THF (3×100 mL).

Synthesis of resin 150 as illustrated in FIG. 21 Wittig reaction of ylide resin 148 with aldehyde 149 (vida supra). A solution of aldehyde 149 (2.50 g, 10.22 mmol, 2.0 equiv.) in THF (25 mL) was cooled at −78° C. and added to the freshly prepared resin 148 (5.11 mmol, 1.0 equiv.) via canula. The resulting suspension was shaken at 23° C. for 3 h, and the supernatant was filtered off. The polymer was washed with THF (100 ml), MeOH (100 mL), $CH_2Cl_2$ (100 mL), MeOH (100 mL), $CH_2Cl_2$ (100 mL), $Et_2O$ (2×100 mL). The resin under high vacuum to a constant weight of 14.12 g.

Synthesis of resin 145 as illustrated in FIG. 21 Step 1) Desilylation of resin 150 with HF Pyridine complex. Resin 150 (14.0 g, 5.05 mmol, 1.0 equiv.) was suspended in THF (135 mL) and treated at 0° C. with HF.Pyridine complex (15 mL). The mixture was allowed to warm to 23° C. and shaken for 12 h. The suspension was poured into a frit and the polymer was filtered, washed with THF (100 mL), $CH_2Cl_2$ (100 mL), MeOH (100 mL), $CH_2Cl_2$ (100 mL), $Et_2O$ (2×100 mL) and dried under high vacuum to give 13.42 g of deprotected resin.

Step 2) Swern oxidation of deprotected resin. To an Oxalyl Chloride (2.56 g, 1.76 mL, 20.0 mmol, 4.0 equiv.) solution in $CH_2Cl_2$ (50 mL) at −78° C. was added dropwise DMSO (3.12 g, 2.84 mL, 40.0 mmol, 8.0 equiv.). The solution was stirred at −78° C. for 1 h and canulated into a suspension of resin (13.26 g, 5.0 mmol, 1.0 equiv.) in $CH_2Cl_2$, previously cooled to −78° C. The resulting mixture was stirred for an additional hour and treated with $Et_3N$ (6.25 g, 8.0 mL, 62.5 mmol, 12.5 equiv.), allowed to warm to 23° C. and stirred for 1 h. The mixture was filtered and the polymer washed successively with $CH_2Cl_2$ (250 mL), MeOH (250 mL), $CH_2Cl_2$ (250 mL), $Et_2O$ (2×300 mL), and dried under high vacuum to afford 13.25 g of resin 145.

Synthesis of resin 151 as illustrated in FIG. 21 Step 1) Enolate formation. To a precooled solution of LDA (6.60 mmol, 4.4 equiv.) obtained by treating diisopropyl amine (0.92 ml, 6.60 mmol, 4.4 equiv.) in THF (25 mL) at 0° C. with n-butyllithium (1.6 M solution in THF, 4.12 mL, 6.60 mmol, 4.4 equiv.) was added a solution of ketoacid 144 (vida supra) (0.93 g, 3.0 mmol, 2.0 equiv.) in THF (25 mL) at −78° C. via canula. The solution was allowed to warm to −40° C. and stirred for 1 h.

Step 2) Aldol reaction. A suspension of resin 145(4.0 g, 1.50 mmol, 1.0 equiv.), $ZnCl_2$ (1.0 M solution in $Et_2O$, 3.0 mL, 3.0 mmol, 2.0 equiv.) in THF (25 mL), was treated at −78° C. with the enolate solution described above. The suspension was allowed to warm to −40° C., stirred for 2 h, quenched with saturated $NH_4Cl$ aq. (8 mL) and neutralised at 23° C. with AcOH (0.76 mL, 13.2 mmol, 8.8 equiv). The mixture was poured into a frit, the polymer was washed with THF (100 mL), $Et_2O$ (100 mL), $CH_2Cl_2$ (100 mL), $H_2O$ (100 mL), MeOH (100 mL $CH_2Cl_2$ (100 mL), 1% TFA v/v in $CH_2Cl_2$ (3×75 mL), $CH_2Cl_2$ (2×100 mL), $Et_2O$ (2×100 mL) and dried under vacuum to afford 1.96 of resin 151.

Synthesis of resin 152 as illustrated in FIG. 21. Esterification of resin 151 with alcohol 143. A mixture of resin 151 (1.40 g, 0.46 mmol, 1.0 equiv.), alcohol 143 (vide supra) (0.49 g, 2.31 mmol, 5.0 equiv.), 4-DMAP (0.32 g, 2.31 mmol, 5.0 equiv.) and DCC (0.46 g, 2.31 mmol, 5.0 equiv.) in $CH_2Cl_2$ (10 mL) was shaken al 23° C. for 15 h. The polymer was filtered, washed with $CH_2Cl_2$ (2×50 mL), MeOH (2×50 mL), $CH_2Cl_2$ (2×50 mL), $Et_2O$ (2×50 mL) and dried under vacuum to afford 1.48 g of resin 152.

Synthesis of 154 as illustrated in FIG. 21. Metathesis of resin 152. A suspension of resin 152 (500 mg) in $CH_2Cl_2$ (40 mL) was treated with bis(tricyclohexylphosphine) benzylidine ruthenium dichloride (RuCl2(=CHPh)(PCy3) 2) (20 mg) and stirred at 23° C. for 48 h. The polymer was filtered and the filtrate was evaporated and purified by preparative thin layer chromatography (silicagel, 20% ethyl acetate in hexanes) to give compounds 154, 155, 156, 157=ca: 3:3:1:3. 52% yield from the calculated loading of heterocycle in resin 152.

Synthesis of 157 and 158 as illustrated in FIG. 21. trans-Dihydroxy Lactone 157 and 158. Desilylation of Compound 141 and 155. Silyl ether 141 or 155 (44 mg, 0.074 mmol) was treated with a freshly prepared solution of 20% (v/v) trifluoroacetic acid (TFA)-$CH_2Cl_2$ (7.4 mL, 0.01 M) to yield, after flash column chromatography (silica gel, 50% EtOAc in hexanes), trans-dihydroxy ester 157 or 158 (33 mg, 93%).

Synthesis of Eposterones 159 and 1 as illustrated in FIG. 21. Epoxidation of cis-Hydroxy Lactone 157 and 158. To a solution of cis-hydroxy lactone 157 and 158 (19 mg, 0.039 mmol) in acetonitrile (390 mL, 0.1 M) is added a 0.0004 M aqueous solution of disodium salt of ethylenediaminetetraacetic acid ($Na_2EDTA$, 200 mL,0.2 M) and the reaction mixture is cooled to 0° C. Excess of 1,1,1-trifluoroacetone (80 mL, 0.5 M) is added, followed by a portionwise addition of Oxone®) (120 mg, 0.20 mmol, 5.0 equiv) and $NaHCO_3$ (26 mg, 0.31 mmol, 8.0 equiv) with stirring, until the disappearance of starting material is detected by TLC. The reaction mixture is then directly passed through silica gel and eluted with 50% EtOAc in hexanes. Purification by preparative thin layer chromatography (250 mm silica gel plate, 70% EtOAc in hexanes) provides the diastereomeric eposterones 159 or 1 (epothilone A).

Synthesis of alcohol 163. Allylboration of Aldehyde 162 as illuststrated in FIG. 25. Aldehyde 162 (1.0 equiv) was dissolved in anhydrous ether (0.3 M) and the solution was cooled to −100° C. (+)-Diisopinocampheylallyl borane (1.2 equiv in pentane, prepared from (−)-Ipc2BOMe and 1.0 equiv of allyl magnesium bromide) was added dropwise under vigorous stirring, and the reaction mixture was allowed to stir for 1 h at the same temperature. Methanol was added at −100° C., and the reaction mixture was allowed to warm up to room temperature. Amino ethanol (10.0 equiv) was added and stirring was continued for 15 h. The work-up procedure was completed by the addition of saturated aqueous $NH_4Cl$ solution, extraction with EtOAc and drying of the combined organic layers with $MgSO_4$. Filtration, followed by evaporation of the solvents under reduced pressure and flash column chromatography (silica gel, 35% ether in hexanes for several fractions until all the boron complexes were removed; then 70% ether in hexanes) provided alcohol 163 (91%).

Synthesis of hydroxy Esters 164 and 165. EDC Coupling of Carboxylic Acids 45 and 46 and Alcohol 163 as illustrated in FIG. 25. Synthesized according to the procedure as described above as shown in FIG. 7 using 163 instead of 6; see conditions in the description of Figures.

Synthesis of 161, 170, 171 and 172. Synthesized according to the procedure as described above as shown in FIG. 6 using 164 instead of 35 or 36; see conditions in the description of Figures.

Synthesis of Epoxalones 177, 178, 179 and 180 as illustrated in FIG. 27. Synthesized according to the procedure as described above as shown in FIG. 6 using 165 instead of 35 or 36; see conditions in the description of Figures.

Synthesis of cis-Bis(TBS) Ether 183 as illustrated in FIG. 29 A solution of alcohol 181 (148 mg, 0.32 mmol) and 2,6-lutidine (560 ml, 4.8 mmol, 15 equiv) in $CH_2Cl_2$ (3.2 mL, 0.1 M), at 0° C., is treated with tert-butyldimethylsilyl trifluoromethanesulfonate (TESOTf, 735 mL, 3.2 mmol, 10 equiv) and stirred at this temperature for 30 minutes, whereupon no starting material is detected by TLC. The reaction mixture is quenched by pouring it into saturated aqueous $NH_4Cl$ (10 mL). Extractions with ether (2×10 mL), drying ($MgSO_4$) and concentration is followed by flash chromatographic purification (silica gel, 7% EtOAc in hexanes) to provide bis(TBS)ether 183 (182 mg, 99%).

Synthesis of trans-Bis(TBS) Ether 184 as illustrated in FIG. 29. Silylation of Alcohol 182. In accordance with the procedure describing the silylation of alcohol 181, a solution of alcohol 182 (77 mg, 0.17 mmol) and 2,6-lutidine (300 ml, 2.6 mmol, 15 equiv) in $CH_2Cl_2$ (1.7 mL, 0.1 M), at 0° C., is treated with tert-butyldimethylsilyl trifluoromethanesulfonate (TBSOTf, 390 mL, 1.7 mmol, 10 equiv) to provide bis(TBS)ether 183 (92 mg, 97%).

Synthesis of cis-Alcohol 185 as illustrated in FIG. 29. A solution of TBS ether 183 (182 mg, 0.31 mmol) in MeOH (3.1 mL, 0.1 M) is treated with 10-camphorsulfonic acid (CSA, 72 mg, 0.31 mmol, 1.0 equiv) at room temperature for 12 h, until TLC indicates the disappearance of starting material. The mixture is then poured into into saturated aqueous $NaHCO_3$ (10 mL), extracted with ether (3×10 mL) and dried ($MgSO_4$). Flash column chromatography (silica gel, 20% EtOAc in hexanes) yields pure 185 (98 mg, 67%).

Synthesis of trans-Alcohol 186 as illustrated in FIG. 29. In accordance with the procedure describing the desilylation of TPS ether 183, a solution of TPS ether 184 (31 mg, 0.05 mmol) in methanol (1.6 mL, 0.1 M) was treated with 10-camphorsulfonic acid (CSA, 37 mg, 0.16 mmol, 1.0 equiv) to yield diol 186 (51 mg, 69%) as a crystalline solid.

Synthesis of Carboxylic acid 187 as illustrated in FIG. 29 Ethyl bromopyruvate (1.66 mL, 13.2 mmol, 1 equiv) and thioacetamide (1.05 g, 13.9 mmol, 1.05 equiv) are dissolved in 95% aqueous ethanol (14 mL, 1 M) and heated at reflux for 5 minutes. Completion of the reaction is indicated by TLC. The reaction mixture is then cooled to room temperature, concentrated in vacuo, suspended in $CHCl_3$ (20 mL) and washed with saturated aqueous $NaHCO_3$ (2×20 mL) and with $H_2O$ (20 mL). Drying ($MgSO_4$) and concentration is followed by flash chromatographic purification (silica gel, EtOAc) to yield the corresponding ethyl ester of acid 7 (2.26 g, 100%). This ester is dissolved in $THF-H_2O$ (1:1; 14 mL, 1 M) and submitted to the action of lithium hydroxide (1.66 g, 39.6 mmol, 3.0 equiv). After stirring at room temperature for 45 min TLC indicates the disappearance of starting material. The mixture is poured into $H_2O$ (20 mL) and extracted with ether (2×20 mL). Acidification to pH~2 to 3 with aqueous 4 N HCl is followed by extractions with EtOAc (6×20 mL). Drying ($MgSO_4$) and concentration gives pure carboxylic acid 187 (1.36 g, 72%).

Synthesis of cis-Keto Ester 188 as illustrated in FIG. 29. EDC Coupling of Alcohol 185 with Thiazole Acid 187. A suspension of thiazole acid 187 (54 mg, 0.38 mmol, 2.0 equiv), 4-(dimethylamino)pyridine (4-DMAP, 2.3 mg, 0.019 mmol, 0.1 equiv) and alcohol 185 (88 mg, 0.19 mmol, 1.0 equiv) in $CH_2Cl_2$ (3.8 mL, 0.05 M) is cooled to 0° C. and then treated with 1-ethyl-(3-dimethylaminopropyl)-3-carbodiimide hydrochloride (EDC, 109 mg, 0.57 mmol, 3.0 equiv). The reaction mixture is stirred at 0° C. for 2 h and then at 25° C. for 12 h, until TLC indicates completion of the reaction. The solution is separated between EtOAc (10 mL) and water (10 mL). The aqueous layer is extracted with EtOAc (2×10 mL) and dried ($MgSO_4$). Evaporation of the solvents is followed by flash column chromatography (silica gel, 30% EtOAc in hexanes) results in pure keto ester 188 (102 mg, 92%).

Synthesis of trans-Keto Ester 189 as illustrated in FIG. 29. By analogy to the procedure described above for the synthesis of keto ester 188, a solution of thiazole acid 187 (28 mg, 0.198 mmol, 2.0 equiv), 4-dimethylaminopyridine (4-DMAP, 1.2 mg, 0.0099 mmol, 0.1 equiv), and alcohol 186 (46 mg, 0.099 mmol, 1.0 equiv) in $CH_2Cl_2$ (2.0 mL) is treated with 1-ethyl-(3-dimethylaminopropyl)-3-carbodiimide hydrochloride (EDC, 57 mg, 0.297 mmol, 3.0 equiv) to provide, after flash column chromatography (silica gel, 20% EtOAc in hexanes), keto ester 189 (49 mg, 84%).

Synthesis of cis-Hydroxy Lactone 190 as illustrated in FIG. 29. Silyl ether 188 (95 mg, 0.16 mmol) was treated with a freshly prepared solution of 20% (v/v) trifluoroacetic acid-$CH_2Cl_2$ (16 mL, 0.01 M) at 0° C. The reaction mixture was stirred at 0° C. for 45 min (completion of the reaction by TLC), and then poured into sturated aqueous $NaHCO_3$ (50 mL), extracted with EtOAc (3×20 mL), dried over MgSO4 and evaporated under reduced pressure. The crude reaction mixture was purified by flash column chromatography (silica gel, 50% EtOAc in hexanes) to obtain cis-hydroxy lactone 190 (74 mg, 96%).

Synthesis of trans-Dihydroxy Lactone 191 as illustrated in FIG. 29. Silyl ether 189 (44 mg, 0.074 mmol) was treated with a freshly prepared solution of 20% (v/v) trifluoroacetic acid (TFA)-$CH_2Cl_2$ (7.4 mL, 0.01 M), according to the procedure described for cis-dihydroxy lactone 8, to yield, after flash column chromatography (silica gel, 50% EtOAc in hexanes), trans-dihydroxy ester 191 (33 mg, 93%).

Synthesis of Eposterones 192 and 194 as illustrated in FIG. 29. To a solution of cis-hydroxy lactone 190 (19 mg, 0.039 mmol) in acetonitrile (390 mL, 0.1 M) is added a 0.0004 M aqueous solution of disodium salt of ethylenediaminetetraacetic acid ($Na_2EDTA$, 200 mL, 0.2 M) and the reaction mixture is cooled to 0° C. Excess of 1,1,1-trifluoroacetone (80 mL, 0.5 M) is added, followed by a portionwise addition of Oxone® (120 mg, 0.20 mmol, 5.0 equiv) and $NaHCO_3$ (26 mg, 0.31 mmol, 8.0 equiv) with stirring, until the disappearance of starting material is detected by TLC. The reaction mixture is then directly passed through silica gel and eluted with 50% EtOAc in hexanes. Purification by preparative thin layer chromatography (250 mm silica gel plate, 70% EtOAc in hexanes) provides the diastereomeric eposterones 192 (9.5 mg, 48%) and 194 (3.4 mg, 17%).

Synthesis of Eposterones 193 and 195 as illustrated in FIG. 29. As described for the epoxidation of cis-hydroxy lactone 190, trans-hydroxy lactone 191 (22 mg, 0.046 mmol) in MeCN (460 mL, 0.1 M) was treated with a 0.0004 M aqueous solution of disodium salt of ethylenediaminetetraacetic acid ($Na_2EDTA$, 230 mL, 0.2 M), 1,1,1-trifluoroacetone (92 mL, 0.5 M), Oxone® (141 mg, 0.23 mmol, 5.0 equiv) and NaHCO3 (31 mg, 0.37 mmol, 8.0 equiv), to yield, after purification by preparative thin layer chromatography (250 mm silica gel plate, ether), eposterones 193 (7.3 mg, 32%) and 195 (5.2 mg, 23%).

Synthesis of Eposterones 199, 200, 201, 202, 203, 204, 205, 206, 207, 208, 209 and 210 as illustrated in FIG. 30. By simple modification of the esterification step, i.e. replacing the thiazole carboxylic acid 187 in FIG. 29 with the known carboxylic acids found in epoxalone (198), eleutherobin (197) and taxol (196), other members of the eposterone family can be created including the various isomers: 199, 200, 201, 202, 203, 204, 205, 206, 207, 208, 209 and 210.

Synthesis of Phosphonium Salt 220 as illustrated in FIG. 31. Synthesized according to the procedure as described via supra as shown in FIG. 12 using 211 instead of 88; see conditions in the description of Figures.

Synthesis of intermediates en route to and Lactones 230 and 229 as illustrated in FIG. 33. Synthesized according to the procedure as described via supra as shown in FIG. 14 using 220 instead of 79; see conditions in the description of Figures.

Synthesis of intermediates en route to and Epothilone 23 and 24 as illustrated in FIG. 33. Synthesized according to the procedure as described via supra as shown in FIG. 14 using 220 as the initial phosponate instead of 79; see conditions in the description of Figures.

Synthesis of Nitrile 244 and intermediates en route to as illustrated in FIG. 34. Synthesized according to the procedure as described via supra as shown in FIG. 17 using 217 instead of 82; see conditions in the description of Figures.

Synthesis of Carboxylic Acid 249 and intermediates en route to as illustrated in FIG. 35. Synthesized according to the procedure as described via supra as shown in FIG. 19 using 224 instead of 75; see conditions in the description of Figures.

Synthesis of Hydroxy Acid 250 as illustrated in FIG. 35. Synthesized according to the procedure as described via supra as shown in FIG. 18 using 249 instead of 119; see conditions in the description of Figures.

Synthesis of Lactone 229 as illustrated in FIG. 36. Synthesized according to the procedure as described via supra as shown in FIG. 18 using 250 instead of 73; see conditions in the description of Figures.

Synthesis of Compound 252 as illustrated in FIG. 37. Compound 251, trityl chloride (2.0 eq.) and DMAP (1.1 eq.) were dissolved in DMF (0.1 M) and the reaction mixture heated at 60° C. for 12 h. The solvent was removed under reduced pressure and flash column chromatography (silica gel, ether in hexanes) furnished pure 252.

Synthesis of Primary Alcohol 253 as illustrated in FIG. 37. Selective Hydroboration of Olefinic Compound 252. Compound 252 was cooled to 0° C. 9-BBN (7.0 mL, 0.5 M solution in THF, 3.5 mmol, 1.2 equiv) was added, and the reaction mixture was stirred for 2 h at 0° C. Aqueous NaOH (7.0 mL, 3 N solution, 21.0 mmol, 7.2 equiv) was added with stirring, followed by $H_2O_2$ (2.4 mL, 30%, aqueous solution). Stirring was continued for 0.5 h at 0° C., after which time the reaction mixture was diluted with ether (30 mL). The organic solution was separated and the aqueous phase was extracted with ether (2×15 mL). The combined organic layer was washed with brine (2×5 mL), dried ($Na_2SO_4$) and concentrated in vacuo. Flash column chromatography (silica gel, 50 to 80% ether in hexanes) furnished primary alcohol 254 (1.0 g, 91%).

Synthesis of Iodide 254 as illustrated in FIG. 37. Iodide 254 (1.18 g, 92%) was prepared from alcohol 253 (1.0 g, 2.53 mmol) according to the procedure described above for 219.

Synthesis of Hydrazone 255 as illustrated in FIG. 37. Alkylation of SAMP Hydrazone with Iodide 254. SAMP hydrazone (337 mg, 0.2 mmol, 2.0 equiv) in THF (2.5 mL) was added to a freshly prepared solution of LDA at 0° C. [diisopropylamine (277 mL, 0.20 mmol, 2.0 equiv) was added to n-BuLi (1.39 mL, 1.42 M solution in hexanes, 0.20 mmol, 2.0 equiv) in 2.5 mL of THF at 0° C.] at 0° C. After stirring at that temperature for 8 h, the resulting yellow solution was cooled to −100° C., and a solution of iodide 254 (0.5 g, 0.99 mmol, 1.0 equiv) in THF (3 mL) was added dropwise over a period of 5 min. The mixture was allowed to warm to −20° C. over 10 h, and then poured into saturated aqueous $NH_4Cl$ solution (5 mL) and extracted with ether (3×25 mL). The combined organic extracts were dried ($MgSO_4$), filtered and evaporated. Purification by flash column chromatography on silica gel (20 to 40% ether in hexanes) provided hydrazone 255 (380 mg, 70%, de >98% by 1H NMR) as a yellow oil.

Synthesis of Nitrile 256 as illustrated in FIG. 37. Monoperoxyphthalic acid magnesium salt (MMPP.6H2O, 233 mg, 0.38 mmol, 2.5 equiv) was suspended in a rapidly stirred mixture of MeOH and pH 7 phosphate buffer (1:1, 3.0 mL) at 0° C. Hydrazone 255 (83 mg, 0.15 mmol, 1.0 equiv) in MeOH (1.0 mL) was added dropwise, and the mixture was stirred at 0° C. until the reaction was complete by TLC (ca 1 h). The resulting suspension was placed in a separating funnel along with ether (15 mL) and saturated aqueous $NaHCO_3$ solution (5 mL). The organic layer was separated and the aqueous phase was extracted with ether (10 mL). The combined organic solution was washed with water (5 mL) and brine (5 mL), dried ($MgSO_4$) and concentrated. Flash column chromatography (silica gel, 50% ether in hexanes) afforded nitrile 256 (53 mg, 80%) as a colorless oil.

Synthesis of Aldehyde 257 as illustrated in FIG. 37. Nitrile 256 (53 mg, 0.12 mmol) was dissolved in toluene (2.0 mL) and cooled to −78° C. DIBAL (245 mL, 1 M solution in toluene, 0.22 mmol, 2.0 equiv) was added dropwise at −78° C. and the reaction mixture was stirred at that temperature until its completion was verified by TLC (ca 1 h). Methanol (150 mL) and aqueous HCl (150 mL, 1 N solution) were sequentially added and the resulting mixture was brought up to 0° C. and stirred at that temperature for 30 min. Ether (5 mL) and water (2 mL) were added, and the organic layer was separated. The aqueous phase was extracted with ether (2×5 mL) and the combined organic solution was washed with brine (5 mL), dried ($MgSO_4$), filtered and concentrated under reduced pressure. Flash column chromatography (silica gel, 15% ether in hexanes) furnished pure aldehyde 257 (44 mg, 82%).

Synthesis of Hydroxy Acid 263 and intermediates en route to, as illustrated in FIG. 38. Synthesized according to the procedure as described above as shown in FIGS. 16 and 18 using 257 instead of 75; see conditions in the description of Figures.

Synthesis of Epoxyde 266 and intermediates en route to, as illustrated in FIG. 39. Synthesized according to the procedure as described above as shown in FIGS. 16 and 18 using 257 as the starting substrated instead of 75; see conditions in the description of Figures.

Synthesis of Spirocyclopropane Ketoester 276 as illustrated in FIG. 41. Cyclopropanation of Ethyl Propionylacetate 275. Ethyl propionylacetate 275 (75.0 mL, 0.526 mol; Aldrich) was added to a solution of dry $K_2CO_3$ (218.0 g, 1.579 mol, 3.0 equiv) in DMF (526 mL, 1 M) at ambient temperature. This mixture was treated with 1,2-dibromoethane (60.0 mL, 0.684 mol, 1.3 equiv) over a period of 15 min and then rapidly stirred for 15 h, after which time completion of the reaction was indicated by NMR. Following filtration through celite and washing with ether, the solvents were removed in vacuo. Vacuum distillation (bp 64° C./6 mm Hg) of the crude product resulted in pure spirocyclopropane ketoester 276 (53.9 g, 60%) as a colorless oil.

Synthesis of Spirocyclopropane Ketoaldehyde 274 as illustrated in FIG. 41. LiAlH4 Reduction/Swern Oxidation of Spirocyclopropane Ketoester 276. To a solution of spirocyclopropane ketoester 276 (53.9 g, 0.316 mol) in ether (1.5 L, 0.2 M) was added a solution of lithium aluminum hydride (LAH; 1 M solution in THF, 632 mL, 0.632 mol, 2.0 equiv) at −20° C. over a period of 2 h and the reaction mixture stirred at −20° C. for 2 h. The reaction mixture was then diluted with ether (250 mL) and quenched by the sequential dropwise addition of water (24 mL), 15% aqueous sodium hydroxide solution (24 mL) and additional water (72 mL). The resulting slurry was allowed to warm to 25° C. over 10 h and the aluminum salts were removed by filtration through celite. The filtrate was dried ($MgSO_4$), and the solvent removed in vacuo to yield the crude diol (38.5 g, 93%), which was used in the oxidation step without further purification. An analytical sample was prepared by flash column chromatography (silica gel, 33 to 50% EtOAc in hexanes). To a solution of oxalyl chloride (35.5 mL, 0.407 mol, 3.0 equiv) in $CH_2Cl_2$ (360 mL) was added dropwise DMSO (38.5 mL, 0.543 mol, 4.0 equiv) in CH2Cl2 (100 mL) at −78° C. over 1 h. After stirring for 35 min, a solution of crude diol (17.7 g, 0.136 mol) in $CH_2Cl_2$ (200 mL) was added dropwise at −78° C. over a period of 1.5 h. The solution was stirred for a further 1 h at −78° C., before $Et_3N$ (151 mL, 1.085 mol, 8.0 equiv) was added over 40 min. After a further 15 min at −78° C. the resulting slurry was allowed to warm to 0° C. over 1 h. Ether (700 mL) and saturated aqueous $NH_4Cl$ solution (500 mL) were then added and the organic phase separated. The aqueous phase was re-extracted with ether (500 mL) and the combined organic solution washed with saturated aqueous $NH_4Cl$ solution (1.0 L), dried ($Na_2SO_4$), filtered and concentrated under reduced pressure. Purification by flash column chromatography (silica gel, 25% ether in hexanes) afforded spirocyclopropane ketoaldehyde 274 (10.9 g, 64%).

Synthesis of Silylether 273 as illustrated in FIG. 41. Allylboration of Spirocyclopropane Ketoaldehyde 33 and Silylation. Allyllmagnesium bromide (1 M solution in ether, 80 mL, 80.0 mmol, 1.0 equiv) was added dropwise to a well stirred solution of (−)-β-methoxydiisopinocampheyl borane (27.2 g, 86.0 mmol, 1.1 equiv) in ether (500 mL) at 0° C. After the completion of the addition, the gray slurry was stirred at room temperature for 1 h and the solvent was removed under reduced pressure. Pentane (400 mL) was added to the residual solids and the mixture stirred for 10 minutes. The stirring was discontinued to allow Drecipitation of the magnesium salts and the clear supernatant pentane solution was transferred via cannula carefully avoiding the transfer of any solid materials. This process was repeated four times. The combined pentane fractions were concentrated to a volume of ca. 500 mL and then added dropwise, without further purification, to a solution of ketoaldehyde 274 (10.1 g, 79.7 mmol, 1.0 equiv) in ether (250 mL) at −100° C. After the addition was complete, the mixture was stirred at the same temperature for 30 min. Methanol (10 mL) was added at −100° C., and the reaction mixture was allowed to warm to −40° C. over 40 min. Saturated aqueous $NaHCO_3$ solution (125 mL), followed by $H_2O_2$ (50 wt. % solution in $H_2O$, 50 mL) were added and the reaction mixture was allowed to stir at room temperature for 12 h. The organic phase was separated and the aqueous phase extracted with EtOAc (3×250 mL). The combined organic extracts were washed with saturated aqueous $NH_4Cl$ solution (500 mL), dried ($Na_2SO_4$) and the solvents removed in vacuo to yield the crude allylic alcohol which was used without further purification. An analytical sample was prepared by flash column chromatography (silica gel, 3% acetone in $CH_2Cl_2$).

This crude alcohol was dissolved in $CH_2Cl_2$ (750 mL, 0.3 M) and the solution was cooled to −78° C. The solution was treated with 2,6-lutidine (40 mL, 0.368 mol, 4.6 equiv), and after stirring for 5 min, tert-butyldimethyisilyl triflate (70 mL, 0.305 mmol, 3.8 equiv) was added dropwise. The reaction mixture was allowed to stir at −78° C. for 35 min, after which time no starting material was detected by TLC. Saturated aqueous $NH_4Cl$ solution (500 mL) was added, and the reaction mixture was allowed to warm to room temperature. The organic phase was separated, and the aqueous layer was extracted with ether (3×300 mL). The combined organic extracts were dried ($MgSO_4$), filtered through celite and the solvents were removed in vacuo to yield the crude silyl ether 32 which was used without further purification. An analytical sample was prepared by flash column chromatography (silica gel, 2 to 17% ether in hexanes).

Synthesis of Spirocyclopropane Ketoacid 31 as illustrated in FIG. 41. Oxidation of Olefin 273. The crude alkene 273 was dissolved in MeCN (143 mL), $CCl_4$ (143 mL) and $H_2O$ (214 mL) and the mixture cooled to 0° C. Sodium periodate (70 g, 327 mmol, 4.1 equiv) and ruthenium(III) chloride hydrate (898 mg, 3.98 mmol, 0.05 equiv) were added and the mixture was stirred at 0° C. for 10 min. The dark mixture was allowed to warm to ambient temperature and stirred for 3 h, after which time the disappearance of starting material was indicated by TLC. $CH_2Cl_2$ (1.5 L) and saturated aqueous NaCl solution (1.5 L) were added and the layers were separated. Extractions of the aqueous phase with $CH_2Cl_2$ (3×750 mL), filtration through celite, concentration and flash column chromatography (2 to 80% EtOAc in hexanes) yielded pure spirocyclopropane ketoacid 31 (10.2 g, 43% for three steps).

Synthesis of Esters 268 and 269 and intermediates en route to, as illustrated in FIG. 42. Synthesized according to the procedure as described above as shown in FIG. 7 using 272 instead of 8; see conditions in the description of Figures.

Synthesis of 4,4-Ethano-epothilone A Analogs 267, 282, 283, 284, and intermediates en route to, as illustrated in FIG. 43. Synthesized according to the procedure as described via supra as shown in FIG. 8 using 272 instead of 8 as the substrate perturbation; see conditions in the description of Figures.

Synthesis of 4,4-Ethano-epothilone A Analogs 289, 290, 291, 292, and intermediates en route to, as illustrated in FIG. 44. Synthesized according to the procedure as described via supra as shown in FIG. 8 using 272 instead of 8 as the substrate perturbation; see conditions in the description of Figures. Synthesis of Keto Aldehyde 295 as illustrated in FIG. 46. Ozonolysis of Ketone 273. Alkene 273 (3.6 g, 12.7 mmol; synthesized exactly to procedures) was dissolved in $CH_2Cl_2$ (50.0 mL, 0.25 M) and the solution was cooled to −78° C. Oxygen was bubbled through for 2 min, after which time ozone was passed through until the reaction mixture adopted a blue color (ca 30 min). The solution was then purged with oxygen for 2 min at −78° C. (disappearance of blue color) and $Ph_3P$ (6.75 g, 25.4 mmol, 1.2 equiv) was added. The cooling bath was removed and the reaction mixture was allowed to reach room temperature and stirred for an 1 additional hour. The solvent was removed under reduced pressure and the mixture was purified by flash column chromatography (silica gel, 30% ether in hexanes) to provide pure keto aldehyde 295 (3.26 g, 90%). 295.

Synthesis of Ketone 294 as illustrated in FIG. 46. To a solution of aldehyde 295 (2.9 g, 10.2 mol) in THF (50 mL, 0.2 M) at −78° C. was added dropwise lithium tri-tert-butoxyaluminohydride (11.2 mL, 1.0 M solution in THF, 11.2 mmol, 1.1 equiv). After 5 min, the reaction mixture was brought up to 0° C. and stirred at that temperature for 15 min, before quenching with saturated aqueous solution of sodium-potassium tartrate (25 mL). The aqueous phase was extracted with ether (3×75 mL) and the combined organic layer was dried (MgSO$_4$), filtered and concentrated. The crude primary alcohol so obtained was dissolved in CH$_2$Cl$_2$ (50 mL, 0.2 M) and cooled to 0° C. Et$_3$N (68.1 mL, 30.6 mmol, 3.0 equiv), 4-DMAP (120 mg, 0.18 mmol, 0.02 equiv) and tert-butyldimethylsilyl chloride (3.0 g, 20.4 mmol, 2.0 equiv) were added. The reaction mixture was allowed to stir at 0° C. for 2 h, then at 25° C. for 10 h. MeOH (5 mL) was added and the solvents were removed under reduced pressure. Ether (100 mL) was added followed by saturated aqueous NH$_4$Cl solution (25 mL) and the organic phase was separated. The aqueous phase was extracted with ether (2×50 mL) and the combined organic solution was dried (MgSO$_4$), filtered and concentrated under reduced pressure. Purification by flash column chromatography (silica gel, 5% ether in hexanes) provided pure bis (silylether) 294 (1.26 g, 83% yield from 45).

Synthesis of tris(Silylethers) 297 and 298 as illustrated in FIG. 47. Aldol Reaction of Ketone 294 with Aldehyde 75. The aldol reaction of ketone 294 (682 mg, 1.7 mmol, 1.4 equiv) with aldehyde 75 (530 mg, 1.2 mmol, 1.0 equiv; vida supra) was carried out exactly as described for ketone and aldehyde for epothilone synthesis vida supra, and yielded pure 297 (270 mg, 24%) and 298 (480 mg, 47%). 297: Colorless oil.

Synthesis of Epothilones 267, 311–313 and intermediates en route to, as illustrated in FIG. 47. Synthesized according to the procedure as described above as shown in FIG. 19 using 294 instead of 136; see conditions in description of Figures for FIG. 47.

Synthesis of aldehydes 320, 321 and 329 as illustrated in FIG. 49. The synthesis of aldehydes 320, 321 and 329 are simple aldhehydes synthesized exactly as in conditions found for standard epothilone aldehydes 7 (FIG. 3), and aldehyde 221 (vida supra); all reactions are carried out using the transformations shown and standard conditions known well to one of ordinary skill in the art and therefore no further elaboration will be disclosed here.

Synthesis of compounds 339–346 and intermediates en route to, as illustrated in FIG. 50. Synthesized according to the procedure as described via supra as shown in FIG. 21 using 330, 331, and 332 instead of 149, 144, and 143; see conditions as disclosed in description of Figures for FIG. 50.

Synthesis of alcohol 350 as illustrated in FIG. 52. Allyl-magnesium bromide (1.3 equiv) was added dropwise over 45 min to a solution of (Ipc)2BOMe (1.3 equiv) in ether (0.2 M) at 0° C., and the resulting pale gray slurry allowed to warm to 25° C. over 1 h. The ether was removed under reduced pressure and pentane added to the residual solid. The slurry was stirred at 25° C. for 10 min and then the solids were allowed to settle over 30 min. The clear supernatant solution was then carefully transferred to a separate flask via cannula. This process was repeated four times, and the resulting solution was then added dropwise over 1 h to a solution of aldehyde 2 (1.0 equiv) in ether at −100° C. After 1 h at −100° C., methanol was added and the mixture allowed to warm over 40 min. Saturated aqueous NaHCO$_3$ and 50% aqueous H$_2$O$_2$ were then added and the mixture left to warm to 25° C. 4 overnight. The layers were separated, the aqueous phase re-extracted with EtOAc and the combined organic phases washed with saturated aqueous NH$_4$Cl. Drying (Na$_2$SO$_4$) and concentration under reduced pressure gave a residue, which was purified by flash column chromatography (silica gel, 20% ether in hexanes) to give the desired alcohol 350 (91%).

Synthesis of Lactone 352 and 353 and intermediates en route to—as illustrated in FIG. 52. Synthesized according to the coupling and metathesis procedure as described above as shown in FIG. 5 using 350 and 348.

Synthesis of cis-Diol 354 and 355 as illustrated in FIG. 52. To a solution of cis-silyl ether 352 (1.0 equiv) in THF (8.2 mL) at 25° C. was added HFpyr (10 equiv) and the resulting solution stirred at the same temperature for 27 h. The mixture was then added carefully to saturated aqueous sodium bicarbonate and EtOAc, and the resulting two-phase mixture stirred at 25° C. for 2 h. The layers were then separated and the organic layer washed with saturated aqueous sodium bicarbonate and brine. Drying over magnesium sulfate and purification by flash chromatography (silica gel, 20 50% EtOAc in hexanes) afforded the desired diol 354 in 84% yield.

Synthesis of 356 and 357: see above.

Synthesis of 2-(Hydroxy-methyl)-4-(tri-n-butyl-stannyl)-thiazole 363 as illustrated in FIG. 53. To a solution of 2,5-dibromothiazole (358; 1.0 equiv) in anhydrous ether (0.1 M) was added n-BuLi (1.1 equiv) at −78° C., and the resulting solution was stirred at the same temperature for 30 min, before DMF (1.2 equiv) and hexamethylphosphoramide (HMPA, 1.1 equiv) were added at the same time. After being stirred at −78° C. for 30 min, the reaction mixture was slowly warmed up to room temperature over a period of 2 h. Hexane (2.0 mL) was added and the resulting mixture passed through a short silica cake with 30% ethyl acetate in hexanes. The solvents were evaporated to give the crude aldehyde 359 (72% yield), which was used in the next step without further purification.

To the solution of the crude aldehyde 359 in methanol (0.1 M) was added sodium borohydride (2.0 equiv) at 25° C., and the resulting mixture was stirred at the same temperature for 30 min. EtOAc and hexanes were added, and the mixture passed through a short silica cake with ethyl acetate. The solvents were then evaporated and the crude product was purified by flash chromatography (20 50% ethyl acetate in hexanes) to give 2-hydroxymethyl-4-bromothiazole 360 in 88% yield.

To a solution alcohol 360 (1.0 equiv) in methylene chloride (0.1 M) at 25° C. was added imidazole (2.0 equiv), followed by tert-butyldimethylchlorosilane (1.5 equiv). After 30 min, the reaction was quenched with methanol, and the mixture was passed through silica with methylene chloride. Evaporation of solvents gave the silyl ether 361 in 96% yield.

To a solution of 361 (1.0 equiv) in ether (0.1 M) was added n-BuLi (1.2 equiv) at −78° C., and the resulting mixture was stirred at this temperature for 10 min. Tri-n-butyltin chloride (1.2 equiv) was then added, and the reaction mixture was stirred at −78° C. for a further 10 min and then warmed up to 25° C. over a period of 1 h. The reaction mixture was diluted with hexanes and passed through silica with 20% EtOAc in hexanes. The crude product was purified by flash chromatography (silica gel pre-treated with triethylamine, 5% Et$_2$O in hexanes) to afford stannane 362 in 85% yield.

To a solution of silyl ether 362 (1.0 equiv) in THF (0.1 M) was added TBAF (1.0 M in THF, 1.2 equiv) at 25° C. and the reaction mixture was stirred for 20 min at this temperature. Hexanes were added, and the mixture was passed through silica with EtOAc. Evaporation of solvents gave alcohol 363 in 95% yield.

Synthesis of compounds 364–367 as illustrated in FIG. 53. Compounds 364–367 were exactly prepared according to Dondoni et al. *Synthesis*, 1986, 757–760.

Synthesis of 2-(-Acetoxy-pentyl)-4-(trimethyl-stannyl)-thiazole 371 as illustrated in FIG. 53. To a solution of 2,4-dibromothiazole (358; 1.0 equiv) in i-$Pr_2$NH (0.5 M) was added 4-pentyn-1-ol (2.0 equiv), tetrakis (triphenylphosphine)palladium(0) (0.05 equiv) and CuI (0.1 equiv). The reaction mixture was then heated at 70° C. for 2 h and after cooling to 25° C. the solvents were removed under reduced pressure. Purification by flash column chromatography (silica gel, 10% Å 75% EtOAc in hexanes) provided the desired alcohol 368 in 83% yield.

A solution of alcohol 368 (1.0 equiv) and $PtO_2$ (0.1 equiv) in EtOH (0.1 M) was stirred at 25° C. under an atmosphere of hydrogen for 4 h, until the disappearance of starting material was indicated by $^1$H NMR. Subsequent filtration through a short plug of silica, washing with EtOAc, and removal of the solvents under reduced pressure afforded the desired alcohol 369 (100%). A solution of alcohol 369 in pyridine-acetic anhydride (1:1; 0.1 M) was stirred at 25° C. for 2 h, after which TLC indicated completion of the reaction. The reagents were then removed under reduced pressure. Purification by flash column chromatography (silica gel, 10% Å 40% ether in hexanes) gave the desired acetate 370 in 90% yield.

A solution of acetate 370 (1.0 equiv) in degassed toluene (0.1 M), was treated with hexamethyiditin (10 equiv) and tetrakis(triphenylphosphine)palladium(0) (0.1 equiv). The mixture was then heated to 100° C. for 3 h, after which TLC indictated disappearance of the aryl bromide. The reaction mixture was cooled to 25° C. and purified by flash column chromatography (silica gel, 50% ether in hexanes containing $NEt_3$) to afford the desired stannane 371 in 193% yield.

Synthesis of 2-Piperidinyl-4-(trimethylstannyl)thiazole 373 as illustrated in FIG. 53. 2,4-Dibromothiazole (358; 1.0 equiv) was dissolved in piperidine (0.5 M) and the reaction was warmed to 50° C. for 8 h, upon which completion of the reaction was indicated by TLC. The mixture was poured into water and extracted with ether (2×). Drying ($MgSO_4$) and evaporation of the solvents gave 2-piperidinyl-4-bromothiazole 372, which was isolated after flash column chromatography (silica gel, 5% EtOAc in hexanes) in 100% yield.

2-Piperidinyl-4-bromothiazole (372, 1.0 equiv) was taken up in degassed toluene (0.1 M), and hexamethyditin (10 equiv) and tetrakis(triphenylphosphine)palladium(0) (0.1 equiv) were added. The mixture was then heated to 80° C. for 3 h, after which TLC indicated disappearance of the aryl bromide. The reaction mixture was poured into saturated aqueous $NaHCO_3$ solution and extracted with ether, washed with water and with saturated aqueous NaCl solution (120 mL). The organic extract was dried ($Na_2SO_4$) and the solvents and the excess hexamethylditin were removed under reduced pressure. Flash column chromatography (silica gel, 5% $NEt_3$ in hexanes) provided 2-piperidinyl-4-(trimethylstannyl)thiazole 373 in 100% yield.

Synthesis of 2-Thiomethyl-4-(trimethylstannyl)thiazole 375 as illustrated in FIG. 53. 2,4-Dibromothiazole (358; 1.0 equiv) was dissolved in ethanol (0.1 M) and treated with sodium thiomethoxide (3.0 equiv). The reaction mixture was stirred at 25° C. for 3 h, upon which completion of the reaction was indicated by $^1$H NMR. The mixture was poured into water and extracted with ether (2×). Drying ($MgSO_4$) and evaporation of the solvents gave 2-thiomethyl-4-bromothiazole 374, which was isolated, after flash column chromatography (silica gel, 5% EtOAc in hexanes), in 92% yield.

2-Thiomethyl-4-bromothiazole (374) was taken up in degassed toluene (0.1 M), and was then treated with hexamethyldtin (10 equiv) and tetrakis(triphenylphosphine) palladium(0) (0.1 equiv) at 80° C. for 3 h according to the procedure described for the synthesis of 2-pi-peridinyl-4-(trimethylstannyl)thiazole (373), to yield, after flash column chromatography (silica gel, 5% $NEt_3$ in hexanes), 2-thiophenyl-4-(trimethylstannyl)thiazole (375; 100%).

Synthesis of Compounds 376–377 and 378–379 as illustrated in FIG. 53. Compounds 376–377 are commercially available from Aldrich. Compounds 378–379 are exactly prepared according to Dondoni et al. *Synthesis*, 1986, 757; Reynaud et al. *Bull. Soc. Chim. Fr.* 1962, 1735.

Synthesis of 2-Thiophenyl-4-(trimethylstannyl)thiazole 381 as illustrated in FIG. 53. 2,4-Dibromothiazole (358; 1.0 equiv) was dissolved in ethanol (0.1 M) and treated with thiophenol (3.0 equiv) and solid sodium hydroxide (3.0 equiv). The reaction mixture was heated at 45° C. for 4 h, upon which completion of the reaction was indicated by TLC. The mixture was poured into water and extracted with ether (2×). Drying ($MgSO_4$) and evaporation of the solvents gave 2-thiophenyl-4-bromothiazole 380, which was isolated after flash column chromatography (silica gel, 5% EtOAc in hexanes) in 84% yield.

2-Thiophenyl-4-bromothiazole (380; 1.0 equiv) was taken up in degassed toluene (0.1 M), and was then treated hexamethyiditin (10 equiv) and tetrakis(triphenylphosphine) palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% $NEt_3$ in hexanes), 2-thiophenyl-4-(trimethylstannyl)thiazole (381; 100%).

Synthesis of 2-Ethyl(trimethylstannyl)thiazole 384 as illustrated in FIG. 53. A solution of 2,4-dibromothiazole (358; 1.0equiv), tributyl(vinyl)tin (1.1 equiv) and tetrakis (triphenylphosphine)palladium(0) (0.1 equiv) in degassed toluene (0.1 M) were heated at 110° C. for 20 min, after which completion of the reaction was shown by TLC. The reaction mixture was poured into saturated aqueous $NaHCO_3$—NaCl solution and extracted with ether (2×). The organic extract was dried ($Na_2SO_4$), and the solvents were removed under reduced pressure to yield, after purification by preparative thin layer chromatography (silica gel, 5% EtOAc in hexanes), 2-vinyl-4-bromothiazole 382 in 96% yield.

Vinylthizaole 382 (1.0 equiv) was taken up in ethanol (0.1 M) and treated with Adam's catalyst ($PTO_2$, 0.05 equiv) and hydrogen (1 atm) for 4 h at 25° C., in accordance with the procedure describing the hydrogenation of compound 368, to yield, after purification by preparative thin layer chromatography (silica gel, 5% EtOAc in hexanes), 2-ethyl-4-bromothiazole 383 in 100% yield.

2-Ethyl-4-bromothiazole (383; 1.0 equiv) was taken up in degassed toluene (0.1 M), and was then with treated hexamethyldtin (10 equiv) and tetrakis(triphenylphosphine) palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% $NEt_3$ in hexanes), 2-ethyl-4-(trimethylstannyl)thiazole (384) in 100% yield.

Synthesis of 2-Dimethylamino-4-trimethylstannylthiazole 386 as illustrated in FIG. 53. 2,4-

Dibromothiazole (358; 1.0 equiv) was dissolved in DMF (0.1 M) and heated at 150–160° C. for 8 h, upon which completion of the reaction was indicated by TLC. The mixture was poured into water and extracted with ether (2×). Drying (MgSO$_4$) and evaporation of the solvents gave 2-dimethylamino-4-bromothiazole 385, which was isolated after flash column chromatography (silica gel, 5% EtOAc in hexanes) in 89% yield.

2-Dimethylamino-4-bromothiazole (385; 1.0 equiv.) was taken up in degassed toluene (0.1 M), and was then treated with hexamethyiditin (10 equiv) and tetrakis(triphenylphosphine)palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt$_3$ in hexanes), 2-dimethylamino-4-(trimethylstannyl)thiazole (386; 100%).

Synthesis of 2-Acetoxymethyl-4-(trimethylstannyl) thiazole 388 as illustrated in FIG. 53. Alcohol 360 (1.0 equiv) was taken up in pyridine acetic anhydride (1:1; 0.2 M) at 25° C. and stirred at this temperature for 3 h, in accordance with the procedure for the formation of acetate 370, to give, after purification by flash column chromatography (silica gel, 5% EtOAc in hexanes), 2-acetoxymethyl-4-bromothiazole (387) in 95% yield.

2-Acetoxymethyl-4-bromothiazole (387) was taken up in degassed toluene (0.1 M), and was then treated hexamethyldtin (10 equiv) and tetrakis(triphenylphosphine)palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt$_3$ in hexanes), 2-acetoxymethyl-4-(trimethylstannyl)thiazole (388; 100%).

Synthesis of 2-Fluoromethyl-4-(trimethylstannyl)thiazole 390 as illustrated in FIG. 53. A solution of alcohol 360 in CH$_2$Cl$_2$ (0.1 M) was added via syringe to a cold (−78° C.) solution of diethylaminosulfur trifluoride (DAST, 1.1 equiv) in CH$_2$Cl$_2$ (0.1 M). The reaction was allowed to warm slowly to 25° C., and was then quenched by addition of saturated aqueous NaHCO$_3$ solution. The organic layer was separated and washed with saturated aqueous NaCl solution. After drying (MgSO$_4$) and evaporation of the solvent under reduced pressure, purification by flash column chromatography (silica gel, 5% EtOAc in hexanes) resulted in 2-fluoromethyl-4-bromothiazole (389) in 88% yield.

2-Fluoromethyl-4-bromothiazole (389; 1.0 equiv) was taken up in degassed toluene (0.1 M), and was then treated with hexamethyiditin (10 equiv) and tetrakis(triphenylphosphine)palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt$_3$ in hexanes), 2-fluoromethyl-4-(trimethylstannyl)thiazole (390) in 100% yield.

Synthesis of 1-Methyl-2-(trimethylstannyl)imidazole 391 as illustrated in FIG. 53. To a solution of 1-methylimidazole (1.0 equiv) in ether (0.1 M) was added n-BuLi (1.2 equiv) at −78° C., and the resulting mixture was stirred at this temperature for 10 min. Trimethyltin chloride (1.2 equiv) was then added, and the reaction mixture was stirred at −78° C. for 10 more min and then warmed up to 25° C. over a period of 1 h. The reaction mixture was diluted with hexanes and passed through silica with 20% EtOAc in hexanes. The crude product was purified by flash chromatography (silica gel pre-treated with triethylamine, 5% Et$_2$O in hexanes) to afford stannane 391 in 85% yield.

General Procedure for Stille Coupling with Epothilone analogs as illustrated in FIG. 52 and compounds found in FIGS. 54–55—General Procedure A. A solution of vinyl iodide (1.0 equiv, cis- or trans-compound), aryl stannane (2.0 equiv) and tetrakis(triphenylphosphine)palladium(0) (0.1 equiv) in degassed toluene (0.1 M) was heated at 100° C. for 30–40 min. The reaction mixture was poured into saturated aqueous NaHCO$_3$—NaCl solution and extracted with EtOAc. The organic extract was dried (Na$_2$SO$_4$), and the solvents were removed under reduced pressure to yield, after purification by preparative thin layer chromatography (250 μm silica gel plate, 75% ether in hexanes), the corresponding epothilone analogs (see Table for yields).

General Procedure B. A solution of vinyl iodide (1.0 equiv, cis or trans-compound), aryl stannane (2.0 equiv) and palladium(II) bis(benzonitrile) dichloride (0.1 equiv) in degassed DMF (0.1 M) was stirred at 25° C. for 10 h. The reaction mixture was poured into saturated aqueous NaHCO$_3$—NaCl solution and extracted with EtOAc (2×). The organic extract was dried (Na$_2$SO$_4$), and the solvents were removed under reduced pressure to yield after purification by preparative thin layer chromatography (250 μm silica gel plate, 75% ether in hexanes) the corresponding epotholone analogs (see Table for yields).

Synthesis of epoxide 356B from 356A as illustrated in FIG. 56. Conditions exactly as that of the conversion from 110 to 111 as shown in FIG. 14 (see above).

Synthesis of alcohol 392 as illustrated in FIG. 58. Trityl deprotection Method A. To a stirred solution of trityl ether 264(1 equiv.) in CH$_2$Cl$_2$/MeOH (1:1, 0.1 M) at 0° C. was added camphor sulfonic acid (1 equiv.) and the mixture allowed to warm to room temperature. After stirring for 2 hours, Et$_3$N (1.5 equiv.) was added and solvent removed in vacuo. Flash chromatography afforded the product 392 as a colorless oil (70%).

Method B. To a stirred solution of trityl ether 264 (1 equiv.) in MeOH/CH$_2$Cl$_2$ (10:1, 0.1 M) was added PPTS (1 equiv.). The reaction was stirred for 72 hours before solvent was removed in vacuo. Filtration through a plug of silica gel gave the product 392 as a colorless oil (60%).

Method C. To the trityl ether 264 (1 equiv.) at 0° C. was added a mixture of ether:formic acid (1:1, 0.2M). After stirring for 1 hour, the reaction was quenched with saturated aqueous sodium bicarbonate. The layers were separated and the aqueous phase extracted with ether. The combined organic extracts were dried (MgSO$_4$), filtered and concentrated in vacuo. Flash chromatography gave the product 392 as a colorless oil (65%).

Synthesis of compound 393 as illustrated in FIG. 58. Fluorination of allylic alcohol 392. To a stirred solution of allylic alcohol 393 (1 equiv.) in CH$_2$Cl$_2$ at −78° C. was added diethylamino sulfurtrifluoride (DAST, 1 equiv.). The reaction was then allowed to warm slowly to room temperature before being quenched with saturated aqueous sodium bicarbonate solution. The layers were separated and the aqueous phase extracted with CH$_2$Cl$_2$. The combined organic extracts were dried (MgSO$_4$), filtered and concentrated in vacuo. Flash chromatography gave the fluoride 393 as a colorless oil (30%).

Synthesis of compound 394 as illustrated in FIG. 58. Compound 394 was prepared using conditions exactly as described for the conversion of 121 to 71 (vida supra) in FIG. 18.

Synthesis of compound 395 as illustrated in FIG. 58. Compound 395 was prepared using conditions exactly as described for the conversion of 71 to 2 (vida supra) in FIG. 16.

Synthesis of compound 396 as illustrated in FIG. 58. Chlorination of allylic alcohol 392. To a solution of allylic alcohol 392 in $CCl_4$ (0.1 M) was added $PPh_3$ (2.5 equiv.). The reaction was then heated to reflux for 18 hours. After cooling to room temperature, the solvent was removed in vacuo and the resulting residue filtered through a plug of silica gel to provide the chloride 396 as a colorless oil (90%).

Synthesis of compound 397 as illustrated in FIG. 58. Compound 397 was prepared using conditions exactly as described for the conversion of 121 to 71 (see above) in FIG. 18.

Synthesis of compound 398 as illustrated in FIG. 58. Compound 398 was prepared using conditions exactly as described for the conversion of 71 to 2 (see above) in FIG. 16.

Synthesis of compound 399 as illustrated in FIG. 59. O-alkylation of allylic alcohol 392. To a suspension of sodium hydride (1.2 equiv.) in THF (0.1 M) was added a solution of the allylic alcohol 392 in THF. After stirring for 30 minutes, a solution of the alkyl halide in THF (1.0M; alkyl halide can be selected from the group consisting of iodmethane, iodoethane, 2-iodopropane, 1-iodobutane, 1-iodopropane, benzyl iodide and allyl iodide; commercially available from Aldrich/Sigma) was added and the resulting mixture was stirred until TLC indicated completion of the reaction. Saturated aqueous ammonium chloride solution was added and the layers were separated. The aqueous phase was extracted with ether and the combined organic extracts were dried ($MgSO_4$), filtered and concentrated in vacuo. Flash chromatography gave the ether product 399.

Synthesis of Triol 400 as illustrated in FIG. 59. Compound 399 (1 equiv.) was treated with a 30% solution of HF.pyridine in THF. After stirring for 24 hours, the reaction was quenched by pouring into saturated sodium bicarbonate solution. The layers were separated and the aqueous phase extracted with ether. The combined organic extracts were dried ($MgSO_4$), filtered and concentrated in vacuo. Flash chromatography gave 400 (78%).

Synthesis of compound 401 as illustrated in FIG. 59. Compound 398 was prepared using conditions exactly as described for the conversion of 71 to 2 (vida supra) in FIG. 16.

Synthesis of epoxide 403 as illustrated in FIG. 60. To a solution of 9.55 g (53.6 mmol) of alcohol 402 and 0.25 equiv of D-(+)diisopropyl tartrate in 0.1 Molar of dichloromethane was added. The solution was cooled to −30° C. and 0.2 equiv of freshly distilled titanium tetraisopropoxide was added. The clear solution was stirred at −20° C. for 30 min, and an aliquot was quenched for capillary GLC analysis. After an additional 5 min of stirring at −20° C., 2.0 equiv of a 1.5 M solution of ter-butyl hydroperoxide in 2,2,4-timethylpentane was added over 10 min. The resulting mixture was stirred at 20° C. for 3 h after which the reaction was quenched by pouring into saturated sodium bicarbonate solution. The layers were separated and the aqueous phase extracted with ether. The combined organic extracts were dried ($MgSO_4$), filtered and concentrated in vacuo. Flash chromatography gave 403.

Sythesis of esters 404. Method 1. To a stirred solution of 403 (1 equiv.) in THF (0.1 M) was added triethylamine (1.1 equiv.) and the required anhydride (1.1 equiv. ($(RCO)_2O$) selected from the group consisting of acetic anhydride, chloroacetic anhydride, propionic anhydride, trifluoroacetic anhydride, isobutyric anhydride; commercially available from Aldrich/Sigma). After stirring for 2 hours, the reaction was quenched with saturated aqueous sodium bicarbonate solution. The layers were separated and the aqueous phase extracted with ether. The combined organic extracts were dried ($MgSO_4$), filtered and concentrated in vacuo. Flash chromatography gave 403.

Synthesis of esters 404. Method 2 as illustrated in FIG. 60. To a stirred solution of 403 (1 equiv) in $CH_2Cl_2$ (0.1 M) was added triethylamine (1.1 equiv.) and the required acid chloride (1.1 equiv. selected from the group consisting of pivaloyl chloride, cyclopropanecarbonyl chloride, cyclohexanecarbonyl chloride, acryloyl chloride, benzoyl chloride, 2-furoyl chloride, N-benzoyl-(2R,3S)-3-phenylisoserine, cinnamoyl chloride, phenylacetyl chloride, 2-thiophenesulfonyl chloride; commercially available from Aldrich/Sigma). After stirring for 2 h, the reaction was quenched with saturated aqueous sodium bicarbonate solution. The layers were separated and the aqueous phase extracted with ether. The combined organic extracts were dried ($MgSO_4$), filtered and concentrated in vacuo. Flash chromatography gave 404.

Synthesis of thioether 405 as illustrated in FIG. 60. To a stirred solution of allylic alcohol 392 (1 equiv.) in THF (0.1 M) was added the required disulfide (2 equiv.) followed by tributyl phosphite (2 equiv.). After stirring for 4 hours the reaction was quenched with brine and the layers were separated. The aqueous phase was extracted with ether and the combined organic extracts were dried ($MgSO_4$), filtered and concentrated in vacuo. Flash chromatography gave the thioether 405.

Synthesis of compound 406 as illustrated in FIG. 60. Compound 406 was prepared using conditions exactly as described for the conversion of 121 to 71 (vida supra) in FIG. 18.

Synthesis of compound 407 as illustrated in FIG. 60. Compound 407 was prepared using conditions exactly as described for the conversion of 71 to 2 (vida supra) in FIG. 16.

Synthesis of compound 408. Tosylation of allylic alcohol 392 as illustrated in FIG. 61. To a stirred solution of allylic alcohol 392 (1 equiv) in $CH_2Cl_2$ (0.1 M) at 0° C. was added $Et_3N$ (4.0 equiv) followed by tosyl chloride (2.0 eqiuv). The reaction mixture was warmed to room temperature and stirred until complete as determined by TLC. Saturated ammonium chloride solution was added and the layers were separated. The aqueous phase was extracted with ether and the combined organic extracts were dried, ($MgSO_4$), filtered and concentrated in vacuo. Flash chromatography gave the tosylate 408.

Synthesis of azide 409 as illustrated in FIG. 61. To a stirred solution of tosylate (1 equiv.) 408 in DMF was added sodium azide. The reaction was stirred for some hours. Saturated ammonium chloride solution was added and the layers were separated. The aqueous phase was extracted with eteher and the combined organic extracts were dried ($MgSO_4$), filtered and evaporated in vacuo. Flash chromatography then provided the azide 409.

Synthesis of diol 410 as illustrated in FIG. 61. Azide (1 equiv.) 409 was treated with a 30% solution of Hfpyridine in THF. After stirring for 24 hours, the reaction was quenched by pouring into saturated sodium bicarbonate solution. The layers were separated and the aqueous phase extracted with ether. The combined organic extracts were dried ($MgSO_4$), filtered and concentrated in vacuo. Flash chromatography gave 410.

Synthesis of amine 411 as illustrated in FIG. 61. To a stirred solution of azide 411 (1 equiv.) in a mixed solvent system of $THF:H_2O$ (1:1, 0.1 M) was $PPh_3$. The reaction was stirred for 4 hours before being poured into saturated brine. The layers were separated and the aqueous phase extracted with ether. The combined organic extracts were dried (MgSO$_4$), filtered and concentrated in vacuo. Flash chromatography gave 411.

Synthesis of amides 412 as illustrated in FIG. 61. Method 1. To a stirred solution of amine 411 (1 equiv.) in THF (0.1 M) was added triethylamine (1.2 equiv.) and the required anhydride (1.1 equiv. ((RCO)$_2$O) selected from the group consisting of acetic anhydride, chloroacetic anhydride, propionic anhydride, trifluoroacetic anhydride, isobutyric anhydride; commercially available from Aldrich/Sigma). After stirring for 4 hours, the reaction was quenched with saturated aqueous sodium bicarbonate solution. The layers were separated and the aqueous phase extracted with ether. The combined organic extracts were dried (MgSO$_4$), filtered and concentrated in vacuo. Flash chromatography gave 412.

Amides 412. Method 2. To a stirred solution of amine 411 (1 equiv) in CH$_2$Cl$_2$ (0.1 M) was added triethylamine (1.2 equiv.) and the required acid chloride (1.1 equiv. selected from the group consisting of pivaloyl chloride, cyclopropanecarbonyl chloride, cyclohexanecarbonyl chloride, acryloyl chloride, benzoyl chloride, 2-furoyl chloride, N-benzoyl-(2R,3S)-3-phenylisoserine, cinnamoyl chloride, phenylacetyl chloride, 2-thiophenesulfonyl chloride; commercially available from Aldrich/Sigma). After stirring for 4 hours, the reaction was quenched with saturated aqueous sodium bicarbonate solution. The layers were separated and the aqueous phase extracted with ether. The combined organic extracts were dried (MgSO$_4$), filtered and concentrated in vacuo. Flash chromatography gave 412.

Synthesis of compound 413 as illustrated in FIG. 61. Compound 413 was prepared using conditions exactly as described for the conversion of 71 to 2 (vida supra) in FIG. 16.

Synthesis of Aldehyde 414. Oxidation of Alcohol 403 as illustrated in FIG. 62. To a solution of alcohol 403 (1.0 equiv.) in CH$_2$Cl$_2$ (0.1 M) was added at −78° C. TEMPO (2,2,6,6-tetramethyl-1-piperidinyloxy, free radical.) (0.008 M solution in CH2Cl2, 1.5 equiv), KBr (0.2 M aqueous solution, 0.1 equiv), and NaOCl (0.035 M solution in 5% aqueous NaHCO$_3$, 1.0 equiv). After stirring for 0.5 h, the organic layer was dried (MgSO$_4$), filtered and concentrated under reduced pressure. Purification by preparative chromatography provided aldehyde 414 (75%).

Synthesis of carboxylic Acid 415. Oxidation of Aldehyde 414 as illustrated in FIG. 62. Aldehyde 414 (1 equiv.), 'BuOH (0.1 M), isobutylene (3.0 equiv.), H$_2$O (0.02M), NaClO$_2$ (3.0 equiv.) and NaH$_2$PO$_4$ (3 equiv.) were combined and stirred at room temperature for 1 h. The reaction mixture was concentrated under reduced pressure and the residue was subjected to flash column chromatography to afford carboxylic acid 415.

Synthesis of ester 416. Coupling of acid 415 with different alcohols and amines as illustrated in FIG. 62. A solution of acid 415 (1.0 equiv), 4-(dimethylamino)pyridine (4-DMAP, 0.1 equiv) and alcohol or amine selected from the group consisting of methanol, t-butanol, i-propanol, phenol, benzyl alcohol, furfurylamine N-benzoyl-(2R,3S)-3-phenylisoserine, dimethyl amine, diethyl amine, benzyl amine (1.0 equiv) in CH$_2$Cl$_2$ (0.3 M) was cooled to 0° C. and then treated with 1-ethyl-(3-dimethylaminopropyl)-3-carbodiimide hydrochloride (EDC, 1.2 equiv). The reaction mixture was stirred at 0° C. for 2 h and then at 25° C. for 5 h. The solution was concentrated to dryness in vacuo, and the residue was taken up in EtOAc (10 mL) and water (10 mL). The organic layer was separated, washed with saturated NH$_4$Cl solution (10 mL) and water (10 mL) and dried (MgSO$_4$). Evaporation of the solvents followed by flash column chromatography resulted in pure ester 416.

Synthesis of variable ring size Compounds shown in FIG. 68. Synthesized according to the procedure as described above as shown in FIGS. 12–19 using 1015, 1016, 1033, 1035 (synthesis shown) instead of 75; see conditions in the description of Figures for FIG. 68.

Synthesis of variable ring size Compounds shown in FIG. 69. Synthesized according to the procedure as described above as shown in FIGS. 12–19 using 1015, 1016, 1033, 1035 (synthesis shown) instead of 75; see conditions in the description of Figures for FIG. 69.

Synthesis of variable ring size Compounds shown in FIG. 70. Synthesized according to the procedure as described above as shown in FIGS. 12–19 using 1015, 1016, 1033, 1035 (synthesis shown) instead of 75; see conditions in the description of Figures for FIG. 70.

Synthesis of Compound look as shown in FIG. 72. Diol 414 (1.0 equiv) was dissolved in CH$_2$Cl$_2$ (0.1 M), the solution was cooled to 0° C. and Et$_3$N (10 equiv) was added. After stirring for 5 min, chloro trimethylsilane (5.0 equiv) was added dropwise and the reaction mixture was allowed to stir at 0° C. for 1 h, and then at 25° C. for 11 h, after which time no starting alcohol was detected by TLC. Methanol (2 mL) was added at 0° C. and the solvent was removed under reduced pressure. Flash column chromatography provided pure 2000 (67%). Next, methyltriphenylphosphonium bromide (1.5 equiv) was dissolved in THF (0.2 M) and the solution was cooled to 0° C. Sodium hexamethyldisilylamide (NaHMDS, 1.4 equiv) was slowly added and the resulting mixture was stirred for 15 min before aldehyde 2000 (1.0 equiv) was added at the same temperature. Stirring was continued for another 0.5 h at 25° C. and then, the reaction mixture was quenched with saturated aqueous NH$_4$Cl solution. Ether was added and the organic phase was separated and washed with brine, dried (MgSO$_4$) and concentrated under vacuo. The crude product was purified by flash column chromatography to afford olefin 2001 (75%). The deprotection of compound 2001 to compound 1000K' was done in 99%, according to the procedures described above (using HF.pyridinepyridineTHF mixture).

Synthesis of Compound 2003 as shown In FIG. 73. To a stirred solution of alcohol 403 (1 equiv) in CH$_2$Cl$_2$ (0.1 M) at 0° C. was added Et$_3$N (4.0 equiv) followed by tosyl chloride (2.0 equiv) and DMAP (0.1 equiv). The reaction mixture was warmed to room temperature and stirred until complete as determined by TLC (1 h). Saturated ammonium chloride solution was added and the layers were separated. The aqueous phase was extracted with ether and the combined organic extracts were dried, (MgSO$_4$), filtered and concentrated in vacuo. Flash chromatography gave the tosylate 2002 (85%). Next, To a stirred solution of tosylate (1 equiv) 2002 in acetone (0.1 M) was added sodium iodide. The reaction was stirred for 12 hours. Saturated ammonium chloride solution was added and the layers were separated. The aqueous phase was extracted with ether, and the combined organic extracts were dried (MgSO$_4$), filtered and evaporated in vacuo. Flash chromatography then provided the iodide 2003 (85%).

Synthesis of Compound 1000n as illustrated in FIG. 74 To a solution of allylic alcohol 392 in Et$_2$O (0.1 M) was added MnO$_2$ (5.0 equiv.). The reaction was then stirred for 3 hours at 25° C. The suspension was filtered through a plug of celite to provide after flash column chromatography, compound 2004 as a colorless oil (85%). Next, To a stirred solution of trimethylsilyl diazomethane (1.5 equiv.) in THF (0.1 M) at −78° C. was added n-BuLi (1.3 equiv.). The solution was stirred at the same temperature for 1 h prior addition of aldehyde 2004 (1.0 equiv.). Stirring was maintained for another hour at −78° C., and the solution was then allowed to warm slowly to 0° C. before being quenched with saturated aqueous sodium bicarbonate solution. The layers were separated and the aqueous phase extracted with $CH_2Cl_2$. The combined organic extracts were dried ($MgSO_4$), filtered and concentrated in vacuo. Flash chromatography gave the compound 2005 as a colorless oil (75%). The deprotection of compound 2005 to afford 1000n was done in 91%, according to the procedure described vida supra (using HFpyridine in THF).

Synthesis of Compound 1001' as illustrated in FIG. 75. To a stirred solution of compound 2005 (1.0 equiv.) in ethylacetate (0.1 M) at 25° C. was added under argon, Lindlar catalyst (0.1 equiv.). The solution was then stirred at the same temperature under an atmosphere of hydrogen ($H_2$) for 0.25 h or until reaction was completed. The suspension was filtered over celite and the solution concentrated in vacuo. Flash chromatography gave the compound 2006 as a colorless oil (30%). The deprotection of compound 2006 to afford 2007 was done in 90%, according to the procedure described for the synthesis of diol 2007 (using HF.pyridine in THF). Finally, the oxidation was carried out identically as that of epothilone B synthesis to provide 1001(l').

Synthesis of epoxide 2008. Epoxide 2008 was prepared from 392 using the same conditions as that of conversion of compound 402 to 403 with the use of (−) diethyl-L-tartrate instead of (+) diethyl-D-tartrate) wherein compound 2008 was obtained in 76% yield.

Synthesis of allylic Alcohol 2009. To a stirred solution of 2008 in a mixed solvent system of MeCN:ether (3:1, 0.1 M) at 0° C. was added triphenylphosphine (2.5 eq.) and iodine (1.2 eq.). After stirring at this temperature for 1 hour, the reaction was quenched with water and the layers were separated. The aqueous phase was extracted with ether (3 times) and the combined organic extracts then washed with saturated aqueous $Na_2S_2O_3$ solution. After drying ($MgSO_4$), the organic solution was filtered and concentrated in vacuo. Flash chromatography provided the allylic alcohol 2009.

Synthesis of stannane 2010. To a stirred solution of allylic alcohol 2009 in THF (0.1 M) at RT was added solid palladium hydroxide (0.2 eq.) followed by very slow addition of $Bu_3SnH$ (1.5 eq.). After stirring for one hour, the solvent was removed in vacuo, and the residue filtered through silica gel to give 2010.

Synthesis of cyclopropyl compound 2011. To a stirred solution of stannane 2010 in $CH_2Cl_2$ (0.1 M) at −15 C. was added triethylamine (4 eq.) followed by methane sulfonyl chloride (2 eq.). After stirring at this temperature for 1 hour, the reaction was quenched by the addition of saturated aqueous sodium bicarbonate solution. The layers were separated and the aqueous phase extracted with $CH_2Cl_2$ (3 times). The combined organic extracts were dried, filtered and concentrated in vacuo. Flash chromatography gave the product 2011.

Synthesis of cyclopropane epothilone A 2012. Product 2011 was deprotected as described previously for the conversion of 2001 to 1000k' using HF.pyr in THF.

What is claimed is:

1. A method for treating a mammal having a proliferative disease, the method comprising the step of administering to said mammal a therapeutically effective dose for inhibiting said proliferative disease of a compound, said compound being represented by the following structure (formula (I)):

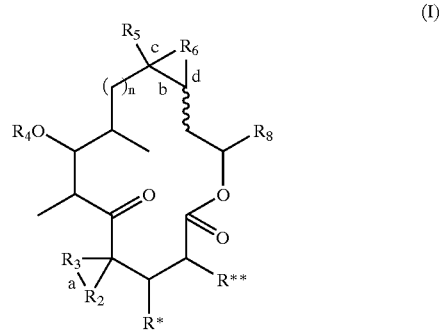

wherein n is 1 to 5;

either $R^*$ is $-OR_1$ and $R^{**}$ is hydrogen, or $R^*$ and $R^{**}$ together form a further bond so that a double bond is present between the two carbon atoms carrying $R^*$ and $R^{**}$;

$R_1$ is a radical selected from the group consisting of hydrogen or methyl, or a protecting group;

$R_2$ is a radical selected from the group consisting of hydrogen, methylene and methyl;

$R_3$ is a radical selected from the group consisting of hydrogen, methylene and methyl;

$R_4$ is a radical selected from the group consisting of hydrogen or methyl, or is a protecting group;

$R_5$ is a radical selected from the group consisting of hydrogen, methyl, —CHO, —COOH, —$CO_2$Me, —$CO_2$(tert-butyl), —$CO_2$(iso-propyl), —$CO_2$(phenyl), —$CO_2$(benzyl), —CONH(furfuryl), —$CO_2$(N-benzoyl-(2R,3S)-3-phenyliso-serine), —CON(methyl)$_2$, —CON(ethyl)$_2$, —CONH(benzyl), —CH=$CH_2$, HCC— and —$CH_2R_{11}$;

$R_{11}$ is a radical selected from the group consisting of —OH, —O-Trityl, —O—($C_1$-$C_6$ alkyl), —($C_1$-$C_6$ alkyl), —O-benzyl, —O-allyl, —O—$COCH_3$, —O—$COCH_2Cl$, —O—$COCH_2CH_3$, —O—$COCF_3$; —O—COCH($CH_3$)$_2$, —O—CO—C($CH_3$)$_3$, —O—CO(cyclopropane), —OCO(cyclohexane), —O—COCH=$CH_2$, —O—CO-Phenyl, —O-(2-furoyl), —O-(N-benzoyl-(2R,3S)-3-phenyliso-serine), —O-cinnamoyl, —O-(acetylphenyl), —O-(2-thiophenesulfonyl), —S-($C_1$-$C_6$ alkyl), —SH, —S-Phenyl, —S-Benzyl, —S-furfuryl, —$NH_2$, —$N_3$, —$NHCOCH_3$, —$NHCOCH_2Cl$, —$NHCOCH_2CH_3$, —$NHCOCF_3$, —NHCOCH($CH_3$)$_2$, —NHCO—C($CH_3$)$_3$, —NHCO(cyclopropane), —NHCO(cyclohexane), —NHCOCH=$CH_2$, —NHCO-Phenyl, —NH(2-furoyl), —NH-(N-benzoyl-(2R,3S)-3-phenylisoserine), —NH-(cinnamoyl), —NH-(acetylphenyl), —NH-(2-thiophenesulfonyl), —F, —Cl, —$CH_2CO_2H$ and methyl;

$R_6$ is absent, methylene, or oxygen; $R_8$ is a radical selected from the group represented by the formulas:

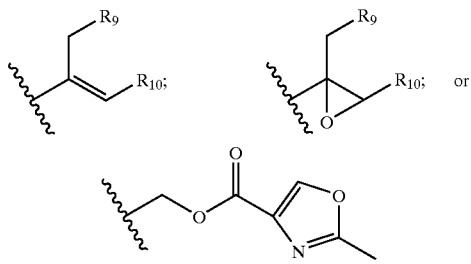

wherein
R$_9$ is a radical selected from the group consisting of hydrogen and methyl;
R$_{10}$ is a radical represented by the formula:

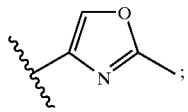

or a salt thereof where a salt-forming group is present;
where, in the above structures,
"a" can be either absent or a single bond;
"b" can be either a single or double bond;
"c" can be either absent or a single bond;
"d" can be either absent or a single bond, and the following provisos pertain:
a. if R$_2$ is methylene, then R$_3$ is methylene;
b. if R$_2$ and R$_3$ are both methylene, then "a" is a single bond;
c. if R$_2$ and R$_3$ are selected from the group consisting of hydrogen and methyl, then the single bond "a" is absent;
d. if R$_6$ is oxygen, then "c" and "d" are both a single bond and "b" is a single bond;
e. if R$_6$ is absent, then "c" and "d" are absent and "b" is a double bond; and
f. if "b" is a double bond then R$_6$, "c", and "d" are absent.

2. A compound represented by formula II,

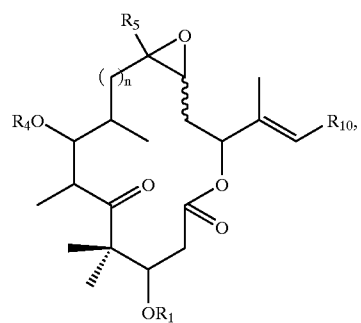

(II)

wherein n is 3,
R$_1$ is a radical selected from the group consisting of hydrogen, methyl or a protecting group,
R$_4$ is a radical selected from the group consisting of hydrogen, methyl or a protecting group,
R$_5$ is a radical selected from the group consisting of hydrogen, methyl, —CHO, —COOH, —CO$_2$Me, —CO$_2$(tert-butyl), —CO$_2$(iso-propyl), —CO$_2$(phenyl), —CO$_2$(benzyl), —CONH(furfuryl), —CO$_2$(N-benzoyl-(2R,3S)-3-phenylisoserine), —CON(methyl)$_2$, —CON(ethyl)$_2$, —CONH(benzyl), —CH$_2$R$_{11}$, —CH=CH$_2$, and HCC—; where R$_{11}$ is a radical selected from the group consisting of —OH, —O-Trityl, —O-(C$_1$-C$_6$ alkyl), —O-benzyl, —O-allyl, —O—COCH$_3$, —O—COCH$_2$Cl, —O—COCH$_2$CH$_3$, —O—COCF$_3$; —O—COCH(CH$_3$)$_2$, —O—CO—C(CH$_3$)$_3$, —O—CO(cyclopropane), —OCO(cyclohexane), —O—COCH=CH$_2$, —O—CO-phenyl, —O-(2-furoyl), —O-(N-benzoyl-(2R,3S)-3-phenylisoserine), —O-cinnamoyl, —O-(acetyl-phenyl), —O-(2-thiophenesulfonyl), —S-(C$_1$-C$_6$ alkyl), —SH, —S-Phenyl, —S-Benzyl, —S-fururyl, —NH$_2$, —N$_3$, —NHCOCH$_3$, —NHCOCH$_2$Cl, —NHCOCH$_2$CH$_3$, —NHCOCF$_3$, —NHCOCH(CH$_3$)$_2$, —NHCO—C(CH$_3$)$_3$, —NHCO(cyclopropane), —NHCO(cyclohexane), —NHCOCH=CH$_2$, —NHCO-phenyl, —NH(2-furoyl), —NH-(N-benzoyl-(2R,3S)-3-phenylisoserine), —NH-(cinnamoyl), —NH-(acetyl-phenyl), —NH-(2-thiophenesulfonyl), —F, —Cl, —CH$_2$CO$_2$H, —(C$_1$-C$_6$ alkyl) and methyl; and
R$_{10}$ is a radical represented by the formula:

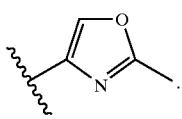

3. A compound of the formula IIa

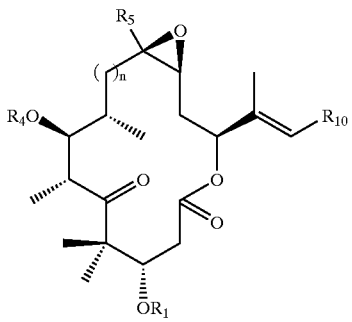

wherein n is 3,
R$_1$ is a radical selected from the group consisting of hydrogen, methyl or a protecting group,
R$_4$ is a radical selected from the group consisting of hydrogen, methyl or a protecting group,
R$_5$ is a radical selected from the group consisting of hydrogen, methyl, —CHO, —COOH, —CO$_2$Me, —CO$_2$(tert-butyl), —CO$_2$(iso-propyl), —CO$_2$(phenyl), —CO$_2$(benzyl), —CONH(furfuryl), —CO$_2$(N-benzoyl-(2R,3S)-3-phenylisoserine), —CON(methyl)$_2$, —CON(ethyl)$_2$, —CONH(benzyl), —CH$_2$R$_{11}$, —CH=CH$_2$, HCC—;
where R$_{11}$ is a radical selected from the group consisting of —OH, —O-Trityl, —O-(C$_1$-C$_6$ alkyl), —O-benzyl, —O-allyl, —O—COCH$_3$, —O—COCH$_2$Cl, —O—COCH$_2$CH$_3$, —O—COCF$_3$; —O—COCH(CH$_3$)$_2$, —O—CO—C(CH$_3$)$_3$, —O—CO(cyclopropane), —OCO(cyclohexane), —O—COCH=CH$_2$, —O—CO-phenyl, —O-(2-furoyl), —O-(N-benzoyl-(2R,3S)-3- phenylisoserine), —O-cinnamoyl, —O-(acetyl-phenyl), —O-(2-thiophenesulfonyl), —S-(C₁-C₆ alkyl), —SH, —S-Phenyl, —S-Benzyl, —S-furfuryl, —NH₂, —N₃, —NHCOCH₃, —NHCOCH₂Cl, —NHCOCH₂CH₃, —NHCOCF₃, —NHCOCH(CH₃)₂, —NHCO—C(CH₃)₃, —NHCO(cyclopropane), —NHCO(cyclohexane), —NHCOCH=CH₂, —NHCO-phenyl, —NH(2-furoyl), —NH-(N-benzoyl-(2R,3S)-3-phenylisoserine),—NH-(cinnamoyl),—NH-(acetyl-phenyl), —NH-(2-thiophene-sulfonyl), —F, —Cl, —CH₂CO₂H, —(C₁-C₆ alkyl) and methyl; and $R_{10}$ is a radical represented by the formula:

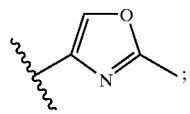

or a salt thereof where a salt-forming group is present.

4. A compound according to claim 3 the formula

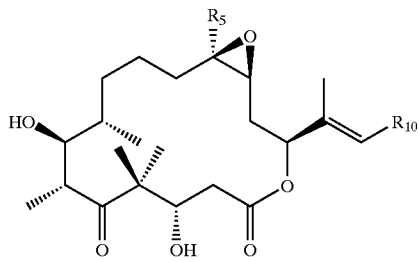

wherein $R_{10}$ is as defined in claim 3 and
$R_5$ is —CH₂F, —CH₂Cl, CH₂OOCCH₃, —CH₂CH₃ or —CH=CH₂.

5. A compound of the formula III,

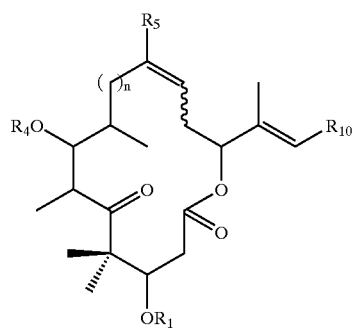

(III)

wherein n is 3;

$R_1$ is a radical selected from the group consisting of hydrogen, methyl or a protecting group, $R_4$ is a radical selected from the group consisting of hydrogen, methyl or a protecting group, $R_5$ is a radical selected from the group consisting of hydrogen, methyl, —CHO, —COOH, —CO₂Me, —CO₂(tert-butyl), —CO₂(iso-propyl), —CO₂(phenyl), —CO₂(benzyl), —CONH(furfuryl), —CO₂(N-benzoyl-(2R,3S)-3-phenylisoserine), —CON(methyl)₂, —CON(ethyl)₂, —CONH(benzyl), and —CH₂R₁₁; or in a broader aspect also from —CH=CH₂ and HCC—;

where $R_{11}$ is a radical selected from the group consisting of —OH, —O-Trityl, —O-(C₁-C₆ alkyl), —O-benzyl, —O-allyl, —O—COCH₃, —O—COCH₂Cl, —O—COCH₂CH₃, —O—COCF₃; —O—COCH(CH₃)₂, —O—CO—C(CH₃)₃, —O—CO(cyclopropane), —OCO(cyclohexane), —O—COCH=CH₂, —O—CO-phenyl, —O-(2-furoyl), —O-(N-benzoyl-(2R,3S)-3-phenylisoserine), —O-cinnamoyl, —O-(acetyl-phenyl), —O-(2-thiophenesulfonyl), —S-(C₁-C₆ alkyl), —SH, —S-Phenyl, —S-Benzyl, —S-furfuryl, —NH₂, —N₃, —NHCOCH₃, —NHCOCH₂Cl, —NHCOCH₂CH₃, —NHCOCF₃, —NHCOCH(CH₃)₂, —NHCO—C(CH₃)₃, —NHCO(cyclopropane), —NHCO(cyclohexane), —NHCOCH=CH₂, —NHCO-phenyl, —NH(2-furoyl), —NH-(N-benzoyl-(2R,3S)-3-phenylisoserine),—NH-(cinnamoyl),—NH-(acetyl-phenyl), —NH-(2-thiophenesulfonyl), —F, —Cl, —CH₂CO₂H; and from —(C₁-C₆ alkyl) and methyl; and $R_{10}$ is a radical represented by the formula:

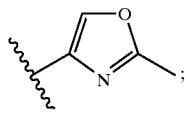

or a salt thereof if a salt-forming group is present.

6. A compound of formula III according to claim 5 wherein $R_5$ is —CH₂F, —CH₂Cl, CH₂OOCCH₃, —CH₂CH₃ or —CH=CH₂, the double bond with the wavered line is in cis form and the remaining moieties are as defined in claim 5.

7. A compound according to claim 1 of the formula V

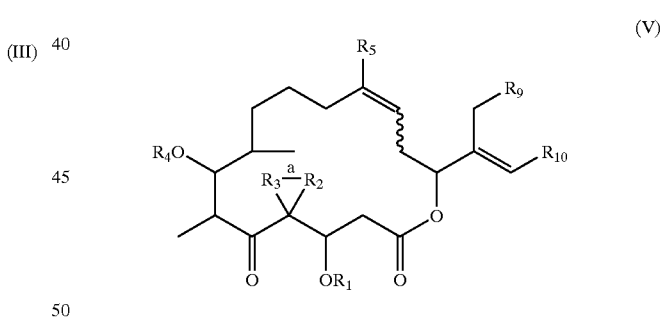

(V)

wherein $R_1$ is a radical selected from the group consisting of hydrogen, methyl or a protecting group, $R_4$ is a radical selected from the group consisting of hydrogen, methyl or a protecting group, $R_5$ is a radical selected from the group consisting of hydrogen and methyl, $R_{10}$ is a radical represented by the formula:

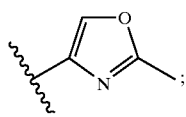

$R_3$ is a radical selected from hydrogen, methylene or methyl;

$R_2$ is hydrogen, methylene or methyl; and $R_9$ is hydrogen or methyl;

or a salt thereof if a salt-forming group is present.

8. A compound represented by the following structure (formula (I)):

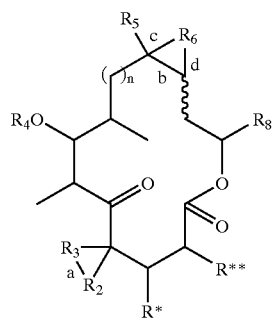

wherein n is 1 to 5;

either $R^*$ is $—OR_1$ and $R^{**}$ is hydrogen, or $R^*$ and $R^{**}$ together form a further bond so that a double bond is present between the two carbon atoms carrying $R^*$ and $R^{**}$;

$R_1$ is a radical selected from the group consisting of hydrogen or methyl, or a protecting group;

$R_2$ is a radical selected from the group consisting of hydrogen, methylene and methyl;

$R_3$ is a radical selected from the group consisting of hydrogen, methylene and methyl;

$R_4$ is a radical selected from the group consisting of hydrogen or methyl, or is a protecting group;

$R_5$ is a radical selected from the group consisting of $—CH_2F$, $—CH_2—CH_3$, $—CH=CH_2$, $—CH_2OOCCH_3$ and $—CH_2Cl$;

$R_6$ is absent, methylene, or oxygen;

$R_8$ is a radical selected from the group represented by the formulas:

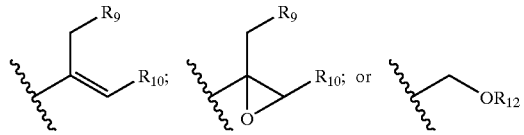

wherein $R_9$ is a radical selected from the group consisting of hydrogen and methyl;

$R_{10}$ is a radical represented by the formula:

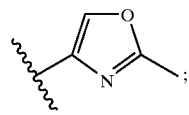

$R_{12}$ is a radical selected from the group consisting of hydrogen, methyl or a protecting group, preferably tert-butyldiphenylsilyl, tert-butyldimethylsilyl, trimethylsilyl, acetyl, benzoyl, tert-butoxycarbonyl and a group represented by any one of the following formulae:

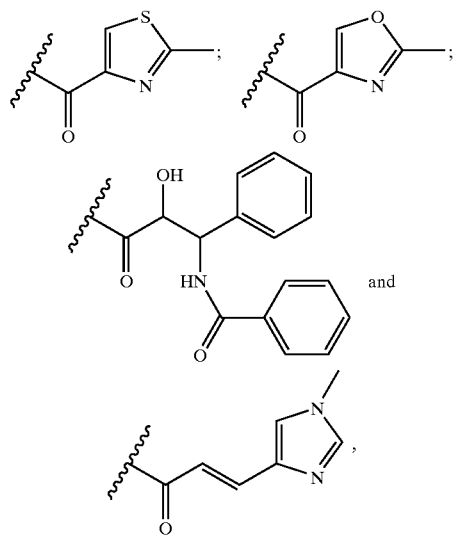

or a salt thereof where a salt-forming group is present;

where, in the above structures,

"a" can be either absent or a single bond;

"b" can be either a single or double bond;

"c" can be either absent or a single bond;

"d" can be either absent or a single bond, and the following provisos pertain:

a. if $R_2$ is methylene, then $R_3$ is methylene;

b. if $R_2$ and $R_3$ are both methylene, then "a" is a single bond;

c. if $R_2$ and $R_3$ are selected from the group consisting of hydrogen and methyl, then the single bond "a" is absent;

d. if $R_6$ is oxygen, then "c" and "d" are both a single bond and "b" is a single bond;

e. if $R_6$ is absent, then "c" and "d" are absent and "b" is a double bond;

f. if "b" is a double bond then $R_6$, "c", and "d" are absent; or a salt thereof if a salt-forming group is present.

9. A compound of the formula I according to claim 8, wherein $R_5$ is $—CH_2F$ and the remaining definitions are as in claim 8, or a salt thereof if a salt-forming group is present.

10. A compound of the formula III

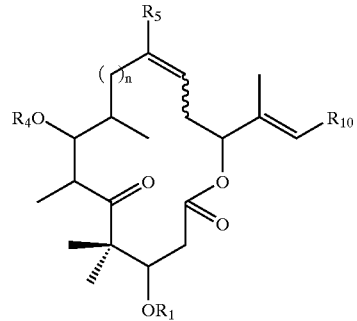

wherein n is 3;

$R_1$ is a radical selected from the group consisting of hydrogen, methyl or a protecting group, $R_4$ is a radical selected from the group consisting of hydrogen, methyl or a protecting group, $R_5$ is a radical selected from the group consisting of —$CH_2F$, —$CH_2$—$CH_3$, —$CH=CH_2$, —$CH_2OOCCH_3$ and —$CH_2$—Cl; and $R_{10}$ is a radical represented by the formula:

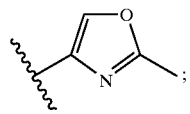

or a salt thereof if a salt-forming group is present.

11. A compound of the formula III according to claim 10, wherein $R_5$ is —$CH_2F$ and the remaining definitions are as in claim 8, or a salt thereof if a salt-forming group is present.

12. A compound according to claim 3, represented by the following formula:

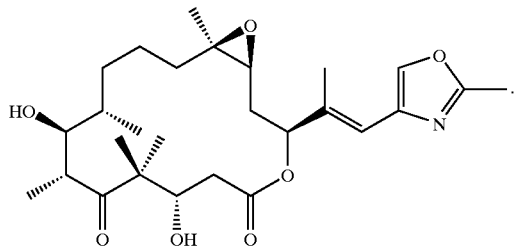

13. A pharmaceutical composition comprising a pharmaceutically acceptable carrier admixed with a compound represented by the following structure (formula (I)):

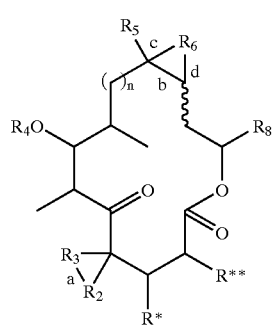

(I)

wherein n is 1 to 5;

either R* is —$OR_1$ and R** is hydrogen, or R* and R** together form a further bond so that a double bond is present between the two carbon atoms carrying R* and R**;

$R_1$ is a radical selected from the group consisting of hydrogen or methyl, or a protecting group;

$R_2$ is a radical selected from the group consisting of hydrogen, methylene and methyl;

$R_3$ is a radical selected from the group consisting of hydrogen, methylene and methyl;

$R_4$ is a radical selected from the group consisting of hydrogen or methyl, or is a protecting group;

$R_5$ is a radical selected from the group consisting of hydrogen, methyl, —CHO, —COOH, —$CO_2Me$, —$CO_2$(tert-butyl), —$CO_2$(iso-propyl), —$CO_2$(phenyl), —$CO_2$(benzyl), —CONH(furfuryl), —$CO_2$(N-benzoyl-(2R,3S)-3-phenyliso-serine), —CON(methyl)$_2$, —CON(ethyl)$_2$, —CONH(benzyl), —$CH=CH_2$, HCC— and —$CH_2R_{11}$;

$R_{11}$ is a radical selected from the group consisting of —OH, —O-Trityl, —O-($C_1$-$C_6$ alkyl), —($C_1$-$C_6$ alkyl), —O-benzyl, —O-allyl, —O—$COCH_3$, —O—$COCH_2Cl$, —O—$COCH_2CH_3$, —O—$COCF_3$; —O—$COCH(CH_3)_2$, —O—CO—$C(CH_3)_3$, —O—CO(cyclopropane), —OCO(cyclohexane), —O—$COCH=CH_2$, —O—CO-Phenyl, —O-(2-furoyl), —O-(N-benzoyl-(2R,3S)-3-phenyliso-serine), —O-cinnamoyl, —O-(acetyl-phenyl), —O-(2-thiophenesulfonyl), —S-($C_1$-$C_6$ alkyl), —SH, —S-Phenyl, —S-Benzyl, —S-furfuryl, —$NH_2$, —$N_3$, —$NHCOCH_3$, —$NHCOCH_2Cl$, —$NHCOCH_2CH_3$, —$NHCOCF_3$, —$NHCOCH(CH_3)_2$, —NHCO—C$(CH_3)_3$, —NHCO(cyclopropane), —NHCO(cyclohexane), —$NHCOCH=CH_2$, —NHCO-Phenyl, —NH(2-furoyl), —NH-(N-benzoyl-(2R,3S)-3-phenylisoserine), —NH-(cinnamoyl), —NH-(acetyl-phenyl), —NH-(2-thiophenesulfonyl), —F, —Cl, —$CH_2CO_2H$ and methyl;

$R_6$ is absent, methylene, or oxygen; $R_8$ is a radical selected from the group represented by the formulas:

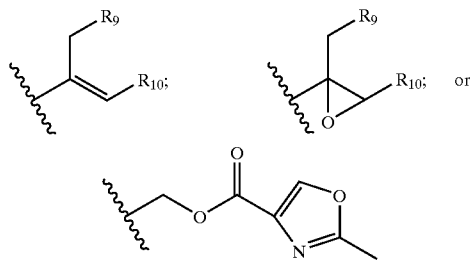

wherein $R_9$ is a radical selected from the group consisting of hydrogen and methyl;

$R_{10}$ is a radical represented by the formula:

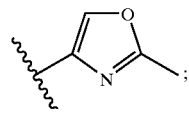

or a salt thereof where a salt-forming group is present;

where, in the above structures,

"a" can be either absent or a single bond;

"b" can be either a single or double bond;

"c" can be either absent or a single bond;

"d" can be either absent or a single bond, and the following provisos pertain:

a. if $R_2$ is methylene, then $R_3$ is methylene;

b. if $R_2$ and $R_3$ are both methylene, then "a" is a single bond;

c. if $R_2$ and $R_3$ are selected from the group consisting of hydrogen and methyl, then the single bond "a" is absent;

d. if $R_6$ is oxygen, then "c" and "d" are both a single bond and "b" is a single bond;

e. if $R_6$ is absent, then "c" and "d" are absent and "b" is a double bond; and f. if "b" is a double bond then $R_6$, "c", and "d" are absent.

* * * * *